US012692325B2

(12) United States Patent
Spillner et al.

(10) Patent No.: US 12,692,325 B2
(45) Date of Patent: Jul. 28, 2026

(54) DISPLACERS OF IGE-FCERI

(71) Applicants: ALK-Abelló, Hørsholm (DK); Aarhus Universitet, Århus (DK)

(72) Inventors: Edzard Spillner, Aarhus (DK); Sivelle Coline, Aarhus (DK); Lars Harder Christensen, Hørsholm (DK); Peter Sejer Andersen, Hørsholm (DK); Gitte Lund, Hørsholm (DK); Teit Johansen, Hørsholm (DK); Frederic Jabs, Hørsholm (DK); Anne-Sofie Ravn Ballegaard, Aarhus (DK); Andrea Maria Kemter, Hørsholm (DK)

(73) Assignees: ALK-Abelló, Hørsholm (DK); Aarhus Universitet, Århus (DK)

( * ) Notice: Subject to any disclaimer, the term of this patent is extended or adjusted under 35 U.S.C. 154(b) by 0 days.

(21) Appl. No.: 18/880,418

(22) PCT Filed: Jun. 30, 2023

(86) PCT No.: PCT/EP2023/068078
§ 371 (c)(1),
(2) Date: Dec. 31, 2024

(87) PCT Pub. No.: WO2024/003376
PCT Pub. Date: Jan. 4, 2024

(65) Prior Publication Data
US 2025/0171562 A1     May 29, 2025

(30) Foreign Application Priority Data

| | | | |
|---|---|---|---|
| Jul. 1, 2022 | (EP) | .................................. | 22182630 |
| Oct. 11, 2022 | (EP) | .................................. | 22200911 |
| Oct. 12, 2022 | (EP) | .................................. | 22201172 |
| Jan. 27, 2023 | (EP) | .................................. | 23153730 |
| Jan. 27, 2023 | (EP) | .................................. | 23153731 |

(51) Int. Cl.
*C07K 16/42*      (2006.01)
*A61K 39/00*      (2006.01)

(52) U.S. Cl.
CPC .... *C07K 16/4291* (2013.01); *A61K 2039/505* (2013.01); *C07K 2317/24* (2013.01); *C07K 2317/31* (2013.01); *C07K 2317/53* (2013.01); *C07K 2317/565* (2013.01); *C07K 2317/569* (2013.01); *C07K 2317/70* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,541,087 A | * | 7/1996 | Lo ........................... C07K 14/55 530/391.1 |
| 7,404,956 B2 | * | 7/2008 | Peters ................ A61K 47/6835 530/387.3 |
| 2012/0149876 A1 | | 6/2012 | Von Kreudenstein et al. |
| 2018/0118836 A1 | | 5/2018 | Bernett et al. |
| 2023/0250191 A1 | | 8/2023 | Deng et al. |

FOREIGN PATENT DOCUMENTS

| | | | | |
|---|---|---|---|---|
| CN | 111875706 B | 3/2021 | | |
| CN | 113461823 B | 12/2022 | | |
| WO | 2004041867 A2 | 5/2004 | | |
| WO | WO-2012175740 A1 | * 12/2012 | ............. | A61P 37/08 |
| WO | WO 2014/087010 A1 | 6/2014 | | |
| WO | 2014145806 A2 | 9/2014 | | |
| WO | WO 2017/211928 A1 | 12/2017 | | |
| WO | 2020208177 A1 | 10/2020 | | |
| WO | WO 2022/007965 A1 | 7/2021 | | |
| WO | WO 2022/061240 A1 | 3/2022 | | |

OTHER PUBLICATIONS

Janeway et al., Immunobiology, 3rd edition, 1997, Garland Publishing Inc., pp. 3:1 -3:11.*
Ghahroudi et al., FEBS Letters Sep. 15, 1997; 414(3): 521-526.*
Ying et al., J Biol Chem. Apr. 19, 2012;287(23):19399-19408. doi: 10.1074/jbc.M112.368647 PMCID: PMC3365978 PMID: 22518843.*
Czajkowsky et al., EMBO Mol Med. Oct. 2012;4(10):1015-28. doi: 10.1002/emmm.201201379. Epub Jul. 26, 2012. PMID: 22837174 PMCID: PMC3491832.*
Dondelinger et al., Front Immunol. Oct. 16, 2018:9:2278. doi: 10.3389/fimmu.2018.02278. eCollection 2018. PMID: 30386328 PMCID: PMC6198058.*
Kipriyanov et al., Mol Biotechnol. Jan. 2004;26(1):39-60. doi: 10.1385/MB:26:1:39. PMID: 14734823.*
Lefranc et al., Immunol Rev. Oct. 4, 2024;328(1):473-506. doi: 10.1111/imr.13399 PMCID: PMC11659927 PMID: 39367563.*
Stryer, L., Biochemistry, 4th edition, W. H. Freeman and Company, 1995, pp. 18-23.*
Rudikoff et al., Proc Natl Acad Sci USA. Mar. 1982;79(6):1979-83.*
Winkler et al., J Immunol. Oct. 15, 2000;165(8):4505-14. doi: 10.4049/jimmunol.165.8.4505. PMID: 11035090.*
Hanning, K, et al., "Deep mutational scanning for therapeutic antibody engineering," *Trends in Pharmacological Sciences*, 2022, vol. 43(2), pp. 123-125.
Jabs, F., et al., "Trapping IgE in a closed conformation by mimicking CD23 binding prevents and disrupts FceRI interaction," *Nature Communications*, 2018, vol. 9(7), pp. 1-11.

(Continued)

*Primary Examiner* — Michael Szperka

(74) *Attorney, Agent, or Firm* — Womble Bond Dickinson (US) LLP

(57) ABSTRACT

Disclosed are single domain antibody-based constructs, which are useful for treating IgE-related disorders or conditions by facilitating the dissociation of IgE from the high-affinity IgE receptor. Further disclosed are compositions comprising the constructs. Also nucleic acids and vectors are provides, as is methods of treatment of IgE related disorders.

12 Claims, 15 Drawing Sheets

Figure 6A:
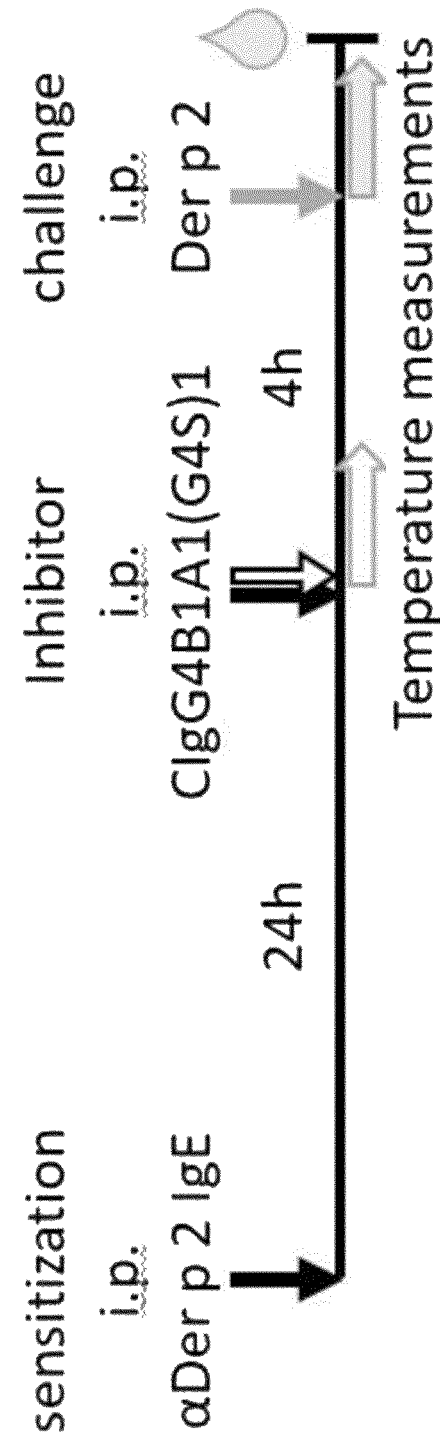

Specification includes a Sequence Listing.

(56) References Cited

OTHER PUBLICATIONS

Jabs, F., et al. "Trapping IgE in a closed conformation by mimicking CD23 binding prevents and disrupts FcεRI interaction," *Nature Communications*, 2018, vol. 9(7), pp. 1-11.—Supplemental Figures, pp. 1-15.

Jensen, R., et al., "Structure of intact IgE and the mechanism of ligelizumab revealed by electron microscopy," *European Journal of Allergy and Clinical Immunology*, 2020, vol. 75(8), pp. 1956-1965, abstract only.

Pennington, L., et al., "Structure-guided design of ultrapotent disruptive IgE inhibitors to rapidly terminate acute allergic reactions," *J Allergy Clin Immunol*, 2012, vol. 148(4), pp. 1049-1060.

Almagro Juan C. "Identification of differences in the specificity-determining residues of antibodies that recognize antigens of different size: implications for the rational design of antibody repertoires" Journal of Molecular Recognition, 17, 132-143 (2004).

Armour et al. "Recombinant human IgG molecules lacking Fc gamma receptor I binding and monocyte triggering activities" Eur. J. Immunol., 29, 2613-2624 (1999).

Balbino et al. Approaches to target IgE antibodies in allergic diseases', Pharmacology & Therapeutics, 191, 50-64 (2018).

Baumann, et al. "DARPins against a functional IgE epitope" Immunology Letters, 133, 78-84 (2010).

Canfield et al. "The binding affinity of human IgG for its high affinity Fc receptor is determined by multiple amino acids in the CH2 domain and is modulated by the hinge region" J. Exp. Med., 173, 1483-1491 (Jun. 1991).

Carter, Paul "Bispecific human IgG by design" Journal of Immunological Methods, 248, 7-15 (2001).

Chang, Tse Wen "The pharmacological basis of anti-IgE therapy" Nature Biotechnology, 18, 157-162 (Feb. 2000).

Czajkowsky et al. "Fc-fusion proteins: new developments and future perspectives" EMBO Molecular Medicine, 4, 1015-1028 (2012).

Dhaliwal et al. "Crystal structure of IgE bound to its B-cell receptor CD23 reveals a mechanism of reciprocal allosteric inhibition with high affinity receptor FcεRI" PNAS, 109(31) (Jul. 31, 2012).

Drinkwater et al. "Human immunoglobulin E flexes between acutely bent and extended conformations" Nature Structural & Molecular Biology, 21(4), 397-404 (Apr. 2014).

Dondelinger et al. "'Understanding the Significance and Implications of Antibody Numbering and Antigen-Binding Surface/Residue Definition" Frontiers in Immunol., 9 (Oct. 16, 2018).

Duncan et al. "Localization of the binding site for the human high-affinity Fc receptor on IgG" Nature, 332, 563-564 (Apr. 1988).

Eggel et al. "Accelerated dissociation of IgE-FcεRI complexes by disruptive inhibitors actively desensitizes allergic effector cells" Journal of Allergy and Clinical Immunology, 133(6), 1709-1719 (Jun. 2014).

Holdom et al. "Conformational changes in IgE contribute to its uniquely slow dissociation rate from receptor Fc epsilon RI" Nature Structural & Molecular Biology, 18(5), 571-576 (2011).

Incorvaia et al. "Omalizumab, an anti-immunoglobulin E antibody: state of the art" Drug Design, Development and Therapy, 197-207 (2014).

Jabs et al. "Supplementary Figures: Supplementary Figure 1: Purification of the IgE Fc:026 sdab complex for crystallization-A-B: Non-reducing SDS-PAGE analysis of the purification of the recombinant IgE Fc and the purification of the recombinant 026 sdab C: Analytical size-exclusion chromatography of the IgE Fc" Nature Communications (2018).

Lefranc, Marie-Paule "IMGT, the international ImMunoGeneTics database: a high-quality information system for comparative immunogenetics and immunology" Developmental and Comparative Immunology, 26, 697-705 (2002).

Kim et al. "Accelerated disassembly of IgE-receptor complexes by a disruptive macromolecular inhibitor" Nature (2012).

Mitchell et al. "Comparative analysis of nanobody sequence and structure data" Proteins, 697-706 (2018).

Ofran et al. "Automated identification of complementarity determining regions (CDRs) reveals peculiar characteristics of CDRs and B cell epitopes" J. Immunol., 181(9), 6230-6235 (2008).

Padlan et al. "Identification of specificity-determining residues in antibodies" FASEB J., 9, 133-139 (1995).

Riechmann et al. "Single domain antibodies: comparison of camel VH and camelised human VH domains" J. Immunol. Methods, 231, 25-38 (1999).

Rossotti et al. "Immunogenicity and humanization of single-domain antibodies" FEBS Journal, 289, 4304-4327 (2022).

Rozan et al. "Single-Domain Antibody-Based and Linker-Free Bispecific Antibodies Targeting FcγRIII Induce Potent Antitumor Activity without Recruiting Regulatory T Cells" Molecular Cancer Therapeutics, 12(8), 1481-1491 (Aug. 2013).

Shields et al. "High Resolution Mapping of the Binding Site on Human IgG1 for FcγRI, FcγRII, FcγRIII, and FcRn and Design of IgG1 Variants with Improved Binding to the FcγR" J. Biol. Chem., 276(9), 6591-6604 (2001).

Strohl, William R. "Fusion Proteins for Half-Life Extension of Biologics as a Strategy to Make Biobetters" BioDrugs, 29, 215-239, (2015).

Sulea, Traian "Humanization of Camelid Single-Domain Antibodies" in Methods in Molecular Biology 2446, 299-312, Humana Press (2022).

Tao et al. "Structural features of human immunoglobulin G that determine isotype-specific differences in complement activation" J. Exp. Med., 178, 661-667 (Aug. 1993).

Wurzburg et al., "An Engineered Disulfide Bond Reversibly Traps the IgE-Fc3-4 in a Closed, Nonreceptor Binding Conformation" Journal of Biological Chemistry, 287(43), 36251-36257 (Oct. 19, 2012).

* cited by examiner

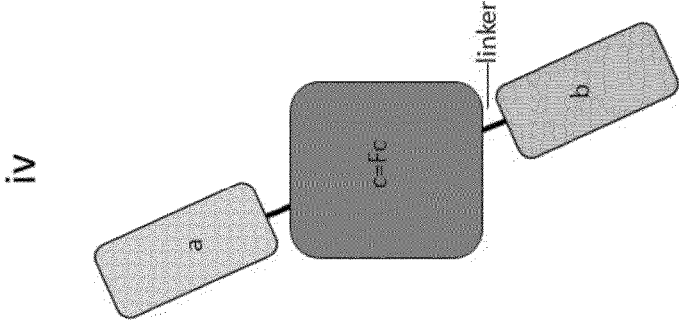
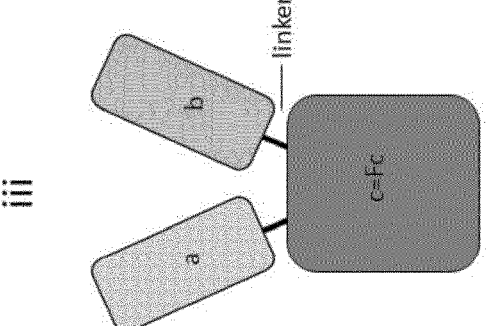
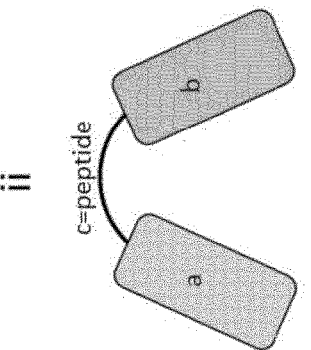
Figure 1

A
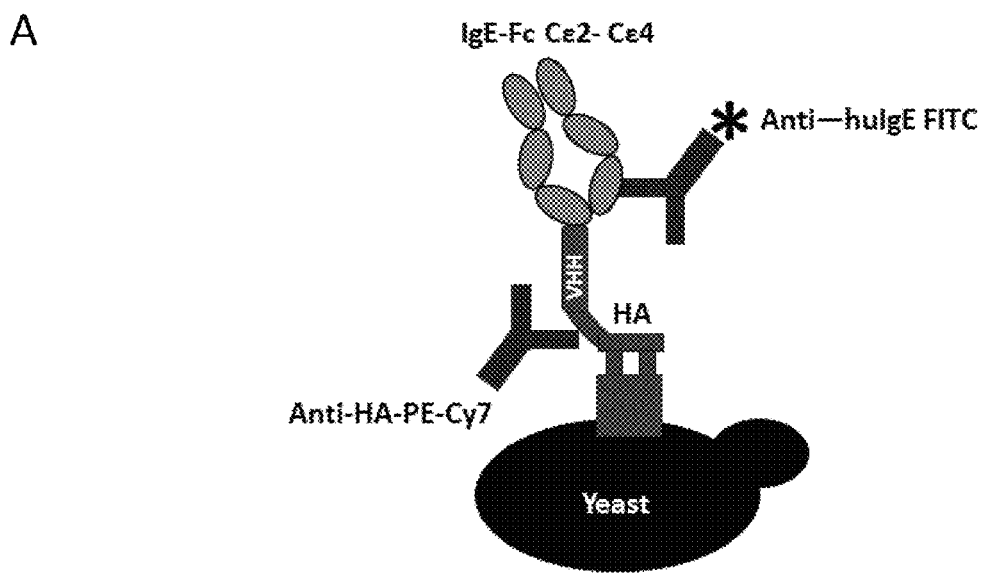
B
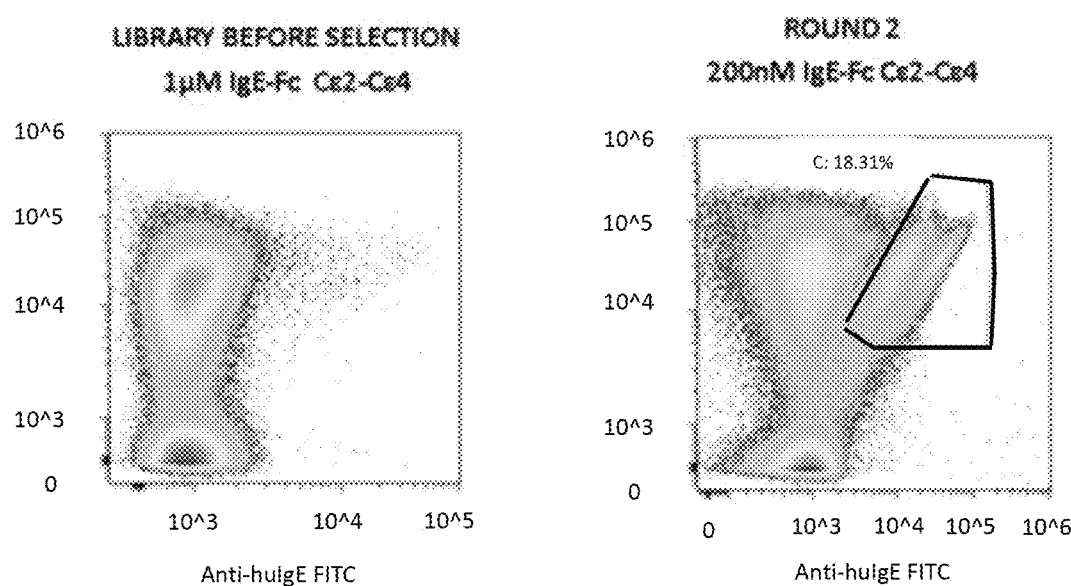
Figure 2A-B

|     | A1  | B1  | B2  | B3  | D1  | D2  |
| --- | --- | --- | --- | --- | --- | --- |
| A1  | x   |     |     |     |     |     |
| B1  |     | x   |     |     |     |     |
| B2  |     |     | x   |     |     |     |
| B3  |     |     |     | x   |     |     |
| D1  |     |     |     |     | x   |     |
| D2  |     |     |     |     |     | x   |

Figure 3

| | A1 Sequence | POSITIVE 28 T | POSITIVE 45 P | POSITIVE 93 V | NEGATIVE 28 T | NEGATIVE 45 P | NEGATIVE 93 V |
|---|---|---|---|---|---|---|---|
| | STOP | 0.3 | 0.3 | D | D | 1.0 | 0.1 |
| Hydrophobic — Aromatic | F | 1.3 | D | 0.5 | D | 0.4 | D |
| | W | 1.9 | 2.8 | 2.8 | D | 0.4 | D |
| | Y | 2.9 | 7.4 | 0.6 | D | 0.4 | D |
| Non polar aliphatic | P | 2.5 | 0.5 | D | D | 1.0 | 0.1 |
| | M | 1.6 | D | 6.0 | D | 0.6 | D |
| | I | 1.6 | D | 3.9 | D | 0.8 | D |
| | L | 2.1 | 0.1 | 0.1 | 0.1 | 0.7 | 0.1 |
| | V | 1.9 | D | 2.2 | D | 0.6 | D |
| SMALL | A | 1.7 | 0.2 | 0.1 | D | 0.8 | D |
| | G | 0.8 | D | D | D | 0.4 | D |
| | C | D | D | 1.1 | D | 0.6 | 0.1 |
| | S | 1.6 | 0.6 | 0.2 | D | 0.6 | 0.1 |
| Polar uncharged | T | 1.5 | 0.1 | 7.3 | 0.1 | 0.7 | D |
| | N | 2.0 | D | D | D | 0.6 | D |
| | Q | 2.6 | 0.4 | 1.9 | D | 1.3 | D |
| Negatively charged | D | D | D | 3.7 | D | 1.0 | D |
| | E | 0.4 | D | 12.8 | D | 1.8 | D |
| Positively charged | H | 2.2 | 0.5 | 0.1 | D | 0.6 | D |
| | K | 4.3 | D | 0.2 | 0.2 | 6.8 | D |
| | R | 6.9 | D | D | D | 1.3 | 0.1 |

Hydrophobic / Hydrophillic

Figure 4

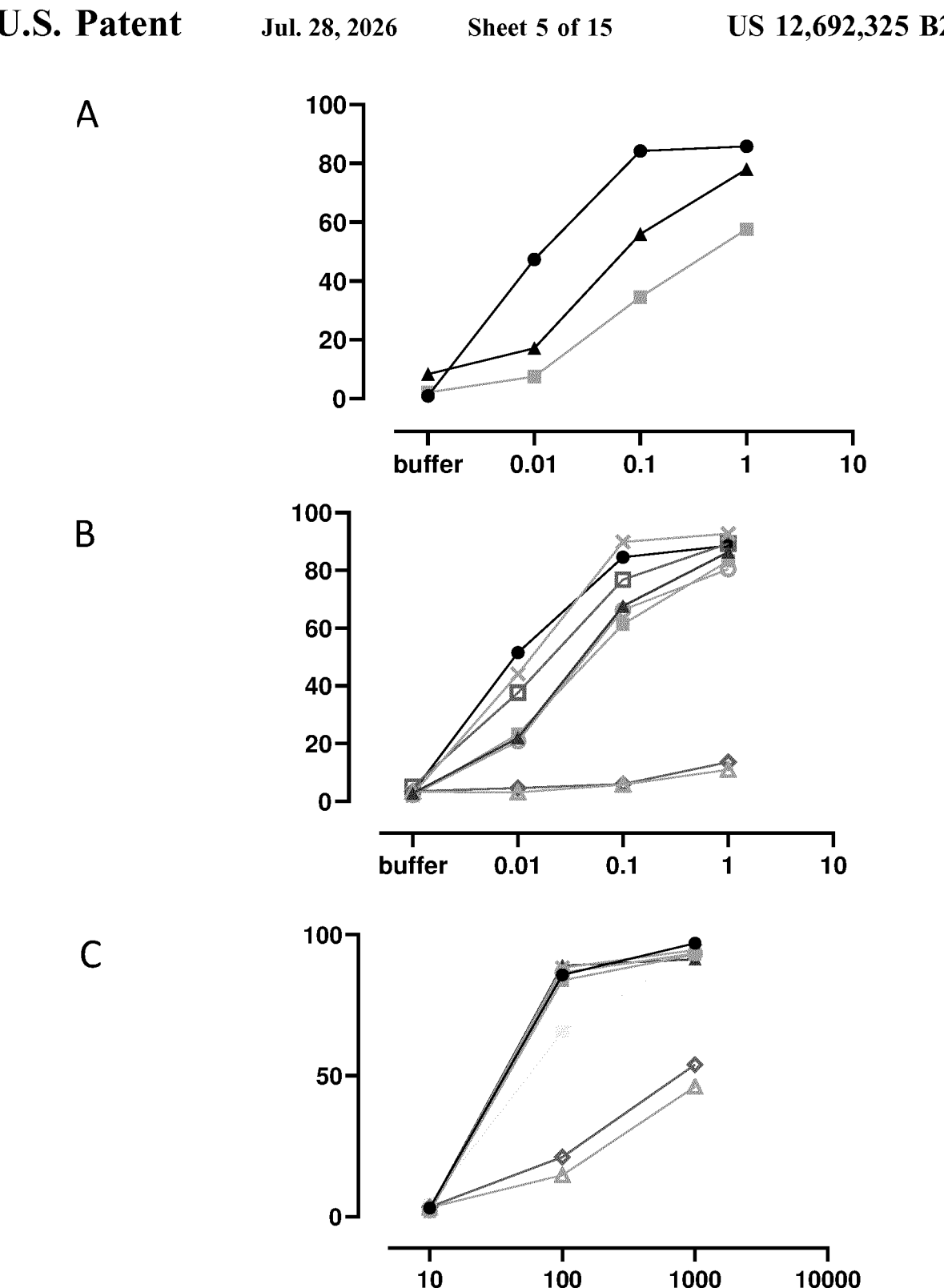
Figure 5A-C

D
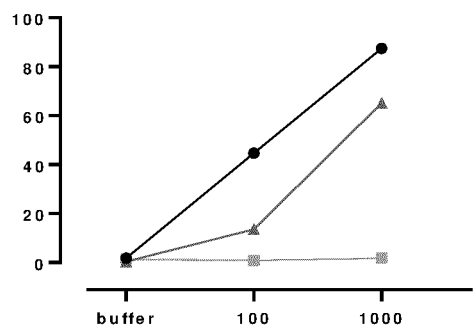
E
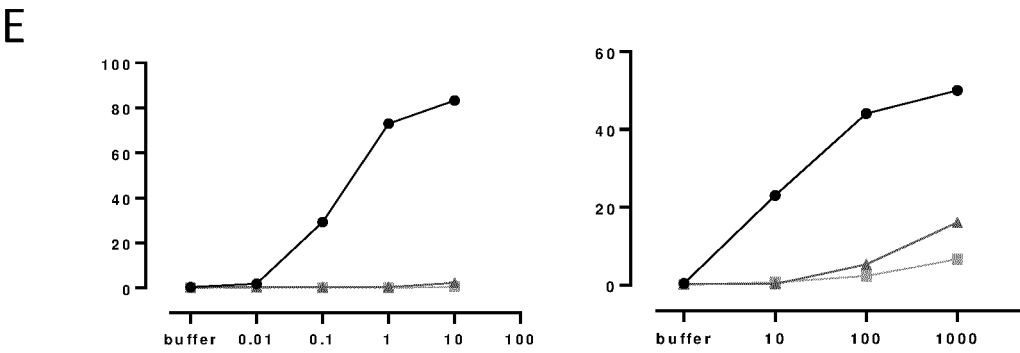
F
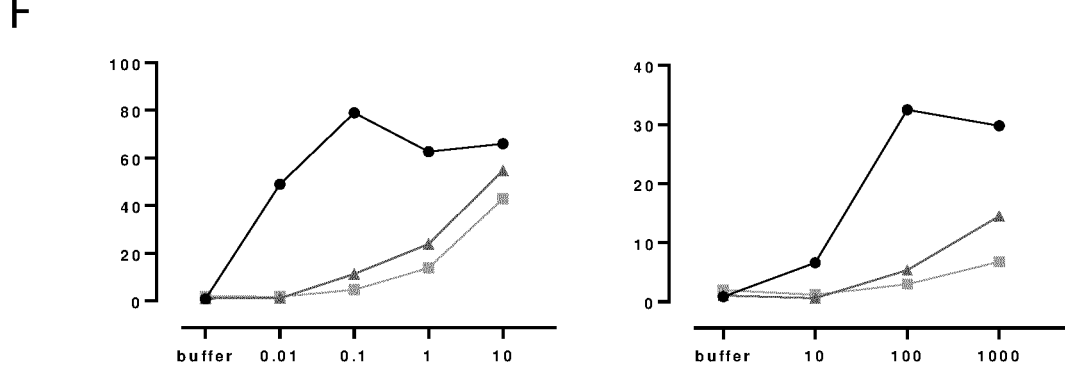
Figure 5D-F

B
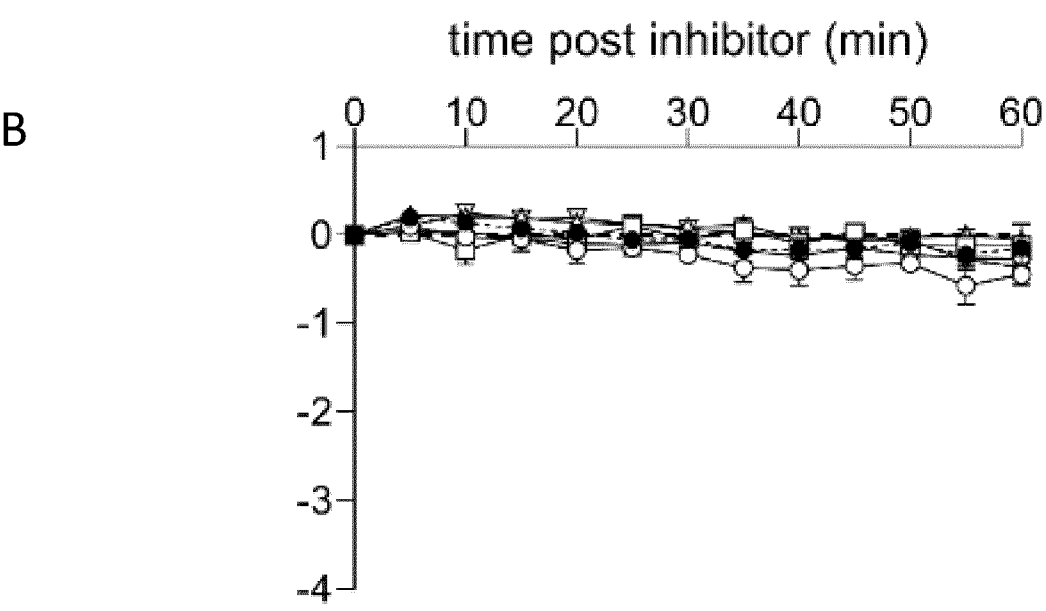
C
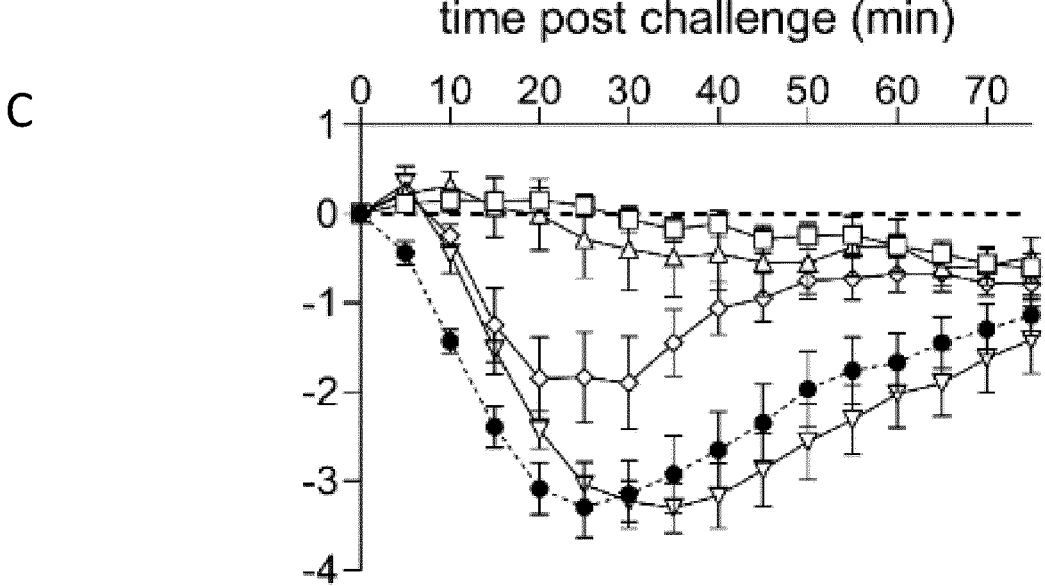
Figure 6B-C

D
E
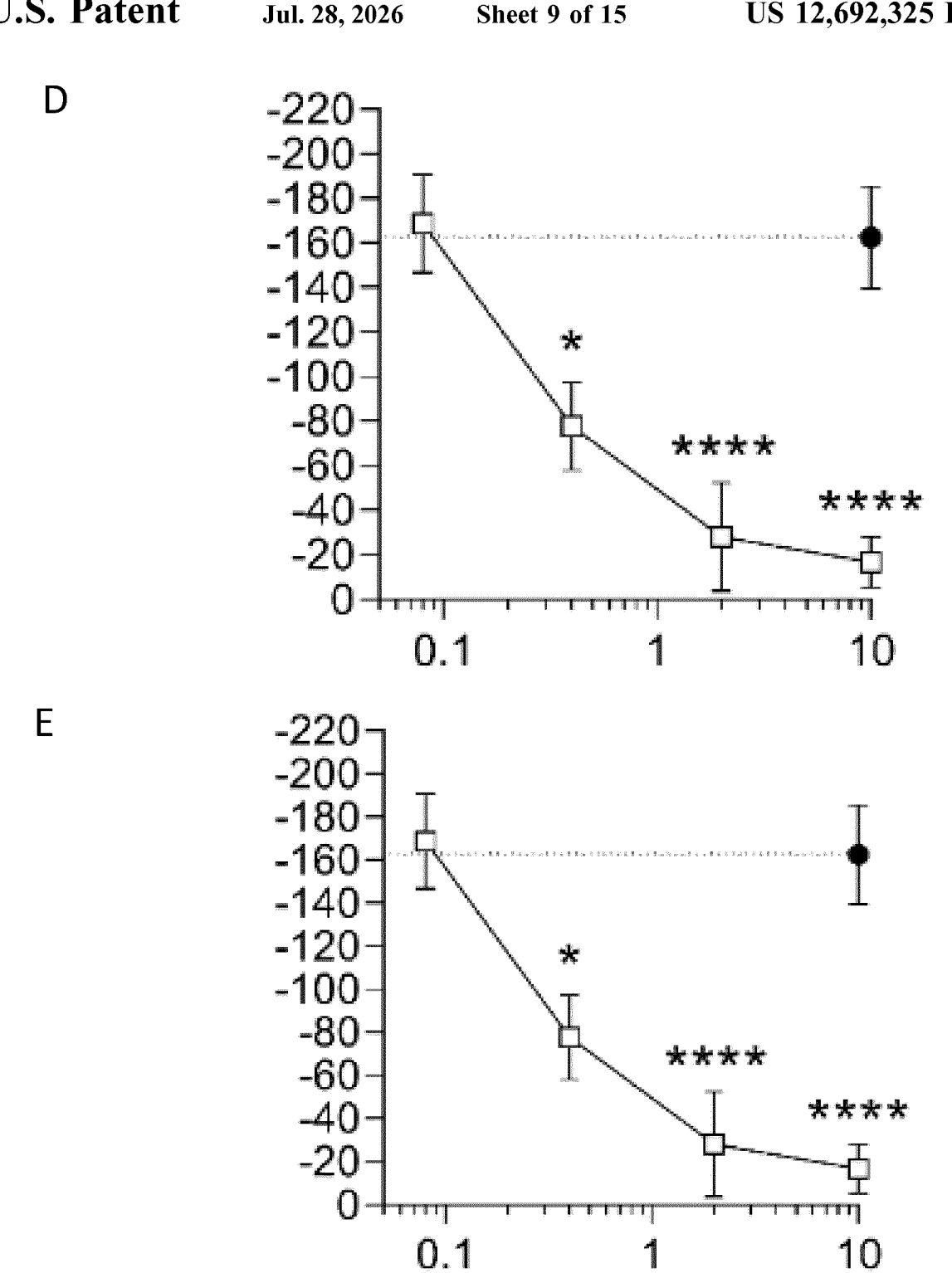
Figure 6D-E

A

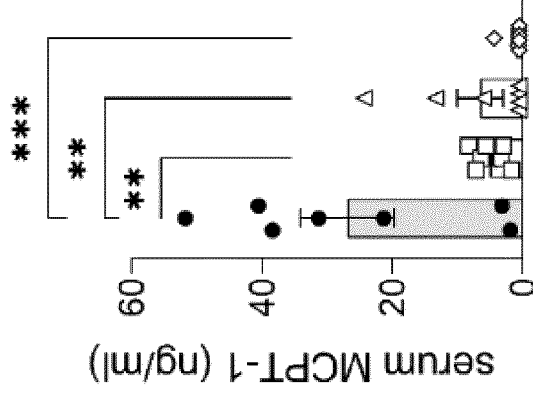
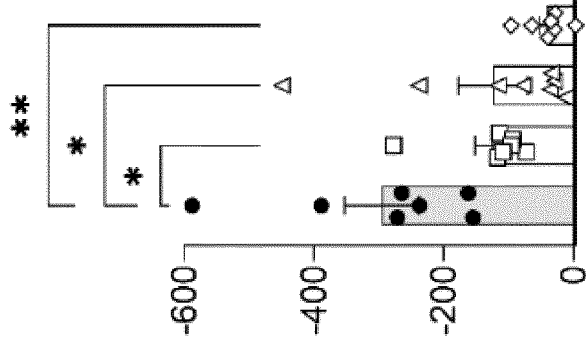
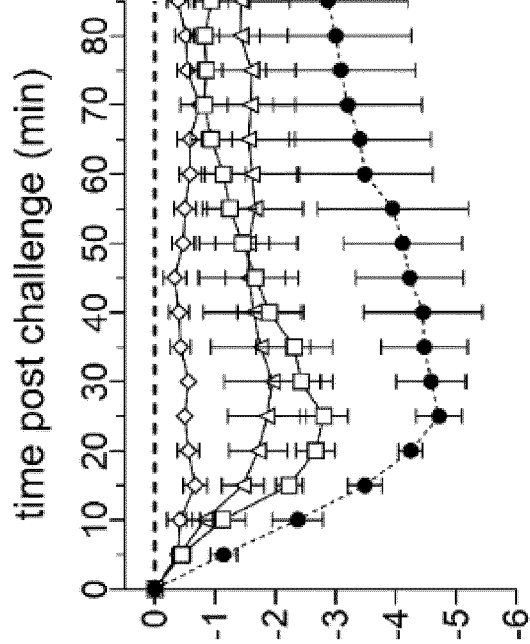
Figure 7B

A
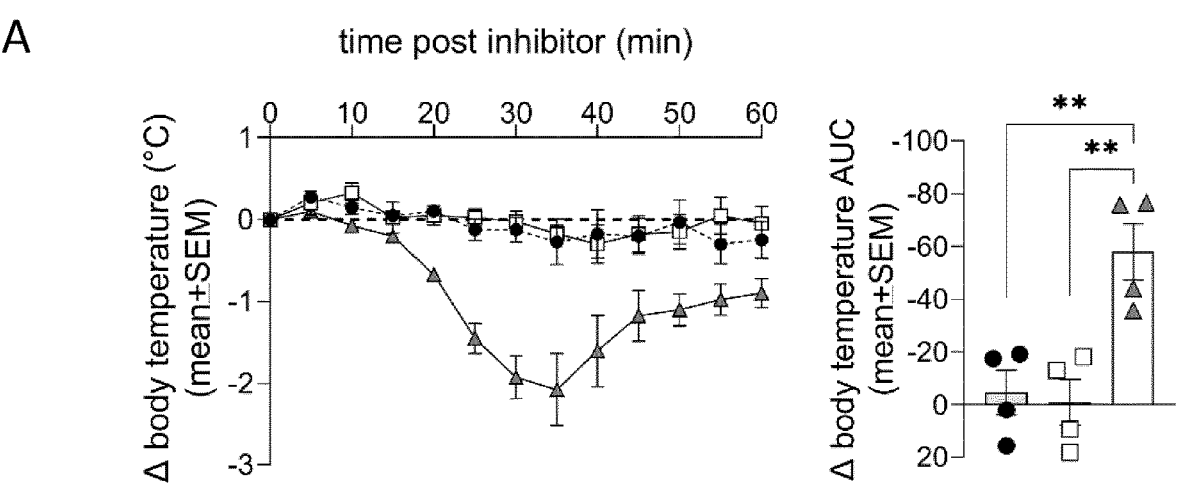
B
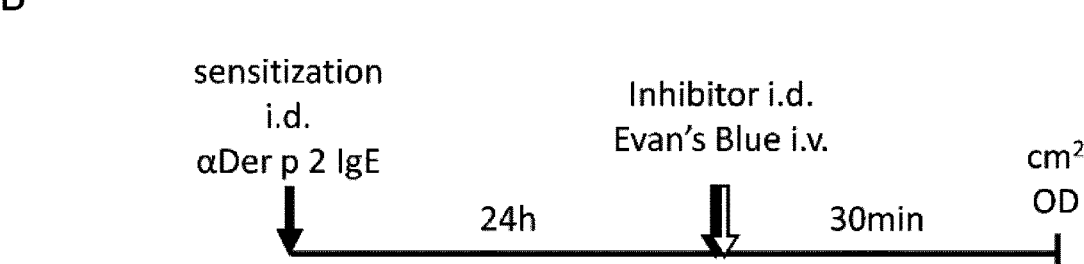
Figure 8A-B

C
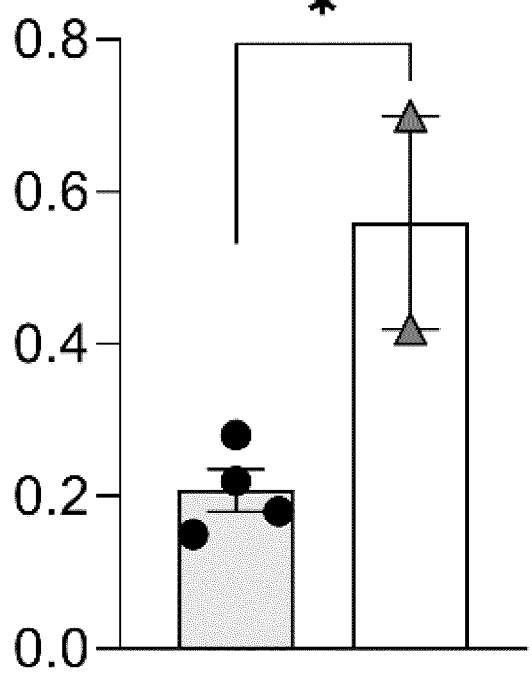
D
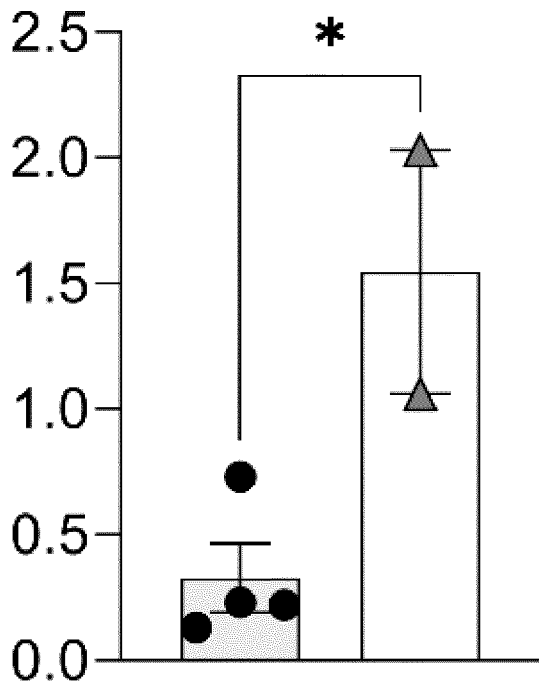
Figure 8C-D

Figure 9D:
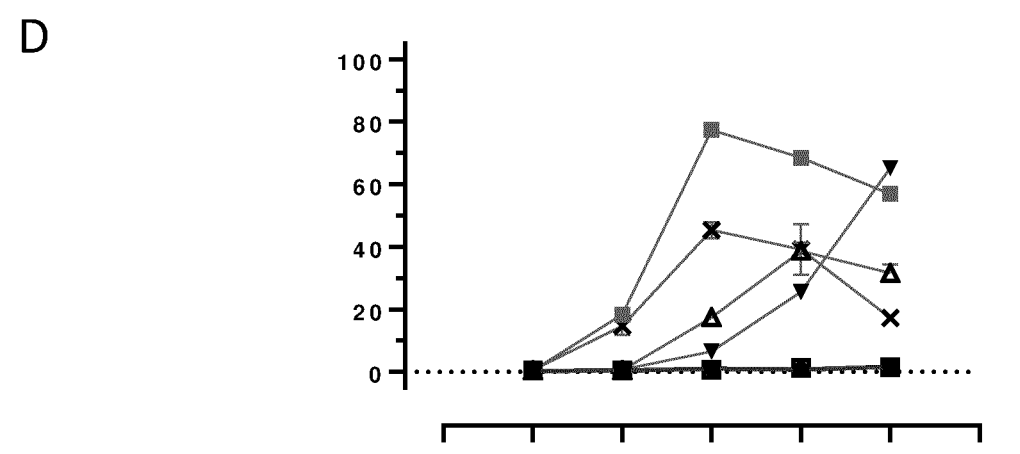

A
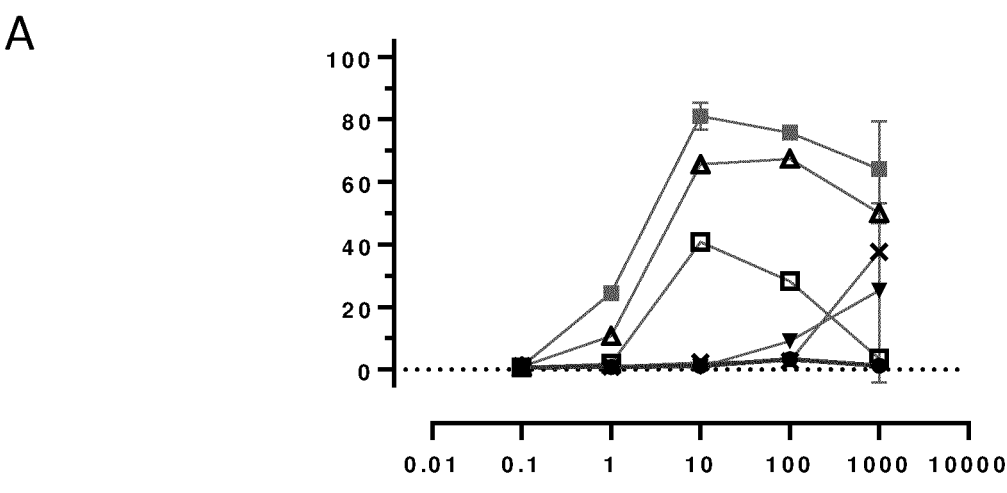
B
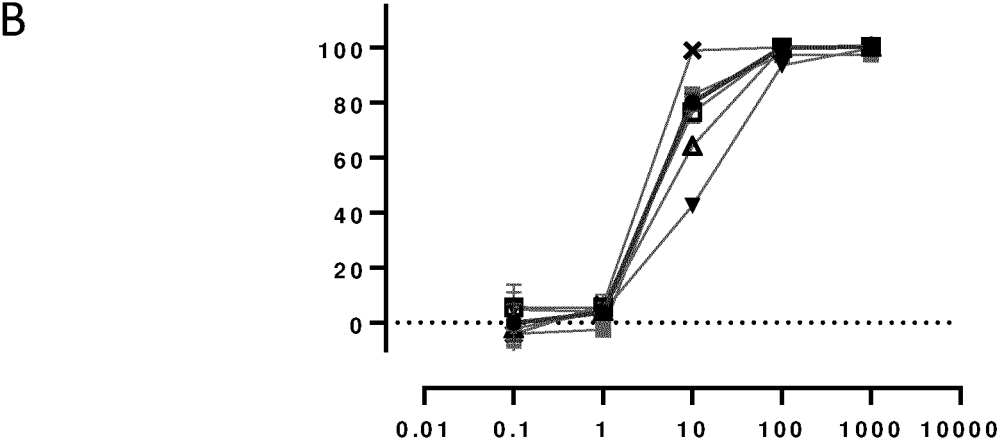
C
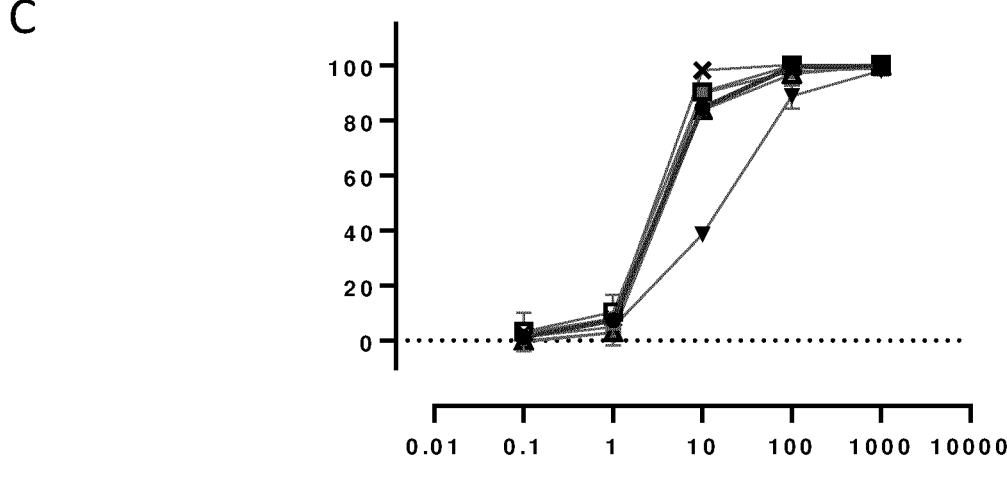
Figure 9A-C

D

SEQUENCE LISTING

```
Sequence total quantity: 463
SEQ ID NO: 1              moltype = AA  length = 122
FEATURE                   Location/Qualifiers
source                    1..122
                          mol_type = protein
                          organism = Synthetic construct
SEQUENCE: 1
EVQLLESGGG LVQPGGSLRL SCAASGFTFG NYDMAWVRQA PGKRPEWVSS IDTGGDITHY  60
ADSVKGRFTI SRDNAKNTLY LQMNSLRPED TAVYWCATDE EYALGPNEFD YYGQGTLVTV  120
SS                                                                 122

SEQ ID NO: 2              moltype = AA  length = 9
FEATURE                   Location/Qualifiers
source                    1..9
                          mol_type = protein
                          organism = Synthetic construct
SEQUENCE: 2
FTFGNYDMA                                                          9

SEQ ID NO: 3              moltype = AA  length = 10
FEATURE                   Location/Qualifiers
source                    1..10
                          mol_type = protein
                          organism = Synthetic construct
SEQUENCE: 3
SIDTGGDITH                                                         10

SEQ ID NO: 4              moltype = AA  length = 16
FEATURE                   Location/Qualifiers
source                    1..16
                          mol_type = protein
                          organism = Synthetic construct
SEQUENCE: 4
ATDEEYALGP NEFDYY                                                  16

SEQ ID NO: 5              moltype = AA  length = 121
FEATURE                   Location/Qualifiers
source                    1..121
                          mol_type = protein
                          organism = Synthetic construct
SEQUENCE: 5
EVQLLESGGG LVQPGGSLRL SCAASGFRFG NYDMAWVRQA PGKRYEWVSS IDTGGDITHY  60
ADSVKGRFTI SRDNAKNTLY LQMNSLRPED TAEYWCATDE EYALGPNEFD YYGQGTLVTV  120
S                                                                  121

SEQ ID NO: 6              moltype = AA  length = 9
FEATURE                   Location/Qualifiers
source                    1..9
                          mol_type = protein
                          organism = Synthetic construct
SEQUENCE: 6
FRFGNYDMA                                                          9
```

-continued

```
SEQ ID NO: 7               moltype = AA   length = 10
FEATURE                    Location/Qualifiers
source                     1..10
                           mol_type = protein
                           organism = Synthetic construct
SEQUENCE: 7
SIDTGGDITH                                                       10

SEQ ID NO: 8               moltype = AA   length = 16
FEATURE                    Location/Qualifiers
source                     1..16
                           mol_type = protein
                           organism = Synthetic construct
SEQUENCE: 8
ATDEEYALGP NEFDYY                                                16

SEQ ID NO: 9               moltype = AA   length = 127
FEATURE                    Location/Qualifiers
source                     1..127
                           mol_type = protein
                           organism = Synthetic construct
SEQUENCE: 9
QVQLQESGGG LVQTGGSLRL SCAVHGRTFS NTGMGWFRQA PGNERQFVAI ISPSGTSTYY   60
ADSVKGRFTI SRDPAKNTVY LQMNSLKMDD TAVYYCAASY GSNWSTLRHQ RRNEYDAWGQ  120
GTQVAVS                                                          127

SEQ ID NO: 10              moltype = AA   length = 9
FEATURE                    Location/Qualifiers
source                     1..9
                           mol_type = protein
                           organism = Synthetic construct
SEQUENCE: 10
RTFSNTGMG                                                         9

SEQ ID NO: 11              moltype = AA   length = 10
FEATURE                    Location/Qualifiers
source                     1..10
                           mol_type = protein
                           organism = Synthetic construct
SEQUENCE: 11
IISPSGTSTY                                                        10

SEQ ID NO: 12              moltype = AA   length = 22
FEATURE                    Location/Qualifiers
source                     1..22
                           mol_type = protein
                           organism = Synthetic construct
SEQUENCE: 12
AASYGSNWST LRHQRRNEYD AW                                          22

SEQ ID NO: 13              moltype = AA   length = 119
FEATURE                    Location/Qualifiers
source                     1..119
                           mol_type = protein
                           organism = Synthetic construct
SEQUENCE: 13
QVQLVESGGG LVQAGGSLRL SCAVFGSTFS NNVADWYRQA PGKQRELVAR ISASGATREY   60
GDSVKGRFTI SRDDAKNTMY LQMNNLKPED TAVYRCHKIE WEDLSRKDYW GQGTQVTVS   119

SEQ ID NO: 14              moltype = AA   length = 9
FEATURE                    Location/Qualifiers
source                     1..9
                           mol_type = protein
                           organism = Synthetic construct
SEQUENCE: 14
STFSNNVAD                                                         9

SEQ ID NO: 15              moltype = AA   length = 10
FEATURE                    Location/Qualifiers
source                     1..10
                           mol_type = protein
                           organism = Synthetic construct
SEQUENCE: 15
RISASGATRE                                                        10

SEQ ID NO: 16              moltype = AA   length = 14
FEATURE                    Location/Qualifiers
source                     1..14
```

```
                              mol_type = protein
                              organism = Synthetic construct
SEQUENCE: 16
HKIEWEDLSR KDYW                                                        14

SEQ ID NO: 17          moltype = AA   length = 117
FEATURE                Location/Qualifiers
source                 1..117
                       mol_type = protein
                       organism = Synthetic construct
SEQUENCE: 17
DVQLQESGGG LVQAGGSLRL SCAASGFIFR LAGMSWVRQA PGKGFEWVSG ITMDGSTTNY    60
ADSVKGRFTI SRDNSKNRLY LQMNSLKPED TAVYYCARGA KGGYNDPRGQ GTQVTVS       117

SEQ ID NO: 18          moltype = AA   length = 9
FEATURE                Location/Qualifiers
source                 1..9
                       mol_type = protein
                       organism = Synthetic construct
SEQUENCE: 18
FIFRLAGMS                                                             9

SEQ ID NO: 19          moltype = AA   length = 10
FEATURE                Location/Qualifiers
source                 1..10
                       mol_type = protein
                       organism = Synthetic construct
SEQUENCE: 19
GITMDGSTTN                                                            10

SEQ ID NO: 20          moltype = AA   length = 12
FEATURE                Location/Qualifiers
source                 1..12
                       mol_type = protein
                       organism = Synthetic construct
SEQUENCE: 20
ARGAKGGYND PR                                                         12

SEQ ID NO: 21          moltype = AA   length = 120
FEATURE                Location/Qualifiers
source                 1..120
                       mol_type = protein
                       organism = Synthetic construct
SEQUENCE: 21
DVQLQESGGG LVQAGGSLRL SCAASGLTFS RCDMGWFRQA PGKEREFVAR ISANGASTHY    60
ADFVKGRFTI SRDNAKNTVY LQMNYLKPED TAVYICAAAR VPVTWQLYDY WGQGTQVTVS    120

SEQ ID NO: 22          moltype = AA   length = 9
FEATURE                Location/Qualifiers
source                 1..9
                       mol_type = protein
                       organism = Synthetic construct
SEQUENCE: 22
LTFSRCDMG                                                             9

SEQ ID NO: 23          moltype = AA   length = 10
FEATURE                Location/Qualifiers
source                 1..10
                       mol_type = protein
                       organism = Synthetic construct
SEQUENCE: 23
RISANGASTH                                                            10

SEQ ID NO: 24          moltype = AA   length = 15
FEATURE                Location/Qualifiers
source                 1..15
                       mol_type = protein
                       organism = Synthetic construct
SEQUENCE: 24
AAARVPVTWQ LYDYW                                                      15

SEQ ID NO: 25          moltype = AA   length = 126
FEATURE                Location/Qualifiers
source                 1..126
                       mol_type = protein
                       organism = Synthetic construct
SEQUENCE: 25
DVQLQESGGG LVEAGGSLRL SCVASGRTFS GWSMGWFRQA PGKEREFVAA ISWVGSWIGG    60
TVYSNSVKGR FTISRDNART TVYLQMNSLK PEDTAVYFCA AANSETPRIF ASEYDYWGQG    120
```

-continued

```
TQVTVS                                                                        126

SEQ ID NO: 26           moltype = AA   length = 9
FEATURE                 Location/Qualifiers
source                  1..9
                        mol_type = protein
                        organism = Synthetic construct
SEQUENCE: 26
RTFSGWSMG                                                                     9

SEQ ID NO: 27           moltype = AA   length = 10
FEATURE                 Location/Qualifiers
source                  1..10
                        mol_type = protein
                        organism = Synthetic construct
SEQUENCE: 27
AISWVGSWIG                                                                    10

SEQ ID NO: 28           moltype = AA   length = 18
FEATURE                 Location/Qualifiers
source                  1..18
                        mol_type = protein
                        organism = Synthetic construct
SEQUENCE: 28
AAANSETPRI FASEYDYW                                                           18

SEQ ID NO: 29           moltype = AA   length = 127
FEATURE                 Location/Qualifiers
source                  1..127
                        mol_type = protein
                        organism = Synthetic construct
SEQUENCE: 29
DVQLQESGGG LVQAGGSLKL SCAASGRTFS SYSMGWFRQA PGKEREFVAG ITWSGGRTYY            60
ADFVKGRFTI SRDNAKNTVY LQMNSLKPED TAVYYCAGLW GVGSWYEELR NKHEYDYWGQ            120
GTQVTVS                                                                       127

SEQ ID NO: 30           moltype = AA   length = 9
FEATURE                 Location/Qualifiers
source                  1..9
                        mol_type = protein
                        organism = Synthetic construct
SEQUENCE: 30
RTFSSYSMG                                                                     9

SEQ ID NO: 31           moltype = AA   length = 9
FEATURE                 Location/Qualifiers
source                  1..9
                        mol_type = protein
                        organism = Synthetic construct
SEQUENCE: 31
ITWSGGRTY                                                                     9

SEQ ID NO: 32           moltype = AA   length = 22
FEATURE                 Location/Qualifiers
source                  1..22
                        mol_type = protein
                        organism = Synthetic construct
SEQUENCE: 32
AGLWGVGSWY EELRNKHEYD YW                                                      22

SEQ ID NO: 33           moltype = AA   length = 128
FEATURE                 Location/Qualifiers
source                  1..128
                        mol_type = protein
                        organism = Synthetic construct
SEQUENCE: 33
DVQLQESGGG LVQAGGSLRL SCLASGRTFT TTSGYNMGWF RQAPGKEREF VAGIKWVSGS            60
NRAYAESVKG RFTISRDNAK NTVYLQMNSL KPEDTAVYYC AAATGQSYVP IREYEYVYWG            120
QGTQVTVS                                                                      128

SEQ ID NO: 34           moltype = AA   length = 12
FEATURE                 Location/Qualifiers
source                  1..12
                        mol_type = protein
                        organism = Synthetic construct
SEQUENCE: 34
RTFTTTSGYN MG                                                                 12

SEQ ID NO: 35           moltype = AA   length = 11
```

-continued

```
FEATURE               Location/Qualifiers
source                1..11
                      mol_type = protein
                      organism = Synthetic construct
SEQUENCE: 35
GIKWVSGSNR A                                                         11

SEQ ID NO: 36         moltype = AA  length = 19
FEATURE               Location/Qualifiers
source                1..19
                      mol_type = protein
                      organism = Synthetic construct
SEQUENCE: 36
AAATGQSYVP IREYEYVYW                                                 19

SEQ ID NO: 37         moltype = AA  length = 124
FEATURE               Location/Qualifiers
source                1..124
                      mol_type = protein
                      organism = Synthetic construct
SEQUENCE: 37
DVQLQESGGG LVQAGGSLRL SCAASGRTIS RYAVGWFRRP PAKEREFIGI NWSGGSTTYA    60
DSAEGRFIIS RDNAKNTVYL QMNSLKPEDT AVYYCAVPSV LVQGGISNPS QYDYWGQGTQ    120
VTVS                                                                124

SEQ ID NO: 38         moltype = AA  length = 9
FEATURE               Location/Qualifiers
source                1..9
                      mol_type = protein
                      organism = Synthetic construct
SEQUENCE: 38
RTISRYAVG                                                            9

SEQ ID NO: 39         moltype = AA  length = 13
FEATURE               Location/Qualifiers
source                1..13
                      mol_type = protein
                      organism = Synthetic construct
SEQUENCE: 39
GINWSGGSTT YAD                                                       13

SEQ ID NO: 40         moltype = AA  length = 20
FEATURE               Location/Qualifiers
source                1..20
                      mol_type = protein
                      organism = Synthetic construct
SEQUENCE: 40
AVPSVLVQGG ISNPSQYDYW                                                20

SEQ ID NO: 41         moltype = AA  length = 125
FEATURE               Location/Qualifiers
source                1..125
                      mol_type = protein
                      organism = Synthetic construct
SEQUENCE: 41
DVQLQESGGG LVQAGGSLRL ACAASGRTLS SYVVSWFRQA PGKERKFVAA ITWSGLSTTY    60
LDSVQGRFTI SRDNTKDTVY LQMNSLKPQD TAIYYCAAGP NIPSILRTRE SEYAYWGQGT    120
QVTVS                                                                125

SEQ ID NO: 42         moltype = AA  length = 9
FEATURE               Location/Qualifiers
source                1..9
                      mol_type = protein
                      organism = Synthetic construct
SEQUENCE: 42
RTLSSYVVS                                                            9

SEQ ID NO: 43         moltype = AA  length = 13
FEATURE               Location/Qualifiers
source                1..13
                      mol_type = protein
                      organism = Synthetic construct
SEQUENCE: 43
AITWSGLSTT YLD                                                       13

SEQ ID NO: 44         moltype = AA  length = 20
FEATURE               Location/Qualifiers
source                1..20
                      mol_type = protein
```

```
                          organism = Synthetic construct
SEQUENCE: 44
AAGPNIPSIL RTRESEYAYW                                               20

SEQ ID NO: 45            moltype = AA   length = 113
FEATURE                  Location/Qualifiers
source                   1..113
                         mol_type = protein
                         organism = Synthetic construct
SEQUENCE: 45
DVQLQESGGG LVQPGGSLRL SCAASGFRFS NYAMRWYRQA PGKEREFVAR ISSTGFITRY  60
TASVRDRFTI SRDNDKNMMY LQLNKLTPQD TAHYYCNAES TDYWGQGTQV TVS         113

SEQ ID NO: 46            moltype = AA   length = 9
FEATURE                  Location/Qualifiers
source                   1..9
                         mol_type = protein
                         organism = Synthetic construct
SEQUENCE: 46
FRFSNYAMR                                                          9

SEQ ID NO: 47            moltype = AA   length = 10
FEATURE                  Location/Qualifiers
source                   1..10
                         mol_type = protein
                         organism = Synthetic construct
SEQUENCE: 47
RISSTGFITR                                                         10

SEQ ID NO: 48            moltype = AA   length = 8
FEATURE                  Location/Qualifiers
source                   1..8
                         mol_type = protein
                         organism = Synthetic construct
SEQUENCE: 48
NAESTDYW                                                           8

SEQ ID NO: 49            moltype = AA   length = 124
FEATURE                  Location/Qualifiers
source                   1..124
                         mol_type = protein
                         organism = Synthetic construct
SEQUENCE: 49
DVQLQESGGG LVQAGGSLKL SCAASGGSLS RYDMGWFRQA PGKEREFVAR ISWSGTTKYY  60
ADAVKGRFAI SRDNAKNTVY LQMNSLKPED TAVYYCAAAF YGNRGYYDVN AYTSSGQGTQ  120
VTVS                                                               124

SEQ ID NO: 50            moltype = AA   length = 9
FEATURE                  Location/Qualifiers
source                   1..9
                         mol_type = protein
                         organism = Synthetic construct
SEQUENCE: 50
GSLSRYDMG                                                          9

SEQ ID NO: 51            moltype = AA   length = 10
FEATURE                  Location/Qualifiers
source                   1..10
                         mol_type = protein
                         organism = Synthetic construct
SEQUENCE: 51
RISWSGTTKY                                                         10

SEQ ID NO: 52            moltype = AA   length = 19
FEATURE                  Location/Qualifiers
source                   1..19
                         mol_type = protein
                         organism = Synthetic construct
SEQUENCE: 52
AAAFYGNRGY YDVNAYTSS                                               19

SEQ ID NO: 53            moltype = AA   length = 124
FEATURE                  Location/Qualifiers
source                   1..124
                         mol_type = protein
                         organism = Synthetic construct
SEQUENCE: 53
DVQLQESGGG LVQAGGSLKL SCAASGGSLS RYDMGWFRQA PGKEREFVAR ISWSGDTKYY  60
ADAVEGRFAI SRDNAQNTVY LQMNSLKPED TAVYYCAVAL YGNRGYYDVN TYSYWGQGTR  120
```

-continued

```
VTVS                                                                    124

SEQ ID NO: 54          moltype = AA  length = 9
FEATURE                Location/Qualifiers
source                 1..9
                       mol_type = protein
                       organism = Synthetic construct
SEQUENCE: 54
GSLSRYDMG                                                               9

SEQ ID NO: 55          moltype = AA  length = 10
FEATURE                Location/Qualifiers
source                 1..10
                       mol_type = protein
                       organism = Synthetic construct
SEQUENCE: 55
RISWSGDTKY                                                              10

SEQ ID NO: 56          moltype = AA  length = 19
FEATURE                Location/Qualifiers
source                 1..19
                       mol_type = protein
                       organism = Synthetic construct
SEQUENCE: 56
AVALYGNRGY YDVNTYSYW                                                    19

SEQ ID NO: 57          moltype = AA  length = 124
FEATURE                Location/Qualifiers
source                 1..124
                       mol_type = protein
                       organism = Synthetic construct
SEQUENCE: 57
DVQLQESGGG LVQAGGSLKL SCAASRGSLS RWDVAWFRQA PGKERSFVTR ISWSGTTSYY       60
ADAVKGRFAI SRDNAKNTVY LQMNSLKPED TAVYYCAVAL YGNRGYYDVN AHSYWGQGTQ       120
VTVS                                                                    124

SEQ ID NO: 58          moltype = AA  length = 9
FEATURE                Location/Qualifiers
source                 1..9
                       mol_type = protein
                       organism = Synthetic construct
SEQUENCE: 58
GSLSRWDVA                                                               9

SEQ ID NO: 59          moltype = AA  length = 10
FEATURE                Location/Qualifiers
source                 1..10
                       mol_type = protein
                       organism = Synthetic construct
SEQUENCE: 59
RISWSGTTSY                                                              10

SEQ ID NO: 60          moltype = AA  length = 19
FEATURE                Location/Qualifiers
source                 1..19
                       mol_type = protein
                       organism = Synthetic construct
SEQUENCE: 60
AVALYGNRGY YDVNAHSYW                                                    19

SEQ ID NO: 61          moltype = AA  length = 126
FEATURE                Location/Qualifiers
source                 1..126
                       mol_type = protein
                       organism = Synthetic construct
SEQUENCE: 61
DVQLQESGGG LVQAGGSLRL SCAVSGLSFS SMGWFRQPPG KEREFVAAIS LYSGSTYYAD       60
SVKGRFTISS DNAKSTVYLQ MNSLKPEDAA VYFCAADRQR TWSTFYASRQ ATYNYWGQGT       120
QVTVTS                                                                  126

SEQ ID NO: 62          moltype = AA  length = 7
FEATURE                Location/Qualifiers
source                 1..7
                       mol_type = protein
                       organism = Synthetic construct
SEQUENCE: 62
LSFSSMG                                                                 7

SEQ ID NO: 63          moltype = AA  length = 10
```

-continued

```
FEATURE            Location/Qualifiers
source             1..10
                   mol_type = protein
                   organism = Synthetic construct
SEQUENCE: 63
AISLYSGSTY                                                          10

SEQ ID NO: 64      moltype = AA  length = 22
FEATURE            Location/Qualifiers
source             1..22
                   mol_type = protein
                   organism = Synthetic construct
SEQUENCE: 64
AADRQRTWST FYASRQATYN YW                                            22

SEQ ID NO: 65      moltype = AA  length = 118
FEATURE            Location/Qualifiers
source             1..118
                   mol_type = protein
                   organism = Synthetic construct
SEQUENCE: 65
DVQLQESGGG LVQPGGSLRL SCAASGSIFS IDIMGWYRQA PGKQRELVAT MPEGNYINYA   60
DSVKGRLTLS RDKGKNTVYL QLNSLKPEDT AVYYCYGFGV REGRGNVYWG QGTQVTVS     118

SEQ ID NO: 66      moltype = AA  length = 9
FEATURE            Location/Qualifiers
source             1..9
                   mol_type = protein
                   organism = Synthetic construct
SEQUENCE: 66
SIFSIDIMG                                                           9

SEQ ID NO: 67      moltype = AA  length = 9
FEATURE            Location/Qualifiers
source             1..9
                   mol_type = protein
                   organism = Synthetic construct
SEQUENCE: 67
TMPEGNYIN                                                           9

SEQ ID NO: 68      moltype = AA  length = 14
FEATURE            Location/Qualifiers
source             1..14
                   mol_type = protein
                   organism = Synthetic construct
SEQUENCE: 68
YGFGVREGRG NVYW                                                     14

SEQ ID NO: 69      moltype = AA  length = 117
FEATURE            Location/Qualifiers
source             1..117
                   mol_type = protein
                   organism = Synthetic construct
SEQUENCE: 69
DVQLQESGGG LVQAGGSLRL SCAASGLTFG SYDMGWYRQA PGKQRELVGR IRNDGITYYA   60
DSVKGRFTMS RDNAKNTVYL QMNSLKPEDT AVYYCAADGT GLGHYDYWGQ GTQVTVS      117

SEQ ID NO: 70      moltype = AA  length = 9
FEATURE            Location/Qualifiers
source             1..9
                   mol_type = protein
                   organism = Synthetic construct
SEQUENCE: 70
LTFGSYDMG                                                           9

SEQ ID NO: 71      moltype = AA  length = 9
FEATURE            Location/Qualifiers
source             1..9
                   mol_type = protein
                   organism = Synthetic construct
SEQUENCE: 71
RIRNDGITY                                                           9

SEQ ID NO: 72      moltype = AA  length = 13
FEATURE            Location/Qualifiers
source             1..13
                   mol_type = protein
                   organism = Synthetic construct
SEQUENCE: 72
```

-continued

```
AADGTGLGHY DYW                                                     13

SEQ ID NO: 73            moltype = AA   length = 118
FEATURE                  Location/Qualifiers
source                   1..118
                         mol_type = protein
                         organism = Synthetic construct
SEQUENCE: 73
DVQLQESGGG LVQAGGSLRL SCAASGFIVS DNVMSWYRQA PGKQRDMVAT IMLNGDTAHA   60
DSVKGRFTIS RDHAKNTVYL QMNSLKPEDT AVYYCNARDS MLEPGRGAWG QGTLVTVS     118

SEQ ID NO: 74            moltype = AA   length = 9
FEATURE                  Location/Qualifiers
source                   1..9
                         mol_type = protein
                         organism = Synthetic construct
SEQUENCE: 74
FIVSDNVMS                                                          9

SEQ ID NO: 75            moltype = AA   length = 9
FEATURE                  Location/Qualifiers
source                   1..9
                         mol_type = protein
                         organism = Synthetic construct
SEQUENCE: 75
TIMLNGDTA                                                          9

SEQ ID NO: 76            moltype = AA   length = 14
FEATURE                  Location/Qualifiers
source                   1..14
                         mol_type = protein
                         organism = Synthetic construct
SEQUENCE: 76
NARDSMLEPG RGAW                                                    14

SEQ ID NO: 77            moltype = AA   length = 127
FEATURE                  Location/Qualifiers
source                   1..127
                         mol_type = protein
                         organism = Synthetic construct
SEQUENCE: 77
QVQLVETGGG LVQPGGSLRL SCAVHGRTFS NTGMGWFRQA PRKGFEWVSG ITMDGSTTNY   60
ADSVKGRFTI SRDPAKNTVY LQMNSLKMDD TAVYYCAASY GSNWSTLRHQ RRNEYDAWGQ   120
GTQVTVS                                                            127

SEQ ID NO: 78            moltype = AA   length = 262
FEATURE                  Location/Qualifiers
source                   1..262
                         mol_type = protein
                         organism = Synthetic construct
SEQUENCE: 78
EVQLLESGGG LVQPGGSLRL SCAASGFTFG NYDMAWVRQA PGKRPEWVSS IDTGGDITHY   60
ADSVKGRFTI SRDNAKNTLY LQMNSLRPED TAVYWCATDE EYALGPNEFD YYGQGTLVTV   120
SGGGGSGGGG SGGGGSGGGG SEVQLLESGG GLVQPGGSLR LSCAASGFTF GNYDMAWVRQ   180
APGKRPEWVS SIDTGGDITH YADSVKGRFT ISRDNAKNTL YLQMNSLRPE DTAVYWCATD   240
EEYALGPNEF DYYGQGTLVT VS                                           262

SEQ ID NO: 79            moltype = AA   length = 258
FEATURE                  Location/Qualifiers
source                   1..258
                         mol_type = protein
                         organism = Synthetic construct
SEQUENCE: 79
DVQLQESGGG LVQAGGSLRL SCAASGFIFR LAGMSWVRQA PGKGFEWVSG ITMDGSTTNY   60
ADSVKGRFTI SRDNSKNRLY LQMNSLKPED TAVYYCARGA KGGYNDPRGQ GTQVTVSGGG   120
GSGGGGSGGG GSGGGGSEVQ LLESGGGLVQ PGGSLRLSCA ASGFTFGNYD MAWVRQAPGK   180
RPEWVSSIDT GGDITHYADS VKGRFTISRD NAKNTLYLQM NSLRPEDTAV YWCATDEEYA   240
LGPNEFDYYG QGTLVTVS                                                258

SEQ ID NO: 80            moltype = AA   length = 258
FEATURE                  Location/Qualifiers
source                   1..258
                         mol_type = protein
                         organism = Synthetic construct
SEQUENCE: 80
EVQLLESGGG LVQPGGSLRL SCAASGFTFG NYDMAWVRQA PGKRPEWVSS IDTGGDITHY   60
ADSVKGRFTI SRDNAKNTLY LQMNSLRPED TAVYWCATDE EYALGPNEFD YYGQGTLVTV   120
SGGGGSGGGG SGGGGSGGGG SDVQLQESGG GLVQAGGSLR LSCAASGFIF RLAGMSWVRQ   180
APGKGFEWVS GITMDGSTTN YADSVKGRFT ISRDNSKNRL YLQMNSLKPE DTAVYYCARG   240
```

```
AKGGYNDPRG QGTQVTVS                                                           258

SEQ ID NO: 81              moltype = AA  length = 260
FEATURE                    Location/Qualifiers
source                     1..260
                           mol_type = protein
                           organism = Synthetic construct
SEQUENCE: 81
QVQLVESGGG LVQAGGSLRL SCAVFGSTFS NNVADWYRQA PGKQRELVAR ISASGATREY          60
GDSVKGRFTI SRDDAKNTMY LQMNNLKPED TAVYRCHKIE WEDLSRKDYW GQGTQVTVSG          120
GGGSGGGGSG GGGSGGGGSE VQLLESGGGL VQPGGSLRLS CAASGFTFGN YDMAWVRQAP          180
GKRPEWVSSI DTGGDITHYA DSVKGRFTIS RDNAKNTLYL QMNSLRPEDT AVYWCATDEE          240
YALGPNEFDY YGQGTLVTVS                                                       260

SEQ ID NO: 82              moltype = AA  length = 260
FEATURE                    Location/Qualifiers
source                     1..260
                           mol_type = protein
                           organism = Synthetic construct
SEQUENCE: 82
EVQLLESGGG LVQPGGSLRL SCAASGFTFG NYDMAWVRQA PGKRPEWVSS IDTGGDITHY          60
ADSVKGRFTI SRDNAKNTLY LQMNSLRPED TAVYWCATDE EYALGPNEFD YYGQGTLVTV          120
SGGGGSGGGG SGGGGSGGGG SQVQLVESGG GLVQAGGSLR LSCAVFGSTF SNNVADWYRQ          180
APGKQRELVA RISASGATRE YGDSVKGRFT ISRDDAKNTM YLQMNNLKPE DTAVYRCHKI          240
EWEDLSRKDY WGQGTQVTVS                                                       260

SEQ ID NO: 83              moltype = AA  length = 267
FEATURE                    Location/Qualifiers
source                     1..267
                           mol_type = protein
                           organism = Synthetic construct
SEQUENCE: 83
DVQLQESGGG LVEAGGSLRL SCVASGRTFS GWSMGWFRQA PGKEREFVAA ISWVGSWIGG          60
TVYSNSVKGR FTISRDNART TVYLQMNSLK PEDTAVYFCA AANSETPRIF ASEYDYWGQG          120
TQVTVSGGGG SGGGGSGGGG SGGGGSEVQL LESGGGLVQP GGSLRLSCAA SGFTFGNYDM          180
AWVRQAPGKR PEWVSSIDTG GDITHYADSV KGRFTISRDN AKNTLYLQMN SLRPEDTAVY          240
WCATDEEYAL GPNEFDYYGQ GTLVTVS                                               267

SEQ ID NO: 84              moltype = AA  length = 267
FEATURE                    Location/Qualifiers
source                     1..267
                           mol_type = protein
                           organism = Synthetic construct
SEQUENCE: 84
EVQLLESGGG LVQPGGSLRL SCAASGFTFG NYDMAWVRQA PGKRPEWVSS IDTGGDITHY          60
ADSVKGRFTI SRDNAKNTLY LQMNSLRPED TAVYWCATDE EYALGPNEFD YYGQGTLVTV          120
SGGGGSGGGG SGGGGSGGGG SDVQLQESGG GLVEAGGSLR LSCVASGRTF SGWSMGWFRQ          180
APGKEREFVA AISWVGSWIG GTVYSNSVKG RFTISRDNAR TTVYLQMNSL KPEDTAVYFC          240
AAANSETPRI FASEYDYWGQ GTQVTVS                                               267

SEQ ID NO: 85              moltype = AA  length = 268
FEATURE                    Location/Qualifiers
source                     1..268
                           mol_type = protein
                           organism = Synthetic construct
SEQUENCE: 85
QVQLQESGGG LVQTGGSLRL SCAVHGRTFS NTGMGWFRQA PGNERQFVAI ISPSGTSTYY          60
ADSVKGRFTI SRDPAKNTVY LQMNSLKMDD TAVYYCAASY GSNWSTLRHQ RRNEYDAWGQ          120
GTQVAVSGGG GSGGGGSGGG GSGGGGSEVQ LLESGGGLVQ PGGSLRLSCA ASGFTFGNYD          180
MAWVRQAPGK RPEWVSSIDT GGDITHYADS VKGRFTISRD NAKNTLYLQM NSLRPEDTAV          240
YWCATDEEYA LGPNEFDYYG QGTLVTVS                                              268

SEQ ID NO: 86              moltype = AA  length = 268
FEATURE                    Location/Qualifiers
source                     1..268
                           mol_type = protein
                           organism = Synthetic construct
SEQUENCE: 86
EVQLLESGGG LVQPGGSLRL SCAASGFTFG NYDMAWVRQA PGKRPEWVSS IDTGGDITHY          60
ADSVKGRFTI SRDNAKNTLY LQMNSLRPED TAVYWCATDE EYALGPNEFD YYGQGTLVTV          120
SGGGGSGGGG SGGGGSGGGG SQVQLQESGG GLVQTGGSLR LSCAVHGRTF SNTGMGWFRQ          180
APGNERQFVA IISPSGTSTY YADSVKGRFT ISRDPAKNTV YLQMNSLKMD DTAVYYCAAS          240
YGSNWSTLRH QRRNEYDAWG QGTQVAVS                                              268

SEQ ID NO: 87              moltype = AA  length = 1470
FEATURE                    Location/Qualifiers
source                     1..1470
                           mol_type = protein
                           organism = Synthetic construct
```

```
SEQUENCE: 87
TCPPCPAPEL LGGPSVFLFP PKPKDTLMIS RTPEVTCVVV DVSHEDPEVK FNWYVDGVEV    60
HNAKTKPREE QYNSTYRVVS VLTVLHQDWL NGKEYKCKVS NKALPAPIEK TISKAKGQPR   120
EPQVYTLPPS RDELTKNQVS LYCLVKGFYP SDIAVEWESN GQPENNYKTT PPVLDSDGSF   180
FLYSKLTVDK SRWQQGNVFS CSVMHEALHN HYTQKSLSLS PGKGGGGSGG GGSGSDLGKK   240
LLEAARAGQD DEVRILTANG ADVNANDYWG HTPLHLAAML GHLEIVEVLL KNGADVNATG   300
NTGRTPLHLA AWADHLEIVE VLLKHGADVN AQDKFGKTAF DISIDNGNED LAEILQKLTC   360
PPCPAPELLG GPSVFLFPPK PKDTLMISRT PEVTCVVVDV SHEDPEVKFN WYVDGVEVHN   420
AKTKPREEQY NSTYRVVSVL TVLHQDWLNG KEYKCKVSNK ALPAPIEKTI SKAKGQPREP   480
QVYTLPPSRD ELTKNQVSLY CLVKGFYPSD IAVEWESNGQ PENNYKTTPP VLDSDGSFFL   540
YSKLTVDKSR WQQGNVFSCS VMHEALHNHY TQKSLSLSPG KGGGGSGGGG SGSDLGKKLL   600
EAARAGQDDE VRILTANGAD VNANDYWGHT PLHLAAMLGH LEIVEVLLKN GADVNATGNT   660
GRTPLHLAAW ADHLEIVEVL LKHGADVNAQ DKFGKTAFDI SIDNGNEDLA EILQKLTCPP   720
CPAPELLGGP SVFLFPPKPK DTLMISRTPE VTCVVVDVSH EDPEVKFNWY VDGVEVHNAK   780
TKPREEQYNS TYRVVSVLTV LHQDWLNGKE YKCKVSNKAL PAPIEKTISK AKGQPREPQV   840
YTLPPSRDEL TKNQVSLYCL VKGFYPSDIA VEWESNGQPE NNYKTTPPVL DSDGSFFLYS   900
KLTVDKSRWQ QGNVFSCSVM HEALHNHYTQ KSLSLSPGKG GGGSGGGGSG SDLGKKLLEA   960
ARAGQDDEVR ILTANGADVN ANDYWGHTPL HLAAMLGHLE IVEVLLKNGA DVNATGNTGR  1020
TPLHLAAWAD HLEIVEVLLK HGADVNAQDK FGKTAFDISI DNGNEDLAEI LQKLTCPPCP  1080
APELLGGPSV FLFPPKPKDT LMISRTPEVT CVVVDVSHED PEVKFNWYVD GVEVHNAKTK  1140
PREEQYNSTY RVVSVLTVLH QDWLNGKEYK CKVSNKALPA PIEKTISKAK GQPREPQVYT  1200
LPPSRDELTK NQVSLTCLVK GFYPSDIAVE WESNGQPENN YKTTPPVLDS DGSFFLTSKL  1260
TVDKSRWQQG NVFSCSVMHE ALHNHYTQKS LSLSPGKGGG GSGGGGSGSD DDDKSSDLGK  1320
KLLEAARAGQ DDEVRILMAN GADVNAIDHN GDTPLHLAAY VGRLEIVEVL LKHGADVNAR  1380
DLRGFTPLHL AAQYGHMEIV EVLLKYGADV NADDDYGTTP LHLAAQYGHM EIVEVLLKYG  1440
ADVNAQDKFG KTAFDISIDN GNEDLAEILQ                                  1470

SEQ ID NO: 88          moltype = AA   length = 5
FEATURE                Location/Qualifiers
source                 1..5
                       mol_type = protein
                       organism = Synthetic construct
SEQUENCE: 88
GGGGS                                                                5

SEQ ID NO: 89          moltype = AA   length = 10
FEATURE                Location/Qualifiers
source                 1..10
                       mol_type = protein
                       organism = Synthetic construct
SEQUENCE: 89
GGGGSGGGGS                                                          10

SEQ ID NO: 90          moltype = AA   length = 15
FEATURE                Location/Qualifiers
source                 1..15
                       mol_type = protein
                       organism = Synthetic construct
SEQUENCE: 90
GGGGSGGGGS GGGGS                                                    15

SEQ ID NO: 91          moltype = AA   length = 20
FEATURE                Location/Qualifiers
source                 1..20
                       mol_type = protein
                       organism = Synthetic construct
SEQUENCE: 91
GGGGSGGGGS GGGGSGGGGS                                               20

SEQ ID NO: 92          moltype = AA   length = 4
FEATURE                Location/Qualifiers
source                 1..4
                       mol_type = protein
                       organism = Synthetic construct
SEQUENCE: 92
RSRS                                                                 4

SEQ ID NO: 93          moltype = AA   length = 349
FEATURE                Location/Qualifiers
source                 1..349
                       mol_type = protein
                       organism = Synthetic construct
SEQUENCE: 93
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
SFFLVSRLTV DKSRWQEGNV FSCSVMHEAL HNHYTQKSLS LSLGKRSEVQ LLESGGGLVQ   240
PGGSLRLSCA ASGFTFGNYD MAWVRQAPGK RPEWVSSIDT GGDITHYADS VKGRFTISRD   300
NAKNTLYLQM NSLRPEDTAV YWCATDEEYA LGPNEFDYYG QGTLVTVSS              349
```

-continued

```
SEQ ID NO: 94                moltype = AA  length = 352
FEATURE                      Location/Qualifiers
source                       1..352
                             mol_type = protein
                             organism = Synthetic construct
SEQUENCE: 94
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
SFFLVSRLTV DKSRWQEGNV FSCSVMHEAL HNHYTQKSLS LSLGKGGGGS EVQLLESGGG   240
LVQPGGSLRL SCAASGFTFG NYDMAWVRQA PGKRPEWVSS IDTGGDITHY ADSVKGRFTI   300
SRDNAKNTLY LQMNSLRPED TAVYWCATDE EYALGPNEFD YYGQGTLVTV SS           352

SEQ ID NO: 95                moltype = AA  length = 357
FEATURE                      Location/Qualifiers
source                       1..357
                             mol_type = protein
                             organism = Synthetic construct
SEQUENCE: 95
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
SFFLVSRLTV DKSRWQEGNV FSCSVMHEAL HNHYTQKSLS LSLGKGGGGS GGGGSEVQLL   240
ESGGGLVQPG GSLRLSCAAS GFTFGNYDMA WVRQAPGKRP EWVSSIDTGG DITHYADSVK   300
GRFTISRDNA KNTLYLQMNS LRPEDTAVYW CATDEEYALG PNEFDYYGQG TLVTVSS      357

SEQ ID NO: 96                moltype = AA  length = 362
FEATURE                      Location/Qualifiers
source                       1..362
                             mol_type = protein
                             organism = Synthetic construct
SEQUENCE: 96
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
SFFLVSRLTV DKSRWQEGNV FSCSVMHEAL HNHYTQKSLS LSLGKGGGGS GGGGSGGGGS   240
EVQLLESGGG LVQPGGSLRL SCAASGFTFG NYDMAWVRQA PGKRPEWVSS IDTGGDITHY   300
ADSVKGRFTI SRDNAKNTLY LQMNSLRPED TAVYWCATDE EYALGPNEFD YYGQGTLVTV   360
SS                                                                 362

SEQ ID NO: 97                moltype = AA  length = 344
FEATURE                      Location/Qualifiers
source                       1..344
                             mol_type = protein
                             organism = Synthetic construct
SEQUENCE: 97
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKRSDVQ LQESGGGLVQ   240
AGGSLRLSCA ASGFIFRLAG MSWVRQAPGK GFEWVSGITM DGSTTNYADS VKGRFTISRD   300
NSKNRLYLQM NSLKPEDTAV YYCARGAKGG YNDPRGQGTQ VTVS                   344

SEQ ID NO: 98                moltype = AA  length = 347
FEATURE                      Location/Qualifiers
source                       1..347
                             mol_type = protein
                             organism = Synthetic construct
SEQUENCE: 98
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS DVQLQESGGG   240
LVQAGGSLRL SCAASGFIFR LAGMSWVRQA PGKGFEWVSG ITMDGSTTNY ADSVKGRFTI   300
SRDNSKNRLY LQMNSLKPED TAVYYCARGA KGGYNDPRGQ GTQVTVS                347

SEQ ID NO: 99                moltype = AA  length = 352
FEATURE                      Location/Qualifiers
source                       1..352
                             mol_type = protein
                             organism = Synthetic construct
SEQUENCE: 99
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSDVQLQ   240
ESGGGLVQAG GSLRLSCAAS GFIFRLAGMS WVRQAPGKGF EWVSGITMDG STTNYADSVK   300
GRFTISRDNS KNRLYLQMNS LKPEDTAVYY CARGAKGGYN DPRGQGTQVT VS           352
```

-continued

```
SEQ ID NO: 100            moltype = AA  length = 357
FEATURE                   Location/Qualifiers
source                    1..357
                          mol_type = protein
                          organism = Synthetic construct
SEQUENCE: 100
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSGGGGS   240
DVQLQESGGG LVQAGGSLRL SCAASGFIFR LAGMSWVRQA PGKGFEWVSG ITMDGSTTNY   300
ADSVKGRFTI SRDNSKNRLY LQMNSLKPED TAVYYCARGA KGGYNDPRGQ GTQVTVS      357

SEQ ID NO: 101            moltype = AA  length = 354
FEATURE                   Location/Qualifiers
source                    1..354
                          mol_type = protein
                          organism = Synthetic construct
SEQUENCE: 101
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKRSQVQ LQESGGGLVQ   240
TGGSLRLSCA VHGRTFSNTG MGWFRQAPGN ERQFVAIISP SGTSTYYADS VKGRFTISRD   300
PAKNTVYLQM NSLKMDDTAV YYCAASYGSN WSTLRHQRRN EYDAWGQGTQ VAVS         354

SEQ ID NO: 102            moltype = AA  length = 357
FEATURE                   Location/Qualifiers
source                    1..357
                          mol_type = protein
                          organism = Synthetic construct
SEQUENCE: 102
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS QVQLQESGGG   240
LVQTGGSLRL SCAVHGRTFS NTGMGWFRQA PGNERQFVAI ISPSGTSTYY ADSVKGRFTI   300
SRDPAKNTVY LQMNSLKMDD TAVYYCAASY GSNWSTLRHQ RRNEYDAWGQ GTQVAVS      357

SEQ ID NO: 103            moltype = AA  length = 362
FEATURE                   Location/Qualifiers
source                    1..362
                          mol_type = protein
                          organism = Synthetic construct
SEQUENCE: 103
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSQVQLQ   240
ESGGGLVQTG GSLRLSCAVH GRTFSNTGMG WFRQAPGNER QFVAIISPSG TSTYYADSVK   300
GRFTISRDPA KNTVYLQMNS LKMDDTAVYY CAASYGSNWS TLRHQRRNEY DAWGQGTQVA   360
VS                                                                  362

SEQ ID NO: 104            moltype = AA  length = 367
FEATURE                   Location/Qualifiers
source                    1..367
                          mol_type = protein
                          organism = Synthetic construct
SEQUENCE: 104
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSGGGGS   240
QVQLQESGGG LVQTGGSLRL SCAVHGRTFS NTGMGWFRQA PGNERQFVAI ISPSGTSTYY   300
ADSVKGRFTI SRDPAKNTVY LQMNSLKMDD TAVYYCAASY GSNWSTLRHQ RRNEYDAWGQ   360
GTQVAVS                                                             367

SEQ ID NO: 105            moltype = AA  length = 349
FEATURE                   Location/Qualifiers
source                    1..349
                          mol_type = protein
                          organism = Synthetic construct
SEQUENCE: 105
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKRSEVQ LLESGGGLVQ   240
PGGSLRLSCA ASGFTFGNYD MAWVRQAPGK RPEWVSSIDT GGDITHYADS VKGRFTISRD   300
```

```
NAKNTLYLQM NSLRPEDTAV YWCATDEEYA LGPNEFDYYG QGTLVTVSS              349

SEQ ID NO: 106          moltype = AA   length = 352
FEATURE                 Location/Qualifiers
source                  1..352
                        mol_type = protein
                        organism = Synthetic construct
SEQUENCE: 106
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS EVQLLESGGG  240
LVQPGGSLRL SCAASGFTFG NYDMAWVRQA PGKRPEWVSS IDTGGDITHY ADSVKGRFTI  300
SRDNAKNTLY LQMNSLRPED TAVYWCATDE EYALGPNEFD YYGQGTLVTV SS          352

SEQ ID NO: 107          moltype = AA   length = 357
FEATURE                 Location/Qualifiers
source                  1..357
                        mol_type = protein
                        organism = Synthetic construct
SEQUENCE: 107
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSEVQLL  240
ESGGGLVQPG GSLRLSCAAS GFTFGNYDMA WVRQAPGKRP EWVSSIDTGG DITHYADSVK  300
GRFTISRDNA KNTLYLQMNS LRPEDTAVYW CATDEEYALG PNEFDYYGQG TLVTVSS     357

SEQ ID NO: 108          moltype = AA   length = 362
FEATURE                 Location/Qualifiers
source                  1..362
                        mol_type = protein
                        organism = Synthetic construct
SEQUENCE: 108
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSGGGGS  240
EVQLLESGGG LVQPGGSLRL SCAASGFTFG NYDMAWVRQA PGKRPEWVSS IDTGGDITHY  300
ADSVKGRFTI SRDNAKNTLY LQMNSLRPED TAVYWCATDE EYALGPNEFD YYGQGTLVTV  360
SS                                                                362

SEQ ID NO: 109          moltype = AA   length = 349
FEATURE                 Location/Qualifiers
source                  1..349
                        mol_type = protein
                        organism = Synthetic construct
SEQUENCE: 109
EVQLLESGGG LVQPGGSLRL SCAASGFTFG NYDMAWVRQA PGKRPEWVSS IDTGGDITHY   60
ADSVKGRFTI SRDNAKNTLY LQMNSLRPED TAVYWCATDE EYALGPNEFD YYGQGTLVTV  120
SSRSGPPCPP CPAPEFLGGP SVFLFPPKPK DTLMISRTPE VTCVVVDVSQ EDPEVQFNWY  180
VDGVEVHNAK TKPREEQFNS TYRVVSVLTV LHQDWLNGKE YKCKVSNKGL PSSIEKTISK  240
AKGQPREPQV YTLPPCQEEM TKNQVSLWCL VKGFYPSDIA VEWESNGQPE NNYKTTPPVL  300
DSDGSFFLYS RLTVDKSRWQ EGNVFSCSVM HEALHNHYTQ KSLSLSLGK             349

SEQ ID NO: 110          moltype = AA   length = 352
FEATURE                 Location/Qualifiers
source                  1..352
                        mol_type = protein
                        organism = Synthetic construct
SEQUENCE: 110
EVQLLESGGG LVQPGGSLRL SCAASGFTFG NYDMAWVRQA PGKRPEWVSS IDTGGDITHY   60
ADSVKGRFTI SRDNAKNTLY LQMNSLRPED TAVYWCATDE EYALGPNEFD YYGQGTLVTV  120
SSGGGGSGPP CPPCPAPEFL GGPSVFLFPP KPKDTLMISR TPEVTCVVVD VSQEDPEVQF  180
NWYVDGVEVH NAKTKPREEQ FNSTYRVVSV LTVLHQDWLN GKEYKCKVSN KGLPSSIEKT  240
ISKAKGQPRE PQVYTLPPCQ EEMTKNQVSL WCLVKGFYPS DIAVEWESNG QPENNYKTTP  300
PVLDSDGSFF LYSRLTVDKS RWQEGNVFSC SVMHEALHNH YTQKSLSLSL GK          352

SEQ ID NO: 111          moltype = AA   length = 357
FEATURE                 Location/Qualifiers
source                  1..357
                        mol_type = protein
                        organism = Synthetic construct
SEQUENCE: 111
EVQLLESGGG LVQPGGSLRL SCAASGFTFG NYDMAWVRQA PGKRPEWVSS IDTGGDITHY   60
ADSVKGRFTI SRDNAKNTLY LQMNSLRPED TAVYWCATDE EYALGPNEFD YYGQGTLVTV  120
SSGGGGSGGG GSGGPPCPPCP APEFLGGPSV FLFPPKPKDT LMISRTPEVT CVVVDVSQED  180
PEVQFNWYVD GVEVHNAKTK PREEQFNSTY RVVSVLTVLH QDWLNGKEYK CKVSNKGLPS  240
SIEKTISKAK GQPREPQVYT LPPCQEEMTK NQVSLWCLVK GFYPSDIAVE WESNGQPENN  300
```

```
YKTTPPVLDS DGSFFLYSRL TVDKSRWQEG NVFSCSVMHE ALHNHYTQKS LSLSLGK          357

SEQ ID NO: 112              moltype = AA   length = 362
FEATURE                     Location/Qualifiers
source                      1..362
                            mol_type = protein
                            organism = Synthetic construct
SEQUENCE: 112
EVQLLESGGG LVQPGGSLRL SCAASGFTFG NYDMAWVRQA PGKRPEWVSS IDTGGDITHY       60
ADSVKGRFTI SRDNAKNTLY LQMNSLRPED TAVYWCATDE EYALGPNEFD YYGQGTLVTV       120
SSGGGGSGGG GSGGGGSGPP CPPCPAPEFL GGPSVFLFPP KPKDTLMISR TPEVTCVVVD       180
VSQEDPEVQF NWYVDGVEVH NAKTKPREEQ FNSTYRVVSV LTVLHQDWLN GKEYKCKVSN       240
KGLPSSIEKT ISKAKGQPRE PQVYTLPPCQ EEMTKNQVSL WCLVKGFYPS DIAVEWESNG       300
QPENNYKTTP PVLDSDGSFF LYSRLTVDKS RWQEGNVFSC SVMHEALHNH YTQKSLSLSL       360
GK                                                                      362

SEQ ID NO: 113              moltype = AA   length = 349
FEATURE                     Location/Qualifiers
source                      1..349
                            mol_type = protein
                            organism = Synthetic construct
SEQUENCE: 113
EVQLLESGGG LVQPGGSLRL SCAASGFTFG NYDMAWVRQA PGKRPEWVSS IDTGGDITHY       60
ADSVKGRFTI SRDNAKNTLY LQMNSLRPED TAVYWCATDE EYALGPNEFD YYGQGTLVTV       120
SSRSGPPCPP CPAPEFLGGP SVFLFPPKPK DTLMISRTPE VTCVVVDVSQ EDPEVQFNWY       180
VDGVEVHNAK TKPREEQFNS TYRVVSVLTV LHQDWLNGKE YKCKVSNKGL PSSIEKTISK       240
AKGQPREPQV CTLPPSQEEM TKNQVSLSCA VKGFYPSDIA VEWESNGQPE NNYKTTPPVL       300
DSDGSFFLVS RLTVDKSRWQ EGNVFSCSVM HEALHNHYTQ KSLSLSLGK                   349

SEQ ID NO: 114              moltype = AA   length = 352
FEATURE                     Location/Qualifiers
source                      1..352
                            mol_type = protein
                            organism = Synthetic construct
SEQUENCE: 114
EVQLLESGGG LVQPGGSLRL SCAASGFTFG NYDMAWVRQA PGKRPEWVSS IDTGGDITHY       60
ADSVKGRFTI SRDNAKNTLY LQMNSLRPED TAVYWCATDE EYALGPNEFD YYGQGTLVTV       120
SSGGGGSGPP CPPCPAPEFL GGPSVFLFPP KPKDTLMISR TPEVTCVVVD VSQEDPEVQF       180
NWYVDGVEVH NAKTKPREEQ FNSTYRVVSV LTVLHQDWLN GKEYKCKVSN KGLPSSIEKT       240
ISKAKGQPRE PQVCTLPPSQ EEMTKNQVSL SCAVKGFYPS DIAVEWESNG QPENNYKTTP       300
PVLDSDGSFF LVSRLTVDKS RWQEGNVFSC SVMHEALHNH YTQKSLSLSL GK               352

SEQ ID NO: 115              moltype = AA   length = 357
FEATURE                     Location/Qualifiers
source                      1..357
                            mol_type = protein
                            organism = Synthetic construct
SEQUENCE: 115
EVQLLESGGG LVQPGGSLRL SCAASGFTFG NYDMAWVRQA PGKRPEWVSS IDTGGDITHY       60
ADSVKGRFTI SRDNAKNTLY LQMNSLRPED TAVYWCATDE EYALGPNEFD YYGQGTLVTV       120
SSGGGGSGGG GSGPPCPPCP APEFLGGPSV FLFPPKPKDT LMISRTPEVT CVVVDVSQED       180
PEVQFNWYVD GVEVHNAKTK PREEQFNSTY RVVSVLTVLH QDWLNGKEYK CKVSNKGLPS       240
SIEKTISKAK GQPREPQVCT LPPSQEEMTK NQVSLSCAVK GFYPSDIAVE WESNGQPENN       300
YKTTPPVLDS DGSFFLVSRL TVDKSRWQEG NVFSCSVMHE ALHNHYTQKS LSLSLGK          357

SEQ ID NO: 116              moltype = AA   length = 362
FEATURE                     Location/Qualifiers
source                      1..362
                            mol_type = protein
                            organism = Synthetic construct
SEQUENCE: 116
EVQLLESGGG LVQPGGSLRL SCAASGFTFG NYDMAWVRQA PGKRPEWVSS IDTGGDITHY       60
ADSVKGRFTI SRDNAKNTLY LQMNSLRPED TAVYWCATDE EYALGPNEFD YYGQGTLVTV       120
SSGGGGSGGG GSGGGGSGPP CPPCPAPEFL GGPSVFLFPP KPKDTLMISR TPEVTCVVVD       180
VSQEDPEVQF NWYVDGVEVH NAKTKPREEQ FNSTYRVVSV LTVLHQDWLN GKEYKCKVSN       240
KGLPSSIEKT ISKAKGQPRE PQVCTLPPSQ EEMTKNQVSL SCAVKGFYPS DIAVEWESNG       300
QPENNYKTTP PVLDSDGSFF LVSRLTVDKS RWQEGNVFSC SVMHEALHNH YTQKSLSLSL       360
GK                                                                      362

SEQ ID NO: 117              moltype = AA   length = 344
FEATURE                     Location/Qualifiers
source                      1..344
                            mol_type = protein
                            organism = Synthetic construct
SEQUENCE: 117
DVQLQESGGG LVQAGGSLRL SCAASGFIFR LAGMSWVRQA PGKGFEWVSG ITMDGSTTNY       60
ADSVKGRFTI SRDNSKNRLY LQMNSLKPED TAVYYCARGA KGGYNDPRGQ GTQVTVSRSG       120
PPCPPCPAPE FLGGPSVFLF PPKPKDTLMI SRTPEVTCVV VDVSQEDPEV QFNWYVDGVE       180
VHNAKTKPRE EQFNSTYRVV SVLTVLHQDW LNGKEYKCKV SNKGLPSSIE KTISKAKGQP       240
```

-continued

```
REPQVYTLPP CQEEMTKNQV SLWCLVKGFY PSDIAVEWES NGQPENNYKT TPPVLDSDGS    300
FFLYSRLTVD KSRWQEGNVF SCSVMHEALH NHYTQKSLSL SLGK                      344

SEQ ID NO: 118           moltype = AA   length = 347
FEATURE                  Location/Qualifiers
source                   1..347
                         mol_type = protein
                         organism = Synthetic construct
SEQUENCE: 118
DVQLQESGGG LVQAGGSLRL SCAASGFIFR LAGMSWVRQA PGKGFEWVSG ITMDGSTTNY    60
ADSVKGRFTI SRDNSKNRLY LQMNSLKPED TAVYYCARGA KGGYNDPRGQ GTQVTVSGGG    120
GSGPPCPPCP APEFLGGPSV FLFPPKPKDT LMISRTPEVT CVVVDVSQED PEVQFNWYVD    180
GVEVHNAKTK PREEQFNSTY RVVSVLTVLH QDWLNGKEYK CKVSNKGLPS SIEKTISKAK    240
GQPREPQVYT LPPCQEEMTK NQVSLWCLVK GFYPSDIAVE WESNGQPENN YKTTPPVLDS    300
DGSFFLYSRL TVDKSRWQEG NVFSCSVMHE ALHNHYTQKS LSLSLGK                  347

SEQ ID NO: 119           moltype = AA   length = 352
FEATURE                  Location/Qualifiers
source                   1..352
                         mol_type = protein
                         organism = Synthetic construct
SEQUENCE: 119
DVQLQESGGG LVQAGGSLRL SCAASGFIFR LAGMSWVRQA PGKGFEWVSG ITMDGSTTNY    60
ADSVKGRFTI SRDNSKNRLY LQMNSLKPED TAVYYCARGA KGGYNDPRGQ GTQVTVSGGG    120
GSGGGGSGPP CPPCPAPEFL GGPSVFLFPP KPKDTLMISR TPEVTCVVVD VSQEDPEVQF    180
NWYVDGVEVH NAKTKPREEQ FNSTYRVVSV LTVLHQDWLN GKEYKCKVSN KGLPSSIEKT    240
ISKAKGQPRE PQVYTLPPCQ EEMTKNQVSL WCLVKGFYPS DIAVEWESNG QPENNYKTTP    300
PVLDSDGSFF LYSRLTVDKS RWQEGNVFSC SVMHEALHNH YTQKSLSLSL GK            352

SEQ ID NO: 120           moltype = AA   length = 357
FEATURE                  Location/Qualifiers
source                   1..357
                         mol_type = protein
                         organism = Synthetic construct
SEQUENCE: 120
DVQLQESGGG LVQAGGSLRL SCAASGFIFR LAGMSWVRQA PGKGFEWVSG ITMDGSTTNY    60
ADSVKGRFTI SRDNSKNRLY LQMNSLKPED TAVYYCARGA KGGYNDPRGQ GTQVTVSGGG    120
GSGGGSGGP GSGPPCPPCP APEFLGGPSV FLFPPKPKDT LMISRTPEVT CVVVDVSQED    180
PEVQFNWYVD GVEVHNAKTK PREEQFNSTY RVVSVLTVLH QDWLNGKEYK CKVSNKGLPS    240
SIEKTISKAK GQPREPQVYT LPPCQEEMTK NQVSLWCLVK GFYPSDIAVE WESNGQPENN    300
YKTTPPVLDS DGSFFLYSRL TVDKSRWQEG NVFSCSVMHE ALHNHYTQKS LSLSLGK      357

SEQ ID NO: 121           moltype = AA   length = 354
FEATURE                  Location/Qualifiers
source                   1..354
                         mol_type = protein
                         organism = Synthetic construct
SEQUENCE: 121
QVQLQESGGG LVQTGGSLRL SCAVHGRTFS NTGMGWFRQA PGNERQFVAI ISPSGTSTYY    60
ADSVKGRFTI SRDPAKNTVY LQMNSLKMDD TAVYYCAASY GSNWSTLRHQ RRNEYDAWGQ    120
GTQVAVSRSG PPCPPCPAPE FLGGPSVFLF PPKPKDTLMI SRTPEVTCVV VDVSQEDPEV    180
QFNWYVDGVE VHNAKTKPRE EQFNSTYRVV SVLTVLHQDW LNGKEYKCKV SNKGLPSSIE    240
KTISKAKGQP REPQVYTLPP CQEEMTKNQV SLWCLVKGFY PSDIAVEWES NGQPENNYKT    300
TPPVLDSDGS FFLYSRLTVD KSRWQEGNVF SCSVMHEALH NHYTQKSLSL SLGK          354

SEQ ID NO: 122           moltype = AA   length = 357
FEATURE                  Location/Qualifiers
source                   1..357
                         mol_type = protein
                         organism = Synthetic construct
SEQUENCE: 122
QVQLQESGGG LVQTGGSLRL SCAVHGRTFS NTGMGWFRQA PGNERQFVAI ISPSGTSTYY    60
ADSVKGRFTI SRDPAKNTVY LQMNSLKMDD TAVYYCAASY GSNWSTLRHQ RRNEYDAWGQ    120
GTQVAVSGGG GSGPPCPPCP APEFLGGPSV FLFPPKPKDT LMISRTPEVT CVVVDVSQED    180
PEVQFNWYVD GVEVHNAKTK PREEQFNSTY RVVSVLTVLH QDWLNGKEYK CKVSNKGLPS    240
SIEKTISKAK GQPREPQVYT LPPCQEEMTK NQVSLWCLVK GFYPSDIAVE WESNGQPENN    300
YKTTPPVLDS DGSFFLYSRL TVDKSRWQEG NVFSCSVMHE ALHNHYTQKS LSLSLGK      357

SEQ ID NO: 123           moltype = AA   length = 362
FEATURE                  Location/Qualifiers
source                   1..362
                         mol_type = protein
                         organism = Synthetic construct
SEQUENCE: 123
QVQLQESGGG LVQTGGSLRL SCAVHGRTFS NTGMGWFRQA PGNERQFVAI ISPSGTSTYY    60
ADSVKGRFTI SRDPAKNTVY LQMNSLKMDD TAVYYCAASY GSNWSTLRHQ RRNEYDAWGQ    120
GTQVAVSGGG GSGGGGSGPP CPPCPAPEFL GGPSVFLFPP KPKDTLMISR TPEVTCVVVD    180
VSQEDPEVQF NWYVDGVEVH NAKTKPREEQ FNSTYRVVSV LTVLHQDWLN GKEYKCKVSN    240
KGLPSSIEKT ISKAKGQPRE PQVYTLPPCQ EEMTKNQVSL WCLVKGFYPS DIAVEWESNG    300
```

```
QPENNYKTTP PVLDSDGSFF LYSRLTVDKS RWQEGNVFSC SVMHEALHNH YTQKSLSLSL   360
GK                                                                  362

SEQ ID NO: 124              moltype = AA   length = 367
FEATURE                     Location/Qualifiers
source                      1..367
                            mol_type = protein
                            organism = Synthetic construct
SEQUENCE: 124
QVQLQESGGG LVQTGGSLRL SCAVHGRTFS NTGMGWFRQA PGNERQFVAI ISPSGTSTYY   60
ADSVKGRFTI SRDPAKNTVY LQMNSLKMDD TAVYYCAASY GSNWSTLRHQ RRNEYDAWGQ   120
GTQVAVSGGG GSGGGGSGGG GSGPPCPPCP APEFLGGPSV FLFPPKPKDT LMISRTPEVT   180
CVVVDVSQED PEVQFNWYVD GVEVHNAKTK PREEQFNSTY RVVSVLTVLH QDWLNGKEYK   240
CKVSNKGLPS SIEKTISKAK GQPREPQVYT LPPCQEEMTK NQVSLWCLVK GFYPSDIAVE   300
WESNGQPENN YKTTPPVLDS DGSFFLYSRL TVDKSRWQEG NVFSCSVMHE ALHNHYTQKS   360
LSLSLGK                                                             367

SEQ ID NO: 125              moltype = AA   length = 229
FEATURE                     Location/Qualifiers
source                      1..229
                            mol_type = protein
                            organism = Synthetic construct
SEQUENCE: 125
ESKYGPPCPS CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK              229

SEQ ID NO: 126              moltype = AA   length = 225
FEATURE                     Location/Qualifiers
source                      1..225
                            mol_type = protein
                            organism = Synthetic construct
SEQUENCE: 126
GPPCPSCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PSQEEMTKNQ VSLTCLVKGF YPSDIAVEWE SNGQPENNYK TTPPVLDSDG   180
SFFLYSRLTV DKSRWQEGNV FSCSVMHEAL HNHYTQKSLS LSLGK                  225

SEQ ID NO: 127              moltype = AA   length = 389
FEATURE                     Location/Qualifiers
source                      1..389
                            mol_type = protein
                            organism = Synthetic construct
SEQUENCE: 127
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGKGGG GSDLGKKLLE   240
AARAGQDDEV RILMANGADV NAIDHNGDTP LHLAAYVGRL EIVEVLLKHG ADVNARDLRG   300
FTPLHLAAQY GHMEIVEVLL KYGADVNADD DYGTTPLHLA AQYGHMEIVE VLLKYGADVN   360
AQDKFGKTAF DISIDNGNED LAEILQKLN                                     389

SEQ ID NO: 128              moltype = AA   length = 356
FEATURE                     Location/Qualifiers
source                      1..356
                            mol_type = protein
                            organism = Synthetic construct
SEQUENCE: 128
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGKGGG GSDLGKKLLE   240
AARAGQDDEV RILTANGADV NANDYWGHTP LHLAAMLGHL EIVEVLLKNG ADVNATGNTG   300
RTPLHLAAWA DHLEIVEVLL KHGADVNAQD KFGKTAFDIS IDNGNEDLAE ILQKLN       356

SEQ ID NO: 129              moltype = AA   length = 5
FEATURE                     Location/Qualifiers
source                      1..5
                            mol_type = protein
                            organism = Synthetic construct
SEQUENCE: 129
NYDMA                                                               5

SEQ ID NO: 130              moltype = AA   length = 17
FEATURE                     Location/Qualifiers
source                      1..17
                            mol_type = protein
                            organism = Synthetic construct
```

-continued

```
SEQUENCE: 130
SIDTGGDITH YADSVKG                                                                    17

SEQ ID NO: 131        moltype = AA  length = 13
FEATURE               Location/Qualifiers
source                1..13
                      mol_type = protein
                      organism = Synthetic construct
SEQUENCE: 131
DEEYALGPNE FDY                                                                        13

SEQ ID NO: 132        moltype = AA  length = 5
FEATURE               Location/Qualifiers
source                1..5
                      mol_type = protein
                      organism = Synthetic construct
SEQUENCE: 132
NYDMA                                                                                 5

SEQ ID NO: 133        moltype = AA  length = 17
FEATURE               Location/Qualifiers
source                1..17
                      mol_type = protein
                      organism = Synthetic construct
SEQUENCE: 133
SIDTGGDITH YADSVKG                                                                    17

SEQ ID NO: 134        moltype = AA  length = 13
FEATURE               Location/Qualifiers
source                1..13
                      mol_type = protein
                      organism = Synthetic construct
SEQUENCE: 134
DEEYALGPNE FDY                                                                        13

SEQ ID NO: 135        moltype = AA  length = 5
FEATURE               Location/Qualifiers
source                1..5
                      mol_type = protein
                      organism = Synthetic construct
SEQUENCE: 135
NTGMG                                                                                 5

SEQ ID NO: 136        moltype = AA  length = 17
FEATURE               Location/Qualifiers
source                1..17
                      mol_type = protein
                      organism = Synthetic construct
SEQUENCE: 136
IISPSGTSTY YADSVKG                                                                    17

SEQ ID NO: 137        moltype = AA  length = 19
FEATURE               Location/Qualifiers
source                1..19
                      mol_type = protein
                      organism = Synthetic construct
SEQUENCE: 137
SYGSNWSTLR HQRRNEYDA                                                                  19

SEQ ID NO: 138        moltype = AA  length = 5
FEATURE               Location/Qualifiers
source                1..5
                      mol_type = protein
                      organism = Synthetic construct
SEQUENCE: 138
NNVAD                                                                                 5

SEQ ID NO: 139        moltype = AA  length = 17
FEATURE               Location/Qualifiers
source                1..17
                      mol_type = protein
                      organism = Synthetic construct
SEQUENCE: 139
RISASGATRE YGDSVKG                                                                    17

SEQ ID NO: 140        moltype = AA  length = 11
FEATURE               Location/Qualifiers
source                1..11
                      mol_type = protein
```

-continued

```
                        organism = Synthetic construct
SEQUENCE: 140
IEWEDLSRKD Y                                                         11

SEQ ID NO: 141          moltype = AA   length = 5
FEATURE                 Location/Qualifiers
source                  1..5
                        mol_type = protein
                        organism = Synthetic construct
SEQUENCE: 141
LAGMS                                                                5

SEQ ID NO: 142          moltype = AA   length = 17
FEATURE                 Location/Qualifiers
source                  1..17
                        mol_type = protein
                        organism = Synthetic construct
SEQUENCE: 142
GITMDGSTTN YADSVKG                                                   17

SEQ ID NO: 143          moltype = AA   length = 9
FEATURE                 Location/Qualifiers
source                  1..9
                        mol_type = protein
                        organism = Synthetic construct
SEQUENCE: 143
GAKGGYNDP                                                            9

SEQ ID NO: 144          moltype = AA   length = 5
FEATURE                 Location/Qualifiers
source                  1..5
                        mol_type = protein
                        organism = Synthetic construct
SEQUENCE: 144
RCDMG                                                                5

SEQ ID NO: 145          moltype = AA   length = 17
FEATURE                 Location/Qualifiers
source                  1..17
                        mol_type = protein
                        organism = Synthetic construct
SEQUENCE: 145
RISANGASTH YADFVKG                                                   17

SEQ ID NO: 146          moltype = AA   length = 12
FEATURE                 Location/Qualifiers
source                  1..12
                        mol_type = protein
                        organism = Synthetic construct
SEQUENCE: 146
ARVPVTWQLY DY                                                        12

SEQ ID NO: 147          moltype = AA   length = 5
FEATURE                 Location/Qualifiers
source                  1..5
                        mol_type = protein
                        organism = Synthetic construct
SEQUENCE: 147
GWSMG                                                                5

SEQ ID NO: 148          moltype = AA   length = 20
FEATURE                 Location/Qualifiers
source                  1..20
                        mol_type = protein
                        organism = Synthetic construct
SEQUENCE: 148
AISWVGSWIG GTVYSNSVKG                                                20

SEQ ID NO: 149          moltype = AA   length = 15
FEATURE                 Location/Qualifiers
source                  1..15
                        mol_type = protein
                        organism = Synthetic construct
SEQUENCE: 149
ANSETPRIFA SEYDY                                                     15

SEQ ID NO: 150          moltype = AA   length = 5
FEATURE                 Location/Qualifiers
source                  1..5
```

-continued

```
                        mol_type = protein
                        organism = Synthetic construct
SEQUENCE: 150
SYSMG                                                                      5

SEQ ID NO: 151          moltype = AA   length = 17
FEATURE                 Location/Qualifiers
source                  1..17
                        mol_type = protein
                        organism = Synthetic construct
SEQUENCE: 151
GITWSGGRTY YADFVKG                                                        17

SEQ ID NO: 152          moltype = AA   length = 19
FEATURE                 Location/Qualifiers
source                  1..19
                        mol_type = protein
                        organism = Synthetic construct
SEQUENCE: 152
LWGVGSWYEE LRNKHEYDY                                                      19

SEQ ID NO: 153          moltype = AA   length = 8
FEATURE                 Location/Qualifiers
source                  1..8
                        mol_type = protein
                        organism = Synthetic construct
SEQUENCE: 153
TTSGYNMG                                                                   8

SEQ ID NO: 154          moltype = AA   length = 18
FEATURE                 Location/Qualifiers
source                  1..18
                        mol_type = protein
                        organism = Synthetic construct
SEQUENCE: 154
GIKWVSGSNR AYAESVKG                                                       18

SEQ ID NO: 155          moltype = AA   length = 16
FEATURE                 Location/Qualifiers
source                  1..16
                        mol_type = protein
                        organism = Synthetic construct
SEQUENCE: 155
ATGQSYVPIR EYEYVY                                                         16

SEQ ID NO: 156          moltype = AA   length = 5
FEATURE                 Location/Qualifiers
source                  1..5
                        mol_type = protein
                        organism = Synthetic construct
SEQUENCE: 156
RYAVG                                                                      5

SEQ ID NO: 157          moltype = AA   length = 16
FEATURE                 Location/Qualifiers
source                  1..16
                        mol_type = protein
                        organism = Synthetic construct
SEQUENCE: 157
INWSGGSTTY ADSAEG                                                         16

SEQ ID NO: 158          moltype = AA   length = 17
FEATURE                 Location/Qualifiers
source                  1..17
                        mol_type = protein
                        organism = Synthetic construct
SEQUENCE: 158
PSVLVQGGIS NPSQYDY                                                        17

SEQ ID NO: 159          moltype = AA   length = 5
FEATURE                 Location/Qualifiers
source                  1..5
                        mol_type = protein
                        organism = Synthetic construct
SEQUENCE: 159
SYVVS                                                                      5

SEQ ID NO: 160          moltype = AA   length = 17
FEATURE                 Location/Qualifiers
```

-continued

```
source                  1..17
                        mol_type = protein
                        organism = Synthetic construct
SEQUENCE: 160
AITWSGLSTT YLDSVQG                                              17

SEQ ID NO: 161          moltype = AA   length = 17
FEATURE                 Location/Qualifiers
source                  1..17
                        mol_type = protein
                        organism = Synthetic construct
SEQUENCE: 161
GPNIPSILRT RESEYAY                                              17

SEQ ID NO: 162          moltype = AA   length = 5
FEATURE                 Location/Qualifiers
source                  1..5
                        mol_type = protein
                        organism = Synthetic construct
SEQUENCE: 162
NYAMR                                                           5

SEQ ID NO: 163          moltype = AA   length = 17
FEATURE                 Location/Qualifiers
source                  1..17
                        mol_type = protein
                        organism = Synthetic construct
SEQUENCE: 163
RISSTGFITR YTASVRD                                              17

SEQ ID NO: 164          moltype = AA   length = 5
FEATURE                 Location/Qualifiers
source                  1..5
                        mol_type = protein
                        organism = Synthetic construct
SEQUENCE: 164
ESTDY                                                           5

SEQ ID NO: 165          moltype = AA   length = 5
FEATURE                 Location/Qualifiers
source                  1..5
                        mol_type = protein
                        organism = Synthetic construct
SEQUENCE: 165
RYDMG                                                           5

SEQ ID NO: 166          moltype = AA   length = 17
FEATURE                 Location/Qualifiers
source                  1..17
                        mol_type = protein
                        organism = Synthetic construct
SEQUENCE: 166
RISWSGTTKY YADAVKG                                              17

SEQ ID NO: 167          moltype = AA   length = 16
FEATURE                 Location/Qualifiers
source                  1..16
                        mol_type = protein
                        organism = Synthetic construct
SEQUENCE: 167
AFYGNRGYYD VNAYTS                                               16

SEQ ID NO: 168          moltype = AA   length = 5
FEATURE                 Location/Qualifiers
source                  1..5
                        mol_type = protein
                        organism = Synthetic construct
SEQUENCE: 168
RYDMG                                                           5

SEQ ID NO: 169          moltype = AA   length = 17
FEATURE                 Location/Qualifiers
source                  1..17
                        mol_type = protein
                        organism = Synthetic construct
SEQUENCE: 169
RISWSGDTKY YADAVEG                                              17

SEQ ID NO: 170          moltype = AA   length = 16
```

-continued

```
FEATURE                Location/Qualifiers
source                 1..16
                       mol_type = protein
                       organism = Synthetic construct
SEQUENCE: 170
ALYGNRGYYD VNTYSY                                                  16

SEQ ID NO: 171         moltype = AA  length = 5
FEATURE                Location/Qualifiers
source                 1..5
                       mol_type = protein
                       organism = Synthetic construct
SEQUENCE: 171
RWDVA                                                              5

SEQ ID NO: 172         moltype = AA  length = 17
FEATURE                Location/Qualifiers
source                 1..17
                       mol_type = protein
                       organism = Synthetic construct
SEQUENCE: 172
RISWSGTTSY YADAVKG                                                 17

SEQ ID NO: 173         moltype = AA  length = 16
FEATURE                Location/Qualifiers
source                 1..16
                       mol_type = protein
                       organism = Synthetic construct
SEQUENCE: 173
ALYGNRGYYD VNAHSY                                                  16

SEQ ID NO: 174         moltype =   length =
SEQUENCE: 174
000

SEQ ID NO: 175         moltype = AA  length = 17
FEATURE                Location/Qualifiers
source                 1..17
                       mol_type = protein
                       organism = Synthetic construct
SEQUENCE: 175
AISLYSGSTY YADSVKG                                                 17

SEQ ID NO: 176         moltype = AA  length = 19
FEATURE                Location/Qualifiers
source                 1..19
                       mol_type = protein
                       organism = Synthetic construct
SEQUENCE: 176
DRQRTWSTFY ASRQATYNY                                               19

SEQ ID NO: 177         moltype = AA  length = 5
FEATURE                Location/Qualifiers
source                 1..5
                       mol_type = protein
                       organism = Synthetic construct
SEQUENCE: 177
IDIMG                                                              5

SEQ ID NO: 178         moltype = AA  length = 16
FEATURE                Location/Qualifiers
source                 1..16
                       mol_type = protein
                       organism = Synthetic construct
SEQUENCE: 178
TMPEGNYINY ADSVKG                                                  16

SEQ ID NO: 179         moltype = AA  length = 11
FEATURE                Location/Qualifiers
source                 1..11
                       mol_type = protein
                       organism = Synthetic construct
SEQUENCE: 179
FGVREGRGNV Y                                                       11

SEQ ID NO: 180         moltype = AA  length = 5
FEATURE                Location/Qualifiers
source                 1..5
                       mol_type = protein
```

-continued

```
                          organism = Synthetic construct
SEQUENCE: 180
SYDMG                                                                  5

SEQ ID NO: 181           moltype = AA   length = 16
FEATURE                  Location/Qualifiers
source                   1..16
                         mol_type = protein
                         organism = Synthetic construct
SEQUENCE: 181
RIRNDGITYY ADSVKG                                                     16

SEQ ID NO: 182           moltype = AA   length = 10
FEATURE                  Location/Qualifiers
source                   1..10
                         mol_type = protein
                         organism = Synthetic construct
SEQUENCE: 182
DGTGLGHYDY                                                           10

SEQ ID NO: 183           moltype = AA   length = 5
FEATURE                  Location/Qualifiers
source                   1..5
                         mol_type = protein
                         organism = Synthetic construct
SEQUENCE: 183
DNVMS                                                                 5

SEQ ID NO: 184           moltype = AA   length = 16
FEATURE                  Location/Qualifiers
source                   1..16
                         mol_type = protein
                         organism = Synthetic construct
SEQUENCE: 184
TIMLNGDTAH ADSVKG                                                    16

SEQ ID NO: 185           moltype = AA   length = 11
FEATURE                  Location/Qualifiers
source                   1..11
                         mol_type = protein
                         organism = Synthetic construct
SEQUENCE: 185
RDSMLEPGRG A                                                         11

SEQ ID NO: 186           moltype = AA   length = 7
FEATURE                  Location/Qualifiers
source                   1..7
                         mol_type = protein
                         organism = Synthetic construct
SEQUENCE: 186
GFTFGNY                                                               7

SEQ ID NO: 187           moltype = AA   length = 6
FEATURE                  Location/Qualifiers
source                   1..6
                         mol_type = protein
                         organism = Synthetic construct
SEQUENCE: 187
DTGGDI                                                                6

SEQ ID NO: 188           moltype = AA   length = 13
FEATURE                  Location/Qualifiers
source                   1..13
                         mol_type = protein
                         organism = Synthetic construct
SEQUENCE: 188
DEEYALGPNE FDY                                                       13

SEQ ID NO: 189           moltype = AA   length = 7
FEATURE                  Location/Qualifiers
source                   1..7
                         mol_type = protein
                         organism = Synthetic construct
SEQUENCE: 189
GFRFGNY                                                               7

SEQ ID NO: 190           moltype = AA   length = 6
FEATURE                  Location/Qualifiers
source                   1..6
```

-continued

```
                              mol_type = protein
                              organism = Synthetic construct
SEQUENCE: 190
DTGGDI                                                        6

SEQ ID NO: 191       moltype = AA   length = 13
FEATURE              Location/Qualifiers
source               1..13
                     mol_type = protein
                     organism = Synthetic construct
SEQUENCE: 191
DEEYALGPNE FDY                                               13

SEQ ID NO: 192       moltype = AA   length = 7
FEATURE              Location/Qualifiers
source               1..7
                     mol_type = protein
                     organism = Synthetic construct
SEQUENCE: 192
GRTFSNT                                                       7

SEQ ID NO: 193       moltype = AA   length = 6
FEATURE              Location/Qualifiers
source               1..6
                     mol_type = protein
                     organism = Synthetic construct
SEQUENCE: 193
SPSGTS                                                        6

SEQ ID NO: 194       moltype = AA   length = 19
FEATURE              Location/Qualifiers
source               1..19
                     mol_type = protein
                     organism = Synthetic construct
SEQUENCE: 194
SYGSNWSTLR HQRRNEYDA                                         19

SEQ ID NO: 195       moltype = AA   length = 7
FEATURE              Location/Qualifiers
source               1..7
                     mol_type = protein
                     organism = Synthetic construct
SEQUENCE: 195
GSTFSNN                                                       7

SEQ ID NO: 196       moltype = AA   length = 6
FEATURE              Location/Qualifiers
source               1..6
                     mol_type = protein
                     organism = Synthetic construct
SEQUENCE: 196
SASGAT                                                        6

SEQ ID NO: 197       moltype = AA   length = 11
FEATURE              Location/Qualifiers
source               1..11
                     mol_type = protein
                     organism = Synthetic construct
SEQUENCE: 197
IEWEDLSRKD Y                                                 11

SEQ ID NO: 198       moltype = AA   length = 7
FEATURE              Location/Qualifiers
source               1..7
                     mol_type = protein
                     organism = Synthetic construct
SEQUENCE: 198
GFIFRLA                                                       7

SEQ ID NO: 199       moltype = AA   length = 6
FEATURE              Location/Qualifiers
source               1..6
                     mol_type = protein
                     organism = Synthetic construct
SEQUENCE: 199
TMDGST                                                        6

SEQ ID NO: 200       moltype = AA   length = 9
FEATURE              Location/Qualifiers
```

-continued

```
source                  1..9
                        mol_type = protein
                        organism = Synthetic construct
SEQUENCE: 200
GAKGGYNDP                                                          9

SEQ ID NO: 201          moltype = AA   length = 7
FEATURE                 Location/Qualifiers
source                  1..7
                        mol_type = protein
                        organism = Synthetic construct
SEQUENCE: 201
GLTFSRC                                                            7

SEQ ID NO: 202          moltype = AA   length = 6
FEATURE                 Location/Qualifiers
source                  1..6
                        mol_type = protein
                        organism = Synthetic construct
SEQUENCE: 202
SANGAS                                                             6

SEQ ID NO: 203          moltype = AA   length = 12
FEATURE                 Location/Qualifiers
source                  1..12
                        mol_type = protein
                        organism = Synthetic construct
SEQUENCE: 203
ARVPVTWQLY DY                                                      12

SEQ ID NO: 204          moltype = AA   length = 7
FEATURE                 Location/Qualifiers
source                  1..7
                        mol_type = protein
                        organism = Synthetic construct
SEQUENCE: 204
GRTFSGW                                                            7

SEQ ID NO: 205          moltype = AA   length = 9
FEATURE                 Location/Qualifiers
source                  1..9
                        mol_type = protein
                        organism = Synthetic construct
SEQUENCE: 205
SWVGSWIGG                                                          9

SEQ ID NO: 206          moltype = AA   length = 15
FEATURE                 Location/Qualifiers
source                  1..15
                        mol_type = protein
                        organism = Synthetic construct
SEQUENCE: 206
ANSETPRIFA SEYDY                                                   15

SEQ ID NO: 207          moltype = AA   length = 7
FEATURE                 Location/Qualifiers
source                  1..7
                        mol_type = protein
                        organism = Synthetic construct
SEQUENCE: 207
GRTFSSY                                                            7

SEQ ID NO: 208          moltype = AA   length = 6
FEATURE                 Location/Qualifiers
source                  1..6
                        mol_type = protein
                        organism = Synthetic construct
SEQUENCE: 208
TWSGGR                                                             6

SEQ ID NO: 209          moltype = AA   length = 19
FEATURE                 Location/Qualifiers
source                  1..19
                        mol_type = protein
                        organism = Synthetic construct
SEQUENCE: 209
LWGVGSWYEE LRNKHEYDY                                               19

SEQ ID NO: 210          moltype = AA   length = 10
```

-continued

```
FEATURE              Location/Qualifiers
source               1..10
                     mol_type = protein
                     organism = Synthetic construct
SEQUENCE: 210
GRTFTTTSGY                                                           10

SEQ ID NO: 211       moltype = AA   length = 7
FEATURE              Location/Qualifiers
source               1..7
                     mol_type = protein
                     organism = Synthetic construct
SEQUENCE: 211
KWVSGSN                                                               7

SEQ ID NO: 212       moltype = AA   length = 16
FEATURE              Location/Qualifiers
source               1..16
                     mol_type = protein
                     organism = Synthetic construct
SEQUENCE: 212
ATGQSYVPIR EYEYVY                                                    16

SEQ ID NO: 213       moltype = AA   length = 7
FEATURE              Location/Qualifiers
source               1..7
                     mol_type = protein
                     organism = Synthetic construct
SEQUENCE: 213
GRTISRY                                                               7

SEQ ID NO: 214       moltype = AA   length = 5
FEATURE              Location/Qualifiers
source               1..5
                     mol_type = protein
                     organism = Synthetic construct
SEQUENCE: 214
WSGGS                                                                 5

SEQ ID NO: 215       moltype = AA   length = 17
FEATURE              Location/Qualifiers
source               1..17
                     mol_type = protein
                     organism = Synthetic construct
SEQUENCE: 215
PSVLVQGGIS NPSQYDY                                                   17

SEQ ID NO: 216       moltype = AA   length = 7
FEATURE              Location/Qualifiers
source               1..7
                     mol_type = protein
                     organism = Synthetic construct
SEQUENCE: 216
GRTLSSY                                                               7

SEQ ID NO: 217       moltype = AA   length = 6
FEATURE              Location/Qualifiers
source               1..6
                     mol_type = protein
                     organism = Synthetic construct
SEQUENCE: 217
TWSGLS                                                                6

SEQ ID NO: 218       moltype = AA   length = 17
FEATURE              Location/Qualifiers
source               1..17
                     mol_type = protein
                     organism = Synthetic construct
SEQUENCE: 218
GPNIPSILRT RESEYAY                                                   17

SEQ ID NO: 219       moltype = AA   length = 7
FEATURE              Location/Qualifiers
source               1..7
                     mol_type = protein
                     organism = Synthetic construct
SEQUENCE: 219
GFRFSNY                                                               7
```

-continued

```
SEQ ID NO: 220          moltype = AA   length = 6
FEATURE                 Location/Qualifiers
source                  1..6
                        mol_type = protein
                        organism = Synthetic construct
SEQUENCE: 220
SSTGFI                                                            6

SEQ ID NO: 221          moltype = AA   length = 5
FEATURE                 Location/Qualifiers
source                  1..5
                        mol_type = protein
                        organism = Synthetic construct
SEQUENCE: 221
ESTDY                                                            5

SEQ ID NO: 222          moltype = AA   length = 7
FEATURE                 Location/Qualifiers
source                  1..7
                        mol_type = protein
                        organism = Synthetic construct
SEQUENCE: 222
GGSLSRY                                                          7

SEQ ID NO: 223          moltype = AA   length = 6
FEATURE                 Location/Qualifiers
source                  1..6
                        mol_type = protein
                        organism = Synthetic construct
SEQUENCE: 223
SWSGTT                                                           6

SEQ ID NO: 224          moltype = AA   length = 16
FEATURE                 Location/Qualifiers
source                  1..16
                        mol_type = protein
                        organism = Synthetic construct
SEQUENCE: 224
AFYGNRGYYD VNAYTS                                               16

SEQ ID NO: 225          moltype = AA   length = 7
FEATURE                 Location/Qualifiers
source                  1..7
                        mol_type = protein
                        organism = Synthetic construct
SEQUENCE: 225
GGSLSRY                                                          7

SEQ ID NO: 226          moltype = AA   length = 6
FEATURE                 Location/Qualifiers
source                  1..6
                        mol_type = protein
                        organism = Synthetic construct
SEQUENCE: 226
SWSGDT                                                           6

SEQ ID NO: 227          moltype = AA   length = 16
FEATURE                 Location/Qualifiers
source                  1..16
                        mol_type = protein
                        organism = Synthetic construct
SEQUENCE: 227
ALYGNRGYYD VNTYSY                                               16

SEQ ID NO: 228          moltype = AA   length = 7
FEATURE                 Location/Qualifiers
source                  1..7
                        mol_type = protein
                        organism = Synthetic construct
SEQUENCE: 228
RGSLSRW                                                          7

SEQ ID NO: 229          moltype = AA   length = 6
FEATURE                 Location/Qualifiers
source                  1..6
                        mol_type = protein
                        organism = Synthetic construct
SEQUENCE: 229
SWSGTT                                                           6
```

-continued

```
SEQ ID NO: 230          moltype = AA   length = 16
FEATURE                 Location/Qualifiers
source                  1..16
                        mol_type = protein
                        organism = Synthetic construct
SEQUENCE: 230
ALYGNRGYYD VNAHSY                                                16

SEQ ID NO: 231          moltype = AA   length = 5
FEATURE                 Location/Qualifiers
source                  1..5
                        mol_type = protein
                        organism = Synthetic construct
SEQUENCE: 231
GLSFS                                                           5

SEQ ID NO: 232          moltype = AA   length = 6
FEATURE                 Location/Qualifiers
source                  1..6
                        mol_type = protein
                        organism = Synthetic construct
SEQUENCE: 232
SLYSGS                                                          6

SEQ ID NO: 233          moltype = AA   length = 19
FEATURE                 Location/Qualifiers
source                  1..19
                        mol_type = protein
                        organism = Synthetic construct
SEQUENCE: 233
DRQRTWSTFY ASRQATYNY                                             19

SEQ ID NO: 234          moltype = AA   length = 7
FEATURE                 Location/Qualifiers
source                  1..7
                        mol_type = protein
                        organism = Synthetic construct
SEQUENCE: 234
GSIFSID                                                         7

SEQ ID NO: 235          moltype = AA   length = 5
FEATURE                 Location/Qualifiers
source                  1..5
                        mol_type = protein
                        organism = Synthetic construct
SEQUENCE: 235
PEGNY                                                           5

SEQ ID NO: 236          moltype = AA   length = 11
FEATURE                 Location/Qualifiers
source                  1..11
                        mol_type = protein
                        organism = Synthetic construct
SEQUENCE: 236
FGVREGRGNV Y                                                     11

SEQ ID NO: 237          moltype = AA   length = 7
FEATURE                 Location/Qualifiers
source                  1..7
                        mol_type = protein
                        organism = Synthetic construct
SEQUENCE: 237
GLTFGSY                                                         7

SEQ ID NO: 238          moltype = AA   length = 5
FEATURE                 Location/Qualifiers
source                  1..5
                        mol_type = protein
                        organism = Synthetic construct
SEQUENCE: 238
RNDGI                                                           5

SEQ ID NO: 239          moltype = AA   length = 10
FEATURE                 Location/Qualifiers
source                  1..10
                        mol_type = protein
                        organism = Synthetic construct
SEQUENCE: 239
```

-continued

```
DGTGLGHYDY                                                    10

SEQ ID NO: 240          moltype = AA  length = 7
FEATURE                 Location/Qualifiers
source                  1..7
                        mol_type = protein
                        organism = Synthetic construct

SEQUENCE: 240
GFIVSDN                                                       7

SEQ ID NO: 241          moltype = AA  length = 5
FEATURE                 Location/Qualifiers
source                  1..5
                        mol_type = protein
                        organism = Synthetic construct

SEQUENCE: 241
MLNGD                                                         5

SEQ ID NO: 242          moltype = AA  length = 11
FEATURE                 Location/Qualifiers
source                  1..11
                        mol_type = protein
                        organism = Synthetic construct

SEQUENCE: 242
RDSMLEPGRG A                                                  11

SEQ ID NO: 243          moltype = AA  length = 8
FEATURE                 Location/Qualifiers
source                  1..8
                        mol_type = protein
                        organism = Synthetic construct

SEQUENCE: 243
GFTFGNYD                                                      8

SEQ ID NO: 244          moltype = AA  length = 8
FEATURE                 Location/Qualifiers
source                  1..8
                        mol_type = protein
                        organism = Synthetic construct

SEQUENCE: 244
IDTGGDIT                                                      8

SEQ ID NO: 245          moltype = AA  length = 15
FEATURE                 Location/Qualifiers
source                  1..15
                        mol_type = protein
                        organism = Synthetic construct

SEQUENCE: 245
ATDEEYALGP NEFDY                                              15

SEQ ID NO: 246          moltype = AA  length = 8
FEATURE                 Location/Qualifiers
source                  1..8
                        mol_type = protein
                        organism = Synthetic construct

SEQUENCE: 246
GFRFGNYD                                                      8

SEQ ID NO: 247          moltype = AA  length = 8
FEATURE                 Location/Qualifiers
source                  1..8
                        mol_type = protein
                        organism = Synthetic construct

SEQUENCE: 247
IDTGGDIT                                                      8

SEQ ID NO: 248          moltype = AA  length = 15
FEATURE                 Location/Qualifiers
source                  1..15
                        mol_type = protein
                        organism = Synthetic construct

SEQUENCE: 248
ATDEEYALGP NEFDY                                              15

SEQ ID NO: 249          moltype = AA  length = 8
FEATURE                 Location/Qualifiers
source                  1..8
                        mol_type = protein
                        organism = Synthetic construct
```

```
SEQUENCE: 249
GRTFSNTG                                                                     8

SEQ ID NO: 250          moltype = AA   length = 8
FEATURE                 Location/Qualifiers
source                  1..8
                        mol_type = protein
                        organism = Synthetic construct
SEQUENCE: 250
ISPSGTST                                                                     8

SEQ ID NO: 251          moltype = AA   length = 21
FEATURE                 Location/Qualifiers
source                  1..21
                        mol_type = protein
                        organism = Synthetic construct
SEQUENCE: 251
AASYGSNWST LRHQRRNEYD A                                                      21

SEQ ID NO: 252          moltype = AA   length = 8
FEATURE                 Location/Qualifiers
source                  1..8
                        mol_type = protein
                        organism = Synthetic construct SEQUENCE: 252
GSTFSNNV                                                                     8

SEQ ID NO: 253          moltype = AA   length = 8
FEATURE                 Location/Qualifiers
source                  1..8
                        mol_type = protein
                        organism = Synthetic construct SEQUENCE: 253
ISASGATR                                                                     8

SEQ ID NO: 254          moltype = AA   length = 13
FEATURE                 Location/Qualifiers
source                  1..13
                        mol_type = protein
                        organism = Synthetic construct SEQUENCE: 254
HKIEWEDLSR KDY                                                               13

SEQ ID NO: 255          moltype = AA   length = 8
FEATURE                 Location/Qualifiers
source                  1..8
                        mol_type = protein
                        organism = Synthetic construct
SEQUENCE: 255
GFIFRLAG                                                                     8

SEQ ID NO: 256          moltype = AA   length = 8
FEATURE                 Location/Qualifiers
source                  1..8
                        mol_type = protein
                        organism = Synthetic construct SEQUENCE: 256
ITMDGSTT                                                                     8

SEQ ID NO: 257          moltype = AA   length = 11
FEATURE                 Location/Qualifiers
source                  1..11
                        mol_type = protein
                        organism = Synthetic construct
SEQUENCE: 257
ARGAKGGYND P                                                                 11

SEQ ID NO: 258          moltype = AA   length = 8
FEATURE                 Location/Qualifiers
source                  1..8
                        mol_type = protein
                        organism = Synthetic construct SEQUENCE: 258
GLTFSRCD                                                                     8

SEQ ID NO: 259          moltype = AA   length = 8
FEATURE                 Location/Qualifiers
source                  1..8
                        mol_type = protein
```

-continued

```
                          organism = Synthetic construct
SEQUENCE: 259
ISANGAST                                                            8

SEQ ID NO: 260           moltype = AA   length = 14
FEATURE                  Location/Qualifiers
source                   1..14
                         mol_type = protein
                         organism = Synthetic construct
SEQUENCE: 260
AAARVPVTWQ LYDY                                                     14

SEQ ID NO: 261           moltype = AA   length = 8
FEATURE                  Location/Qualifiers
source                   1..8
                         mol_type = protein
                         organism = Synthetic construct
SEQUENCE: 261
GRTFSGWS                                                            8

SEQ ID NO: 262           moltype = AA   length = 11
FEATURE                  Location/Qualifiers
source                   1..11
                         mol_type = protein
                         organism = Synthetic construct
SEQUENCE: 262
ISWVGSWIGG T                                                        11

SEQ ID NO: 263           moltype = AA   length = 17
FEATURE                  Location/Qualifiers
source                   1..17
                         mol_type = protein
                         organism = Synthetic construct
SEQUENCE: 263
AAANSETPRI FASEYDY                                                  17

SEQ ID NO: 264           moltype = AA   length = 8
FEATURE                  Location/Qualifiers
source                   1..8
                         mol_type = protein
                         organism = Synthetic construct
SEQUENCE: 264
GRTFSSYS                                                            8

SEQ ID NO: 265           moltype = AA   length = 8
FEATURE                  Location/Qualifiers
source                   1..8
                         mol_type = protein
                         organism = Synthetic construct
SEQUENCE: 265
ITWSGGRT                                                            8

SEQ ID NO: 266           moltype = AA   length = 21
FEATURE                  Location/Qualifiers
source                   1..21
                         mol_type = protein
                         organism = Synthetic construct
SEQUENCE: 266
AGLWGVGSWY EELRNKHEYD Y                                             21

SEQ ID NO: 267           moltype = AA   length = 11
FEATURE                  Location/Qualifiers
source                   1..11
                         mol_type = protein
                         organism = Synthetic construct
SEQUENCE: 267
GRTFTTTSGY N                                                        11

SEQ ID NO: 268           moltype = AA   length = 9
FEATURE                  Location/Qualifiers
source                   1..9
                         mol_type = protein
                         organism = Synthetic construct
SEQUENCE: 268
IKWVSGSNR                                                           9

SEQ ID NO: 269           moltype = AA   length = 18
FEATURE                  Location/Qualifiers
source                   1..18
```

-continued

```
                          mol_type = protein
                          organism = Synthetic construct
SEQUENCE: 269
AAATGQSYVP IREYEYVY                                        18

SEQ ID NO: 270           moltype = AA  length = 8
FEATURE                  Location/Qualifiers
source                   1..8
                         mol_type = protein
                         organism = Synthetic construct
SEQUENCE: 270
GRTISRYA                                                   8

SEQ ID NO: 271           moltype = AA  length = 7
FEATURE                  Location/Qualifiers
source                   1..7
                         mol_type = protein
                         organism = Synthetic construct
SEQUENCE: 271
NWSGGST                                                    7

SEQ ID NO: 272           moltype = AA  length = 19
FEATURE                  Location/Qualifiers
source                   1..19
                         mol_type = protein
                         organism = Synthetic construct
SEQUENCE: 272
AVPSVLVQGG ISNPSQYDY                                       19

SEQ ID NO: 273           moltype = AA  length = 8
FEATURE                  Location/Qualifiers
source                   1..8
                         mol_type = protein
                         organism = Synthetic construct
SEQUENCE: 273
GRTLSSYV                                                   8

SEQ ID NO: 274           moltype = AA  length = 8
FEATURE                  Location/Qualifiers
source                   1..8
                         mol_type = protein
                         organism = Synthetic construct
SEQUENCE: 274
ITWSGLST                                                   8

SEQ ID NO: 275           moltype = AA  length = 19
FEATURE                  Location/Qualifiers
source                   1..19
                         mol_type = protein
                         organism = Synthetic construct
SEQUENCE: 275
AAGPNIPSIL RTRESEYAY                                       19

SEQ ID NO: 276           moltype = AA  length = 8
FEATURE                  Location/Qualifiers
source                   1..8
                         mol_type = protein
                         organism = Synthetic construct
SEQUENCE: 276
GFRFSNYA                                                   8

SEQ ID NO: 277           moltype = AA  length = 8
FEATURE                  Location/Qualifiers
source                   1..8
                         mol_type = protein
                         organism = Synthetic construct
SEQUENCE: 277
ISSTGFIT                                                   8

SEQ ID NO: 278           moltype = AA  length = 7
FEATURE                  Location/Qualifiers
source                   1..7
                         mol_type = protein
                         organism = Synthetic construct
SEQUENCE: 278
NAESTDY                                                    7

SEQ ID NO: 279           moltype = AA  length = 8
FEATURE                  Location/Qualifiers
```

-continued

```
source                   1..8
                         mol_type = protein
                         organism = Synthetic construct
SEQUENCE: 279
GGSLSRYD                                                              8

SEQ ID NO: 280           moltype = AA  length = 8
FEATURE                  Location/Qualifiers
source                   1..8
                         mol_type = protein
                         organism = Synthetic construct
SEQUENCE: 280
ISWSGTTK                                                              8

SEQ ID NO: 281           moltype = AA  length = 18
FEATURE                  Location/Qualifiers
source                   1..18
                         mol_type = protein
                         organism = Synthetic construct
SEQUENCE: 281
AAAFYGNRGY YDVNAYTS                                                   18

SEQ ID NO: 282           moltype = AA  length = 8
FEATURE                  Location/Qualifiers
source                   1..8
                         mol_type = protein
                         organism = Synthetic construct
SEQUENCE: 282
GGSLSRYD                                                              8

SEQ ID NO: 283           moltype = AA  length = 8
FEATURE                  Location/Qualifiers
source                   1..8
                         mol_type = protein
                         organism = Synthetic construct
SEQUENCE: 283
ISWSGDTK                                                              8

SEQ ID NO: 284           moltype = AA  length = 18
FEATURE                  Location/Qualifiers
source                   1..18
                         mol_type = protein
                         organism = Synthetic construct
SEQUENCE: 284
AVALYGNRGY YDVNTYSY                                                   18

SEQ ID NO: 285           moltype = AA  length = 8
FEATURE                  Location/Qualifiers
source                   1..8
                         mol_type = protein
                         organism = Synthetic construct
SEQUENCE: 285
RGSLSRWD                                                              8

SEQ ID NO: 286           moltype = AA  length = 8
FEATURE                  Location/Qualifiers
source                   1..8
                         mol_type = protein
                         organism = Synthetic construct
SEQUENCE: 286
ISWSGTTS                                                              8

SEQ ID NO: 287           moltype = AA  length = 18
FEATURE                  Location/Qualifiers
source                   1..18
                         mol_type = protein
                         organism = Synthetic construct
SEQUENCE: 287
AVALYGNRGY YDVNAHSY                                                   18

SEQ ID NO: 288           moltype = AA  length = 6
FEATURE                  Location/Qualifiers
source                   1..6
                         mol_type = protein
                         organism = Synthetic construct
SEQUENCE: 288
GLSFSS                                                                6

SEQ ID NO: 289           moltype = AA  length = 8
```

```
FEATURE           Location/Qualifiers
source            1..8
                  mol_type = protein
                  organism = Synthetic construct
SEQUENCE: 289
ISLYSGST                                                          8

SEQ ID NO: 290    moltype = AA  length = 21
FEATURE           Location/Qualifiers
source            1..21
                  mol_type = protein
                  organism = Synthetic construct
SEQUENCE: 290
AADRQRTWST FYASRQATYN Y                                          21

SEQ ID NO: 291    moltype = AA  length = 8
FEATURE           Location/Qualifiers
source            1..8
                  mol_type = protein
                  organism = Synthetic construct
SEQUENCE: 291
GSIFSIDI                                                          8

SEQ ID NO: 292    moltype = AA  length = 7
FEATURE           Location/Qualifiers
source            1..7
                  mol_type = protein
                  organism = Synthetic construct
SEQUENCE: 292
MPEGNYI                                                           7

SEQ ID NO: 293    moltype = AA  length = 13
FEATURE           Location/Qualifiers
source            1..13
                  mol_type = protein
                  organism = Synthetic construct
SEQUENCE: 293
YGFGVREGRG NVY                                                   13

SEQ ID NO: 294    moltype = AA  length = 8
FEATURE           Location/Qualifiers
source            1..8
                  mol_type = protein
                  organism = Synthetic construct
SEQUENCE: 294
GLTFGSYD                                                          8

SEQ ID NO: 295    moltype = AA  length = 7
FEATURE           Location/Qualifiers
source            1..7
                  mol_type = protein
                  organism = Synthetic construct
SEQUENCE: 295
IRNDGIT                                                           7

SEQ ID NO: 296    moltype = AA  length = 12
FEATURE           Location/Qualifiers
source            1..12
                  mol_type = protein
                  organism = Synthetic construct
SEQUENCE: 296
AADGTGLGHY DY                                                    12

SEQ ID NO: 297    moltype = AA  length = 8
FEATURE           Location/Qualifiers
source            1..8
                  mol_type = protein
                  organism = Synthetic construct
SEQUENCE: 297
GFIVSDNV                                                          8

SEQ ID NO: 298    moltype = AA  length = 7
FEATURE           Location/Qualifiers
source            1..7
                  mol_type = protein
                  organism = Synthetic construct
SEQUENCE: 298
IMLNGDT                                                           7
```

-continued

```
SEQ ID NO: 299          moltype = AA   length = 13
FEATURE                 Location/Qualifiers
source                  1..13
                        mol_type = protein
                        organism = Synthetic construct
SEQUENCE: 299
NARDSMLEPG RGA                                                           13

SEQ ID NO: 300          moltype = AA   length = 269
FEATURE                 Location/Qualifiers
source                  1..269
                        mol_type = protein
                        organism = Synthetic construct
SEQUENCE: 300
DVQLQESGGG LVQAGGSLRL SCLASGRTFT TTSGYNMGWF RQAPGKEREF VAGIKWVSGS   60
NRAYAESVKG RFTISRDNAK NTVYLQMNSL KPEDTAVYYC AAATGQSYVP IREYEYVYWG  120
QGTQVTVSGG GGSGGGGSGG GGSGGGGSEV QLLESGGGLV QPGGSLRLSC AASGFTFGNY  180
DMAWVRQAPG KRPEWVSSID TGGDITHYAD SVKGRFTISR DNAKNTLYLQ MNSLRPEDTA  240
VYWCATDEEY ALGPNEFDYY GQGTLVTVS                                    269

SEQ ID NO: 301          moltype = AA   length = 265
FEATURE                 Location/Qualifiers
source                  1..265
                        mol_type = protein
                        organism = Synthetic construct
SEQUENCE: 301
DVQLQESGGG LVQAGGSLRL SCAASGRTIS RYAVGWFRRP PAKEREFIGI NWSGGSTTYA   60
DSAEGRFIIS RDNAKNTVYL QMNSLKPEDT AVYYCAVPSV LVQGGISNPS QYDYWGQGTQ  120
VTVSGGGGSG GGGSGGGGSG GGGSEVQLLE SGGGLVQPGG SLRLSCAASG FTFGNYDMAW  180
VRQAPGKRPE WVSSIDTGGD ITHYADSVKG RFTISRDNAK NTLYLQMNSL RPEDTAVYWC  240
ATDEEYALGP NEFDYYGQGT LVTVS                                        265

SEQ ID NO: 302          moltype = AA   length = 254
FEATURE                 Location/Qualifiers
source                  1..254
                        mol_type = protein
                        organism = Synthetic construct
SEQUENCE: 302
DVQLQESGGG LVQPGGSLRL SCAASGFRFS NYAMRWYRQA PGKEREFVAR ISSTGFITRY   60
TASVRDRFTI SRDNDKNMMY LQLNKLTPQD TAHYYCNAES TDYWGQGTQV TVSGGGGSGG  120
GGSGGGGSGG GGSEVQLLES GGGLVQPGGS LRLSCAASGF TFGNYDMAWV RQAPGKRPEW  180
VSSIDTGGDI THYADSVKGR FTISRDNAKN TLYLQMNSLR PEDTAVYWCA TDEEYALGPN  240
EFDYYGQGTL VTVS                                                    254

SEQ ID NO: 303          moltype = AA   length = 269
FEATURE                 Location/Qualifiers
source                  1..269
                        mol_type = protein
                        organism = Synthetic construct
SEQUENCE: 303
EVQLLESGGG LVQPGGSLRL SCAASGFTFG NYDMAWVRQA PGKRPEWVSS IDTGGDITHY   60
ADSVKGRFTI SRDNAKNTLY LQMNSLRPED TAVYWCATDE EYALGPNEFD YYGQGTLVTV  120
SGGGGSGGGG SGGGGSGGGG SDVQLQESGG GLVQAGGSLR LSCLASGRTF TTTSGYNMGW  180
FRQAPGKERE FVAGIKWVSG SNRAYAESVK GRFTISRDNA KNTVYLQMNS LKPEDTAVYY  240
CAAATGQSYV PIREYEYVYW GQGTQVTVS                                    269

SEQ ID NO: 304          moltype = AA   length = 265
FEATURE                 Location/Qualifiers
source                  1..265
                        mol_type = protein
                        organism = Synthetic construct
SEQUENCE: 304
EVQLLESGGG LVQPGGSLRL SCAASGFTFG NYDMAWVRQA PGKRPEWVSS IDTGGDITHY   60
ADSVKGRFTI SRDNAKNTLY LQMNSLRPED TAVYWCATDE EYALGPNEFD YYGQGTLVTV  120
SGGGGSGGGG SGGGGSGGGG SDVQLQESGG GLVQAGGSLR LSCAASGRTI SRYAVGWFRR  180
PPAKEREFIG INWSGGSTTY ADSAEGRFII SRDNAKNTVY LQMNSLKPED TAVYYCAVPS  240
VLVQGGISNP SQYDYWGQGT QVTVS                                        265

SEQ ID NO: 305          moltype = AA   length = 254
FEATURE                 Location/Qualifiers
source                  1..254
                        mol_type = protein
                        organism = Synthetic construct
SEQUENCE: 305
EVQLLESGGG LVQPGGSLRL SCAASGFTFG NYDMAWVRQA PGKRPEWVSS IDTGGDITHY   60
ADSVKGRFTI SRDNAKNTLY LQMNSLRPED TAVYWCATDE EYALGPNEFD YYGQGTLVTV  120
SGGGGSGGGG SGGGGSGGGG SDVQLQESGG GLVQPGGSLR LSCAASGFRF SNYAMRWYRQ  180
APGKEREFVA RISSTGFITR YTASVRDRFT ISRDNDKNMM YLQLNKLTPQ DTAHYYCNAE  240
STDYWGQGTQ VTVS                                                    254
```

-continued

```
SEQ ID NO: 306           moltype = AA   length = 265
FEATURE                  Location/Qualifiers
source                   1..265
                         mol_type = protein
                         organism = Synthetic construct
SEQUENCE: 306
DVQLQESGGG LVQAGGSLKL SCAASGGSLS RYDMGWFRQA PGKEREFVAR ISWSGTTKYY    60
ADAVKGRFAI SRDNAKNTVY LQMNSLKPED TAVYYCAAAF YGNRGYYDVN AYTSSGQGTQ   120
VTVSGGGGSG GGGSGGGGSG GGGSEVQLLE SGGGLVQPGG SLRLSCAASG FTFGNYDMAW   180
VRQAPGKRPE WVSSIDTGGD ITHYADSVKG RFTISRDNAK NTLYLQMNSL RPEDTAVYWC   240
ATDEEYALGP NEFDYYGQGT LVTVS                                         265

SEQ ID NO: 307           moltype = AA   length = 265
FEATURE                  Location/Qualifiers
source                   1..265
                         mol_type = protein
                         organism = Synthetic construct
SEQUENCE: 307
DVQLQESGGG LVQAGGSLKL SCAASRGSLS RWDVAWFRQA PGKERSFVTR ISWSGTTSYY    60
ADAVKGRFAI SRDNAKNTVY LQMNSLKPED TAVYYCAVAL YGNRGYYDVN AHSYWGQGTQ   120
VTVSGGGGSG GGGSGGGGSG GGGSEVQLLE SGGGLVQPGG SLRLSCAASG FTFGNYDMAW   180
VRQAPGKRPE WVSSIDTGGD ITHYADSVKG RFTISRDNAK NTLYLQMNSL RPEDTAVYWC   240
ATDEEYALGP NEFDYYGQGT LVTVS                                         265

SEQ ID NO: 308           moltype = AA   length = 267
FEATURE                  Location/Qualifiers
source                   1..267
                         mol_type = protein
                         organism = Synthetic construct
SEQUENCE: 308
DVQLQESGGG LVQAGGSLRL SCAVSGLSFS SMGWFRQPPG KEREFVAAIS LYSGSTYYAD    60
SVKGRFTISS DNAKSTVYLQ MNSLKPEDAA VYFCAADRQR TWSTFYASRQ ATYNYWGQGT   120
QVTVTSGGGG SGGGGSGGGG SGGGGSEVQL LESGGGLVQP GGSLRLSCAA SGFTFGNYDM   180
AWVRQAPGKR PEWVSSIDTG GDITHYADSV KGRFTISRDN AKNTLYLQMN SLRPEDTAVY   240
WCATDEEYAL GPNEFDYYGQ GTLVTVS                                       267

SEQ ID NO: 309           moltype = AA   length = 259
FEATURE                  Location/Qualifiers
source                   1..259
                         mol_type = protein
                         organism = Synthetic construct
SEQUENCE: 309
DVQLQESGGG LVQPGGSLRL SCAASGSIFS IDIMGWYRQA PGKQRELVAT MPEGNYINYA    60
DSVKGRLTLS RDKGKNTVYL QLNSLKPEDT AVYYCYGFGV REGRGNVYWG QGTQVTVSGG   120
GGSGGGGSGG GGSGGGGSEV QLLESGGGLV QPGGSLRLSC AASGFTFGNY DMAWVRQAPG   180
KRPEWVSSID TGGDITHYAD SVKGRFTISR DNAKNTLYLQ MNSLRPEDTA VYWCATDEEY   240
ALGPNEFDYY GQGTLVTVS                                                259

SEQ ID NO: 310           moltype = AA   length = 258
FEATURE                  Location/Qualifiers
source                   1..258
                         mol_type = protein
                         organism = Synthetic construct
SEQUENCE: 310
DVQLQESGGG LVQAGGSLRL SCAASGLTFG SYDMGWYRQA PGKQRELVGR IRNDGITYYA    60
DSVKGRFTMS RDNAKNTVYL QMNSLKPEDT AVYYCAADGT GLGHYDYWGQ GTQVTVSGGG   120
GSGGGGSGGG GSGGGGSEVQ LLESGGGLVQ PGGSLRLSCA ASGFTFGNYD MAWVRQAPGK   180
RPEWVSSIDT GGDITHYADS VKGRFTISRD NAKNTLYLQM NSLRPEDTAV YWCATDEEYA   240
LGPNEFDYYG QGTLVTVS                                                 258

SEQ ID NO: 311           moltype = AA   length = 265
FEATURE                  Location/Qualifiers
source                   1..265
                         mol_type = protein
                         organism = Synthetic construct
SEQUENCE: 311
EVQLLESGGG LVQPGGSLRL SCAASGFTFG NYDMAWVRQA PGKRPEWVSS IDTGGDITHY    60
ADSVKGRFTI SRDNAKNTLY LQMNSLRPED TAVYWCATDE EYALGPNEFD YYGQGTLVTV   120
SGGGGSGGGG SGGGGSGGGG SDVQLQESGG GLVQAGGSLK LSCAASGGSL SRYDMGWFRQ   180
APGKEREFVA RISWSGTTKY YADAVKGRFA ISRDNAKNTV YLQMNSLKPE DTAVYYCAAA   240
FYGNRGYYDV NAYTSSGQGT QVTVS                                         265

SEQ ID NO: 312           moltype = AA   length = 265
FEATURE                  Location/Qualifiers
source                   1..265
                         mol_type = protein
                         organism = Synthetic construct
SEQUENCE: 312
```

-continued

```
EVQLLESGGG LVQPGGSLRL SCAASGFTFG NYDMAWVRQA PGKRPEWVSS IDTGGDITHY  60
ADSVKGRFTI SRDNAKNTLY LQMNSLRPED TAVYWCATDE EYALGPNEFD YYGQGTLVTV  120
SGGGGSGGGG SGGGGSGGGG SDVQLQESGG GLVQAGGSLK LSCAASRGSL SRWDVAWFRQ  180
APGKERSFVT RISWSGTTSY YADAVKGRFA ISRDNAKNTV YLQMNSLKPE DTAVYYCAVA  240
LYGNRGYYDV NAHSYWGQGT QVTVS                                        265

SEQ ID NO: 313          moltype = AA  length = 267
FEATURE                 Location/Qualifiers
source                  1..267
                        mol_type = protein
                        organism = Synthetic construct
SEQUENCE: 313
EVQLLESGGG LVQPGGSLRL SCAASGFTFG NYDMAWVRQA PGKRPEWVSS IDTGGDITHY  60
ADSVKGRFTI SRDNAKNTLY LQMNSLRPED TAVYWCATDE EYALGPNEFD YYGQGTLVTV  120
SGGGGSGGGG SGGGGSGGGG SDVQLQESGG GLVQAGGSLR LSCAVSGLSF SSMGWFRQPP  180
GKEREFVAAI SLYSGSTYYA DSVKGRFTIS SDNAKSTVYL QMNSLKPEDA AVYFCAADRQ  240
RTWSTFYASR QATYNYWGQG TQVTVTS                                      267

SEQ ID NO: 314          moltype = AA  length = 259
FEATURE                 Location/Qualifiers
source                  1..259
                        mol_type = protein
                        organism = Synthetic construct
SEQUENCE: 314
EVQLLESGGG LVQPGGSLRL SCAASGFTFG NYDMAWVRQA PGKRPEWVSS IDTGGDITHY  60
ADSVKGRFTI SRDNAKNTLY LQMNSLRPED TAVYWCATDE EYALGPNEFD YYGQGTLVTV  120
SGGGGSGGGG SGGGGSGGGG SDVQLQESGG GLVQPGGSLR LSCAASGSIF SIDIMGWYRQ  180
APGKQRELVA TMPEGNYINY ADSVKGRLTL SRDKGKNTVY LQLNSLKPED TAVYYCYGFG  240
VREGRGNVYW GQGTQVTVS                                               259

SEQ ID NO: 315          moltype = AA  length = 258
FEATURE                 Location/Qualifiers
source                  1..258
                        mol_type = protein
                        organism = Synthetic construct
SEQUENCE: 315
EVQLLESGGG LVQPGGSLRL SCAASGFTFG NYDMAWVRQA PGKRPEWVSS IDTGGDITHY  60
ADSVKGRFTI SRDNAKNTLY LQMNSLRPED TAVYWCATDE EYALGPNEFD YYGQGTLVTV  120
SGGGGSGGGG SGGGGSGGGG SDVQLQESGG GLVQAGGSLR LSCAASGLTF GSYDMGWYRQ  180
APGKQRELVG RIRNDGITYY ADSVKGRFTM SRDNAKNTVY LQMNSLKPED TAVYYCAADG  240
TGLGHYDYWG QGTQVTVS                                                258

SEQ ID NO: 316          moltype = AA  length = 122
FEATURE                 Location/Qualifiers
source                  1..122
                        mol_type = protein
                        organism = Synthetic construct
SEQUENCE: 316
EVQLVESGGG LVQPGGSLRL SCAASGFTFG SYDMSWVRQA PGKGPEWVSS TOTGGDITHY  60
ADSVKGRFTI SRDNANNMLY LQMNSLKPED TAVYWCATDE DYALGPNEYD YYGQGTQVTV  120
SS                                                                122

SEQ ID NO: 317          moltype = AA  length = 122
FEATURE                 Location/Qualifiers
source                  1..122
                        mol_type = protein
                        organism = Synthetic construct
SEQUENCE: 317
EVQLLESGGG LVQPGGSLRL SCAASGFTFG SYDMSWVRQA PGKGPEWVSS IDTGGDITHY  60
ADSVKGRFTI SRDNANNTLY LQMNSLRPED TAVYWCATDE DYALGPNEYD YYGQGTLVTV  120
SS                                                                122

SEQ ID NO: 318          moltype = AA  length = 122
FEATURE                 Location/Qualifiers
source                  1..122
                        mol_type = protein
                        organism = Synthetic construct
SEQUENCE: 318
EVQLLESGGG LVQPGGSLRL SCAASGFTFG SYDMSWVRQA PGKGPEWVSS IDTGGDITHY  60
ADSVKGRFTI SRDNANNLLY LQMNSLRPED TAVYWCATDE DYALGPNEYD YYGQGTLVTV  120
SS                                                                122

SEQ ID NO: 319          moltype = AA  length = 122
FEATURE                 Location/Qualifiers
source                  1..122
                        mol_type = protein
                        organism = Synthetic construct
SEQUENCE: 319
EVQLLESGGG LVQPGGSLRL SCAASGFTFG SYDMSWVRQA PGKGPEWVSS IDTGGDITHY  60
```

```
ADSVKGRFTI SRDNANNTLY LQMNSLRPED TAVYYCATDE DYALGPNEYD YYGQGTLVTV   120
SS                                                                  122

SEQ ID NO: 320          moltype = AA  length = 122
FEATURE                 Location/Qualifiers
source                  1..122
                        mol_type = protein
                        organism = Synthetic construct
SEQUENCE: 320
EVQLLESGGG LVQPGGSLRL SCAASGFTFG SYDMSWVRQA PGKGPEWVSS IDTGGDITHY    60
ADSVKGRFTI SRDNANNLLY LQMNSLRPED TAVYYCATDE DYALGPNEYD YYGQGTLVTV   120
SS                                                                  122

SEQ ID NO: 321          moltype = AA  length = 346
FEATURE                 Location/Qualifiers
source                  1..346
                        mol_type = protein
                        organism = Synthetic construct
SEQUENCE: 321
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKRSQVQ LVESGGGLVQ   240
AGGSLRLSCA VFGSTFSNNV ADWYRQAPGK QRELVARISA SGATREYGDS VKGRFTISRD   300
DAKNTMYLQM NNLKPEDTAV YRCHKIEWED LSRKDYWGQG TQVTVS                  346

SEQ ID NO: 322          moltype = AA  length = 349
FEATURE                 Location/Qualifiers
source                  1..349
                        mol_type = protein
                        organism = Synthetic construct
SEQUENCE: 322
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS QVQLVESGGG   240
LVQAGGSLRL SCAVFGSTFS NNVADWYRQA PGKQRELVAR ISASGATREY GDSVKGRFTI   300
SRDDAKNTMY LQMNNLKPED TAVYRCHKIE WEDLSRKDYW GQGTQVTVS               349

SEQ ID NO: 323          moltype = AA  length = 354
FEATURE                 Location/Qualifiers
source                  1..354
                        mol_type = protein
                        organism = Synthetic construct
SEQUENCE: 323
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSQVQLV   240
ESGGGLVQAG GSLRLSCAVF GSTFSNNVAD WYRQAPGKQR ELVARISASG ATREYGDSVK   300
GRFTISRDDA KNTMYLQMNN LKPEDTAVYR CHKIEWEDLS RKDYWGQGTQ VTVS         354

SEQ ID NO: 324          moltype = AA  length = 359
FEATURE                 Location/Qualifiers
source                  1..359
                        mol_type = protein
                        organism = Synthetic construct
SEQUENCE: 324
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSGGGGS   240
QVQLVESGGG LVQAGGSLRL SCAVFGSTFS NNVADWYRQA PGKQRELVAR ISASGATREY   300
GDSVKGRFTI SRDDAKNTMY LQMNNLKPED TAVYRCHKIE WEDLSRKDYW GQGTQVTVS    359

SEQ ID NO: 325          moltype = AA  length = 346
FEATURE                 Location/Qualifiers
source                  1..346
                        mol_type = protein
                        organism = Synthetic construct
SEQUENCE: 325
QVQLVESGGG LVQAGGSLRL SCAVFGSTFS NNVADWYRQA PGKQRELVAR ISASGATREY    60
GDSVKGRFTI SRDDAKNTMY LQMNNLKPED TAVYRCHKIE WEDLSRKDYW GQGTQVTVSR   120
SGPPCPPCPA PEFLGGPSVF LFPPKPKDTL MISRTPEVTC VVVDVSQEDP EVQFNWYVDG   180
VEVHNAKTKP REEQFNSTYR VVSVLTVLHQ DWLNGKEYKC KVSNKGLPSS IEKTISKAKG   240
QPREPQVYTL PPCQEEMTKN QVSLWCLVKG FYPSDIAVEW ESNGQPENNY KTTPPVLDSD   300
GSFFLYSRLT VDKSRWQEGN VFSCSVMHEA LHNHYTQKSL SLSLGK                 346

SEQ ID NO: 326          moltype = AA  length = 349
```

```
FEATURE            Location/Qualifiers
source             1..349
                   mol_type = protein
                   organism = Synthetic construct
SEQUENCE: 326
QVQLVESGGG LVQAGGSLRL SCAVFGSTFS NNVADWYRQA PGKQRELVAR ISASGATREY   60
GDSVKGRFTI SRDDAKNTMY LQMNNLKPED TAVYRCHKIE WEDLSRKDYW GQGTQVTVSG  120
GGGSGPPCPP CPAPEFLGGP SVFLFPPKPK DTLMISRTPE VTCVVVDVSQ EDPEVQFNWY  180
VDGVEVHNAK TKPREEQFNS TYRVVSVLTV LHQDWLNGKE YKCKVSNKGL PSSIEKTISK  240
AKGQPREPQV YTLPPCQEEM TKNQVSLWCL VKGFYPSDIA VEWESNGQPE NNYKTTPPVL  300
DSDGSFFLYS RLTVDKSRWQ EGNVFSCSVM HEALHNHYTQ KSLSLSLGK             349

SEQ ID NO: 327     moltype = AA   length = 354
FEATURE            Location/Qualifiers
source             1..354
                   mol_type = protein
                   organism = Synthetic construct
SEQUENCE: 327
QVQLVESGGG LVQAGGSLRL SCAVFGSTFS NNVADWYRQA PGKQRELVAR ISASGATREY   60
GDSVKGRFTI SRDDAKNTMY LQMNNLKPED TAVYRCHKIE WEDLSRKDYW GQGTQVTVSG  120
GGGSGGGGSG PPCPPCPAPE FLGGPSVFLF PPKPKDTLMI SRTPEVTCVV VDVSQEDPEV  180
QFNWYVDGVE VHNAKTKPRE EQFNSTYRVV SVLTVLHQDW LNGKEYKCKV SNKGLPSSIE  240
KTISKAKGQP REPQVYTLPP CQEEMTKNQV SLWCLVKGFY PSDIAVEWES NGQPENNYKT  300
TPPVLDSDGS FFLYSRLTVD KSRWQEGNVF SCSVMHEALH NHYTQKSLSL SLGK       354

SEQ ID NO: 328     moltype = AA   length = 359
FEATURE            Location/Qualifiers
source             1..359
                   mol_type = protein
                   organism = Synthetic construct
SEQUENCE: 328
QVQLVESGGG LVQAGGSLRL SCAVFGSTFS NNVADWYRQA PGKQRELVAR ISASGATREY   60
GDSVKGRFTI SRDDAKNTMY LQMNNLKPED TAVYRCHKIE WEDLSRKDYW GQGTQVTVSG  120
GGGSGGGGSG GGGSGPPCPP CPAPEFLGGP SVFLFPPKPK DTLMISRTPE VTCVVVDVSQ  180
EDPEVQFNWY VDGVEVHNAK TKPREEQFNS TYRVVSVLTV LHQDWLNGKE YKCKVSNKGL  240
PSSIEKTISK AKGQPREPQV YTLPPCQEEM TKNQVSLWCL VKGFYPSDIA VEWESNGQPE  300
NNYKTTPPVL DSDGSFFLYS RLTVDKSRWQ EGNVFSCSVM HEALHNHYTQ KSLSLSLGK  359

SEQ ID NO: 329     moltype = AA   length = 347
FEATURE            Location/Qualifiers
source             1..347
                   mol_type = protein
                   organism = Synthetic construct
SEQUENCE: 329
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKRSDVQ LQESGGGLVQ  240
AGGSLRLSCA ASGLTFSRCD MGWFRQAPGK EREFVARISA NGASTHYADF VKGRFTISRD  300
NAKNTVYLQM NYLKPEDTAV YICAAARVPV TWQLYDYWGQ GTQVTVS              347

SEQ ID NO: 330     moltype = AA   length = 350
FEATURE            Location/Qualifiers
source             1..350
                   mol_type = protein
                   organism = Synthetic construct
SEQUENCE: 330
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS DVQLQESGGG  240
LVQAGGSLRL SCAASGLTFS RCDMGWFRQA PGKEREFVAR ISANGASTHY ADFVKGRFTI  300
SRDNAKNTVY LQMNYLKPED TAVYICAAAR VPVTWQLYDY WGQGTQVTVS           350

SEQ ID NO: 331     moltype = AA   length = 355
FEATURE            Location/Qualifiers
source             1..355
                   mol_type = protein
                   organism = Synthetic construct
SEQUENCE: 331
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSDVQLQ  240
ESGGGLVQAG GSLRLSCAAS GLTFSRCDMG WFRQAPGKER EFVARISANG ASTHYADFVK  300
GRFTISRDNA KNTVYLQMNY LKPEDTAVYI CAAARVPVTW QLYDYWGQGT QVTVS      355

SEQ ID NO: 332     moltype = AA   length = 360
FEATURE            Location/Qualifiers
```

```
source                  1..360
                        mol_type = protein
                        organism = Synthetic construct
SEQUENCE: 332
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSGGGGS   240
DVQLQESGGG LVQAGGSLRL SCAASGLTFS RCDMGWFRQA PGKEREFVAR ISANGASTHY   300
ADFVKGRFTI SRDNAKNTVY LQMNYLKPED TAVYICAAAR VPVTWQLYDY WGQGTQVTVS   360

SEQ ID NO: 333            moltype = AA   length = 347
FEATURE                   Location/Qualifiers
source                    1..347
                          mol_type = protein
                          organism = Synthetic construct
SEQUENCE: 333
DVQLQESGGG LVQAGGSLRL SCAASGLTFS RCDMGWFRQA PGKEREFVAR ISANGASTHY   60
ADFVKGRFTI SRDNAKNTVY LQMNYLKPED TAVYICAAAR VPVTWQLYDY WGQGTQVTVS   120
RSGPPCPPCP APEFLGGPSV FLFPPKPKDT LMISRTPEVT CVVVDVSQED PEVQFNWYVD   180
GVEVHNAKTK PREEQFNSTY RVVSVLTVLH QDWLNGKEYK CKVSNKGLPS SIEKTISKAK   240
GQPREPQVYT LPPCQEEMTK NQVSLWCLVK GFYPSDIAVE WESNGQPENN YKTTPPVLDS   300
DGSFFLYSRL TVDKSRWQEG NVFSCSVMHE ALHNHYTQKS LSLSLGK             347

SEQ ID NO: 334            moltype = AA   length = 350
FEATURE                   Location/Qualifiers
source                    1..350
                          mol_type = protein
                          organism = Synthetic construct
SEQUENCE: 334
DVQLQESGGG LVQAGGSLRL SCAASGLTFS RCDMGWFRQA PGKEREFVAR ISANGASTHY   60
ADFVKGRFTI SRDNAKNTVY LQMNYLKPED TAVYICAAAR VPVTWQLYDY WGQGTQVTVS   120
GGGGSGPPCP PCPAPEFLGG PSVFLFPPKP KDTLMISRTP EVTCVVVDVS QEDPEVQFNW   180
YVDGVEVHNA KTKPREEQFN STYRVVSVLT VLHQDWLNGK EYKCKVSNKG LPSSIEKTIS   240
KAKGQPREPQ VYTLPPCQEE MTKNQVSLWC LVKGFYPSDI AVEWESNGQP ENNYKTTPPV   300
LDSDGSFFLY SRLTVDKSRW QEGNVFSCSV MHEALHNHYT QKSLSLSLGK             350

SEQ ID NO: 335            moltype = AA   length = 355
FEATURE                   Location/Qualifiers
source                    1..355
                          mol_type = protein
                          organism = Synthetic construct
SEQUENCE: 335
DVQLQESGGG LVQAGGSLRL SCAASGLTFS RCDMGWFRQA PGKEREFVAR ISANGASTHY   60
ADFVKGRFTI SRDNAKNTVY LQMNYLKPED TAVYICAAAR VPVTWQLYDY WGQGTQVTVS   120
GGGGSGGGGS GPPCPPCPAP EFLGGPSVFL FPPKPKDTLM ISRTPEVTCV VVDVSQEDPE   180
VQFNWYVDGV EVHNAKTKPR EEQFNSTYRV VSVLTVLHQD WLNGKEYKCK VSNKGLPSSI   240
EKTISKAKGQ PREPQVYTLP PCQEEMTKNQ VSLWCLVKGF YPSDIAVEWE SNGQPENNYK   300
TTPPVLDSDG SFFLYSRLTV DKSRWQEGNV FSCSVMHEAL HNHYTQKSLS LSLGK       355

SEQ ID NO: 336            moltype = AA   length = 360
FEATURE                   Location/Qualifiers
source                    1..360
                          mol_type = protein
                          organism = Synthetic construct
SEQUENCE: 336
DVQLQESGGG LVQAGGSLRL SCAASGLTFS RCDMGWFRQA PGKEREFVAR ISANGASTHY   60
ADFVKGRFTI SRDNAKNTVY LQMNYLKPED TAVYICAAAR VPVTWQLYDY WGQGTQVTVS   120
GGGGSGGGGS GGGGSGPPCP PCPAPEFLGG PSVFLFPPKP KDTLMISRTP EVTCVVVDVS   180
QEDPEVQFNW YVDGVEVHNA KTKPREEQFN STYRVVSVLT VLHQDWLNGK EYKCKVSNKG   240
LPSSIEKTIS KAKGQPREPQ VYTLPPCQEE MTKNQVSLWC LVKGFYPSDI AVEWESNGQP   300
ENNYKTTPPV LDSDGSFFLY SRLTVDKSRW QEGNVFSCSV MHEALHNHYT QKSLSLSLGK   360

SEQ ID NO: 337            moltype = AA   length = 353
FEATURE                   Location/Qualifiers
source                    1..353
                          mol_type = protein
                          organism = Synthetic construct
SEQUENCE: 337
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKRSDVQ LQESGGGLVE   240
AGGSLRLSCV ASGRTFSGWS MGWFRQAPGK EREFVAAISW VGSWIGGTVY SNSVKGRFTI   300
SRDNARTTVY LQMNSLKPED TAVYFCAAAN SETPRIFASE YDYWGQGTQV TVS         353

SEQ ID NO: 338            moltype = AA   length = 356
FEATURE                   Location/Qualifiers
source                    1..356
```

-continued

```
                        mol_type = protein
                        organism = Synthetic construct
SEQUENCE: 338
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS DVQLQESGGG   240
LVEAGGSLRL SCVASGRTFS GWSMGWFRQA PGKEREFVAA ISWVGSWIGG TVYSNSVKGR   300
FTISRDNART TVYLQMNSLK PEDTAVYFCA AANSETPRIF ASEYDYWGQG TQVTVS       356

SEQ ID NO: 339           moltype = AA   length = 361
FEATURE                  Location/Qualifiers
source                   1..361
                         mol_type = protein
                         organism = Synthetic construct
SEQUENCE: 339
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSDVQLQ   240
ESGGGLVEAG GSLRLSCVAS GRTFSGWSMG WFRQAPGKER EFVAAISWVG SWIGGTVYSN   300
SVKGRFTISR DNARTTVYLQ MNSLKPEDTA VYFCAAANSE TPRIFASEYD YWGQGTQVTV   360
S                                                                   361

SEQ ID NO: 340           moltype = AA   length = 366
FEATURE                  Location/Qualifiers
source                   1..366
                         mol_type = protein
                         organism = Synthetic construct
SEQUENCE: 340
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSGGGGS   240
DVQLQESGGG LVEAGGSLRL SCVASGRTFS GWSMGWFRQA PGKEREFVAA ISWVGSWIGG   300
TVYSNSVKGR FTISRDNART TVYLQMNSLK PEDTAVYFCA AANSETPRIF ASEYDYWGQG   360
TQVTVS                                                              366

SEQ ID NO: 341           moltype = AA   length = 353
FEATURE                  Location/Qualifiers
source                   1..353
                         mol_type = protein
                         organism = Synthetic construct
SEQUENCE: 341
DVQLQESGGG LVEAGGSLRL SCVASGRTFS GWSMGWFRQA PGKEREFVAA ISWVGSWIGG    60
TVYSNSVKGR FTISRDNART TVYLQMNSLK PEDTAVYFCA AANSETPRIF ASEYDYWGQG   120
TQVTVSRSGP PCPPCPAPEF LGGPSVFLFP PKPKDTLMIS RTPEVTCVVV DVSQEDPEVQ   180
FNWYVDGVEV HNAKTKPREE QFNSTYRVVS VLTVLHQDWL NGKEYKCKVS NKGLPSSIEK   240
TISKAKGQPR EPQVYTLPPC QEEMTKNQVS LWCLVKGFYP SDIAVEWESN GQPENNYKTT   300
PPVLDSDGSF FLYSRLTVDK SRWQEGNVFS CSVMHEALHN HYTQKSLSLS LGK          353

SEQ ID NO: 342           moltype = AA   length = 356
FEATURE                  Location/Qualifiers
source                   1..356
                         mol_type = protein
                         organism = Synthetic construct
SEQUENCE: 342
DVQLQESGGG LVEAGGSLRL SCVASGRTFS GWSMGWFRQA PGKEREFVAA ISWVGSWIGG    60
TVYSNSVKGR FTISRDNART TVYLQMNSLK PEDTAVYFCA AANSETPRIF ASEYDYWGQG   120
TQVTVSGGGG SGPPCPPCPA PEFLGGPSVF LFPPKPKDTL MISRTPEVTC VVVDVSQEDP   180
EVQFNWYVDG VEVHNAKTKP REEQFNSTYR VVSVLTVLHQ DWLNGKEYKC KVSNKGLPSS   240
IEKTISKAKG QPREPQVYTL PPCQEEMTKN QVSLWCLVKG FYPSDIAVEW ESNGQPENNY   300
KTTPPVLDSD GSFFLYSRLT VDKSRWQEGN VFSCSVMHEA LHNHYTQKSL SLSLGK       356

SEQ ID NO: 343           moltype = AA   length = 361
FEATURE                  Location/Qualifiers
source                   1..361
                         mol_type = protein
                         organism = Synthetic construct
SEQUENCE: 343
DVQLQESGGG LVEAGGSLRL SCVASGRTFS GWSMGWFRQA PGKEREFVAA ISWVGSWIGG    60
TVYSNSVKGR FTISRDNART TVYLQMNSLK PEDTAVYFCA AANSETPRIF ASEYDYWGQG   120
TQVTVSGGGG SGGGGSGPPC PPCPAPEFLG GPSVFLFPPK PKDTLMISRT PEVTCVVVDV   180
SQEDPEVQFN WYVDGVEVHN AKTKPREEQE NSTYRVVSVL TVLHQDWLNG KEYKCKVSNK   240
GLPSSIEKTI SKAKGQPREP QVYTLPPCQE EMTKNQVSLW CLVKGFYPSD IAVEWESNGQ   300
PENNYKTTPP VLDSDGSFFL YSRLTVDKSR WQEGNVFSCS VMHEALHNHY TQKSLSLSLG   360
K                                                                   361

SEQ ID NO: 344           moltype = AA   length = 366
```

```
FEATURE                     Location/Qualifiers
source                      1..366
                            mol_type = protein
                            organism = Synthetic construct
SEQUENCE: 344
DVQLQESGGG LVEAGGSLRL SCVASGRTFS GWSMGWFRQA PGKEREFVAA ISWVGSWIGG     60
TVYSNSVKGR FTISRDNART TVYLQMNSLK PEDTAVYFCA AANSETPRIF ASEYDYWGQG    120
TQVTVSGGGG SGGGGSGGGG SGPPCPPCPA PEFLGGPSVF LFPPKPKDTL MISRTPEVTC    180
VVVDVSQEDP EVQFNWYVDG VEVHNAKTKP REEQFNSTYR VVSVLTVLHQ DWLNGKEYKC    240
KVSNKGLPSS IEKTISKAKG QPREPQVYTL PPCQEEMTKN QVSLWCLVKG FYPSDIAVEW    300
ESNGQPENNY KTTPPVLDSD GSFFLYSRLT VDKSRWQEGN VFSCSVMHEA LHNHYTQKSL    360
SLSLGK                                                              366

SEQ ID NO: 345             moltype = AA  length = 355
FEATURE                     Location/Qualifiers
source                      1..355
                            mol_type = protein
                            organism = Synthetic construct
SEQUENCE: 345
GPPCPPCPAP EFLGGPSVFL FPPKPKDTLM ISRTPEVTCV VVDVSQEDPE VQFNWYVDGV     60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKRSDVQ LQESGGGLVQ    240
AGGSLRLSCL ASGRTFTTTS GYNMGWFRQA PGKEREFVAG IKWVSGSNRA YAESVKGRFT    300
ISRDNAKNTV YLQMNSLKPE DTAVYYCAAA TGQSYVPIRE YEYVYWGQGT QVTVS         355

SEQ ID NO: 346             moltype = AA  length = 358
FEATURE                     Location/Qualifiers
source                      1..358
                            mol_type = protein
                            organism = Synthetic construct
SEQUENCE: 346
GPPCPPCPAP EFLGGPSVFL FPPKPKDTLM ISRTPEVTCV VVDVSQEDPE VQFNWYVDGV     60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS DVQLQESGGG    240
LVQAGGSLRL SCLASGRTFT TTSGYNMGWF RQAPGKEREF VAGIKWVSGS NRAYAESVKG    300
RFTISRDNAK NTVYLQMNSL KPEDTAVYYC AAATGQSYVP IREYEYVYWG QGTQVTVS      358

SEQ ID NO: 347             moltype = AA  length = 363
FEATURE                     Location/Qualifiers
source                      1..363
                            mol_type = protein
                            organism = Synthetic construct
SEQUENCE: 347
GPPCPPCPAP EFLGGPSVFL FPPKPKDTLM ISRTPEVTCV VVDVSQEDPE VQFNWYVDGV     60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS GGGGSDVQLQ    240
ESGGGLVQAG GSLRLSCLAS GRTFTTTSGY NMGWFRQAPG KEREFVAGIK WVSGSNRAYA    300
ESVKGRFTIS RDNAKNTVYL QMNSLKPEDT AVYYCAAATG QSYVPIREYE YVYWGQGTQV    360
TVS                                                                 363

SEQ ID NO: 348             moltype = AA  length = 368
FEATURE                     Location/Qualifiers
source                      1..368
                            mol_type = protein
                            organism = Synthetic construct
SEQUENCE: 348
GPPCPPCPAP EFLGGPSVFL FPPKPKDTLM ISRTPEVTCV VVDVSQEDPE VQFNWYVDGV     60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS GGGGSGGGGS    240
DVQLQESGGG LVQAGGSLRL SCLASGRTFT TTSGYNMGWF RQAPGKEREF VAGIKWVSGS    300
NRAYAESVKG RFTISRDNAK NTVYLQMNSL KPEDTAVYYC AAATGQSYVP IREYEYVYWG    360
QGTQVTVS                                                            368

SEQ ID NO: 349             moltype = AA  length = 355
FEATURE                     Location/Qualifiers
source                      1..355
                            mol_type = protein
                            organism = Synthetic construct
SEQUENCE: 349
DVQLQESGGG LVQAGGSLRL SCLASGRTFT TTSGYNMGWF RQAPGKEREF VAGIKWVSGS     60
NRAYAESVKG RFTISRDNAK NTVYLQMNSL KPEDTAVYYC AAATGQSYVP IREYEYVYWG    120
QGTQVTVSRS GPPCPPCPAP EFLGGPSVFL FPPKPKDTLM ISRTPEVTCV VVDVSQEDPE    180
VQFNWYVDGV EVHNAKTKPR EEQFNSTYRV VSVLTVLHQD WLNGKEYKCK VSNKGLPSSI    240
EKTISKAKGQ PREPQVYTLP PCQEEMTKNQ VSLWCLVKGF YPSDIAVEWE SNGQPENNYK    300
TTPPVLDSDG SFFLYSRLTV DKSRWQEGNV FSCSVMHEAL HNHYTQKSLS LSLGK         355
```

```
SEQ ID NO: 350              moltype = AA   length = 358
FEATURE                     Location/Qualifiers
source                      1..358
                            mol_type = protein
                            organism = Synthetic construct
SEQUENCE: 350
DVQLQESGGG LVQAGGSLRL SCLASGRTFT TTSGYNMGWF RQAPGKEREF VAGIKWVSGS   60
NRAYAESVKG RFTISRDNAK NTVYLQMNSL KPEDTAVYYC AAATGQSYVP IREYEYVYWG   120
QGTQVTVSGG GGSGPPCPPC PAPEFLGGPS VFLFPPKPKD TLMISRTPEV TCVVVDVSQE   180
DPEVQFNWYV DGVEVHNAKT KPREEQFNST YRVVSVLTVL HQDWLNGKEY KCKVSNKGLP   240
SSIEKTISKA KGQPREPQVY TLPPCQEEMT KNQVSLWCLV KGFYPSDIAV EWESNGQPEN   300
NYKTTPPVLD SDGSFFLYSR LTVDKSRWQE GNVFSCSVMH EALHNHYTQK SLSLSLGK     358

SEQ ID NO: 351              moltype = AA   length = 363
FEATURE                     Location/Qualifiers
source                      1..363
                            mol_type = protein
                            organism = Synthetic construct
SEQUENCE: 351
DVQLQESGGG LVQAGGSLRL SCLASGRTFT TTSGYNMGWF RQAPGKEREF VAGIKWVSGS   60
NRAYAESVKG RFTISRDNAK NTVYLQMNSL KPEDTAVYYC AAATGQSYVP IREYEYVYWG   120
QGTQVTVSGG GGSGGGGSGP PCPPCPAPEF LGGPSVFLFP PKPKDTLMIS RTPEVTCVVV   180
DVSQEDPEVQ FNWYVDGVEV HNAKTKPREE QFNSTYRVVS VLTVLHQDWL NGKEYKCKVS   240
NKGLPSSIEK TISKAKGQPR EPQVYTLPPC QEEMTKNQVS LWCLVKGFYP SDIAVEWESN   300
GQPENNYKTT PPVLDSDGSF FLYSRLTVDK SRWQEGNVFS CSVMHEALHN HYTQKSLSLS   360
LGK                                                                 363

SEQ ID NO: 352              moltype = AA   length = 368
FEATURE                     Location/Qualifiers
source                      1..368
                            mol_type = protein
                            organism = Synthetic construct
SEQUENCE: 352
DVQLQESGGG LVQAGGSLRL SCLASGRTFT TTSGYNMGWF RQAPGKEREF VAGIKWVSGS   60
NRAYAESVKG RFTISRDNAK NTVYLQMNSL KPEDTAVYYC AAATGQSYVP IREYEYVYWG   120
QGTQVTVSGG GGSGGGGSGG GGSGPPCPPC PAPEFLGGPS VFLFPPKPKD TLMISRTPEV   180
TCVVVDVSQE DPEVQFNWYV DGVEVHNAKT KPREEQFNST YRVVSVLTVL HQDWLNGKEY   240
KCKVSNKGLP SSIEKTISKA KGQPREPQVY TLPPCQEEMT KNQVSLWCLV KGFYPSDIAV   300
EWESNGQPEN NYKTTPPVLD SDGSFFLYSR LTVDKSRWQE GNVFSCSVMH EALHNHYTQK   360
SLSLSLGK                                                            368

SEQ ID NO: 353              moltype = AA   length = 351
FEATURE                     Location/Qualifiers
source                      1..351
                            mol_type = protein
                            organism = Synthetic construct
SEQUENCE: 353
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKRSDVQ LQESGGGLVQ   240
AGGSLRLSCA ASGRTISRYA VGWFRRPPAK EREFIGINWS GGSTTYADSA EGRFIISRDN   300
AKNTVYLQMN SLKPEDTAVY YCAVPSVLVQ GGISNPSQYD YWGQGTQVTV S            351

SEQ ID NO: 354              moltype = AA   length = 354
FEATURE                     Location/Qualifiers
source                      1..354
                            mol_type = protein
                            organism = Synthetic construct
SEQUENCE: 354
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS DVQLQESGGG   240
LVQAGGSLRL SCAASGRTIS RYAVGWFRRP PAKEREFIGI NWSGGSTTYA DSAEGRFIIS   300
RDNAKNTVYL QMNSLKPEDT AVYYCAVPSV LVQGGISNPS QYDYWGQGTQ VTVS          354

SEQ ID NO: 355              moltype = AA   length = 359
FEATURE                     Location/Qualifiers
source                      1..359
                            mol_type = protein
                            organism = Synthetic construct
SEQUENCE: 355
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGGGS GGGGSDVQLQ   240
ESGGGLVQAG GSLRLSCAAS GRTISRYAVG WFRRPPAKER EFIGINWSGG STTYADSAEG   300
```

```
RFIISRDNAK NTVYLQMNSL KPEDTAVYYC AVPSVLVQGG ISNPSQYDYW GQGTQVTVS    359

SEQ ID NO: 356            moltype = AA   length = 364
FEATURE                   Location/Qualifiers
source                    1..364
                          mol_type = protein
                          organism = Synthetic construct
SEQUENCE: 356
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS GGGGSGGGGS    240
DVQLQESGGG LVQAGGSLRL SCAASGRTIS RYAVGWFRRP PAKEREFIGI NWSGGSTTYA    300
DSAEGRFIIS RDNAKNTVYL QMNSLKPEDT AVYYCAVPSV LVQGGISNPS QYDYWGQGTQ    360
VTVS                                                                364

SEQ ID NO: 357            moltype = AA   length = 351
FEATURE                   Location/Qualifiers
source                    1..351
                          mol_type = protein
                          organism = Synthetic construct
SEQUENCE: 357
DVQLQESGGG LVQAGGSLRL SCAASGRTIS RYAVGWFRRP PAKEREFIGI NWSGGSTTYA    60
DSAEGRFIIS RDNAKNTVYL QMNSLKPEDT AVYYCAVPSV LVQGGISNPS QYDYWGQGTQ    120
VTVSRSGPPC PPCPAPEFLG GPSVFLFPPK PKDTLMISRT PEVTCVVVDV SQEDPEVQFN    180
WYVDGVEVHN AKTKPREEQF NSTYRVVSVL TVLHQDWLNG KEYKCKVSNK GLPSSIEKTI    240
SKAKGQPREP QVYTLPPCQE EMTKNQVSLW CLVKGFYPSD IAVEWESNGQ PENNYKTTPP    300
VLDSDGSFFL YSRLTVDKSR WQEGNVFSCS VMHEALHNHY TQKSLSLSLG K            351

SEQ ID NO: 358            moltype = AA   length = 354
FEATURE                   Location/Qualifiers
source                    1..354
                          mol_type = protein
                          organism = Synthetic construct
SEQUENCE: 358
DVQLQESGGG LVQAGGSLRL SCAASGRTIS RYAVGWFRRP PAKEREFIGI NWSGGSTTYA    60
DSAEGRFIIS RDNAKNTVYL QMNSLKPEDT AVYYCAVPSV LVQGGISNPS QYDYWGQGTQ    120
VTVSGGGGGS PPCPPCPAPE FLGGPSVFLF PPKPKDTLMI SRTPEVTCVV VDVSQEDPEV    180
QFNWYVDGVE VHNAKTKPRE EQFNSTYRVV SVLTVLHQDW LNGKEYKCKV SNKGLPSSIE    240
KTISKAKGQP REPQVYTLPP CQEEMTKNQV SLWCLVKGFY PSDIAVEWES NGQPENNYKT    300
TPPVLDSDGS FFLYSRLTVD KSRWQEGNVF SCSVMHEALH NHYTQKSLSL SLGK         354

SEQ ID NO: 359            moltype = AA   length = 359
FEATURE                   Location/Qualifiers
source                    1..359
                          mol_type = protein
                          organism = Synthetic construct
SEQUENCE: 359
DVQLQESGGG LVQAGGSLRL SCAASGRTIS RYAVGWFRRP PAKEREFIGI NWSGGSTTYA    60
DSAEGRFIIS RDNAKNTVYL QMNSLKPEDT AVYYCAVPSV LVQGGISNPS QYDYWGQGTQ    120
VTVSGGGSGG GGSGPPCPPP CPAPEFLGGP SVFLFPPKPK DTLMISRTPE VTCVVVDVSQ    180
EDPEVQFNWY VDGVEVHNAK TKPREEQFNS TYRVVSVLTV LHQDWLNGKE YKCKVSNKGL    240
PSSIEKTISK AKGQPREPQV YTLPPCQEEM TKNQVSLWCL VKGFYPSDIA VEWESNGQPE    300
NNYKTTPPVL DSDGSFFLYS RLTVDKSRWQ EGNVFSCSVM HEALHNHYTQ KSLSLSLGK    359

SEQ ID NO: 360            moltype = AA   length = 364
FEATURE                   Location/Qualifiers
source                    1..364
                          mol_type = protein
                          organism = Synthetic construct
SEQUENCE: 360
DVQLQESGGG LVQAGGSLRL SCAASGRTIS RYAVGWFRRP PAKEREFIGI NWSGGSTTYA    60
DSAEGRFIIS RDNAKNTVYL QMNSLKPEDT AVYYCAVPSV LVQGGISNPS QYDYWGQGTQ    120
VTVSGGGGSG GGSGGGGSG PPCPPCPAPE FLGGPSVFLF PPKPKDTLMI SRTPEVTCVV    180
VDVSQEDPEV QFNWYVDGVE VHNAKTKPRE EQFNSTYRVV SVLTVLHQDW LNGKEYKCKV    240
SNKGLPSSIE KTISKAKGQP REPQVYTLPP CQEEMTKNQV SLWCLVKGFY PSDIAVEWES    300
NGQPENNYKT TPPVLDSDGS FFLYSRLTVD KSRWQEGNVF SCSVMHEALH NHYTQKSLSL    360
SLGK                                                                364

SEQ ID NO: 361            moltype = AA   length = 352
FEATURE                   Location/Qualifiers
source                    1..352
                          mol_type = protein
                          organism = Synthetic construct
SEQUENCE: 361
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKRSDVQ LQESGGGLVQ    240
```

```
AGGSLRLACA ASGRTLSSYV VSWFRQAPGK ERKFVAAITW SGLSTTYLDS VQGRFTISRD  300
NTKDTVYLQM NSLKPQDTAI YYCAAGPNIP SILRTRESEY AYWGQGTQVT VS          352

SEQ ID NO: 362         moltype = AA  length = 355
FEATURE                Location/Qualifiers
source                 1..355
                       mol_type = protein
                       organism = Synthetic construct
SEQUENCE: 362
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS DVQLQESGGG  240
LVQAGGSLRL ACAASGRTLS SYVVSWFRQA PGKERKFVAA ITWSGLSTTY LDSVQGRFTI  300
SRDNTKDTVY LQMNSLKPQD TAIYYCAAGP NIPSILRTRE SEYAYWGQGT QVTVS       355

SEQ ID NO: 363         moltype = AA  length = 360
FEATURE                Location/Qualifiers
source                 1..360
                       mol_type = protein
                       organism = Synthetic construct
SEQUENCE: 363
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSDVQLQ  240
ESGGGLVQAG GSLRLACAAS GRTLSSYVVS WFRQAPGKER KFVAAITWSG LSTTYLDSVQ  300
GRFTISRDNT KDTVYLQMNS LKPQDTAIYY CAAGPNIPSI LRTRESEYAY WGQGTQVTVS  360

SEQ ID NO: 364         moltype = AA  length = 365
FEATURE                Location/Qualifiers
source                 1..365
                       mol_type = protein
                       organism = Synthetic construct
SEQUENCE: 364
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSGGGGS  240
DVQLQESGGG LVQAGGSLRL ACAASGRTLS SYVVSWFRQA PGKERKFVAA ITWSGLSTTY  300
LDSVQGRFTI SRDNTKDTVY LQMNSLKPQD TAIYYCAAGP NIPSILRTRE SEYAYWGQGT  360
QVTVS                                                             365

SEQ ID NO: 365         moltype = AA  length = 352
FEATURE                Location/Qualifiers
source                 1..352
                       mol_type = protein
                       organism = Synthetic construct
SEQUENCE: 365
DVQLQESGGG LVQAGGSLRL ACAASGRTLS SYVVSWFRQA PGKERKFVAA ITWSGLSTTY  60
LDSVQGRFTI SRDNTKDTVY LQMNSLKPQD TAIYYCAAGP NIPSILRTRE SEYAYWGQGT  120
QVTVSRSGPP CPPCPAPEFL GGPSVFLFPP KPKDTLMISR TPEVTCVVVD VSQEDPEVQF  180
NWYVDGVEVH NAKTKPREEQ FNSTYRVVSV LTVLHQDWLN GKEYKCKVSN KGLPSSIEKT  240
ISKAKGQPRE PQVYTLPPCQ EEMTKNQVSL WCLVKGFYPS DIAVEWESNG QPENNYKTTP  300
PVLDSDGSFF LYSRLTVDKS RWQEGNVFSC SVMHEALHNH YTQKSLSLSL GK          352

SEQ ID NO: 366         moltype = AA  length = 355
FEATURE                Location/Qualifiers
source                 1..355
                       mol_type = protein
                       organism = Synthetic construct
SEQUENCE: 366
DVQLQESGGG LVQAGGSLRL ACAASGRTLS SYVVSWFRQA PGKERKFVAA ITWSGLSTTY  60
LDSVQGRFTI SRDNTKDTVY LQMNSLKPQD TAIYYCAAGP NIPSILRTRE SEYAYWGQGT  120
QVTVSGGGGS GPPCPPCPAP EFLGGPSVFL FPPKPKDTLM ISRTPEVTCV VVDVSQEDPE  180
VQFNWYVDGV EVHNAKTKPR EEQFNSTYRV VSVLTVLHQD WLNGKEYKCK VSNKGLPSSI  240
EKTISKAKGQ PREPQVYTLP PCQEEMTKNQ VSLWCLVKGF YPSDIAVEWE SNGQPENNYK  300
TTPPVLDSDG SFFLYSRLTV DKSRWQEGNV FSCSVMHEAL HNHYTQKSLS LSLGK       355

SEQ ID NO: 367         moltype = AA  length = 360
FEATURE                Location/Qualifiers
source                 1..360
                       mol_type = protein
                       organism = Synthetic construct
SEQUENCE: 367
DVQLQESGGG LVQAGGSLRL ACAASGRTLS SYVVSWFRQA PGKERKFVAA ITWSGLSTTY  60
LDSVQGRFTI SRDNTKDTVY LQMNSLKPQD TAIYYCAAGP NIPSILRTRE SEYAYWGQGT  120
QVTVSGGGGS GGGGSGPPCP PCPAPEFLGG PSVFLFPPKP KDTLMISRTP EVTCVVVDVS  180
QEDPEVQFNW YVDGVEVHNA KTKPREEQFN STYRVVSVLT VLHQDWLNGK EYKCKVSNKG  240
```

```
LPSSIEKTIS KAKGQPREPQ VYTLPPCQEE MTKNQVSLWC LVKGFYPSDI AVEWESNGQP  300
ENNYKTTPPV LDSDGSFFLY SRLTVDKSRW QEGNVFSCSV MHEALHNHYT QKSLSLSLGK  360

SEQ ID NO: 368          moltype = AA  length = 365
FEATURE                 Location/Qualifiers
source                  1..365
                        mol_type = protein
                        organism = Synthetic construct
SEQUENCE: 368
DVQLQESGGG LVQAGGSLRL ACAASGRTLS SYVVSWFRQA PGKERKFVAA ITWSGLSTTY  60
LDSVQGRFTI SRDNTKDTVY LQMNSLKPQD TAIYYCAAGP NIPSILRTRE SEYAYWGQGT  120
QVTVSGGGGS GGGGSGGGGS GPPCPPCPAP EFLGGPSVFL FPPKPKDTLM ISRTPEVTCV  180
VVDVSQEDPE VQFNWYVDGV EVHNAKTKPR EEQFNSTYRV VSVLTVLHQD WLNGKEYKCK  240
VSNKGLPSSI EKTISKAKGQ PREPQVYTLP PCQEEMTKNQ VSLWCLVKGF YPSDIAVEWE  300
SNGQPENNYK TTPPVLDSDG SFFLYSRLTV DKSRWQEGNV FSCSVMHEAL HNHYTQKSLS  360
LSLGK                                                                365

SEQ ID NO: 369          moltype = AA  length = 340
FEATURE                 Location/Qualifiers
source                  1..340
                        mol_type = protein
                        organism = Synthetic construct
SEQUENCE: 369
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKRSDVQ LQESGGGLVQ  240
PGGSLRLSCA ASGFRFSNYA MRWYRQAPGK EREFVARISS TGFITRYTAS VRDRFTISRD  300
NDKNMMYLQL NKLTPQDTAH YYCNAESTDY WGQGTQVTVS                        340

SEQ ID NO: 370          moltype = AA  length = 343
FEATURE                 Location/Qualifiers
source                  1..343
                        mol_type = protein
                        organism = Synthetic construct
SEQUENCE: 370
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS DVQLQESGGG  240
LVQPGGSLRL SCAASGFRFS NYAMRWYRQA PGKEREFVAR ISSTGFITRY TASVRDRFTI  300
SRDNDKNMMY LQLNKLTPQD TAHYYCNAES TDYWGQGTQV TVS                    343

SEQ ID NO: 371          moltype = AA  length = 348
FEATURE                 Location/Qualifiers
source                  1..348
                        mol_type = protein
                        organism = Synthetic construct
SEQUENCE: 371
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSDVQLQ  240
ESGGGLVQPG GSLRLSCAAS GFRFSNYAMR WYRQAPGKER EFVARISSTG FITRYTASVR  300
DRFTISRDND KNMMYLQLNK LTPQDTAHYY CNAESTDYWG QGTQVTVS                348

SEQ ID NO: 372          moltype = AA  length = 353
FEATURE                 Location/Qualifiers
source                  1..353
                        mol_type = protein
                        organism = Synthetic construct
SEQUENCE: 372
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSGGGGS  240
DVQLQESGGG LVQPGGSLRL SCAASGFRFS NYAMRWYRQA PGKEREFVAR ISSTGFITRY  300
TASVRDRFTI SRDNDKNMMY LQLNKLTPQD TAHYYCNAES TDYWGQGTQV TVS          353

SEQ ID NO: 373          moltype = AA  length = 340
FEATURE                 Location/Qualifiers
source                  1..340
                        mol_type = protein
                        organism = Synthetic construct
SEQUENCE: 373
DVQLQESGGG LVQPGGSLRL SCAASGFRFS NYAMRWYRQA PGKEREFVAR ISSTGFITRY  60
TASVRDRFTI SRDNDKNMMY LQLNKLTPQD TAHYYCNAES TDYWGQGTQV TVSRSGPPCP  120
PCPAPEFLGG PSVFLFPPKP KDTLMISRTP EVTCVVVDVS QEDPEVQFNW YVDGVEVHNA  180
KTKPREEQFN STYRVVSVLT VLHQDWLNGK EYKCKVSNKG LPSSIEKTIS KAKGQPREPQ  240
```

```
VYTLPPCQEE MTKNQVSLWC LVKGFYPSDI AVEWESNGQP ENNYKTTPPV LDSDGSFFLY    300
SRLTVDKSRW QEGNVFSCSV MHEALHNHYT QKSLSLSLGK                          340

SEQ ID NO: 374            moltype = AA  length = 343
FEATURE                   Location/Qualifiers
source                    1..343
                          mol_type = protein
                          organism = Synthetic construct
SEQUENCE: 374
DVQLQESGGG LVQPGGSLRL SCAASGFRFS NYAMRWYRQA PGKEREFVAR ISSTGFITRY    60
TASVRDRFTI SRDNDKNMMY LQLNKLTPQD TAHYYCNAES TDYWGQGTQV TVSGGGGSGP    120
PCPPCPAPEF LGGPSVFLFP PKPKDTLMIS RTPEVTCVVV DVSQEDPEVQ FNWYVDGVEV    180
HNAKTKPREE QFNSTYRVVS VLTVLHQDWL NGKEYKCKVS NKGLPSSIEK TISKAKGQPR    240
EPQVYTLPPC QEEMTKNQVS LWCLVKGFYP SDIAVEWESN GQPENNYKTT PPVLDSDGSF    300
FLYSRLTVDK SRWQEGNVFS CSVMHEALHN HYTQKSLSLS LGK                     343

SEQ ID NO: 375            moltype = AA  length = 348
FEATURE                   Location/Qualifiers
source                    1..348
                          mol_type = protein
                          organism = Synthetic construct
SEQUENCE: 375
DVQLQESGGG LVQPGGSLRL SCAASGFRFS NYAMRWYRQA PGKEREFVAR ISSTGFITRY    60
TASVRDRFTI SRDNDKNMMY LQLNKLTPQD TAHYYCNAES TDYWGQGTQV TVSGGGGSGG    120
GGSGPPCPPC PAPEFLGGPS VFLFPPKPKD TLMISRTPEV TCVVVDVSQE DPEVQFNWYV    180
DGVEVHNAKT KPREEQFNST YRVVSVLTVL HQDWLNGKEY KCKVSNKGLP SSIEKTISKA    240
KGQPREPQVY TLPPCQEEMT KNQVSLWCLV KGFYPSDIAV EWESNGQPEN NYKTTPPVLD    300
SDGSFFLYSR LTVDKSRWQE GNVFSCSVMH EALHNHYTQK SLSLSLGK                348

SEQ ID NO: 376            moltype = AA  length = 353
FEATURE                   Location/Qualifiers
source                    1..353
                          mol_type = protein
                          organism = Synthetic construct
SEQUENCE: 376
DVQLQESGGG LVQPGGSLRL SCAASGFRFS NYAMRWYRQA PGKEREFVAR ISSTGFITRY    60
TASVRDRFTI SRDNDKNMMY LQLNKLTPQD TAHYYCNAES TDYWGQGTQV TVSGGGGSGG    120
GGSGGGSGGP CPPCPAPEF LGGPSVFLFP PKPKDTLMIS RTPEVTCVVV DVSQEDPEVQ     180
FNWYVDGVEV HNAKTKPREE QFNSTYRVVS VLTVLHQDWL NGKEYKCKVS NKGLPSSIEK    240
TISKAKGQPR EPQVYTLPPC QEEMTKNQVS LWCLVKGFYP SDIAVEWESN GQPENNYKTT    300
PPVLDSDGSF FLYSRLTVDK SRWQEGNVFS CSVMHEALHN HYTQKSLSLS LGK          353

SEQ ID NO: 377            moltype = AA  length = 351
FEATURE                   Location/Qualifiers
source                    1..351
                          mol_type = protein
                          organism = Synthetic construct
SEQUENCE: 377
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKRSDVQ LQESGGGLVQ    240
AGGSLKLSCA ASGGSLSRYD MGWFRQAPGK EREFVARISW SGTTKYYADA VKGRFAISRD    300
NAKNTVYLQM NSLKPEDTAV YYCAAAFYGN RGYYDVNAYT SSGQGTQVTV S            351

SEQ ID NO: 378            moltype = AA  length = 354
FEATURE                   Location/Qualifiers
source                    1..354
                          mol_type = protein
                          organism = Synthetic construct
SEQUENCE: 378
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS DVQLQESGGG    240
LVQAGGSLKL SCAASGGSLS RYDMGWFRQA PGKEREFVAR ISWSGTTKYY ADAVKGRFAI    300
SRDNAKNTVY LQMNSLKPED TAVYYCAAAF YGNRGYYDVN AYTSSGQGTQ VTVS          354

SEQ ID NO: 379            moltype = AA  length = 359
FEATURE                   Location/Qualifiers
source                    1..359
                          mol_type = protein
                          organism = Synthetic construct
SEQUENCE: 379
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS GGGGSDVQLQ    240
ESGGGLVQAG GSLKLSCAAS GGSLSRYDMG WFRQAPGKER EFVARISWSG TTKYYADAVK    300
```

```
GRFAISRDNA KNTVYLQMNS LKPEDTAVYY CAAAFYGNRG YYDVNAYTSS GQGTQVTVS    359

SEQ ID NO: 380          moltype = AA   length = 364
FEATURE                 Location/Qualifiers
source                  1..364
                        mol_type = protein
                        organism = Synthetic construct
SEQUENCE: 380
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS GGGGSGGGGS    240
DVQLQESGGG LVQAGGSLKL SCAASGGSLS RYDMGWFRQA PGKEREFVAR ISWSGTTKYY    300
ADAVKGRFAI SRDNAKNTVY LQMNSLKPED TAVYYCAAAF YGNRGYYDVN AYTSSGQGTQ    360
VTVS                                                                 364

SEQ ID NO: 381          moltype = AA   length = 351
FEATURE                 Location/Qualifiers
source                  1..351
                        mol_type = protein
                        organism = Synthetic construct
SEQUENCE: 381
DVQLQESGGG LVQAGGSLKL SCAASGGSLS RYDMGWFRQA PGKEREFVAR ISWSGTTKYY    60
ADAVKGRFAI SRDNAKNTVY LQMNSLKPED TAVYYCAAAF YGNRGYYDVN AYTSSGQGTQ    120
VTVSRSGPPC PPCPAPEFLG GPSVFLFPPK PKDTLMISRT PEVTCVVVDV SQEDPEVQFN    180
WYVDGVEVHN AKTKPREEQF NSTYRVVSVL TVLHQDWLNG KEYKCKVSNK GLPSSIEKTI    240
SKAKGQPREP QVYTLPPCQE EMTKNQVSLW CLVKGFYPSD IAVEWESNGQ PENNYKTTPP    300
VLDSDGSFFL YSRLTVDKSR WQEGNVFSCS VMHEALHNHY TQKSLSLSLG K             351

SEQ ID NO: 382          moltype = AA   length = 354
FEATURE                 Location/Qualifiers
source                  1..354
                        mol_type = protein
                        organism = Synthetic construct
SEQUENCE: 382
DVQLQESGGG LVQAGGSLKL SCAASGGSLS RYDMGWFRQA PGKEREFVAR ISWSGTTKYY    60
ADAVKGRFAI SRDNAKNTVY LQMNSLKPED TAVYYCAAAF YGNRGYYDVN AYTSSGQGTQ    120
VTVSGGGGSG PPCPPCPAPE FLGGPSVFLF PPKPKDTLMI SRTPEVTCVV VDVSQEDPEV    180
QFNWYVDGVE VHNAKTKPRE EQFNSTYRVV SVLTVLHQDW LNGKEYKCKV SNKGLPSSIE    240
KTISKAKGQP REPQVYTLPP CQEEMTKNQV SLWCLVKGFY PSDIAVEWES NGQPENNYKT    300
TPPVLDSDGS FFLYSRLTVD KSRWQEGNVF SCSVMHEALH NHYTQKSLSL SLGK          354

SEQ ID NO: 383          moltype = AA   length = 359
FEATURE                 Location/Qualifiers
source                  1..359
                        mol_type = protein
                        organism = Synthetic construct
SEQUENCE: 383
DVQLQESGGG LVQAGGSLKL SCAASGGSLS RYDMGWFRQA PGKEREFVAR ISWSGTTKYY    60
ADAVKGRFAI SRDNAKNTVY LQMNSLKPED TAVYYCAAAF YGNRGYYDVN AYTSSGQGTQ    120
VTVSGGGSGP PCPAPEFLGGP SVFLFPPKPK DTLMISRTPE VTCVVVDVSQ              180
EDPEVQFNWY VDGVEVHNAK TKPREEQFNS TYRVVSVLTV LHQDWLNGKE YKCKVSNKGL    240
PSSIEKTISK AKGQPREPQV YTLPPCQEEM TKNQVSLWCL VKGFYPSDIA VEWESNGQPE    300
NNYKTTPPVL DSDGSFFLYS RLTVDKSRWQ EGNVFSCSVM HEALHNHYTQ KSLSLSLGK     359

SEQ ID NO: 384          moltype = AA   length = 364
FEATURE                 Location/Qualifiers
source                  1..364
                        mol_type = protein
                        organism = Synthetic construct
SEQUENCE: 384
DVQLQESGGG LVQAGGSLKL SCAASGGSLS RYDMGWFRQA PGKEREFVAR ISWSGTTKYY    60
ADAVKGRFAI SRDNAKNTVY LQMNSLKPED TAVYYCAAAF YGNRGYYDVN AYTSSGQGTQ    120
VTVSGGGGSG GGGSGGGGSG PPCPPCPAPE FLGGPSVFLF PPKPKDTLMI SRTPEVTCVV    180
VDVSQEDPEV QFNWYVDGVE VHNAKTKPRE EQFNSTYRVV SVLTVLHQDW LNGKEYKCKV    240
SNKGLPSSIE KTISKAKGQP REPQVYTLPP CQEEMTKNQV SLWCLVKGFY PSDIAVEWES    300
NGQPENNYKT TPPVLDSDGS FFLYSRLTVD KSRWQEGNVF SCSVMHEALH NHYTQKSLSL    360
SLGK                                                                 364

SEQ ID NO: 385          moltype = AA   length = 351
FEATURE                 Location/Qualifiers
source                  1..351
                        mol_type = protein
                        organism = Synthetic construct
SEQUENCE: 385
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKRSDVQ LQESGGGLVQ    240
```

-continued

```
AGGSLKLSCA ASGGSLSRYD MGWFRQAPGK EREFVARISW SGDTKYYADA VEGRFAISRD  300
NAQNTVYLQM NSLKPEDTAV YYCAVALYGN RGYYDVNTYS YWGQGTRVTV S           351

SEQ ID NO: 386          moltype = AA   length = 354
FEATURE                 Location/Qualifiers
source                  1..354
                        mol_type = protein
                        organism = Synthetic construct
SEQUENCE: 386
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS DVQLQESGGG  240
LVQAGGSLKL SCAASGGSLS RYDMGWFRQA PGKEREFVAR ISWSGDTKYY ADAVEGRFAI  300
SRDNAQNTVY LQMNSLKPED TAVYYCAVAL YGNRGYYDVN TYSYWGQGTR VTVS         354

SEQ ID NO: 387          moltype = AA   length = 359
FEATURE                 Location/Qualifiers
source                  1..359
                        mol_type = protein
                        organism = Synthetic construct
SEQUENCE: 387
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSDVQLQ  240
ESGGGLVQAG GSLKLSCAAS GGSLSRYDMG WFRQAPGKER EFVARISWSG DTKYYADAVE  300
GRFAISRDNA QNTVYLQMNS LKPEDTAVYY CAVALYGNRG YYDVNTYSYW GQGTRVTVS   359

SEQ ID NO: 388          moltype = AA   length = 364
FEATURE                 Location/Qualifiers
source                  1..364
                        mol_type = protein
                        organism = Synthetic construct
SEQUENCE: 388
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSGGGGS  240
DVQLQESGGG LVQAGGSLKL SCAASGGSLS RYDMGWFRQA PGKEREFVAR ISWSGDTKYY  300
ADAVEGRFAI SRDNAQNTVY LQMNSLKPED TAVYYCAVAL YGNRGYYDVN TYSYWGQGTR  360
VTVS                                                               364

SEQ ID NO: 389          moltype = AA   length = 351
FEATURE                 Location/Qualifiers
source                  1..351
                        mol_type = protein
                        organism = Synthetic construct
SEQUENCE: 389
DVQLQESGGG LVQAGGSLKL SCAASGGSLS RYDMGWFRQA PGKEREFVAR ISWSGDTKYY  60
ADAVEGRFAI SRDNAQNTVY LQMNSLKPED TAVYYCAVAL YGNRGYYDVN TYSYWGQGTR  120
VTVSRSGPPC PPCPAPEFLG GPSVFLFPPK PKDTLMISRT PEVTCVVVDV SQEDPEVQFN  180
WYVDGVEVHN AKTKPREEQF NSTYRVVSVL TVLHQDWLNG KEYKCKVSNK GLPSSIEKTI  240
SKAKGQPREP QVYTLPPCQE EMTKNQVSLW CLVKGFYPSD IAVEWESNGQ PENNYKTTPP  300
VLDSDGSFFL YSRLTVDKSR WQEGNVFSCS VMHEALHNHY TQKSLSLSLG K           351

SEQ ID NO: 390          moltype = AA   length = 354
FEATURE                 Location/Qualifiers
source                  1..354
                        mol_type = protein
                        organism = Synthetic construct
SEQUENCE: 390
DVQLQESGGG LVQAGGSLKL SCAASGGSLS RYDMGWFRQA PGKEREFVAR ISWSGDTKYY  60
ADAVEGRFAI SRDNAQNTVY LQMNSLKPED TAVYYCAVAL YGNRGYYDVN TYSYWGQGTR  120
VTVSGGGGSG PPCPPCPAPE FLGGPSVFLF PPKPKDTLMI SRTPEVTCVV VDVSQEDPEV  180
QFNWYVDGVE VHNAKTKPRE EQFNSTYRVV SVLTVLHQDW LNGKEYKCKV SNKGLPSSIE  240
KTISKAKGQP REPQVYTLPP CQEEMTKNQV SLWCLVKGFY PSDIAVEWES NGQPENNYKT  300
TPPVLDSDGS FFLYSRLTVD KSRWQEGNVF SCSVMHEALH NHYTQKSLSL SLGK         354

SEQ ID NO: 391          moltype = AA   length = 359
FEATURE                 Location/Qualifiers
source                  1..359
                        mol_type = protein
                        organism = Synthetic construct
SEQUENCE: 391
DVQLQESGGG LVQAGGSLKL SCAASGGSLS RYDMGWFRQA PGKEREFVAR ISWSGDTKYY  60
ADAVEGRFAI SRDNAQNTVY LQMNSLKPED TAVYYCAVAL YGNRGYYDVN TYSYWGQGTR  120
VTVSGGGGSG GGGSGPPCPP CPAPEFLGGP SVFLFPPKPK DTLMISRTPE VTCVVVDVSQ  180
EDPEVQFNWY VDGVEVHNAK TKPREEQFNS TYRVVSVLTV LHQDWLNGKE YKCKVSNKGL  240
```

```
PSSIEKTISK AKGQPREPQV YTLPPCQEEM TKNQVSLWCL VKGFYPSDIA VEWESNGQPE 300
NNYKTTPPVL DSDGSFFLYS RLTVDKSRWQ EGNVFSCSVM HEALHNHYTQ KSLSLSLGK  359

SEQ ID NO: 392          moltype = AA  length = 364
FEATURE                 Location/Qualifiers
source                  1..364
                        mol_type = protein
                        organism = Synthetic construct
SEQUENCE: 392
DVQLQESGGG LVQAGGSLKL SCAASGGSLS RYDMGWFRQA PGKEREFVAR ISWSGDTKYY 60
ADAVEGRFAI SRDNAQNTVY LQMNSLKPED TAVYYCAVAL YGNRGYYDVN TYSYWGQGTR 120
VTVSGGGGSG GGGSGGGGSG PPCPPCPAPE FLGGPSVFLF PPKPKDTLMI SRTPEVTCVV 180
VDVSQEDPEV QFNWYVDGVE VHNAKTKPRE EQFNSTYRVV SVLTVLHQDW LNGKEYKCKV 240
SNKGLPSSIE KTISKAKGQP REPQVYTLPP CQEEMTKNQV SLWCLVKGFY PSDIAVEWES 300
NGQPENNYKT TPPVLDSDGS FFLYSRLTVD KSRWQEGNVF SCSVMHEALH NHYTQKSLSL 360
SLGK                                                              364

SEQ ID NO: 393          moltype = AA  length = 351
FEATURE                 Location/Qualifiers
source                  1..351
                        mol_type = protein
                        organism = Synthetic construct
SEQUENCE: 393
GPPCPPCPAP EFLGGPSVFL FPPKPKDTLM ISRTPEVTCV VVDVSQEDPE VQFNWYVDGV 60
EVHNAKTKPR EEQFNSTYRV VSVLTVLHQD WLNGKEYKCK VSNKGLPSSI EKTISKAKGQ 120
PREPQVYTLP PCQEEMTKNQ VSLWCLVKGF YPSDIAVEWE SNGQPENNYK TTPPVLDSDG 180
SFFLYSRLTV DKSRWQEGNV FSCSVMHEAL HNHYTQKSLS LSLGKRSDVQ LQESGGGLVQ 240
AGGSLKLSCA ASRGSLSRWD VAWFRQAPGK ERSFVTRISW SGTTSYYADA VKGRFAISRD 300
NAKNTVYLQM NSLKPEDTAV YYCAVALYGN RGYYDVNAHS YWGQGTQVTV S          351

SEQ ID NO: 394          moltype = AA  length = 354
FEATURE                 Location/Qualifiers
source                  1..354
                        mol_type = protein
                        organism = Synthetic construct
SEQUENCE: 394
GPPCPPCPAP EFLGGPSVFL FPPKPKDTLM ISRTPEVTCV VVDVSQEDPE VQFNWYVDGV 60
EVHNAKTKPR EEQFNSTYRV VSVLTVLHQD WLNGKEYKCK VSNKGLPSSI EKTISKAKGQ 120
PREPQVYTLP PCQEEMTKNQ VSLWCLVKGF YPSDIAVEWE SNGQPENNYK TTPPVLDSDG 180
SFFLYSRLTV DKSRWQEGNV FSCSVMHEAL HNHYTQKSLS LSLGKGGGGS DVQLQESGGG 240
LVQAGGSLKL SCAASRGSLS RWDVAWFRQA PGKERSFVTR ISWSGTTSYY ADAVKGRFAI 300
SRDNAKNTVY LQMNSLKPED TAVYYCAVAL YGNRGYYDVN AHSYWGQGTQ VTVS        354

SEQ ID NO: 395          moltype = AA  length = 359
FEATURE                 Location/Qualifiers
source                  1..359
                        mol_type = protein
                        organism = Synthetic construct
SEQUENCE: 395
GPPCPPCPAP EFLGGPSVFL FPPKPKDTLM ISRTPEVTCV VVDVSQEDPE VQFNWYVDGV 60
EVHNAKTKPR EEQFNSTYRV VSVLTVLHQD WLNGKEYKCK VSNKGLPSSI EKTISKAKGQ 120
PREPQVYTLP PCQEEMTKNQ VSLWCLVKGF YPSDIAVEWE SNGQPENNYK TTPPVLDSDG 180
SFFLYSRLTV DKSRWQEGNV FSCSVMHEAL HNHYTQKSLS LSLGKGGGGS GGGGSDVQLQ 240
ESGGGLVQAG GSLKLSCAAS RGSLSRWDVA WFRQAPGKER SFVTRISWSG TTSYYADAVK 300
GRFAISRDNA KNTVYLQMNS LKPEDTAVYY CAVALYGNRG YYDVNAHSYW GQGTQVTVS  359

SEQ ID NO: 396          moltype = AA  length = 364
FEATURE                 Location/Qualifiers
source                  1..364
                        mol_type = protein
                        organism = Synthetic construct
SEQUENCE: 396
GPPCPPCPAP EFLGGPSVFL FPPKPKDTLM ISRTPEVTCV VVDVSQEDPE VQFNWYVDGV 60
EVHNAKTKPR EEQFNSTYRV VSVLTVLHQD WLNGKEYKCK VSNKGLPSSI EKTISKAKGQ 120
PREPQVYTLP PCQEEMTKNQ VSLWCLVKGF YPSDIAVEWE SNGQPENNYK TTPPVLDSDG 180
SFFLYSRLTV DKSRWQEGNV FSCSVMHEAL HNHYTQKSLS LSLGKGGGGS GGGGSGGGGS 240
DVQLQESGGG LVQAGGSLKL SCAASRGSLS RWDVAWFRQA PGKERSFVTR ISWSGTTSYY 300
ADAVKGRFAI SRDNAKNTVY LQMNSLKPED TAVYYCAVAL YGNRGYYDVN AHSYWGQGTQ 360
VTVS                                                              364

SEQ ID NO: 397          moltype = AA  length = 351
FEATURE                 Location/Qualifiers
source                  1..351
                        mol_type = protein
                        organism = Synthetic construct
SEQUENCE: 397
DVQLQESGGG LVQAGGSLKL SCAASRGSLS RWDVAWFRQA PGKERSFVTR ISWSGTTSYY 60
ADAVKGRFAI SRDNAKNTVY LQMNSLKPED TAVYYCAVAL YGNRGYYDVN AHSYWGQGTQ 120
VTVSRSGPPC PPCPAPEFLG GPSVFLFPPK PKDTLMISRT PEVTCVVVDV SQEDPEVQFN 180
```

```
WYVDGVEVHN AKTKPREEQF NSTYRVVSVL TVLHQDWLNG KEYKCKVSNK GLPSSIEKTI  240
SKAKGQPREP QVYTLPPCQE EMTKNQVSLW CLVKGFYPSD IAVEWESNGQ PENNYKTTPP  300
VLDSDGSFFL YSRLTVDKSR WQEGNVFSCS VMHEALHNHY TQKSLSLSLG K           351

SEQ ID NO: 398          moltype = AA  length = 354
FEATURE                 Location/Qualifiers
source                  1..354
                        mol_type = protein
                        organism = Synthetic construct
SEQUENCE: 398
DVQLQESGGG LVQAGGSLKL SCAASRGSLS RWDVAWFRQA PGKERSFVTR ISWSGTTSYY  60
ADAVKGRFAI SRDNAKNTVY LQMNSLKPED TAVYYCAVAL YGNRGYYDVN AHSYWGQGTQ  120
VTVSGGGGSG PPCPPCPAPE FLGGPSVFLF PPKPKDTLMI SRTPEVTCVV VDVSQEDPEV  180
QFNWYVDGVE VHNAKTKPRE EQFNSTYRVV SVLTVLHQDW LNGKEYKCKV SNKGLPSSIE  240
KTISKAKGQP REPQVYTLPP CQEEMTKNQV SLWCLVKGFY PSDIAVEWES NGQPENNYKT  300
TPPVLDSDGS FFLYSRLTVD KSRWQEGNVF SCSVMHEALH NHYTQKSLSL SLGK        354

SEQ ID NO: 399          moltype = AA  length = 359
FEATURE                 Location/Qualifiers
source                  1..359
                        mol_type = protein
                        organism = Synthetic construct
SEQUENCE: 399
DVQLQESGGG LVQAGGSLKL SCAASRGSLS RWDVAWFRQA PGKERSFVTR ISWSGTTSYY  60
ADAVKGRFAI SRDNAKNTVY LQMNSLKPED TAVYYCAVAL YGNRGYYDVN AHSYWGQGTQ  120
VTVSGGGGSG GGGSGPPCPP CPAPEFLGGP SVFLFPPPKPK DTLMISRTPE VTCVVVDVSQ  180
EDPEVQFNWY VDGVEVHNAK TKPREEQFNS TYRVVSVLTV LHQDWLNGKE YKCKVSNKGL  240
PSSIEKTISK AKGQPREPQV YTLPPCQEEM TKNQVSLWCL VKGFYPSDIA VEWESNGQPE  300
NNYKTTPPVL DSDGSFFLYS RLTVDKSRWQ EGNVFSCSVM HEALHNHYTQ KSLSLSLGK   359

SEQ ID NO: 400          moltype = AA  length = 364
FEATURE                 Location/Qualifiers
source                  1..364
                        mol_type = protein
                        organism = Synthetic construct
SEQUENCE: 400
DVQLQESGGG LVQAGGSLKL SCAASRGSLS RWDVAWFRQA PGKERSFVTR ISWSGTTSYY  60
ADAVKGRFAI SRDNAKNTVY LQMNSLKPED TAVYYCAVAL YGNRGYYDVN AHSYWGQGTQ  120
VTVSGGGGSG GGGSGGGGSG PPCPPCPAPE FLGGPSVFLF PPKPKDTLMI SRTPEVTCVV  180
VDVSQEDPEV QFNWYVDGVE VHNAKTKPRE EQFNSTYRVV SVLTVLHQDW LNGKEYKCKV  240
SNKGLPSSIE KTISKAKGQP REPQVYTLPP CQEEMTKNQV SLWCLVKGFY PSDIAVEWES  300
NGQPENNYKT TPPVLDSDGS FFLYSRLTVD KSRWQEGNVF SCSVMHEALH NHYTQKSLSL  360
SLGK                                                                364

SEQ ID NO: 401          moltype = AA  length = 353
FEATURE                 Location/Qualifiers
source                  1..353
                        mol_type = protein
                        organism = Synthetic construct
SEQUENCE: 401
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKRSDVQ LQESGGGLVQ  240
AGGSLRLSCA VSGLSFSSMG WFRQPPGKER EFVAAISLYS GSTYYADSVK GRFTISSDNA  300
KSTVYLQMNS LKPEDAAVYF CAADRQRTWS TFYASRQATY NYWGQGTQVT VTS         353

SEQ ID NO: 402          moltype = AA  length = 356
FEATURE                 Location/Qualifiers
source                  1..356
                        mol_type = protein
                        organism = Synthetic construct
SEQUENCE: 402
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS DVQLQESGGG  240
LVQAGGSLRL SCAVSGLSFS SMGWFRQPPG KEREFVAAIS LYSGSTYYAD SVKGRFTISS  300
DNAKSTVYLQ MNSLKPEDAA VYFCAADRQR TWSTFYASR ATYNYWGQGT QVTVTS       356

SEQ ID NO: 403          moltype = AA  length = 361
FEATURE                 Location/Qualifiers
source                  1..361
                        mol_type = protein
                        organism = Synthetic construct
SEQUENCE: 403
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
```

```
SFFLYSRLTV DKSRWQEGNV FSCSVMHEAL HNHYTQKSLS LSLGKGGGGS GGGGSDVQLQ  240
ESGGGLVQAG GSLRLSCAVS GLSFSSMGWF RQPPGKEREF VAAISLYSGS TYYADSVKGR  300
FTISSDNAKS TVYLQMNSLK PEDAAVYFCA ADRQRTWSTF YASRQATYNY WGQGTQVTVT  360
S                                                                361

SEQ ID NO: 404            moltype = AA  length = 366
FEATURE                   Location/Qualifiers
source                    1..366
                          mol_type = protein
                          organism = Synthetic construct
SEQUENCE: 404
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSGGGGS  240
DVQLQESGGG LVQAGGSLRL SCAVSGLSFS SMGWFRQPPG KEREFVAAIS LYSGSTYYAD  300
SVKGRFTISS DNAKSTVYLQ MNSLKPEDAA VYFCAADRQR TWSTFYASRQ ATYNYWGQGT  360
QVTVTS                                                            366

SEQ ID NO: 405            moltype = AA  length = 353
FEATURE                   Location/Qualifiers
source                    1..353
                          mol_type = protein
                          organism = Synthetic construct
SEQUENCE: 405
DVQLQESGGG LVQAGGSLRL SCAVSGLSFS SMGWFRQPPG KEREFVAAIS LYSGSTYYAD  60
SVKGRFTISS DNAKSTVYLQ MNSLKPEDAA VYFCAADRQR TWSTFYASRQ ATYNYWGQGT  120
QVTVTSRSGP PCPPCPAPEF LGGPSVFLFP PKPKDTLMIS RTPEVTCVVV DVSQEDPEVQ  180
FNWYVDGVEV HNAKTKPREE QFNSTYRVVS VLTVLHQDWL NGKEYKCKVS NKGLPSSIEK  240
TISKAKGQPR EPQVYTLPPC QEEMTKNQVS LWCLVKGFYP SDIAVEWESN GQPENNYKTT  300
PPVLDSDGSF FLYSRLTVDK SRWQEGNVFS CSVMHEALHN HYTQKSLSLS LGK         353

SEQ ID NO: 406            moltype = AA  length = 356
FEATURE                   Location/Qualifiers
source                    1..356
                          mol_type = protein
                          organism = Synthetic construct
SEQUENCE: 406
DVQLQESGGG LVQAGGSLRL SCAVSGLSFS SMGWFRQPPG KEREFVAAIS LYSGSTYYAD  60
SVKGRFTISS DNAKSTVYLQ MNSLKPEDAA VYFCAADRQR TWSTFYASRQ ATYNYWGQGT  120
QVTVTSGGGG SGPPCPPCPA PEFLGGPSVF LFPPKPKDTL MISRTPEVTC VVVDVSQEDP  180
EVQFNWYVDG VEVHNAKTKP REEQFNSTYR VVSVLTVLHQ DWLNGKEYKC KVSNKGLPSS  240
IEKTISKAKG QPREPQVYTL PPCQEEMTKN QVSLWCLVKG FYPSDIAVEW ESNGQPENNY  300
KTTPPVLDSD GSFFLYSRLT VDKSRWQEGN VFSCSVMHEA LHNHYTQKSL SLSLGK      356

SEQ ID NO: 407            moltype = AA  length = 361
FEATURE                   Location/Qualifiers
source                    1..361
                          mol_type = protein
                          organism = Synthetic construct
SEQUENCE: 407
DVQLQESGGG LVQAGGSLRL SCAVSGLSFS SMGWFRQPPG KEREFVAAIS LYSGSTYYAD  60
SVKGRFTISS DNAKSTVYLQ MNSLKPEDAA VYFCAADRQR TWSTFYASRQ ATYNYWGQGT  120
QVTVTSGGGG SGGGGSGPPC PPCPAPEFLG GPSVFLFPPK PKDTLMISRT PEVTCVVVDV  180
SQEDPEVQFN WYVDGVEVHN AKTKPREEQF NSTYRVVSVL TVLHQDWLNG KEYKCKVSNK  240
GLPSSIEKTI SKAKGQPREP QVYTLPPCQE EMTKNQVSLW CLVKGFYPSD IAVEWESNGQ  300
PENNYKTTPP VLDSDGSFFL YSRLTVDKSR WQEGNVFSCS VMHEALHNHY TQKSLSLSLG  360
K                                                                361

SEQ ID NO: 408            moltype = AA  length = 366
FEATURE                   Location/Qualifiers
source                    1..366
                          mol_type = protein
                          organism = Synthetic construct
SEQUENCE: 408
DVQLQESGGG LVQAGGSLRL SCAVSGLSFS SMGWFRQPPG KEREFVAAIS LYSGSTYYAD  60
SVKGRFTISS DNAKSTVYLQ MNSLKPEDAA VYFCAADRQR TWSTFYASRQ ATYNYWGQGT  120
QVTVTSGGGG SGGGGSGGGG SGPPCPPCPA PEFLGGPSVF LFPPKPKDTL MISRTPEVTC  180
VVVDVSQEDP EVQFNWYVDG VEVHNAKTKP REEQFNSTYR VVSVLTVLHQ DWLNGKEYKC  240
KVSNKGLPSS IEKTISKAKG QPREPQVYTL PPCQEEMTKN QVSLWCLVKG FYPSDIAVEW  300
ESNGQPENNY KTTPPVLDSD GSFFLYSRLT VDKSRWQEGN VFSCSVMHEA LHNHYTQKSL  360
SLSLGK                                                            366

SEQ ID NO: 409            moltype = AA  length = 345
FEATURE                   Location/Qualifiers
source                    1..345
                          mol_type = protein
                          organism = Synthetic construct
SEQUENCE: 409
```

-continued

```
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKRSDVQ LQESGGGLVQ  240
PGGSLRLSCA ASGSIFSIDI MGWYRQAPGK QRELVATMPE GNYINYADSV KGRLTLSRDK  300
GKNTVYLQLN SLKPEDTAVY YCYGFGVREG RGNVYWGQGT QVTVS  345
```

```
SEQ ID NO: 410              moltype = AA   length = 348
FEATURE                     Location/Qualifiers
source                      1..348
                            mol_type = protein
                            organism = Synthetic construct
SEQUENCE: 410
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS DVQLQESGGG  240
LVQPGGSLRL SCAASGSIFS IDIMGWYRQA PGKQRELVAT MPEGNYINYA DSVKGRLTLS  300
RDKGKNTVYL QLNSLKPEDT AVYYCYGFGV REGRGNVYWG QGTQVTVS  348
```

```
SEQ ID NO: 411              moltype = AA   length = 353
FEATURE                     Location/Qualifiers
source                      1..353
                            mol_type = protein
                            organism = Synthetic construct
SEQUENCE: 411
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSDVQLQ  240
ESGGGLVQPG GSLRLSCAAS GSIFSIDIMG WYRQAPGKQR ELVATMPEGN YINYADSVKG  300
RLTLSRDKGK NTVYLQLNSL KPEDTAVYYC YGFGVREGRG NVYWGQGTQV TVS  353
```

```
SEQ ID NO: 412              moltype = AA   length = 358
FEATURE                     Location/Qualifiers
source                      1..358
                            mol_type = protein
                            organism = Synthetic construct
SEQUENCE: 412
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGGS GGGGSGGGGS  240
DVQLQESGGG LVQPGGSLRL SCAASGSIFS IDIMGWYRQA PGKQRELVAT MPEGNYINYA  300
DSVKGRLTLS RDKGKNTVYL QLNSLKPEDT AVYYCYGFGV REGRGNVYWG QGTQVTVS  358
```

```
SEQ ID NO: 413              moltype = AA   length = 345
FEATURE                     Location/Qualifiers
source                      1..345
                            mol_type = protein
                            organism = Synthetic construct
SEQUENCE: 413
DVQLQESGGG LVQPGGSLRL SCAASGSIFS IDIMGWYRQA PGKQRELVAT MPEGNYINYA  60
DSVKGRLTLS RDKGKNTVYL QLNSLKPEDT AVYYCYGFGV REGRGNVYWG QGTQVTVSRS  120
GPPCPPCPAP EFLGGPSVFL FPPKPKDTLM ISRTPEVTCV VVDVSQEDPE VQFNWYVDGV  180
EVHNAKTKPR EEQFNSTYRV VSVLTVLHQD WLNGKEYKCK VSNKGLPSSI EKTISKAKGQ  240
PREPQVYTLP PCQEEMTKNQ VSLWCLVKGF YPSDIAVEWE SNGQPENNYK TTPPVLDSDG  300
SFFLYSRLTV DKSRWQEGNV FSCSVMHEAL HNHYTQKSLS LSLGK  345
```

```
SEQ ID NO: 414              moltype = AA   length = 348
FEATURE                     Location/Qualifiers
source                      1..348
                            mol_type = protein
                            organism = Synthetic construct
SEQUENCE: 414
DVQLQESGGG LVQPGGSLRL SCAASGSIFS IDIMGWYRQA PGKQRELVAT MPEGNYINYA  60
DSVKGRLTLS RDKGKNTVYL QLNSLKPEDT AVYYCYGFGV REGRGNVYWG QGTQVTVSGG  120
GGSGPPCPPC PAPEFLGGPS VFLFPPKPKD TLMISRTPEV TCVVVDVSQE DPEVQFNWYV  180
DGVEVHNAKT KPREEQFNST YRVVSVLTVL HQDWLNGKEY KCKVSNKGLP SSIEKTISKA  240
KGQPREPQVY TLPPCQEEMT KNQVSLWCLV KGFYPSDIAV EWESNGQPEN NYKTTPPVLD  300
SDGSFFLYSR LTVDKSRWQE GNVFSCSVMH EALHNHYTQK SLSLSLGK  348
```

```
SEQ ID NO: 415              moltype = AA   length = 353
FEATURE                     Location/Qualifiers
source                      1..353
                            mol_type = protein
                            organism = Synthetic construct
SEQUENCE: 415
DVQLQESGGG LVQPGGSLRL SCAASGSIFS IDIMGWYRQA PGKQRELVAT MPEGNYINYA  60
```

```
DSVKGRLTLS RDKGKNTVYL QLNSLKPEDT AVYYCYGFGV REGRGNVYWG QGTQVTVSGG    120
GGSGGGGSGP PCPPCPAPEF LGGPSVFLFP PKPKDTLMIS RTPEVTCVVV DVSQEDPEVQ    180
FNWYVDGVEV HNAKTKPREE QFNSTYRVVS VLTVLHQDWL NGKEYKCKVS NKGLPSSIEK    240
TISKAKGQPR EPQVYTLPPC QEEMTKNQVS LWCLVKGFYP SDIAVEWESN GQPENNYKTT    300
PPVLDSDGSF FLYSRLTVDK SRWQEGNVFS CSVMHEALHN HYTQKSLSLS LGK           353

SEQ ID NO: 416          moltype = AA  length = 358
FEATURE                 Location/Qualifiers
source                  1..358
                        mol_type = protein
                        organism = Synthetic construct
SEQUENCE: 416
DVQLQESGGG LVQPGGSLRL SCAASGSIFS IDIMGWYRQA PGKQRELVAT MPEGNYINYA    60
DSVKGRLTLS RDKGKNTVYL QLNSLKPEDT AVYYCYGFGV REGRGNVYWG QGTQVTVSGG    120
GGSGGGGSGG GGSGPPCPPC PAPEFLGGPS VFLFPPKPKD TLMISRTPEV TCVVVDVSQE    180
DPEVQFNWYV DGVEVHNAKT KPREEQFNST YRVVSVLTVL HQDWLNGKEY KCKVSNKGLP    240
SSIEKTISKA KGQPREPQVY TLPPCQEEMT KNQVSLWCLV KGFYPSDIAV EWESNGQPEN    300
NYKTTPPVLD SDGSFFLYSR LTVDKSRWQE GNVFSCSVMH EALHNHYTQK SLSLSLGK      358

SEQ ID NO: 417          moltype = AA  length = 344
FEATURE                 Location/Qualifiers
source                  1..344
                        mol_type = protein
                        organism = Synthetic construct
SEQUENCE: 417
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKRSDVQ LQESGGGLVQ    240
AGGSLRLSCA ASGLTFGSYD MGWYRQAPGK QRELVGRIRN DGITYYADSV KGRFTMSRDN    300
AKNTVYLQMN SLKPEDTAVY YCAADGTGLG HYDYWGQGTQ VTVS                     344

SEQ ID NO: 418          moltype = AA  length = 347
FEATURE                 Location/Qualifiers
source                  1..347
                        mol_type = protein
                        organism = Synthetic construct
SEQUENCE: 418
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS DVQLQESGGG    240
LVQAGGSLRL SCAASGLTFG SYDMGWYRQA PGKQRELVGR IRNDGITYYA DSVKGRFTMS    300
RDNAKNTVYL QMNSLKPEDT AVYYCAADGT GLGHYDYWGQ GTQVTVS                  347

SEQ ID NO: 419          moltype = AA  length = 352
FEATURE                 Location/Qualifiers
source                  1..352
                        mol_type = protein
                        organism = Synthetic construct
SEQUENCE: 419
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS GGGGSDVQLQ    240
ESGGGLVQAG GSLRLSCAAS GLTFGSYDMG WYRQAPGKQR ELVGRIRNDG ITYYADSVKG    300
RFTMSRDNAK NTVYLQMNSL KPEDTAVYYC AADGTGLGHY DYWGQGTQVT VS            352

SEQ ID NO: 420          moltype = AA  length = 357
FEATURE                 Location/Qualifiers
source                  1..357
                        mol_type = protein
                        organism = Synthetic construct
SEQUENCE: 420
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGGGGS GGGGSGGGGS    240
DVQLQESGGG LVQAGGSLRL SCAASGLTFG SYDMGWYRQA PGKQRELVGR IRNDGITYYA    300
DSVKGRFTMS RDNAKNTVYL QMNSLKPEDT AVYYCAADGT GLGHYDYWGQ GTQVTVS       357

SEQ ID NO: 421          moltype = AA  length = 344
FEATURE                 Location/Qualifiers
source                  1..344
                        mol_type = protein
                        organism = Synthetic construct
SEQUENCE: 421
DVQLQESGGG LVQAGGSLRL SCAASGLTFG SYDMGWYRQA PGKQRELVGR IRNDGITYYA    60
DSVKGRFTMS RDNAKNTVYL QMNSLKPEDT AVYYCAADGT GLGHYDYWGQ GTQVTVSRSG    120
```

```
PPCPPCPAPE FLGGPSVFLF PPKPKDTLMI SRTPEVTCVV VDVSQEDPEV QFNWYVDGVE   180
VHNAKTKPRE EQFNSTYRVV SVLTVLHQDW LNGKEYKCKV SNKGLPSSIE KTISKAKGQP   240
REPQVYTLPP CQEEMTKNQV SLWCLVKGFY PSDIAVEWES NGQPENNYKT TPPVLDSDGS   300
FFLYSRLTVD KSRWQEGNVF SCSVMHEALH NHYTQKSLSL SLGK                   344

SEQ ID NO: 422              moltype = AA  length = 347
FEATURE                     Location/Qualifiers
source                      1..347
                            mol_type = protein
                            organism = Synthetic construct
SEQUENCE: 422
DVQLQESGGG LVQAGGSLRL SCAASGLTFG SYDMGWYRQA PGKQRELVGR IRNDGITYYA   60
DSVKGRFTMS RDNAKNTVYL QMNSLKPEDT AVYYCAADGT GLGHYDYWGQ GTQVTVSGGG   120
GSGPPCPPCP APEFLGGPSV FLFPPKPKDT LMISRTPEVT CVVVDVSQED PEVQFNWYVD   180
GVEVHNAKTK PREEQFNSTY RVVSVLTVLH QDWLNGKEYK CKVSNKGLPS SIEKTISKAK   240
GQPREPQVYT LPPCQEEMTK NQVSLWCLVK GFYPSDIAVE WESNGQPENN YKTTPPVLDS   300
DGSFFLYSRL TVDKSRWQEG NVFSCSVMHE ALHNHYTQKS LSLSLGK               347

SEQ ID NO: 423              moltype = AA  length = 352
FEATURE                     Location/Qualifiers
source                      1..352
                            mol_type = protein
                            organism = Synthetic construct
SEQUENCE: 423
DVQLQESGGG LVQAGGSLRL SCAASGLTFG SYDMGWYRQA PGKQRELVGR IRNDGITYYA   60
DSVKGRFTMS RDNAKNTVYL QMNSLKPEDT AVYYCAADGT GLGHYDYWGQ GTQVTVSGGG   120
GSGGGGSGPP CPPCPAPEFL GGPSVFLFPP KPKDTLMISR TPEVTCVVVD VSQEDPEVQF   180
NWYVDGVEVH NAKTKPREEQ FNSTYRVVSV LTVLHQDWLN GKEYKCKVSN KGLPSSIEKT   240
ISKAKGQPRE PQVYTLPPCQ EEMTKNQVSL WCLVKGFYPS DIAVEWESNG QPENNYKTTP   300
PVLDSDGSFF LYSRLTVDKS RWQEGNVFSC SVMHEALHNH YTQKSLSLSL GK          352

SEQ ID NO: 424              moltype = AA  length = 357
FEATURE                     Location/Qualifiers
source                      1..357
                            mol_type = protein
                            organism = Synthetic construct
SEQUENCE: 424
DVQLQESGGG LVQAGGSLRL SCAASGLTFG SYDMGWYRQA PGKQRELVGR IRNDGITYYA   60
DSVKGRFTMS RDNAKNTVYL QMNSLKPEDT AVYYCAADGT GLGHYDYWGQ GTQVTVSGGG   120
GSGGGGSGGG GSGPPCPPCP APEFLGGPSV FLFPPKPKDT LMISRTPEVT CVVVDVSQED   180
PEVQFNWYVD GVEVHNAKTK PREEQFNSTY RVVSVLTVLH QDWLNGKEYK CKVSNKGLPS   240
SIEKTISKAK GQPREPQVYT LPPCQEEMTK NQVSLWCLVK GFYPSDIAVE WESNGQPENN   300
YKTTPPVLDS DGSFFLYSRL TVDKSRWQEG NVFSCSVMHE ALHNHYTQKS LSLSLGK     357

SEQ ID NO: 425              moltype = AA  length = 348
FEATURE                     Location/Qualifiers
source                      1..348
                            mol_type = protein
                            organism = Synthetic construct
SEQUENCE: 425
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
SFFLVSRLTV DKSRWQEGNV FSCSVMHEAL HNHYTQKSLS LSLGKRSEVQ LLESGGGLVQ   240
PGGSLRLSCA ASGFRFGNYD MAWVRQAPGK RYEWVSSIDT GGDITHYADS VKGRFTISRD   300
NAKNTLYLQM NSLRPEDTAE YWCATDEEYA LGPNEFDYYG QGTLVTVS               348

SEQ ID NO: 426              moltype = AA  length = 351
FEATURE                     Location/Qualifiers
source                      1..351
                            mol_type = protein
                            organism = Synthetic construct
SEQUENCE: 426
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
SFFLVSRLTV DKSRWQEGNV FSCSVMHEAL HNHYTQKSLS LSLGKGGGGS EVQLLESGGG   240
LVQPGGSLRL SCAASGFRFG NYDMAWVRQA PGKRYEWVSS IDTGGDITHY ADSVKGRFTI   300
SRDNAKNTLY LQMNSLRPED TAEYWCATDE EYALGPNEFD YYGQGTLVTV S           351

SEQ ID NO: 427              moltype = AA  length = 356
FEATURE                     Location/Qualifiers
source                      1..356
                            mol_type = protein
                            organism = Synthetic construct
SEQUENCE: 427
GPPCPPCPAP EFLGGPSVFL FPPKPKDTLM ISRTPEVTCV VVDVSQEDPE VQFNWYVDGV   60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
```

-continued

```
SFFLVSRLTV DKSRWQEGNV FSCSVMHEAL HNHYTQKSLS LSLGKGGGGS GGGGSEVQLL  240
ESGGGLVQPG GSLRLSCAAS GFRFGNYDMA WVRQAPGKRY EWVSSIDTGG DITHYADSVK  300
GRFTISRDNA KNTLYLQMNS LRPEDTAEYW CATDEEYALG PNEFDYYGQG TLVTVS      356

SEQ ID NO: 428            moltype = AA   length = 361
FEATURE                   Location/Qualifiers
source                    1..361
                          mol_type = protein
                          organism = Synthetic construct
SEQUENCE: 428
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVCTLP PSQEEMTKNQ VSLSCAVKGF YPSDIAVEWE SNGQPENNYK TTPPVLDSDG  180
SFFLVSRLTV DKSRWQEGNV FSCSVMHEAL HNHYTQKSLS LSLGKGGGGS GGGGSGGGGS  240
EVQLLESGGG LVQPGGSLRL SCAASGFRFG NYDMAWVRQA PGKRYEWVSS IDTGGDITHY  300
ADSVKGRFTI SRDNAKNTLY LQMNSLRPED TAEYWCATDE EYALGPNEFD YYGQGTLVTV  360
S                                                                  361

SEQ ID NO: 429            moltype = AA   length = 348
FEATURE                   Location/Qualifiers
source                    1..348
                          mol_type = protein
                          organism = Synthetic construct
SEQUENCE: 429
EVQLLESGGG LVQPGGSLRL SCAASGFRFG NYDMAWVRQA PGKRYEWVSS IDTGGDITHY  60
ADSVKGRFTI SRDNAKNTLY LQMNSLRPED TAEYWCATDE EYALGPNEFD YYGQGTLVTV  120
SRSGPPCPPC PAPEFLGGPS VFLFPPKPKD TLMISRTPEV TCVVVDVSQE DPEVQFNWYV  180
DGVEVHNAKT KPREEQFNST YRVVSVLTVL HQDWLNGKEY KCKVSNKGLP SSIEKTISKA  240
KGQPREPQVC TLPPSQEEMT KNQVSLSCAV KGFYPSDIAV EWESNGQPEN NYKTTPPVLD  300
SDGSFFLVSR LTVDKSRWQE GNVFSCSVMH EALHNHYTQK SLSLSLGK             348

SEQ ID NO: 430            moltype = AA   length = 351
FEATURE                   Location/Qualifiers
source                    1..351
                          mol_type = protein
                          organism = Synthetic construct
SEQUENCE: 430
EVQLLESGGG LVQPGGSLRL SCAASGFRFG NYDMAWVRQA PGKRYEWVSS IDTGGDITHY  60
ADSVKGRFTI SRDNAKNTLY LQMNSLRPED TAEYWCATDE EYALGPNEFD YYGQGTLVTV  120
SGGGGSGPPC PPCPAPEFLG GPSVFLFPPK PKDTLMISRT PEVTCVVVDV SQEDPEVQFN  180
WYVDGVEVHN AKTKPREEQF NSTYRVVSVL TVLHQDWLNG KEYKCKVSNK GLPSSIEKTI  240
SKAKGQPREP QVCTLPPSQE EMTKNQVSLS CAVKGFYPSD IAVEWESNGQ PENNYKTTPP  300
VLDSDGSFFL VSRLTVDKSR WQEGNVFSCS VMHEALHNHY TQKSLSLSLG K          351

SEQ ID NO: 431            moltype = AA   length = 356
FEATURE                   Location/Qualifiers
source                    1..356
                          mol_type = protein
                          organism = Synthetic construct
SEQUENCE: 431
EVQLLESGGG LVQPGGSLRL SCAASGFRFG NYDMAWVRQA PGKRYEWVSS IDTGGDITHY  60
ADSVKGRFTI SRDNAKNTLY LQMNSLRPED TAEYWCATDE EYALGPNEFD YYGQGTLVTV  120
SGGGGSGGGG SGPPCPPCPA PEFLGGPSVF LFPPKPKDTL MISRTPEVTC VVVDVSQEDP  180
EVQFNWYVDG VEVHNAKTKP REEQFNSTYR VVSVLTVLHQ DWLNGKEYKC KVSNKGLPSS  240
IEKTISKAKG QPREPQVCTL PPSQEEMTKN QVSLSCAVKG FYPSDIAVEW ESNGQPENNY  300
KTTPPVLDSD GSFFLVSRLT VDKSRWQEGN VFSCSVMHEA LHNHYTQKSL SLSLGK     356

SEQ ID NO: 432            moltype = AA   length = 361
FEATURE                   Location/Qualifiers
source                    1..361
                          mol_type = protein
                          organism = Synthetic construct
SEQUENCE: 432
EVQLLESGGG LVQPGGSLRL SCAASGFRFG NYDMAWVRQA PGKRYEWVSS IDTGGDITHY  60
ADSVKGRFTI SRDNAKNTLY LQMNSLRPED TAEYWCATDE EYALGPNEFD YYGQGTLVTV  120
SGGGGSGGGG SGGGGSGPPC PPCPAPEFLG GPSVFLFPPK PKDTLMISRT PEVTCVVVDV  180
SQEDPEVQFN WYVDGVEVHN AKTKPREEQF NSTYRVVSVL TVLHQDWLNG KEYKCKVSNK  240
GLPSSIEKTI SKAKGQPREP QVCTLPPSQE EMTKNQVSLS CAVKGFYPSD IAVEWESNGQ  300
PENNYKTTPP VLDSDGSFFL VSRLTVDKSR WQEGNVFSCS VMHEALHNHY TQKSLSLSLG  360
K                                                                  361

SEQ ID NO: 433            moltype = AA   length = 225
FEATURE                   Location/Qualifiers
source                    1..225
                          mol_type = protein
                          organism = Homo sapiens
SEQUENCE: 433
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
```

```
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGK                    225

SEQ ID NO: 434          moltype = AA  length = 225
FEATURE                 Location/Qualifiers
source                  1..225
                        mol_type = protein
                        organism = Homo sapiens
SEQUENCE: 434
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVCTLP PSQEEMTKNQ VSLSCAVKGF YPSDIAVEWE SNGQPENNYK TTPPVLDSDG    180
SFFLVSRLTV DKSRWQEGNV FSCSVMHEAL HNHYTQKSLS LSLGK                    225

SEQ ID NO: 435          moltype = AA  length = 229
FEATURE                 Location/Qualifiers
source                  1..229
                        mol_type = protein
                        organism = Homo sapiens
SEQUENCE: 435
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPCQEEM TKNQVSLWCL VKGFYPSDIA VEWESNGQPE NNYKTTPPVL    180
DSDGSFFLYS RLTVDKSRWQ EGNVFSCSVM HEALHNHYTQ KSLSLSLGK               229

SEQ ID NO: 436          moltype = AA  length = 229
FEATURE                 Location/Qualifiers
source                  1..229
                        mol_type = protein
                        organism = Homo sapiens
SEQUENCE: 436
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPCQEEM TKNQVSLWCL VKGFYPSDIA VEWESNGQPE NNYKTTPPVL    180
DSDGSFFLYS RLTVDKSRWQ EGNVFSCSVM HEALHNHYTQ KSLSLSLGK               229

SEQ ID NO: 437          moltype = AA  length = 357
FEATURE                 Location/Qualifiers
source                  1..357
                        mol_type = protein
                        organism = Synthetic construct
SEQUENCE: 437
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVCTLP PSQEEMTKNQ VSLSCAVKGF YPSDIAVEWE SNGQPENNYK TTPPVLDSDG    180
SFFLVSRLTV DKSRWQEGNV FSCSVMHEAL HNHYTQKSLS LSLGKGGGGS QVQLQESGGG    240
LVQTGGSLRL SCAVHGRTFS NTGMGWFRQA PGNERQFVAI ISPSGTSTYY ADSVKGRFTI    300
SRDPAKNTVY LQMNSLKMDD TAVYYCAASY GSNWSTLRHQ RRNEYDAWGQ GTQVAVS       357

SEQ ID NO: 438          moltype = AA  length = 354
FEATURE                 Location/Qualifiers
source                  1..354
                        mol_type = protein
                        organism = Synthetic construct
SEQUENCE: 438
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVYTLP PCQEEMTKNQ VSLWCLVKGF YPSDIAVEWE SNGQPENNYK TTPPVLDSDG    180
SFFLYSRLTV DKSRWQEGNV FSCSVMHEAL HNHYTQKSLS LSLGKGSQVQ LQESGGGLVQ    240
TGGSLRLSCA VHGRTFSNTG MGWFRQAPGN ERQFVAIISP SGTSTYYADS VKGRFTISRD    300
PAKNTVYLQM NSLKMDDTAV YYCAASYGSN WSTLRHQRRN EYDAWGQGTQ VAVS          354

SEQ ID NO: 439          moltype = AA  length = 349
FEATURE                 Location/Qualifiers
source                  1..349
                        mol_type = protein
                        organism = Synthetic construct
SEQUENCE: 439
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ    120
PREPQVCTLP PSQEEMTKNQ VSLSCAVKGF YPSDIAVEWE SNGQPENNYK TTPPVLDSDG    180
SFFLVSRLTV DKSRWQEGNV FSCSVMHEAL HNHYTQKSLS LSLGKGSEVQ LLESGGGLVQ    240
PGGSLRLSCA ASGFTFGNYD MAWVRQAPGK RPEWVSSIDT GGDITHYADS VKGRFTISRD    300
NAKNTLYLQM NSLRPEDTAV YWCATDEEYA LGPNEFDYYG QGTLVTVSS               349

SEQ ID NO: 440          moltype = AA  length = 355
FEATURE                 Location/Qualifiers
source                  1..355
                        mol_type = protein
```

```
                            organism = Synthetic construct
SEQUENCE: 440
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGSQV QLQESGGGLV  240
QTGGSLRLSC AVHGRTFSNT GMGWFRQAPG NERQFVAIIS PSGTSTYYAD SVKGRFTISR  300
DPAKNTVYLQ MNSLKMDDTA VYYCAASYGS NWSTLRHQRR NEYDAWGQGT QVAVS       355

SEQ ID NO: 441             moltype = AA  length = 350
FEATURE                    Location/Qualifiers
source                     1..350
                           mol_type = protein
                           organism = Synthetic construct
SEQUENCE: 441
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVCTLP PSQEEMTKNQ VSLSCAVKGF YPSDIAVEWE SNGQPENNYK TTPPVLDSDG  180
SFFLVSRLTV DKSRWQEGNV FSCSVMHEAL HNHYTQKSLS LSLGKGGSEV QLLESGGGLV  240
QPGGSLRLSC AASGFTFGNY DMAWVRQAPG KRPEWVSSID TGGDITHYAD SVKGRFTISR  300
DNAKNTLYLQ MNSLRPEDTA VYWCATDEEY ALGPNEFDYY GQGTLVTVSS            350

SEQ ID NO: 442             moltype = AA  length = 356
FEATURE                    Location/Qualifiers
source                     1..356
                           mol_type = protein
                           organism = Synthetic construct
SEQUENCE: 442
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKGGGSQ VQLQESGGGL  240
VQTGGSLRLS CAVHGRTFSN TGMGWFRQAP GNERQFVAII SPSGTSTYYA DSVKGRFTIS  300
RDPAKNTVYL QMNSLKMDDT AVYYCAASYG SNWSTLRHQR RNEYDAWGQG TQVAVS      356

SEQ ID NO: 443             moltype = AA  length = 351
FEATURE                    Location/Qualifiers
source                     1..351
                           mol_type = protein
                           organism = Synthetic construct
SEQUENCE: 443
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVCTLP PSQEEMTKNQ VSLSCAVKGF YPSDIAVEWE SNGQPENNYK TTPPVLDSDG  180
SFFLVSRLTV DKSRWQEGNV FSCSVMHEAL HNHYTQKSLS LSLGKGGGSE VQLLESGGGL  240
VQPGGSLRLS CAASGFTFGN YDMAWVRQAP GKRPEWVSSI DTGGDITHYA DSVKGRFTIS  300
RDNAKNTLYL QMNSLRPEDT AVYWCATDEE YALGPNEFDY YGQGTLVTVS S           351

SEQ ID NO: 444             moltype = AA  length = 357
FEATURE                    Location/Qualifiers
source                     1..357
                           mol_type = protein
                           organism = Synthetic construct
SEQUENCE: 444
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PCQEEMTKNQ VSLWCLVKGF YPSDIAVEWE SNGQPENNYK TTPPVLDSDG  180
SFFLYSRLTV DKSRWQEGNV FSCSVMHEAL HNHYTQKSLS LSLGKEAAAK QVQLQESGGG  240
LVQTGGSLRL SCAVHGRTFS NTGMGWFRQA PGNERQFVAI ISPSGTSTYY ADSVKGRFTI  300
SRDPAKNTVY LQMNSLKMDD TAVYYCAASY GSNWSTLRHQ RRNEYDAWGQ GTQVAVS     357

SEQ ID NO: 445             moltype = AA  length = 352
FEATURE                    Location/Qualifiers
source                     1..352
                           mol_type = protein
                           organism = Synthetic construct
SEQUENCE: 445
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVCTLP PSQEEMTKNQ VSLSCAVKGF YPSDIAVEWE SNGQPENNYK TTPPVLDSDG  180
SFFLVSRLTV DKSRWQEGNV FSCSVMHEAL HNHYTQKSLS LSLGKEAAAK EVQLLESGGG  240
LVQPGGSLRL SCAASGFTFG NYDMAWVRQA PGKRPEWVSS IDTGGDITHY ADSVKGRFTI  300
SRDNAKNTLY LQMNSLRPED TAVYWCATDE EYALGPNEFD YYGQGTLVTV SS          352

SEQ ID NO: 446             moltype = AA  length = 362
FEATURE                    Location/Qualifiers
source                     1..362
                           mol_type = protein
                           organism = Synthetic construct
```

-continued

```
SEQUENCE: 446
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKEAAAK EAAAKQVQLQ   240
ESGGGLVQTG GSLRLSCAVH GRTFSNTGMG WFRQAPGNER QFVAIISPSG TSTYYADSVK   300
GRFTISRDPA KNTVYLQMNS LKMDDTAVYY CAASYGSNWS TLRHQRRNEY DAWGQGTQVA   360
VS                                                                 362

SEQ ID NO: 447            moltype = AA   length = 357
FEATURE                   Location/Qualifiers
source                    1..357
                          mol_type = protein
                          organism = Synthetic construct
SEQUENCE: 447
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
SFFLVSRLTV DKSRWQEGNV FSCSVMHEAL HNHYTQKSLS LSLGKEAAAK EAAAKEVQLL   240
ESGGGLVQPG GSLRLSCAAS GFTFGNYDMA WVRQAPGKRP EWVSSIDTGG DITHYADSVK   300
GRFTISRDNA KNTYLYLQMNS LRPEDTAVYW CATDEEYALG PNEFDYYGQG TLVTVSS     357

SEQ ID NO: 448            moltype = AA   length = 358
FEATURE                   Location/Qualifiers
source                    1..358
                          mol_type = protein
                          organism = Synthetic construct
SEQUENCE: 448
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKGGSGG SQVQLQESGG   240
GLVQTGGSLR LSCAVHGRTF SNTGMGWFRQ APGNERQFVA IISPSGTSTY YADSVKGRFT   300
ISRDPAKNTV YLQMNSLKMD DTAVYYCAAS YGSNWSTLRH QRRNEYDAWG QGTQVAVS    358

SEQ ID NO: 449            moltype = AA   length = 353
FEATURE                   Location/Qualifiers
source                    1..353
                          mol_type = protein
                          organism = Synthetic construct
SEQUENCE: 449
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
SFFLVSRLTV DKSRWQEGNV FSCSVMHEAL HNHYTQKSLS LSLGKGGSGG SEVQLLESGG   240
GLVQPGGSLR LSCAASGFTF GNYDMAWVRQ APGKRPEWVS SIDTGGDITH YADSVKGRFT   300
ISRDNAKNTL YLQMNSLRPE DTAVYWCATD EEYALGPNEF DYYGQGTLVT VSS          353

SEQ ID NO: 450            moltype = AA   length = 352
FEATURE                   Location/Qualifiers
source                    1..352
                          mol_type = protein
                          organism = Synthetic construct
SEQUENCE: 450
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVYTLP PCQEEMTKNQ VSLWCLVKGF YPSDIAVEWE SNGQPENNYK TTPPVLDSDG   180
SFFLYSRLTV DKSRWQEGNV FSCSVMHEAL HNHYTQKSLS LSLGKQVQLQ ESGGGLVQTG   240
GSLRLSCAVH GRTFSNTGMG WFRQAPGNER QFVAIISPSG TSTYYADSVK GRFTISRDPA   300
KNTVYLQMNS LKMDDTAVYY CAASYGSNWS TLRHQRRNEY DAWGQGTQVA VS           352

SEQ ID NO: 451            moltype = AA   length = 347
FEATURE                   Location/Qualifiers
source                    1..347
                          mol_type = protein
                          organism = Synthetic construct
SEQUENCE: 451
GPPCPPCPAP EFLGGPSVFL FPPKPKDTLM ISRTPEVTCV VVDVSQEDPE VQFNWYVDGV    60
EVHNAKTKPR EEQFNSTYRV VSVLTVLHQD WLNGKEYKCK VSNKGLPSSI EKTISKAKGQ   120
PREPQVCTLP PSQEEMTKNQ VSLSCAVKGF YPSDIAVEWE SNGQPENNYK TTPPVLDSDG   180
SFFLVSRLTV DKSRWQEGNV FSCSVMHEAL HNHYTQKSLS LSLGKEVQLL ESGGGLVQPG   240
GSLRLSCAAS GFTFGNYDMA WVRQAPGKRP EWVSSIDTGG DITHYADSVK GRFTISRDNA   300
KNTLYLQMNS LRPEDTAVYW CATDEEYALG PNEFDYYGQG TLVTVSS                 347

SEQ ID NO: 452            moltype = AA   length = 4
FEATURE                   Location/Qualifiers
source                    1..4
                          mol_type = protein
                          organism = Synthetic construct
```

```
SEQUENCE: 452
GSGS                                                                   4

SEQ ID NO: 453        moltype = AA  length = 6
FEATURE               Location/Qualifiers
source                1..6
                      mol_type = protein
                      organism = Synthetic construct
SEQUENCE: 453
GGSGGS                                                                 6

SEQ ID NO: 454        moltype = AA  length = 4
FEATURE               Location/Qualifiers
source                1..4
                      mol_type = protein
                      organism = Synthetic construct
SEQUENCE: 454
GGGS                                                                   4

SEQ ID NO: 455        moltype = AA  length = 5
FEATURE               Location/Qualifiers
source                1..5
                      mol_type = protein
                      organism = Synthetic construct
SEQUENCE: 455
EAAAK                                                                  5

SEQ ID NO: 456        moltype = AA  length = 10
FEATURE               Location/Qualifiers
source                1..10
                      mol_type = protein
                      organism = Synthetic construct
SEQUENCE: 456
EAAAKEAAAK                                                             10

SEQ ID NO: 457        moltype = AA  length = 6
FEATURE               Location/Qualifiers
source                1..6
                      mol_type = protein
                      organism = Synthetic construct
SEQUENCE: 457
GGSGGS                                                                 6

SEQ ID NO: 458        moltype = AA  length = 254
FEATURE               Location/Qualifiers
source                1..254
                      mol_type = protein
                      organism = Synthetic construct
SEQUENCE: 458
EVQLLESGGG LVQPGGSLRL SCAASGFTFG NYDMAWVRQA PGKRPEWVSS IDTGGDITHY      60
ADSVKGRFTI SRDNAKNTLY LQMNSLRPED TAVYWCATDE EYALGPNEFD YYGQGTLVTV     120
SSGGGGSQVQ LQESGGGLVQ TGGSLRLSCA VHGRTFSNTG MGWFRQAPGN ERQFVAIISP     180
SGTSTYYADS VKGRFTISRD PAKNTVYLQM NSLKMDDTAV YYCAASYGSN WSTLRHQRRN     240
EYDAWGQGTQ VAVS                                                       254

SEQ ID NO: 459        moltype = AA  length = 254
FEATURE               Location/Qualifiers
source                1..254
                      mol_type = protein
                      organism = Synthetic construct
SEQUENCE: 459
EVQLLESGGG LVQPGGSLRL SCAASGFTFG NYDMAWVRQA PGKRPEWVSS IDTGGDITHY      60
ADSVKGRFTI SRDNAKNTLY LQMNSLRPED TAVYWCATDE EYALGPNEFD YYGQGTLVTV     120
SSGGGGSQVQ LQESGGGLVQ TGGSLRLSCA VHGRTFSNTG MGWFRQAPGN ERQFVAIISP     180
SGTSTYYADS VKGRFTISRD PAKNTVYLQM NSLKMDDTAV YYCAASYGSN WSTLRHQRRN     240
EYDAWGQGTQ VAVS                                                       254

SEQ ID NO: 460        moltype = AA  length = 264
FEATURE               Location/Qualifiers
source                1..264
                      mol_type = protein
                      organism = Synthetic construct
SEQUENCE: 460
EVQLLESGGG LVQPGGSLRL SCAASGFTFG NYDMAWVRQA PGKRPEWVSS IDTGGDITHY      60
ADSVKGRFTI SRDNAKNTLY LQMNSLRPED TAVYWCATDE EYALGPNEFD YYGQGTLVTV     120
SSGGGGSGGG GSGGGGSQVQ LQESGGGLVQ TGGSLRLSCA VHGRTFSNTG MGWFRQAPGN     180
ERQFVAIISP SGTSTYYADS VKGRFTISRD PAKNTVYLQM NSLKMDDTAV YYCAASYGSN     240
WSTLRHQRRN EYDAWGQGTQ VAVS                                            264
```

```
SEQ ID NO: 461          moltype = AA  length = 254
FEATURE                 Location/Qualifiers
source                  1..254
                        mol_type = protein
                        organism = Synthetic construct
SEQUENCE: 461
QVQLQESGGG LVQTGGSLRL SCAVHGRTFS NTGMGWFRQA PGNERQFVAI ISPSGTSTYY   60
ADSVKGRFTI SRDPAKNTVY LQMNSLKMDD TAVYYCAASY GSNWSTLRHQ RRNEYDAWGQ  120
GTQVAVSGGG GSEVQLLESG GGLVQPGGSL RLSCAASGFT FGNYDMAWVR QAPGKRPEWV  180
SSIDTGGDIT HYADSVKGRF TISRDNAKNT LYLQMNSLRP EDTAVYWCAT DEEYALGPNE  240
FDYYGQGTLV TVSS                                                   254

SEQ ID NO: 462          moltype = AA  length = 259
FEATURE                 Location/Qualifiers
source                  1..259
                        mol_type = protein
                        organism = Synthetic construct
SEQUENCE: 462
QVQLQESGGG LVQTGGSLRL SCAVHGRTFS NTGMGWFRQA PGNERQFVAI ISPSGTSTYY   60
ADSVKGRFTI SRDPAKNTVY LQMNSLKMDD TAVYYCAASY GSNWSTLRHQ RRNEYDAWGQ  120
GTQVAVSGGG GSGGGGSEVQ LLESGGGLVQ PGGSLRLSCA ASGFTFGNYD MAWVRQAPGK  180
RPEWVSSIDT GGDITHYADS VKGRFTISRD NAKNTLYLQM NSLRPEDTAV YWCATDEEYA  240
LGPNEFDYYG QGTLVTVSS                                              259

SEQ ID NO: 463          moltype = AA  length = 264
FEATURE                 Location/Qualifiers
source                  1..264
                        mol_type = protein
                        organism = Synthetic construct
SEQUENCE: 463
QVQLQESGGG LVQTGGSLRL SCAVHGRTFS NTGMGWFRQA PGNERQFVAI ISPSGTSTYY   60
ADSVKGRFTI SRDPAKNTVY LQMNSLKMDD TAVYYCAASY GSNWSTLRHQ RRNEYDAWGQ  120
GTQVAVSGGG GSGGGGSGGG GSEVQLLESG GGLVQPGGSL RLSCAASGFT FGNYDMAWVR  180
QAPGKRPEWV SSIDTGGDIT HYADSVKGRF TISRDNAKNT LYLQMNSLRP EDTAVYWCAT  240
DEEYALGPNE FDYYGQGTLV TVSS                                        264
```

DISPLACERS OF IGE-FCERI

CROSS-REFERENCE TO RELATED APPLICATIONS

This application is a national stage filing under 35 U.S.C. 371 of PCT/EP2023/068078, filed Jun. 30, 2023, which was published by the International Bureau in English on Jan. 4, 2024, and which claims the benefit of European Patent Application Nos. 22182630.8, filed Jul. 1, 2022, 22200911.0, filed Oct. 11, 2022, 22201172.8, filed Oct. 12, 2022, 23153730.9, filed Jan. 27, 2023, and 23153731.7, filed Jan. 27, 2023, each of which application is incorporated by reference herein in its entirety.

FIELD OF THE INVENTION

The present invention relates to single domain antibody-based constructs for treating IgE-related disorders or conditions by facilitating the dissociation of IgE from the high-affinity IgE receptor.

BACKGROUND OF THE INVENTION

Allergic diseases are inflammatory disorders with immunoglobulin E (IgE) antibodies playing a key role. IgE recognises allergens via its Fab regions, whilst its effector functions are controlled through interactions of the Fc region with two principal cell surface receptors: the high-affinity IgE receptor (FcεRI) and the low-affinity IgE receptor (FcεRII/CD23). IgE binds with high affinity (KD of 0.01 to 0.1 nM) to FcεRI at a site involving the Cε3 domain of IgE-Fc providing the basis for long-term stability on effector cells and half-life of ~10 days (Chang et al., 2000). IgE binds with much lower affinity to CD23 at a site involving both the Cε3 and Cε4 domains of IgE-Fc. Cross-linking of FcεRI-bound IgE through allergen-binding leads to the activation and degranulation of effector cells (e.g., mast cells and basophils), which triggers the release of histamine and other inflammatory mediators, and synthesis of numerous cytokines and other factors able to produce an inflammatory response. IgE also associates with CD23 located on cell types including B cells, macrophages, platelets, and epithelial cells and plays a number of roles, e.g., in the regulation of IgE synthesis, allergen transcytosis, transportation of IgE: allergen immune complexes across the gut and airways, and facilitated antigen presentation on antigen-presenting cells.

Recent insights have revealed that IgE cannot bind both types of receptors simultaneously, due to the conformational flexibility of the Cε3 domain of IgE (Holdom M., 2011, Dhaliwal et al., 2012). FcεRI binds only to IgE when the Cε3 domains has adopted a so-called "open" conformation, whereas CD23 only binds to IgE when the Cε3 domain have adopted a so-called "closed" conformation. This conformational selectivity has been further described using an engineered IgE-Fc Cε3-4 with a disulfide bond at position Cys-335 (IgE-Fc Cε3-4 335) maintaining IgE-Fc in "closed" conformation. FcεRI can bind this construct only after reduction of the disulfide bond (Wurzburg et al., 2012). Importantly, the FcεRI stabilises IgE in the open conformation, thus preventing binding of CD23 to IgE. And conversely, binding of CD23 to IgE stabilises the closed conformation, thus preventing binding of FcεRI to IgE. This makes binding of both receptors to IgE mutually exclusive and prevent overlap of the two pathways (Drinkwater et al., 2014).

IgE adopts a compact, bent conformation which was evident from the crystal structure of IgE Fc Cε2-Cε4 (PDB: 2WQR) showing the backfolding of the Cε2 domains with extensive contacts to the Cε3 and even Cε4 domains. However, molecular dynamics simulations and biophysical studies revealed a transiently extended conformation with the Cε2 domains "flipping" from one side to the other. Furthermore, this energetically less favoured extended conformation was recently stabilised by two anti-IgE Fab fragments resulting in FcεRI inhibition, revealing a potentially new mode of action for anti-IgE molecules (Drinkwater et al., 2014).

However, there is only one therapeutic anti-IgE antibody (Omalizumab, Xolair® marketed by Novartis/Genentech) approved for the treatment of allergic conditions including asthma, nasal polyps and chronic spontaneous urticaria (CSU). It is a humanised monoclonal IgG1 antibody binding to the Cε3 domain of free IgE and thereby inhibiting the IgE binding to both the FcεRI and CD23. Thus, the binding of circulating IgE to both the FcεRI receptor and CD23 receptor is impaired. Omalizumab presents with several drawbacks, including frequent administration (e.g., every 2-4 weeks), need of injection of high volumes, immunogenicity, and immune complex formation. Since Omalizumab only addresses free IgE, the treatment with Omalizumab might not effectively prevent all types of allergic reactions, such as anaphylactic reactions. It has been shown that even trace amounts of allergen specific IgE bound to FcεRIs can cause cellular degranulation of, e.g., mast cells, and lead to significant allergic reactions.

The concept of specifically targeting IgE as a therapeutic concept has gained a lot of interest in recent years. For example, it has been found that certain antibodies and antibody-mimetics are able to displace bound IgE from FcεRI and CD23. In other words, these antibodies would be able to disrupt IgE:FcεRI complexes (Balbino et al., 2018).

DARPins™ are small and highly stable non-antibody protein scaffolds. Some anti-IgE DARPins have the advantage that they not only neutralise free IgE but also actively disrupt preformed IgE:FcεRI complexes through a facilitated dissociation mechanism. In comparison to Omalizumab, which has a poor displacement activity, the anti-IgE DARPins has been shown to be 10,000-fold more efficient than Omalizumab in both in vitro and ex vivo studies (Kim B et al., 2012 and Baumann, M. J. 2010).

Biparatopic (bi-specific) anti-IgE DARPins engineered by linking two different anti-IgE DARPins (e.g., DARPin bi53_79) have been shown to be more effective than single epitope binding DARPins (Eggel et al., 2014) and lately, Pennington et al. have reported about the highly displacement, fast-acting anti-IgE DARPin molecule (KIH_E07_79) with the potential to treat anaphylaxis and rapidly desensitising allergic individuals without the risk of incurring anaphylactogenic activity (Pennington et al. 2021). The fast-acting anti-IgE DARPin (KIH_E07_79) is IgG1-Fc fused to biparatopic DARPins, via a short peptide linker using the knobs-into-holes mutation strategy. The international patent application WO2022/061240 discloses fast-acting anti-IgE DARPins with displacement activity.

Single-domain antibodies (sdAbs), also known under the name Nanobodies®, are the antigen-binding moieties (VHH) of heavy chain antibodies occurring in camelid species and cartilaginous fishes. SdAb 026 is a llama-derived, humanised sdAb described in the international patent applications WO2012/175740 and WO2014/087010.

The sdAb 026 has been shown to accelerate the dissociation of IgE from FcεRI and CD23 by binding to an epitope within the IgE-Fc domains similar to the CD23 binding site which does not significantly overlap with the FcεRI-binding site. The sdAb 026 inhibits the interaction of IgE with FcεRI by trapping IgE-Fc in a closed conformation mimicking CD23 binding (Jabs et al., 2018). A bispecific sdAb (ALX-0962) targeting IgE as well as human serum albumin to obtain plasma half-life extension has been reported to have dual mode anti-IgE action by neutralisation of soluble (free) IgE with a higher potency than Omalizumab and by binding and displacement of preformed IgE:FcεRI complexes on basophils (Rinaldi et al., 2014).

Further anti-IgE sdAbs are disclosed in the patent applications WO2004/041867, WO2020/208177, CN113461823 and CN111875706.

The present inventors address the unmet clinical need for new treatment and prevention options for allergic diseases, in particular to provide fast-acting anti-IgE constructs.

SUMMARY OF THE INVENTION

The present inventors have found that highly potent anti-IgE construct can be provided by combining at least one single domain antibody (sdAb) with modest ability to displace IgE from its high affinity receptor with another sdAb able to bind IgE but without displacement activity or with low displacement activity. Such combinations of sdAbs have improved displacement activity even when provided as simple mixtures of individual sdAbs. Highly potent displacers can be provided by linking the two sdAbs, either by use of short peptide chains or as Fc-fusion proteins. Methods for providing novel sdAbs with IgE binding activity or displacement activity are demonstrated in examples 1 and 2 and their ability, either alone or in combination with another sdAb, to displace IgE from its high affinity receptor are evaluated by use of a simple ELISA assay (example 6) and results are listed in table 15 of example 6. Notably, with a very few exceptions, the combined sdAbs exhibit improved displacement activity compared to either or the two sdAbs in the combination. Interestingly, the present inventors have made it possible to obtain high and fast displacement activity by incorporation the combined sdAbs into a multi-specific construct with the structural elements shown in FIG. 1 and by use of various linking moieties that might provide, to a various degree, constraint on the free mobility or orientation of each of the two sdAbs. Importantly, the displacement activity can simply be addressed by using ELISA assay, commonly known to the skilled person and therefore it can easily be assessed whether sdAbs with IgE binding affinity can be used in constructs disclosed herein. Further, the present inventors have evaluated the anaphylactogenic activity in vitro as well as in murine models.

In a first aspect the present invention relates to a multi-specific construct comprising a. a first single domain antibody (sdAb) able to displace bound IgE from FcεRI, b. a second sdAb that binds to IgE, c. a moiety that links the first and second sdAb, wherein the first and second sdAb bind non-identical epitopes of IgE, and the multi-specific construct can displace bound IgE from the IgE high-affinity receptor (FcεRI) with improved displacement activity compared to the first or second sdAb.

In a first aspect of the present invention, the multi-specific construct may be a Fc-fusion protein. Thus, moiety c) may be an Fc of an immunoglobulin antibody with the Fc domain directly linked or linked via a linker (simple peptide chain) to the first and second sdAb.

A second aspect relates to novel monomeric sdAbs able to bind to IgE antibodies, and which are eligible for being used in the multi-specific construct of the first aspect. Such sdAbs may have a displacement activity on their own or may facilitate displacement activity in combination with another sdAb. Exemplary monomeric sdAbs are listed in Table 1 (full length amino acid sequence, camelid version) and Tables 2a-d show the complementarity determining regions (CDRs), CDR1, CDR2 and CDR3 regions of each of the novel monomeric sdAbs. Several methods may be applied for determining CDR regions and the resulting CDR region may depend on the method. Tables 2a-d shows the CDRs of novel sdAbs according to Aho, Kabat, Chotia or IMGT determination schemes.

When using the Aho method for determining CDR regions, exemplary monomeric sdAbs might in a second aspect comprise a combination of CDR1, CDR2, and CDR3 having the respective SEQ ID NOS:

6, 7, and 8; 10, 11, and 12; 14, 15, and 16; 18, 19, and 20; 22, 23, and 24; 26, 27, and 28; 30, 31, and 32; 34, 35, and 36; 38, 39, and 40; 42, 43, and 44; 46, 47, and 48; 50, 51, and 52; 54, 55, and 56; 58, 59, and 60; 62, 63, and 64; 66, 67, and 68; 70, 71, and 72; or 74, 75, and 76, wherein each CDR1 may contain 1, 2, or 3 amino acid substitutions, each CDR2 may contain 1, 2, or 3 amino acid substitutions and/or each CDR3 may contain 1, 2, or 3 amino acid substitutions.

A third aspect relates to a pharmaceutical composition comprising a multi-specific construct of the first aspect and any embodiments thereof disclosed herein, or to a pharmaceutical composition comprising one or more monomeric sdAbs of the second aspect and any embodiments thereof disclosed herein, wherein the pharmaceutical composition comprises a pharmaceutically acceptable carrier and/or vehicle and/or diluent and/or excipient.

A still further aspect relates to a method for treatment or prevention of an IgE-related disease or condition, the method comprising administering an effective amount of a) the multi-specific construct of a first aspect of the invention and any embodiments thereof disclosed herein, b) one or more monomeric sdAbs of a second aspect of the invention and any embodiments thereof disclosed herein or c) the pharmaceutical composition of a third aspect of the invention and any embodiments thereof disclosed herein.

A still further aspect relates to a) the multi-specific construct of the first aspect of the invention and any embodiments thereof disclosed herein, b) one or more monomeric sdAbs of the second aspect of the invention and any embodiments thereof disclosed herein or c) the pharmaceutical composition of the third aspect of the invention and any embodiments thereof disclosed herein for use as a medicament, preferably for use in anti-IgE therapy, such as for use in the treatment or prevention of an IgE-related disease or condition.

A still further aspect relates to the use of multi-specific construct of the first aspect of the invention and any embodiments thereof disclosed herein, one or more monomeric sdAbs of the second aspect of the invention and any embodiments thereof disclosed herein or the pharmaceutical composition of the third aspect of the invention and any embodiments thereof disclosed herein in the manufacture of a medicament, such as a medicament for use in anti-IgE therapy or in the treatment or prevention of an IgE related disease or condition.

LEGENDS TO THE FIGURES

FIG. 1 shows an outline of non-limiting examples of various types of multi-specific constructs of the invention including their components. i) an sdAb monomer, either (a) or (b) as described herein. ii) multimeric construct comprising a first sdAb (a) and a second sdAb (b) fused by a moiety (c), which may be a peptide linker (also herein named as a "dimer". iii) a multimeric construct comprising a first sdAb (a) and a second sdAb (b) fused to the same site of (optional via a linker) a moiety (c) which may be a Fc domain. iv) a multimeric construct similar to iii), but where (a) and (b) are fused on the opposite sites of the moiety (c).

FIG. 2 shows sdAb library selection against IgE-Fc Cε2-Cε4 and IgE-Fc Cε2-Cε4/FcεRIα complex. A) The library was incubated with 1 UM IgE-Fc Cε2-Cε4 and analysed by FACS using two parameters (sdAb expression and IgE-Fc binding) to control sdAb expression and IgE-Fc binding before starting selection. First round of selection was performed by MACS with 1 μM biotinylated IgE-Fc Cε2-Cε4. B) Second round of selection performed with 200 nM IgE-Fc Cε2-Cε4 by FACS using 2 parameters (sdAb expression and IgE-Fc binding). Positive populations on both expression and IgE-Fc binding are selected in gate C. C) Alternative, the second round of selection was performed with 200 nM complex IgE-Fc Cε2-Cε4/FcεRIα by FACS using 3 parameters (sdAb expression, Streptavidin for IgE-Fc binding, anti-FcεRIα). A large positive population was visible on both expression and IgE-Fc binding. This population can be discriminated in 3 populations when anti-FcεRIα signal is used. Potential displacement sdAb are selected within the IgE-Fc+/FcεRIα− population using gate E.

FIG. 3: Shows the relative epitope mapping matrix, wherein the combined binding to the same IgE-Fc of different pairs of two sdAbs is evaluated. Dark grey colouring indicates concomitant binding of two sdAbs, and thus binding to distinct epitopes of IgE-FC, whereas white colouring indicates no binding. Light grey colouring indicates potential concomitant binding of two sdAbs, but with inconclusive results due to low affinity.

FIG. 4 shows example of deep mutational scanning matrixes of sdAb A1 for the purpose of improving the binding affinity to IgE-Fc or displacement activity. Positive and negative populations sequencing data analysis. Numerical values are enrichment values (Enrichment=Frequency of the mutant after selection/Frequency before selection), "D" means that the mutant is depleted upon selection. Matrix is coloured in a gray scale proportional to enrichment values. Mutations improving A1 binding/activity are enriched in the A1 positive population and should be depleted or with an enrichment <1 in the A1 negative population. Three mutations of interest improving A1 binding toward IgE-Fc (T28R, P45Y and V93E) are shown in the white box.

FIG. 5 shows inhibition of allergen-induced activation of basophils after in-vitro treatment A) Shows inhibition of allergen-induced activation of basophils in PBMC isolated from HDM allergic donor using monomeric sdAb A1 in a concentration of 1 μM (Black dot: buffer, black triangle: sdAb A1, light grey square: KIH-E07_79). B) Shows inhibition of allergen-induced activation of basophils in PBMC isolated from HDM allergic donor, using monomeric sdAb A2 or mixes of two different monomeric sdAbs in a concentration of 1 μM (Black dot: buffer, grey square: A2, white dot: B1, cross: B3, black triangle A1, white rhombus: A2+B1, white triangle: A2+B2, black triangle: A2+B3). C) Shows inhibition of a-IgE induced activation of basophils in PBMC isolated from HDM allergic donor using monomeric sdAb A2 or mixes of two different monomeric sdAbs in a concentration of 1 μM (Black dot: buffer, grey square: A2, white dot: B1, cross: B3, black triangle A1, white rhombus: A2+B1, white triangle: A2+B2, black triangle: A2+B3). D) Shows inhibition of allergen-induced or a-IgE-induced activation of basophils in PBMC isolated from HDM allergic donor 83 (Black dot: buffer, grey triangle CIgG4B1A1 (G4S)1 10 nM, light grey square: CIgG4B1A1(G4S)1 10000 nM). E) Shows inhibition of allergen-induced or a-IgE-induced activation of basophils in whole blood HDM allergic donor 220 (Black dot: buffer, grey triangle CIgG4B1A1(G4S)1 50 nM, light grey square: CIgG4B1A1 (G4S)1 500 nM). F) Shows inhibition of allergen-induced or a-IgE-induced activation of basophils in whole blood from Birch allergic donor 187 (Black dot: buffer, grey triangle CIgG4B1A1(G4S)1 50 nM, light grey square: CIgG4B1A1 (G4S)1 500 nM). (Y-axis: % CD63 pos basophils, X-axis left: rDerp2/a-IgE/Betv1 ng/ml)

FIG. 6 relates to the inhibition/prevention of anaphylaxis in a murine model of passive systemic anaphylaxis by treatment with the IgG4 Fc-fusion construct comprising the two sdAbs A1 and B1, each linked to the C-terminus of the Fc domain of IgG4 with peptide linker G4S (CIgG4B1A1 (G4S)1). A) Shows the schematic outline of the experimental setup of the performed passive systemic anaphylaxis assay: i) Mice expressing the human FcεRIα chain were sensitised with a mix of three human anti-Der p 2 antibodies, ii) intraperitoneal (i.p.) injected with CIgG4B1A1(G4S)1 and iii) challenged by i.p. injection of rDer p 2 four hours later. Body temperatures as a measure of anaphylaxis severity were measured for one hour after CIgG4B1A1(G4S)1 injection and for 90 min at challenge. At termination, blood was collected to determine serum mast cell protease levels as a secondary readout for anaphylaxis severity. B) Shows the body temperature change upon injection with sterile PBS or different concentrations of CIgG4B1A1(G4S)1 (Y-axis shows temperature in ° C. Black dot is PBS, white circle: 2352.6 ug, white square: 156.8 ug, white triangle point up: 31.4, white rhombus: 6.3 ug and white triangle point down: 1.3 ug). C) shows the body temperature change after challenge with rDer p 2 and injection of sterile PBS or different concentrations of CIgG4B1A1(G4S)1 (Y-axis shows temperature in ° C. black dot is PBS, white square: 156.8 ug, white triangle point up: 31.4, white rhombus: 6.3 ug and white triangle point down: 1.3 ug). D) Shows the mean area under the curve values for body temperature changes after challenge per inhibitor concentration tested (Y-axis: delta-body temp AUC. Black dot: PBS, white square: CIgG4B1A1(G4S)1). E) Shows the mean serum mMCPT1 concentrations 90 minutes after challenge per inhibitor concentration tested (Y-axis: delta-body temp AUC. Black dot: PBS, white square: CIgG4B1A1(G4S)1). Data are shown as mean±SEM; *: P≤0.05; : P≤0.01; *: P≤0.001; ****: P≤0.0001 compared to PBS control.

FIG. 7 shows inhibition/prevention of anaphylaxis in a murine model of passive systemic anaphylaxis by treatment with three different IgG4 Fc-fusion constructs with the sdAb A1 combined with either D2, E1 or F4, each linked to the C-terminus of the Fc domain of IgG4 with one or two iterations of peptide linker G4S. A) Body temperature change upon injection with sterile PBS or a IgG4 Fc-fusion construct. B) Body temperature change after challenge with rDer p 2, with mean area under the curve values for body temperature changes and mean serum mMCPT1 concentrations 90 minutes after challenge per construct tested. Data are shown as mean±SEM; *: P≤0.05; : P≤0.01; *: P≤0.001 compared to PBS control (black dot: PBS, white square: CIgG4D2A1(G4S)2, white triangle: CIgG4E1A1 (G4S)2, white rhombus: CIgG4F4A1(G4S)2), A+B-left: Y axis is delta-body-temp, x-axis is time post challenge in minutes).

FIG. 8 shows anaphylactogenicity testing in both the PSA murine model and a version of the PCA murine model, using the IgG4 Fc-fusion construct with the sdAbs A1 and B1 each linked to the N- or C-terminus of the Fc domain of IgG4 with three iterations of the peptide linker G4S (C/NIgG4B1A1 (G4S)3). A) Body temperature change upon injection with sterile PBS or either inhibitor, with mean area under the curve values for body temperature changes. B) Schematic showing the experimental setup of the performed passive cutaneous anaphylaxis assay for anaphylactogenicity testing: i) Mice expressing the human FcεRIα chain were sensitised intradermally (i.d.) with a mix of three human anti-Der p 2 antibodies, ii) i.d. injected with PBS or NIgG4B1A1(G4S)3 and Evan's Blue dye intravenously, iii) terminated 30 min after injection for measurement of dye extravasation area and dye extraction from the skin. C) Area of dye extravasation into the sensitized section of skin at 30 min after inhibitor+dye injection, and optical density of the dye after extraction from the skin sections. Data are shown as mean±SEM; *: P≤0.05; **: P≤0.01 (dot: PBS, Square: CIgG4B1A1(G4S)3, triangle: NIgG4B1A1(G4S)3).

FIG. 9 shows anaphylactogenicity and IgE displacement as evaluated by in-vitro stimulation of human basophils from two independent allergic donors. CD63 activated basophils in Heparinized whole blood were incubated with IgG4 Fc-fusion constructs in concentrations ranging from 0.1 nM to 1 μM. Donor 1 FIG. 9A and donor 2 FIG. 9B. (Figure A+D-Y-axis: % IgE displaced from basophils, Figure B+C-Y-axis: % CD63+ cells, X-axis: sdAb concentration (nM), Black dot: CIgG4B1A1(G4S)1, white square: CIgG4B1A1 (G4S)2, white triangle CIgG4B1A1(G4S)3, black triangle CIgG4B1A1 (RS), light grey square: NIgG4B1A1 (G4S), black cross: KIH-E07_79).

DETAILED DISCLOSURE OF THE INVENTION

Definitions

The term a "multi-specific construct" is meant to define a compound, molecule or complex which can bind at least two distinct epitopes on IgE, in particular to one and the same IgE antibody. Thus, the wording multi-specific is meant to indicate that the construct is able to bind more than one epitope of an antigen and thus being paratopic. When the construct is able to bind two distinct IgE epitopes, the construct might be named bispecific construct. In the present context, the at least two distinct epitopes are preferably present outside the antigen-binding regions of IgE, such as on IgE-Fc. It will hence be understood that in the present context, a multi-specific construct is not one that binds several different antigens but is able to bind the same antigen (IgE) at several distinct surface exposed sites typically found in the Fc part of IgE. However, a multi-specific construct may be able to interfere with other biological targets. By example can be mentioned constructs comprising an Fc domain able to bind or interfere with other targets than IgE. The phrase "the multi-specific construct can displace bound IgE from the IgE high-affinity receptor (FcεRI receptor)" is meant to define that the multi-specific construct is able to enhance the dissociation of IgE from the FcεRI by, for example facilitated dissociation mechanism, conformational change, and/or sterical hindrance.

The term "displacement activity" or "displacement effect" are interchangeable terms, all meant to define the ability of a compound (such as either monomeric sdAbs, combined sdAbs, linked sdAbs, or compounds comprising sdAbs such as multi-specific constructs as described herein) to displace IgE from its high affinity receptor FcεRI. The ability of such test compounds to displace bound IgE from FcεRI may be evaluated by use of an ELISA-based IgE-FcεRIα displacement assay as described in Example 6 herein. In brief, the assay is based on measuring remaining IgE, which is not removed from immobilised recombinant human FcεRIα pre-loaded with IgE upon addition of a test compound (e.g., an sdAb or multi-specific construct described herein. The test result may be provided as the percent displacement effect calculated as the relative reduction in signal compared to a control with no test compound added and the test compound might be applied in various concentrations. Then the concentration providing half displacement effect may be determined ($EC_{50}$ for displacement effect, i.e., $EC_{50}$ is the molar concentration of the test compound able to dissociate 50% of the IgE preloaded to FcεRIα receptor). In addition, the displacement activity might be evaluated by determining the percentage of IgE that maximally can be dissociated from the pool of IgE preloaded to FcεRIα receptor (maximal displacement activity) and to which extent maximal effect is achieved (100% of the preloaded IgE is dissociated).

The displacement activity may also be evaluated by other assay types, in vitro or ex-vivo assay, as well as in-vivo murine models may be used for evaluation of displacement activity. Such methods are known to the skilled person in the art (Eggel et al., 2014, Pennington et al., 2021 and Jabs et al., 2018).

The displacement effect may be compared to known displacers (comparator displacer), such as sdAb 026 mentioned in patent application WO2012/175740 and herein named (A1) or the Darpin-based construct, KIH_E7_79 (Pennington et al., 2021, and in the patent application WO2022/061240).

A "single-domain antibody" (sdAb) which may be termed "nanobody", is an antibody fragment in the form of a single monomeric variable antibody domain that is able to bind selectively to a specific antigen. Conventionally, an sdAb is a fragment of a heavy chain-only antibody comprising the antibody's VH domain. SdAbs bind antigens using only three complementarity-determining regions (CDR1, CDR2 and CDR3) rather than the six present in conventional VH:VL antibodies. However, an sdAb can also in some cases be derived from a common antibody such as IgG, but this approach requires abrogation of the natural dimerisation of VH and VL domains by amino acid substitution, meaning that antigen affinity is often compromised. Typically, sdAbs are relatively short, such as 100-130 amino acid residues.

Further, sdAbs are antibodies whose CDRs are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. SdAbs may be derived from any species including, but not limited to mouse, human, camel, llama, goat, rabbit, and/or bovine.

In some embodiments, an sdAb as used herein is the variable domain derived from a naturally occurring heavy chain antibody devoid of light chains. For clarity reasons, this variable domain derived from a heavy chain only antibody is known as a VHH domain to distinguish it from the conventional VH of four chain immunoglobulins. In here, the term sdAb is interchangeable with an VHH antibody. When the sdAb is part of a fusion protein/fusion construct, the term sdAb may be interchangeable with VHH domain. Such a VHH domain can be derived from antibodies raised in animals able to produce heavy chain only antibodies. By example are Camelidae species, e.g., camel, llama, dromedary, alpaca and guanaco. Other species besides Camelidae may produce heavy chain only antibodies and such VHHs are within the scope of the disclosure. Therefore, in any construct described herein, wherein an sdAb is part of a larger construct, the term sdAb is exchangeable with the term VHH.

A binding region of an sdAb herein is meant to include one or more or all the three complementarity-determining regions (CDR1, CDR2 and CDR3).

A "complementarity-determining region" or "CDR", is a variable part of an antibody, including sdAbs and thus crucial to the diversity. Not all residues in the CDRs might be responsible for epitope binding. Ex. cysteines in CDR1 and CDR3 of sdAbs are determining for the structure (Pellis et al., 2012)

As previously described, sdAbs and VHH are used interchangeably herein. In some embodiments, an sdAb comprises three CDRs and four framework regions (FRs), arranged in the following order: FR1, CDR1, FR2, CDR2, FR3, CDR3 and FR4. In some embodiments, an sdAb may be truncated at the N-terminus or C-terminus such that it comprises only a partial FR1 and/or FR4, or lacks one or both of those FRs, so long as the VHH/sdAb substantially maintains the desired antigen binding and specificity.

As previously described, the main purpose of CDR regions is to define the regions having specificity to an epitope. However, not all residues in the CDRs might be responsible for epitope binding but might merely determine structural elements (Wilton E. et al 2018 ref 6). In addition, the FRs might not exclusively responsible for the structure as residues of the FRs adjacent to CDRs can influence binding.

Different methods can be applied for determination of the position of the different frameworks and CDR regions of an sdAb.

One method is the "Kabat numbering scheme" or "Kabat", first described by American scientist Elvis Kabat. Here amino acid residues of an immunoglobulin single variable domain can be numbered according to the general numbering of VH domains given by Kabat et al. and applied to VHH domains from camelids as described in the by Riechmann and Muyldemans (Riechmann and Muyldemans, 1999).

In CDR determination according to Kabat, FR1 of a VHH comprises the amino acids residues at position 1-30, CDR1 of a VHH comprises the amino acids residues at position 31-35, FR2 of a VHH comprises the amino acid position 36-49, CDR2 of a VHH comprises the amino acid residues of position 50-65, FR3 of a VHH comprises the amino acids residues at position 66-94, CDR3 of a VHH comprises the amino acid residues at position 95-102, and FR4 of a VHH comprises the amino acid residues at position 103-113.

It should be noted that—as is well known in the art for VH domains and for VHH domains—the total number of amino acid residues in each of the CDRs may vary and may not correspond to the total number of amino acid residues indicated by the Kabat numbering. That is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain may typically be in the range of from 110 to 120, often between 112 and 115. It should however be noted that smaller and longer sequences may also be suitable for the purposes described herein.

Another method for determining CDR regions in VHH is by Chothia numbering scheme. Here amino acid residues of an immunoglobulin single variable domain can be numbered using conserved amino acids, which always have the same position (Dondelinger M et al., 2018).

A further method for determining CDR regions in VHH is by IMGT. Here amino acid residues of an immunoglobulin single variable domain can be numbered using conserved amino acids, which always have the same position. For instance, Cysteine 23, Tryptophane 41, Leucine 89, Cysteine 104. FR1 of a VHH comprises the amino acids residues at position 1-26, CDR1 of a VHH comprises the amino acids residues at position 27-38, FR2 of a VHH comprises the amino acid position 39-55, CDR2 of a VHH comprises the amino acid residues of position 56-65, FR3 of a VHH comprises the amino acids residues at position 66-104, CDR3 of a VHH comprises the amino acid residues at position 105-117, and FR4 of a VHH comprises the amino acid residues at position 118 and the rest of the sequence. The maximum length of CDR is as defined above. For shorter CDRs, gaps are created (Lefranc et al., 2002).

Alternatively, the CDR regions in an sdAb can be determined by using the AbM numbering as described in Kontermann and Dubel (Eds. 2010, Antibody Engineering, vol 2, Springer Verlag Heidelberg Berlin, Martin, Chapter 3, pp. 33-51). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

A further method for determining the CDR regions in an sdAb is by using the Aho numbering scheme (Mitchelle & Colwell, 2017 and Honegger & Pluckthun et al., 2001).

Another alternative for determining CDR regions in VHH is using sdAb-DB described by Emily Wilton in 2018. The method is built on a set of sequence-based rules for identifying CDRs in light and heavy chains of conventional antibodies by Pantazes and Maranas (Wilton E et al 2018 SyntheticBioloogy) and adopted to sdAbs. In sdAb-DB, CDR1 starts 4 residues after the first cysteine, with a length of 6-15 residues followed by a W. CDR2 starts 10-20 residues after end of CDR1 and following sequence [I/L/V/M]-[G/A/S]. The length of CDR2 is 8-15 residues and is followed by the sequence [Y/F/I/L/T/N/S/V/H]-X-X-X-[A/I/L/M/V]-[Q/K/R/A/E/G/L/T]. CDR3 is located 30-50 residues after end of CDR2 and following the sequence C-X-X. The length is 3-25 amino acids and is followed by the sequence [W/A/E/F/H/K/L/Q/Y/G/S/R]-[G/S]-X-G-X-X-X-T-V-S. The all the sequences, "X" can be any amino acid.

Alternative CDR definitions of interest include, without limitation, Ofran et al., Almagro J C (Ofran et al. 2001, Almagro J C 2004), each of which is herein specifically incorporated by reference.

An "antibody", which is also termed an "immunoglobulin", is a protein, which in humans consists of pairwise identical light chains and heavy chains, where the heavy and light chains each comprise a variable domain and a constant region, wherein the variable domains are responsible for the antibody's specific binding to an antigen. Generally, antibodies are grouped into the immunoglobulin isotypes IgA, IgD, IgE, IgG and IgM, which each play different roles as antigen-recognizing agents in the immune system. The specificity for antigen binding of an antibody is determined by variable regions in the variable domains, and in particular by the complementarity determining-regions (CDRs) in the variable domains. Generally, antibodies are molecules, which in principle or in practice can be expressed in its natural conformation in an animal, meaning that the expressed antibody includes all structural elements found in a naturally occurring immunoglobulin.

An "antibody variant" is a protein derived from an antibody, which has the same binding specificity as an antibody, but which would not be a natural expression product in a mammal. As such, the term refers to various fragments of antibodies as well as artificial antibody analogue formats. Also, the term denotes antibody formats that are found in nature, but which are uncommon among mammals, such as heavy-chain antibodies and IgY found in birds and reptiles, but where CDRs from mammalian antibodies or combinatorically produced antibodies have been engineered into an antibody format from which it is not originally derived.

A "heavy chain-only antibody" is an antibody format naturally found in camelids (such as camels, dromedaries, llamas, and alpacas) or in cartilaginous fish (such a sharks, skates, rays, sawfish etc.) and consists of only two heavy chains lacking the two light chains.

The term "Anaphylactogenic" is in here used to describe an effect of a molecule able to activate effector cells like basophils and mast cells to cause degranulation (histamine release) without the presence of an allergen. An example is the multi-specific construct NIgG4B1A1(G4S)1 shown in Example 10, or NIgG4B1A1(G4S)3, which in a murine anaphylaxis model (Example 9) was shown to activate basophils on its own.

The term "IgE binding affinity" is meant to designate the affinity for a test compound (such as sdAbs and multi-specific constructs disclosed herein) to bind free IgE. The ability of a test compound to bind free IgE may be tested by use of the bio-layer interferometry (BLI) as described in Example 5 herein. In short, this assay measures the association and the dissociation of the test molecule to IgE, or alternatively to IgE-Fc. Based on these measurements, the $k_{on}$, $k_{off}$, ratio $k_{off}/k_{on}$ ($=K_D$) may be determined. $k_{on}$ is a constant used to characterise how quickly the test molecule binds to IgE, whereas $k_{off}$ characterises how quickly the test molecule dissociates from IgE. The ratio of $k_{off}/k_{on}$ results in the equilibrium dissociation constant $K_D$. The lower the $K_D$ value the higher the affinity of the test molecule to IgE. In interesting embodiments, monomer sdAbs exhibit improved IgE binding affinity (lower $K_D$ value) and improved maximal effect compared to known IgE binders (comparator IgE binders), such as sdAb 026 (A1). In still other interesting embodiments, the multi-specific constructs (including double sdAbs linked by a peptide linker) exhibit improved IgE binding affinity compared to DARPin KIH-E7_79 or a construct comprising two sdAbs 026 (A1) linked together with a peptide linker. It is envisaged that in other embodiments, the IgE binding affinity may be lower than the comparators. Generally, $K_D$ values in the nanomolar range may be desirable, such as particularly in the low nM affinity range, such as below $3 \times 10^{-10}$ M. Other IgE affinity binding assays can be used and are known to the skilled person in the art.

The term "IgE-related disease or condition" is meant to encompass any disease or condition which will benefit from reducing receptor bound IgE and/or reducing levels of free circulating IgE. Such conditions may also be termed IgE-mediated diseases or conditions. Examples of such specific diseases include allergic diseases including type-I allergic diseases, in particularly allergic diseases with severe allergic symptoms (asthma, atopic dermatitis, urticaria) or where the allergic response develops fast (e.g., anaphylaxis). The term "allergic disease" is known in the art of medicine. In particular, the term allergic disease is meant to be characterised by an allergic and/or atopic immunological reaction to an antigen, such as an allergen, which results in allergic and/or atopic symptoms in the patient suffering from allergic disease. An allergic disease often is typically characterised by the generation of antigen specific IgE antibodies and might be the resultant biological effect of the IgE antibodies.

SPECIFIC EMBODIMENTS OF THE INVENTION

SdAbs/VHH Domains

The present invention provides novel VHH domains (sdAbs) able to bind IgE, which are applicable for being used in the first and second aspects disclosed herein as well as further aspects disclosed herein.

The VHH domain may be expressed as monomeric sdAbs or be incorporated into a larger construct (e.g., be part of a polypeptide/protein construct/fusion protein). Two or more different VHH domains may be expressed as individual monomeric sdAbs, which may further be linked to provide dimers or multimeric sdAbs to form multi-specific constructs. Two or more VHH domains may be incorporated into a larger construct (e.g., be part of a polypeptide/protein construct/fusion protein). The sdAbs may have a displacement activity on their own or may facilitate displacement activity in combination with another sdAb. Of interest are sdAbs which are eligible for being combined in a multi-specific construct described herein or alternatively be combined in any other design that provide the desired displacement activity.

Of interest are monomeric sdAbs exhibiting displacement activity on their own and preferably with improved displacement activity (lower $EC_{50}$ and/or higher maximal effect) compared to the known displacers, e.g., sdAb 026. Such sdAbs exhibiting displacement activity might be used as a first sdAb in multi-specific constructs described herein. In still interesting embodiments, the multi-specific constructs (including double sdAbs linked by a peptide linker) exhibit similar or improved displacement activity (lower $EC_{50}$ and/or higher maximal effect) to the DARPin KIH-E7_79 or alternatively to monomeric sdAb 026, dimeric sdAb 026 (two sdAb 026 linked via peptide linker) or Fc-fusion construct with two sdAb 026 (bivalent construct).

A monomeric sdAb (or in the alternative "a VHH domain") of the present invention may be obtained as a fragment of an antibody obtained from camelids immunised with full-length human IgE or a portion of the IgE, such as IgE-Fc Cε3-Cε4, IgE-Fc Cε2-Cε4, a mutated version of IgE-Fc Cε3-Cε4 (i.e. IgE-Fc Cε3-Cε4 335), where an additional cysteine residue at position 335 is incorporated in order to build an artificial disulphide bridge between the two chains to obtain IgE in a closed formation, or any combination thereof. Such camelid monomeric sdAbs may be subject to further affinity maturation, humanisation or other sequence variation to obtain sdAbs with desirable properties.

Monomeric sdAbs may bind to an IgE epitope outside the variable domain of IgE, such as particularly in the Fc region of IgE, such as in the IgE-Fc Cε2-Cε4. Of interest are sdAbs that displace the binding of IgE to FcεRI and/or having a high binding affinity to IgE. However, it is not excluded that a monomeric sdAb (e.g., the second sdAb) disclosed herein can bind to the CL domain in IgE.

The IgE binding region of the sdAbs comprises CDRs, which are the specific region where an sdAb typically bind its targets. In a single sdAb, three CDRs are present, CDR1, CDR2 and CDR3, and one or more of the CDRs may in combination be the key responsible for the activity of an sdAb. The individual CDR regions can be determined through different methods, including Aho, Kabat or AbM as previous described.

Exemplary novel monomeric sdAbs able to bind IgE are shown in Table 1 and are named A2, B1, B2, B3, D1, D2, D3, E1, E2, E3, E4, F1, F2, F3, F4, F5, F6 and G1, respectively. As shown by the ELISA-based IgE-FcεRIα displacement assay, only the sdAbs named A2 and B1 turned out to exhibit displacement activity (Example 6, table 15). A2 is a mutant of sdAb 026 (herein named A1) and exhibit lower $EC_{50}$ displacement activity than the comparator A1, while maintaining a maximal activity above 90%. SdAb B1 also exhibited improved displacement activity with lower $EC_{50}$ than the comparator A1 but could only displace 60% of the pre-loaded IgE (maximal displacement effect achieved at 60% dissociation of IgE). Therefore, B1 may be regarded as less preferably than A1 and A2 for use as a first sdAb in multi-specific constructs described herein. As shown in Example 6 (table 15), the novel sdAbs without displacement activity or with poor displacement activity (as for B1) might successfully be used as a second sdAb of multi-specific construct herein to obtain compounds with high displacement activity.

Table 1 provides the full-length amino acid sequences of the monomeric sdAbs (camelid version) and with the information about which IgE construct that has been used for immunisation.

Table 1 shows the full-length amino acid sequence of monomeric sdAbs (camelid version).

| sdAb | SEQ ID No | Immunisation |
|------|-----------|--------------|
| A2 | 5 | |
| B1 | 9 | IgE |
| B2 | 13 | IgE |
| B3 | 17 | IgE |
| D1 | 21 | IgE-Fc Cε2-Cε4 |
| D2 | 25 | IgE-Fc Cε2-Cε4 |
| D3 | 29 | IgE-Fc Cε2-Cε4 |

-continued

| sdAb | SEQ ID No | Immunisation |
|------|-----------|--------------|
| E1 | 33 | IgE-Fc Cε2-Cε4 |
| E2 | 37 | IgE-Fc Cε2-Cε4 |
| E3 | 41 | IgE-Fc Cε2-Cε4 |
| E4 | 45 | IgE-Fc Cε2-Cε4 |
| F1 | 49 | IgE-Fc Cε2-Cε4 |
| F2 | 53 | IgE-Fc Cε2-Cε4 |
| F3 | 57 | IgE-Fc Cε2-Cε4 |
| F4 | 61 | IgE-Fc Cε2-Cε4 |
| F5 | 65 | IgE-Fc Cε2-Cε4 |
| F6 | 69 | IgE-Fc Cε2-Cε4 |
| G1 | 73 | IgE |

Accordingly, in some embodiments, an sdAb may comprise or consist of the amino acid sequences selected from any one of SEQ ID NOs: 5, 9, 13, 17, 21, 21, 25, 29, 33, 37, 41, 45, 49, 53, 57, 61, 65, 69, and 73. Since such sdAbs may be subject to affinity maturation, humanisation or other amino acid changes of the amino acid sequence, further embodiments relate to an sdAb having an amino acid sequence that is at least 80%, such as at least 85%, 90%, 95%, 96%, 97%, 98%, or 99% identical to an amino acid sequence selected from the group consisting of SEQ ID NOs: 5, 9, 13, 17, 21, 21, 25, 29, 33, 37, 41, 45, 49, 53, 57, 61, 65, 69, and 73. In preferred embodiments, the said variation in the amino acid sequence is not in the CDR regions, and thus only in the combined frame region. Typically, such variations are introduced with the aim of affinity maturate and/or humanise the sdAbs. Therefore, a novel sdAb may comprise or consist of the amino acid sequences selected from any one of SEQ ID NOs: 5, 9, 13, 17, 21, 21, 25, 29, 33, 37, 41, 45, 49, 53, 57, 61, 65, 69, and 73 including affinity matured and/or humanised variants thereof.

Further, the novel sdAbs might be define according to the individual CDR regions derivable from the entire sdAb amino acid sequence and may be determined by different numbering schemes, such as, but not limited to Kabat, Chothia, IMTG or Aho.

Thus, in one embodiment, an sdAb comprises binding regions CDR1, CDR2, and CDR3 each comprising or consisting of an amino acid sequence determined according to either Kabat, Chothia, IMTG or Aho numbering schemes in the amino acid sequences selected from any one of SEQ ID NOs: 5, 9, 13, 17, 21, 21, 25, 29, 33, 37, 41, 45, 49, 53, 57, 61, 65, 69, and 73, optionally wherein the CDR1 contain 1, 2, or 3 amino acid substitutions, the CDR2 contain 1, 2, or 3 amino acid substitutions and/or the CDR3 contain 1, 2, or 3 amino acid substitutions. The substitutions are meant to be incorporated in view of the CDR1, CDR2, and CDR3 that was determined directly by either Kabat, Chothia, IMTH or Aho in the said sequences.

Specific CDR Regions of Novel sdAbs.

Table 2a shows the amino acid sequences of CDR1, CRD2 and CDR3 of monomeric sdAbs/VHH domains determined by Aho.

| sdAb ID | CDR1 | | CDR2 | | CDR3 | |
|---------|------|------|------|------|------|------|
| | SEQ ID No | Amino acid sequence | SEQ ID No | Amino acid sequence | SEQ ID No | Amino acid sequence |
| A1 | 2 | FTFGNYDMA | 3 | SIDTGGDITH | 4 | ATDEEYALGPNEFDYY |
| A2 | 6 | FRFGNYDMA | 7 | SIDTGGDITH | 8 | ATDEEYALGPNEFDYY |
| B1 | 10 | RTFSNTGMG | 11 | IISPSGTSTY | 12 | AASYGSNWSTLRHQRRNEYDAW |

-continued

| sdAb ID | CDR1 | | CDR2 | | CDR3 | |
|---------|------|------|------|------|------|------|
| | SEQ ID No | Amino acid sequence | SEQ ID No | Amino acid sequence | SEQ ID No | Amino acid sequence |
| B2 | 14 | STFSNNVAD | 15 | RISASGATRE | 16 | HKIEWEDLSRKDYW |
| B3 | 18 | FIFRLAGMS | 19 | GITMDGSTTN | 20 | ARGAKGGYNDPR |
| D1 | 22 | LTFSRCDMG | 23 | RISANGASTH | 24 | AAARVPVTWQLYDYW |
| D2 | 26 | RTFSGWSMG | 27 | AISWVGSWIG | 28 | AAANSETPRIFASEYDYW |
| D3 | 30 | RTFSSYSMG | 31 | ITWSGGRTY | 32 | AGLWGVGSWYEELRNKHEYDYW |
| E1 | 34 | RTFTTTSGYNMG | 35 | GIKWVSGSNRA | 36 | AAATGQSYVPIREYEYVYW |
| E2 | 38 | RTISRYAVG | 39 | GINWSGGSTTYAD | 40 | AVPSVLVQGGISNPSQYDYW |
| E3 | 42 | RTLSSYVVS | 43 | AITWSGLSTTYLD | 44 | AAGPNIPSILRTRESEYAYW |
| E4 | 46 | FRFSNYAMR | 47 | RISSTGFITR | 48 | NAESTDYW |
| F1 | 50 | GSLSRYDMG | 51 | RISWSGTTKY | 52 | AAAFYGNRGYYDVNAYTSS |
| F2 | 54 | GSLSRYDMG | 55 | RISWSGDTKY | 26 | AVALYGNRGYYDVNTYSYW |
| F3 | 58 | GSLSRWDVA | 59 | RISWSGTTSY | 60 | AVALYGNRGYYDVNAHSYW |
| F4 | 62 | LSFSSMG | 63 | AISLYSGSTY | 64 | AADRQRTWSTFYASRQATYNYW |
| F5 | 66 | SIFSIDIMG | 67 | TMPEGNYIN | 68 | YGFGVREGRGNVYW |
| F6 | 70 | LTFGSYDMG | 71 | RIRNDGITY | 72 | AADGTGLGHYDYW |
| G1 | 74 | FIVSDNVMS | 75 | TIMLNGDTA | 76 | NARDSMLEPGRGAW |

Table 2b shows the amino acid sequences of CDR1, CRD2 and CDR3 of monomeric sdAbs/VHH domains determined by the Kabat method.

| sdAb ID | CDR1 | | CDR2 | | CDR3 | |
|---------|------|------|------|------|------|------|
| | SEQ ID No | Amino acid sequence | SEQ ID No | Amino acid sequence | SEQ ID No | Amino acid sequence |
| A1 | 129 | NYDMA | 130 | SIDTGGDITHYADSVKG | 131 | DEEYALGPNEFDY |
| A2 | 132 | NYDMA | 133 | SIDTGGDITHYADSVKG | 134 | DEEYALGPNEFDY |
| B1 | 135 | NTGMG | 136 | SIDTGGDITHYADSVKG | 137 | DEEYALGPNEFDY |
| B2 | 138 | NNVAD | 139 | IISPSGTSTYYADSVKG | 140 | SYGSNWSTLRHQRRNEYDA |
| B3 | 141 | LAGMS | 142 | RISASGATREYGDSVKG | 143 | IEWEDLSRKDY |
| D1 | 144 | RCDMG | 145 | GITMDGSTTNYADSVKG | 146 | GAKGGYNDP |
| D2 | 147 | GWSMG | 148 | RISANGASTHYADFVKG | 149 | ARVPVTWQLYDY |
| D3 | 150 | SYSMG | 151 | AISWVGSWIGGTVYSNSVKG | 152 | ANSETPRIFASEYDY |
| E1 | 153 | TTSGYNMG | 154 | GITWSGGRTYYADFVKG | 155 | LWGVGSWYEELRNKHEYDY |
| E2 | 156 | RYAVG | 157 | GIKWVSGSNRAYAESVKG | 158 | ATGQSYVPIREYEYVY |
| E3 | 159 | SYVVS | 160 | INWSGGSTTYADSAEG | 161 | PSVLVQGGISNPSQYDY |

-continued

| sdAb ID | CDR1 | | CDR2 | | CDR3 | |
|---|---|---|---|---|---|---|
| | SEQ ID No | Amino acid sequence | SEQ ID No | Amino acid sequence | SEQ ID No | Amino acid sequence |
| E4 | 162 | NYAMR | 163 | AITWSGLSTTYLDSVQG | 164 | GPNIPSILRTRESEYAY |
| F1 | 165 | RYDMG | 166 | RISSTGFITRYTASVRD | 167 | ESTDY |
| F2 | 168 | RYDMG | 169 | RISWSGTTKYYADAVKG | 170 | AFYGNRGYYDVNAYTS |
| F3 | 171 | RWDVA | 172 | RISWSGDTKYYADAVEG | 173 | ALYGNRGYYDVNTYSY |
| F4 | 174 | SMG | 175 | RISWSGTTSYYADAVKG | 176 | ALYGNRGYYDVNAHSY |
| F5 | 177 | IDIMG | 178 | AISLYSGSTYYADSVKG | 179 | DRQRTWSTFYASRQATYNY |
| F6 | 180 | SYDMG | 181 | TMPEGNYINYADSVKG | 182 | FGVREGRGNVY |
| G1 | 183 | DNVMS | 184 | RIRNDGITYYADSVKG | 185 | DGTGLGHYDY |

Table 2c shows the amino acid sequences of CDR1, CRD2 and CDR3 of monomeric sdAbs/VHH domains determined by the Chothia method.

| sdAb ID | CDR1 | | CDR2 | | CDR3 | |
|---|---|---|---|---|---|---|
| | SEQ ID No | Amino acid sequence | SEQ ID No | Amino acid sequence | SEQ ID No | Amino acid sequence |
| A1 | 186 | GFTFGNY | 187 | DTGGDI | 188 | DEEYALGPNEFDY |
| A2 | 189 | GFRFGNY | 190 | DTGGDI | 191 | DEEYALGPNEFDY |
| B1 | 192 | GRTFSNT | 193 | SPSGTS | 194 | SYGSNWSTLRHQRRNEYDA |
| B2 | 195 | GSTFSNN | 196 | SASGAT | 197 | IEWEDLSRKDY |
| B3 | 198 | GFIFRLA | 199 | TMDGST | 200 | GAKGGYNDP |
| D1 | 201 | GLTFSRC | 202 | SANGAS | 203 | ARVPVTWQLYDY |
| D2 | 204 | GRTFSGW | 205 | SWVGSWIGG | 206 | ANSETPRIFASEYDY |
| D3 | 207 | GRTFSSY | 208 | TWSGGR | 209 | LWGVGSWYEELRNKHEYDY |
| E1 | 210 | GRTFTTTSGY | 211 | KWVSGSN | 212 | ATGQSYVPIREYEYVY |
| E2 | 213 | GRTISRY | 214 | WSGGS | 215 | PSVLVQGGISNPSQYDY |
| E3 | 216 | GRTLSSY | 217 | TWSGLS | 218 | GPNIPSILRTRESEYAY |
| E4 | 219 | GFRFSNY | 220 | SSTGFI | 221 | ESTDY |
| F1 | 222 | GGSLSRY | 223 | SWSGTT | 224 | AFYGNRGYYDVNAYTS |
| F2 | 225 | GGSLSRY | 226 | SWSGDT | 227 | ALYGNRGYYDVNTYSY |
| F3 | 228 | RGSLSRW | 229 | SWSGTT | 230 | ALYGNRGYYDVNAHSY |
| F4 | 231 | GLSFS | 232 | SLYSGS | 233 | DRQRTWSTFYASRQATYNY |
| F5 | 234 | GSIFSID | 235 | PEGNY | 236 | FGVREGRGNVY |
| F6 | 237 | GLTFGSY | 238 | RNDGI | 239 | DGTGLGHYDY |
| G1 | 240 | GFIVSDN | 241 | MLNGD | 242 | RDSMLEPGRGA |

Table 2d shows the amino acid sequences of CDR1, CRD2 and CDR3 of monomeric sdAbs/VHH domains determined by the IMGT method.

| sdAb ID | CDR1 | | CDR2 | | CDR3 | |
|---------|------|---|------|---|------|---|
| | SEQ ID No | Amino acid sequence | SEQ ID No | Amino acid sequence | SEQ ID No | Amino acid sequence |
| A1 | 243 | GFTFGNYD | 244 | IDTGGDIT | 249 | ATDEEYALGPNEFDY |
| A2 | 246 | GFRFGNYD | 247 | IDTGGDIT | 248 | ATDEEYALGPNEFDY |
| B1 | 249 | GRTFSNTG | 250 | ISPSGTST | 251 | AASYGSNWSTLRHQRRNEYDA |
| B2 | 252 | GSTFSNNV | 253 | ISASGATR | 254 | HKIEWEDLSRKDY |
| B3 | 255 | GFIFRLAG | 256 | ITMDGSTT | 257 | ARGAKGGYNDP |
| D1 | 258 | GLTFSRCD | 259 | ISANGAST | 260 | AAARVPVTWQLYDY |
| D2 | 261 | GRTFSGWS | 262 | ISWVGSWIGGT | 263 | AAANSETPRIFASEYDY |
| D3 | 264 | GRTFSSYS | 265 | ITWSGGRT | 266 | AGLWGVGSWYEELRNKHEYDY |
| E1 | 267 | GRTFTTTSGYN | 268 | IKWVSGSNR | 269 | AAATGQSYVPIREYEYVY |
| E2 | 270 | GRTISRYA | 271 | NWSGGST | 272 | AVPSVLVQGGISNPSQYDY |
| E3 | 273 | GRTLSSYV | 274 | ITWSGLST | 275 | AAGPNIPSILRTRESEYAY |
| E4 | 276 | GFRFSNYA | 277 | ISSTGFIT | 278 | NAESTDY |
| F1 | 279 | GGSLSRYD | 280 | ISWSGTTK | 281 | AAAFYGNRGYYDVNAYTS |
| F2 | 282 | GGSLSRYD | 283 | ISWSGDTK | 284 | AVALYGNRGYYDVNTYSY |
| F3 | 285 | RGSLSRWD | 286 | ISWSGTTS | 287 | AVALYGNRGYYDVNAHSY |
| F4 | 288 | GLSFSS | 289 | ISLYSGST | 290 | AADRQRTWSTFYASRQATYNY |
| F5 | 291 | GSIFSIDI | 292 | MPEGNYI | 293 | YGFGVREGRGNVY |
| F6 | 294 | GLTFGSYD | 295 | IRNDGIT | 296 | AADGTGLGHYDY |
| G1 | 297 | GFIVSDNV | 298 | IMLNGDT | 299 | NARDSMLEPGRGA |

Exemplary monomeric sdAbs comprises a CDR1 having the amino acid sequence, SEQ ID NO: 6, 10, 14, 18, 22, 26, 30, 34, 38, 42, 46, 50, 54, 58, 62, 66, 70, or 74, wherein each of the amino acid sequences may have 1, 2, or 3 amino acid substitutions and wherein the CDR region is determined by Aho.

Exemplary monomeric sdAbs comprises a CDR2 having the amino acid sequence SEQ ID NO: 7, 11, 15, 19, 23, 27, 31, 35, 39, 43, 47, 51, 55, 59, 63, 67, 71, or 75, wherein each of the amino acid sequences may have 1, 2, or 3 amino acid substitutions and wherein the CDR region is determined by Aho.

Exemplary monomeric sdAbs comprises a CDR3 having the amino acid sequence SEQ ID NO: 8, 12, 16, 20, 24, 28, 32, 36, 40, 44, 48, 52, 56, 60, 64, 68, 72, or 76, wherein each of the amino acid sequences may have 1, 2, or 3 amino acid substitutions and wherein the CDR region is determined by Aho.

In the alternative, the exemplary monomeric sdAbs A2, B1, B2, B3, D1, D2, D3, E1, E2, E3, E4, F1, F2, F3, F4, F5, F6, and G1 may be defined with their specific CDR regions determined by Kabat as shown in Table 2b, by Chothia as shown in Table 2c, or by IMGT as shown in Table 2d.

In here, the sdAbs may be defined according to their binding regions CDR1, CDR2, and CDR3 determined in the VHH region in a parent version, e.g., the camelid version. In any of the embodiments disclosed herein each of CDR1, CDR2 and CDR3 may optionally be subject to sequence variation, such as 1, 2 or 3 amino acid substitutions, deletions or additions. The purpose for introducing a variation might be to improve IgE binding activity or displacement activity compared to a comparator IgE binder or displacer.

Thus, in all the following embodiments, the CDR1 may contain 1, 2, or 3 amino acid substitutions, CDR 2 may contain 1, 2, or 3 amino acid substitutions and CDR3 may contain 1, 2, or 3 amino acid substitutions, such as 1 or 2 amino acid substitutions. The resulting variant sdAb may be evaluated by determining the binding affinity to IgE Fc or determining the displacement activity by an ELISA-based IgE-FcεRIα displacement assay. Desired are variants with comparable activity to the parent sdAb or with improved IgE affinity or improved displacement activity.

More specifically, an sdAb comprises binding regions CDR1, CDR2, and CDR3 having the respective SEQ ID Nos:

6, 7, and 8; 10, 11, and 12; 14, 15, and 16; 18, 19, and 20; 22, 23, and 24; 26, 27, and 28; 30, 31, and 32; 34, 35, and 36; 38, 39, and 40; 42, 43, and 44; 46, 47, and 48; 50, 51, and 52; 54, 55, and 56; 58, 59, and 60; 62, 63, and 64; 66, 67, and 68; 70, 71, and 72; or 74, 75, and 76, wherein each CDR is determined according to Aho numbering scheme.

In another embodiment, an sdAb comprises binding regions CDR1, CDR2, and CDR3 having the respective SEQ ID Nos:

132, 133, and 134; 135, 136, and 137; 138, 139, and 140; 141, 142, and 143; 144, 145, and 146; 147, 148, and 149; 150, 151, and 152; 153, 154, and 155; 156, 157, and 158; 159, 160, and 161; 162, 163, and 164; 165, 166, and 167; 168, 169, and 170; 171, 172, and 173; 174, 175, and 176; 177, 178, and 179; 180, 181, and 182; or 183, 184 and 185, wherein each CDR is determined according to Kabat numbering scheme.

In a further embodiment, an sdAb comprises binding regions CDR1, CDR2, and CDR3 having the respective SEQ ID Nos:

189, 190, and 191; 192, 193, and 194; 195, 196, and 197; 198, 199, and 200; 201, 202, and 203; 204, 205, and 206; 207, 208, and 209; 210, 211, and 212; 213, 214, and 215; 216, 217, and 218; 219, 220, and 221; 222, 223, and 224; 225, 226, and 227; 228, 229, and 230; 231, 232, and 233; 234, 235, and 236; 237, 238, and 239; or 240, 241 and 242, wherein each CDR is determined according to Chothia numbering scheme.

In yet a further embodiment, an sdAb comprises binding regions CDR1, CDR2, and CDR3 having the respective SEQ ID Nos:

245, 247, and 248; 249, 250, and 251; 252, 253, and 254; 255, 256, and 257; 258, 259, and 260; 261, 262, and 263; 264, 265, and 266; 267, 268, and 269; 270, 271, and 272; 273, 274, and 275; 276, 277, and 278; 279, 280, and 281; 282, 283, and 284; 285, 286, and 287; 288, 289, and 290; 291, 292, and 293; 294, 295, and 296; or 297, 298 and 299, wherein each CDR is determined according to IMTG numbering scheme.

The monomeric sdAbs, may either alone or in combination be able to improve the biological activity (e.g., displacement activity), improve drug ability (e.g., improving serum circulation half-life, improving biodistribution) or establish binding to additional therapeutical targets other than IgE.

As mentioned, the individual sdAbs A1, A2 and B1 were able to displace IgE from its high affinity receptor. Therefore, interesting embodiments encompasses sdAbs that can be used as a first sdAb in a multi-specific construct described herein.

According to one interesting embodiment, the sdAb has binding regions of A1 (shown in tables 2a-d). Thus, an sdAb may comprise binding regions CDR1, CDR2 and CDR3 having the respective SEQ ID NOS:

2, 3, and 4 determined according to Aho;
129, 130, and 131 determined according to Kabat;
186, 187, and 188 determined according to Chothia; or
243, 244, and 245 determined according to IMGT.

According to another interesting embodiment, the sdAb has binding regions of A2. Thus, an sdAb may comprise binding regions CDR1, CDR2 and CDR3 having the respective SEQ ID NOS:

6, 7, and 8 determined according to Aho;
132, 133, and 134 determined according to Kabat;
189, 190, and 191 determined according to Chothia; or
246, 247, and 248 determined according to IMGT.

According to another interesting embodiment, the sdAb has binding regions of B1. Thus, an sdAb may comprise binding regions CDR1, CDR2 and CDR3 having the respective SEQ ID NOS:

10, 11, and 12 determined according to Aho;
135, 136, and 137 determined according to Kabat;
192, 193, and 194 determined according to Chothia; or 249, 250, and 251 determined according to IMGT.

Further, as seen in Example 6 and 7, monomeric sdAbs as described herein shows an increased displacing activity when for example used in pairs of two individual (not linked) monomeric sdAbs. For example, when A1 and B1 is administered in a combination, without being linked together, the ability to displace IgE from its receptor is increased compared to the individual sdAbs administered alone. Notably, the improved displacement activity is also provided by combining two sdAbs both having individual displacement activity. A combination of a displacement sdAb and a non-displacement sdAb exhibit comparable displacement activity to the combination of A1 and B1 (example 6, table 15 and Example 7, table 16).

In further embodiments, any of the monomeric sdAbs as described herein can be combined in pairs of two sdAbs or as three, such as four sdAbs of which one of the sdAbs exhibit displacement activity. In preferred embodiments, the sdAbs are combined in pairs of two. However, any other non-IgE binding sdAb can be combined with an IgE-binding sdAb to modify the biology or kinetics, for example be combined with an sdAb able to bind albumin to decrease the elimination rate in vivo.

Combinations of sdAbs and preferred embodiments are described further below.

Modifications of Amino Acid Sequences of sdAbs

Any amino acid sequence of CDR's or of the FRs outside the CDR's might be subject to amino acid substitutions, insertions, or deletions for the purpose of modifying biological activity, expression level, stability, or other functional properties. In preferred embodiments, the amino acid changes are only incorporated outside the CDR regions.

In some embodiments, an sdAb consist of affinity-matured, human or humanised amino acid sequences. In further embodiments thereof, the amino acid sequence of the CDR regions of the camelid sdAbs may not change upon performing affinity-maturation or humanisation of the camelid sdAbs. In such embodiments, the sdAbs consist of affinity-matured, human or humanised amino acid sequences, but not in the CDR regions involved in the binding to the target.

In some embodiments, one more of the CDR's of an sdAb (i.e., CDR1, CDR2 and/or CDR3) may independently be subject to amino acid substitution, such as by 1, 2, 3, or more amino acid residue substitutions. The amino acid substitution in the CDR's may be conservative amino acid substitution. "Conservative" amino acid substitutions are generally amino acid substitutions in which an amino acid residue is replaced with another amino acid residue of similar chemical structure and/or charge, which provides little or essentially no influence on the function, activity, or other biological properties of the resulting binding region of an sdAb, or multi-specific construct described herein. Such conservative amino acid substitutions are well known in the art. For example, conservative substitutions preferably are substitutions in which one amino acid residue within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues; His, Arg and Lys; (d) large aliphatic, nonpolar residues: Met, Leu, Ile, Val and Cys; and (e) aromatic residues: Phe, Tyr and Trp.

Particularly preferred conservative amino acid substitutions are as follows: Ala into Gly; Ala into Ser; Arg into Lys; Asn into Gln; Asn into His; Asp into Glu; Cys into Ser; Gln into Asn; Glu into Asp; Gly into Ala; Gly into Pro; His into Asn; His into Gln; Ile into Leu, Ile into Val; Leu into Ile; Leu into Val; Lys into Arg; Lys into Gln; Lys into Glu; Met into Leu; Met into Tyr; Met into Ile; Phe into Met; Phe into Leu; Phe into Tyr; Ser into Thr; Thr into Ser; Trp into Tyr; Tyr into Trp; Phe into Val; Phe into Ile and/or Phe or into Leu.

Conservative amino acid substitutions may also be made in the non-CDR amino acid sequence.

In other embodiments, amino acid substitutions in the amino acid sequence of CDRs might be performed with the purpose to provide sdAbs with modified, such as increased, affinity for binding to IgE, displacement of IgE from FcεRI or for binding to another target of interest. The amino acid sequences of the CDRs are typically more determining for the target affinity than the amino acid sequences outside the CDRs. Accordingly, the sdAbs described herein can also be subjected to affinity maturation by introducing one or more alterations in the amino acid sequence of one or more CDRs, which alterations result in a modified such as an improved affinity of the resulting sdAb for IgE as compared to the first (parent) sdAb. Methods for affinity-maturation of sdAbs may be prepared by methods known in the art, for example, as described in the patent application WO2012/175740.

There might also be amino acid substitutions, insertions or deletions made in one or more of the FRs outside the CDR's. In particularly, humanising substitutions may be made (i.e., replacing one or more amino acid residues in the amino acid sequence of a naturally occurring framework sequence by one or more of the amino acid residues that occur at the corresponding position(s) in the same domain from a conventional antibody from a human being. Potentially useful humanizing substitutions can be ascertained by comparing the sequence of the framework regions of a naturally occurring VHH sequence with the corresponding framework sequence of one or more closely related human VHH sequences, after which one or more of the potentially useful humanising substitutions (or combinations thereof) thus determined can be introduced into said VHH sequence (in any manner known per se) and the resulting humanized VHH sequences can be tested for affinity for the target (IgE binding), IgE displacement activity, for stability, for ease and level of expression, and/or for other desired properties. Thus, sdAbs may be partially humanized or fully humanized. Methods for humanizing sdAbs was previously described by Rossoti et al (Rossoti et al., 2021) and Traian S., (Traian S., 2022).

Any amino acid substitution in the amino acid sequence outside the CDRs may typically provide sdAbs with less modified biological activity compared to substitutions in the CDRs. However, any changes in the amino acid sequence of an sdAb (such as deletions, insertions and/or substitutions) may also be designed to improve the expression level depending on the host organism used to express the sdAbs or multi-specific construct described herein. For example, the changes may be designed in such a way that one or more sites for post-translational modification (such as one or more glycosylation sites) are removed, as will be within the ability of the person skilled in the art. Alternatively, substitutions or insertions may be designed to introduce one or more sites for attachment of functional groups, for example to allow for insertion of affinity tags (His-tags) or for site-specific PEGylation. The possibility of post-translational modification of the N-terminus can be eliminated by changing the N-terminal Glutamic acid (E) into an Aspartic acid (D). Thus, an amino acid difference may be change of Glutamic acid (Glu) at position 1 (said position determined according to Kabat numbering) into an Aspartic acid (Asp).

One embodiment illustrates how amino acid substitutions can modify the IgE binding affinity and/or the displacement activity of an sdAb described herein. The known monomeric sdAb 026 (herein named A1 (SEQ ID No:1 having the binding regions CDR1, CDR2, and CDR3 with SEQ ID Nos: 2, 3 and 4, respectively, determined according to Aho) was optimised for improved IgE binding and displacement activity. Methods for investigating the impact of amino acid substitutions are described in example 4. The resulting sdAb (A2) with SEQ ID No: 5 having the binding regions CDR1, CDR2, and CDR3 with SEQ ID Nos: 6, 7 and 8, respectively, determined according to Aho, had improved displacement activity by 2-4-fold compared to sdAb A1. Notably, the improved sdAb A1 (i.e., sdAb A2) had amino acid substitution in one of the three CDRs as well as outside the CDRs.

In alternative embodiments, the sdAb named A1 (SEQ ID No:1) can be optimised for improved IgE binding and/or displacement activity by implementation of one or more mutations selected from the list consisting of: L11F, L11K, V12F, V12Y, V12G, Q13V, P14M, P14E, P14R, R19K, A23K, A23R, S25K, S25R, G26K, G26R, T28K, T28R, F29Y, G30F, G30W, G30Y, G30D, G30H, G30K, G30K, G30R, K43R, P45W, P45Y, F68W, T69W, T69G, T69N, T69R, I70V, S71N, D73F, D73W, D73Y, D73M, D73I, D73L, D73V, D73A, D73G, D73S, D73T, D73N, D73Q, D73E, D73H, D73K, D73R, A75W, A75Y, A75P, A75M, A75G, A75S, A75N, A75K, A75R, N77Y, N77K, N77R, M78K, M78R, L79F, L79V, L79A, L79A, L79N, L79H, Q82W, Q82Y, M83I, T91A, T91G, T91Q, T91D, T91E, T91H, V93M, V93T, V93E and L104M.

Any of the novel sdAbs disclosed herein may be subject to a similar amino acid mutation evaluation as A1 with the purpose of improving IgE binding.

In one embodiment, the sdAb B2 (SEQ ID NO: 13) can be optimized for improved IgE binding by implementation of one or more mutations selected from the list consisting of: V12T, A23Q, A23D, T28Q, T28H, D35M, D35A, D36V, Q39F, Q39W, Q39Y, Q39I, Q39V, Q39E, Q44P, D74P, D74I, S105I, S105N, S105D and S105E.

In another embodiment, the sdAb B3 (SEQ ID NO: 17) can be optimized for improved IgE binding and/or displacement activity by implementation of one or more mutations selected from the list consisting of: S21E, A23D, A23E, S25D, W36I, V37W, V37Y, A40C, A40R, G44P, G44D, G44E, G44H, F45P, F45M, F45M, F45I, F45L, F45V, F45A, S45A, S45G, T58D, N59E, K65M, K65A, T69Q, S71I, N77G, R78M, R78V, R78E, Q82Y, N84D, N84E, K87L, K87G, K87C, K87S, K87N, K87D, K87E, K87H, P88D, T91A, T91G, T91N, T91Q, T91D, T91E, A97M, A97I, A97L, A97V, N105P, N105D, R108F, R108M, R108I, R108V, R108N, R108Q and R108K.

As mentioned, the parent CDR regions may be subject to sequence variation, such as 1, 2 or 3 amino acid substitutions, deletions or additions. The variant may have the same, improved, or increased IgE binding activity or displacement activity compared to a comparator IgE binder or displacer. In preferred embodiments, the displacement activity is improved or increased compared to sdAb A1 (SEQ ID NO: 1) or a multi-specific construct comprising two sdAb A1.

Multi-Specific Constructs

SdAbs, such as monomeric sdAbs/VHH domain, may be engineered into multimeric, such as multi-specific, constructs with the purpose of improving biological activity (e.g., displacement activity), improving druggability (e.g., improving serum circulation half-life, improving biodistribution) or establishing binding to additional therapeutical targets other than IgE.

In particularly, two or more sdAbs may be combined to form a multimeric, such as a multi-specific construct, which is able to displace bound IgE from FCεRI. Preferably, such a multi-specific construct may in addition limit, prevent, or inhibit free IgE from binding to FCεRI. Even more preferably such constructs also limit, prevent, or inhibit free IgE from binding to CD23. Advantageously, by combining two or more sdAbs in a multimeric construct, in particularly a multi-specific construct, the construct may exhibit an improved ability to i) displace bound IgE from FcεRI compared to the monomeric sdAbs present in the constructs; ii) limit, prevent or inhibit free IgE from binding to FcεRI and/or iii) limit, prevent or inhibit free IgE from binding to CD23.

A multi-specific construct is composed of two or more sdAbs, wherein at least one has displacement activity on its own and the two sdAbs are linked together via a linking moiety as outlined in FIG. 1.

A multi-specific construct comprises
a. a first single domain antibody (sdAb) able to displace bound IgE from FCεRI,
b. a second sdAb that binds to IgE,
c. a moiety that links the first and second sdAb,
wherein
the first and second sdAb bind non-identical epitopes of IgE, and
the multi-specific construct can displace bound IgE from the IgE high-affinity receptor (FcεRI) with improved displacement activity compared to the first or second sdAb.

Where the present construct comprises at least one sdAb able to displace bound IgE, it is envisaged that multi-specific constructs comprising a) a first single domain antibody (sdAb) that binds to IgE and b) a second sdAb that binds to IgE might be able to provide the desired displacement.

Preferably, both the first and second sdAb binds to the same IgE antibody, such as simultaneously to the same IgE antibody to avoid cross-binding of IgE bound to the IgE high affinity receptor, and thus to prevent any degranulation of mast cells or basophils by the anti-IgE multi-specific construct. Methods for evaluating that both sdAbs can bind the same IgE molecule are described in example 3 (relative epitope mapping).

The binding site to IgE may be outside the variable domains of IgE. In some embodiments, it is preferred that at least one of the two sdAbs binds to the Fc region of IgE and in other embodiments, it is preferred that both sdAbs binds to the Fc region of IgE. It is further emphasised that the multi-specific construct may comprise at least one further sdAb that binds another epitope of IgE than any of those bound by the first sdAb and the second sdAb. Preferably, the further sdAb binds to the same IgE molecule as the first and second sdAb.

By implementing an sdAb with displacement activity, into the described multi-specific construct, the displacement activity is increased compared to the individual sdAb.

Since an sdAb consists of the VHH domain of a camelid antibody, the multi-specific constructs may alternatively be worded as follows: The multi-specific constructs comprise a) a first VHH domain that binds to IgE and b) a second VHH domain that binds to IgE. Preferably, both the first and second VHH domain bind the same IgE antibody, such as simultaneously to the same IgE antibody. The binding site to IgE may be outside the variable domains of IgE. In some embodiments, it is preferred that at least one of the two VHH domains bind to the Fc region of IgE and in other embodiments, it is preferred that both VHH domains bind to the Fc region of IgE. It is further emphasised that the multi-specific construct may comprise at least one further VHH domain that binds another epitope of IgE than any of those bound by the first VHH and the second VHH. Preferably, the further VHH domain binds to the same IgE molecule as the first and second VHH domain.

Therefore, in the most interesting embodiments, the multi-specific constructs comprise non-identical sdAbs, such as non-identical VHH domains. Thus, the two sdAbs/VHH domains may be able to bind the same IgE antibody simultaneously as can be assessed by relative epitope mapping.

In the following, any referral to an sdAb may be consistent with a VHH domain.

In interesting embodiments, the multi-specific constructs comprise a first sdAb and/or a second sdAb, which when binding to IgE bound to FcεRI causes the binding affinity between IgE and FcεRI to decrease. Thus, the multi-specific constructs comprise at least one sdAb able to displace bound IgE from FcεRI, such as a first sdAb. Alternatively, neither of the two sdAbs may have displacement activity, but the final multi-specific construct may upon binding to IgE bound to FcεRI cause the binding affinity between IgE and FcεRI to decrease.

In still further interesting embodiments, the multi-specific construct comprises at least one further sdAb, such as the second sdAb, wherein this sdAb facilitates improved or increased binding affinity (i.e., avidity) of the multi-specific construct to IgE compared to the IgE binding affinity of the first sdAb or the second sdAb. Thus, the second sdAb may add to the overall IgE binding affinity (avidity).

For example, the overall binding affinity (i.e., avidity) of the multi-specific construct for IgE is increased such that the sum of the binding affinities observed for either of the first sdAb and the second sdAb is increased. Moreover, the displacement effect of the multi-specific construct is increased such that the sum of the displacement effect observed for either of the first sdAb and the second sdAbs is increased.

The displacement activity of the individual sdAbs or multi-specitic constructs may be evaluated by an ELISA-based IgE-FcεRIα displacement assay, which is based on measuring remaining IgE not removed from immobilised recombinant human FcεRIα pre-loaded with IgE following addition of a test compound (e.g., the sdAb or the multi-specific construct) and determining the percentage displacement activity as the relative reduction in signal compared to a control with no test compound added.

In constructs disclosed herein, the first sdAb may be selected among sdAbs having displacement activity with an $EC_{50}$ in the upper nano molar range to molar range, such as with an $EC_{50}$ in the range of 100 nM to 5000 nM, such as with an $EC_{50}$ above 200, 300, 400, 500 or 600 nM, but below 4000, 3000, 2000 or 1000 nM. Exemplary sdAbs complying with this criterion is sdAbs A1, A2 or B1.

Further or in the alternative, the displacement activity of the first sdAb is such that the maximum displacement activity is at least 80%, preferably at least 85%, 90% or 95%. Exemplary sdAbs complying with this criterion is sdAbs A1 or A2.

Most preferably, a first sdAb has displacement activity with an $EC_{50}$ in the range of 200 nM to 5000 nM, and the maximum displacement effect is at least 80%. Exemplary sdAbs complying with this criterion is sdAbs A1 or A2.

For multi-specific constructs disclosed herein, the second sdAb may be selected among sdAbs exhibiting no displacement activity (e.g., sdAbs exhibiting a lower displacement activity (higher $EC_{50}$) compared to the first sdAb (e.g. sdAbs B2, B3, D1, D2, D3, E1, E2, E3, E4, F1, F2, F3, F4, F5, F6 and G1) or the second sdAb may exhibit a maximum displacement effect below 75% (e.g. B1).

As mentioned, the multi-specific construct has improved displacement activity over the individual sdAbs of the multi-specific construct. The improved displacement activity may be such that the $EC_{50}$ observed for either of the first sdAb or second sdAb or a mix of first and second sdAb result in lower $EC_{50}$ for the construct.

By example the improved displacement activity of the multi-specific construct is such that the $EC_{50}$ is lowered by a factor of at least 20 compared to the $EC_{50}$ of the first sdAb. Preferably, the $EC_{50}$ is lowered by a factor of at least 25, 30, 35, 40, 45, 50, 60, 70, 80, 100, 150, 200, 250, 300, 350, 400, 500, 600, 700, 800, 900 or 1000.

For example, the improved displacement activity of the multi-specific construct is such that the $EC_{50}$ is below 200 nM. Preferably, the $EC_{50}$ is below 150, 100, 75, 50, 25, 20, 15, 10, 5, 4, 3, 2, or 1 nM.

In the alternative or in addition, the improved displacement activity of the multi-specific construct is such that the maximum displacement effect is at least 80%. Preferably, the maximum displacement effect is at least 85%, 90% or 95%, most preferably at least 95%.

In preferred embodiments, the improved displacement activity of the multi-specific construct is such that the $EC_{50}$ is below 100 nM and the maximum displacement is at least 80%, such as at least 85, 90 or 95%.

Generally, the multi-specific construct may comprise as the first sdAb or second sdAb, an sdAb comprising a CDR1 having the amino acid sequence SEQ ID NO: 2, 6, 10, 14, 18, 22, 26, 30, 34, 38, 42, 46, 50, 54, 58, 62, 66, 70, or 74, determined according to Aho, wherein each of the amino acid sequences may have 1, 2, or 3 amino acid substitutions; and/or comprising a CDR2 having the amino acid sequence SEQ ID NO: 3, 7, 11, 15, 19, 23, 27, 31, 35, 39, 43, 47, 51, 55, 59, 63, 67, 71, or 75, determined according to Aho, wherein each of the amino acid sequences may have 1, 2, or 3 amino acid substitutions; and/or comprising a CDR3 having the amino acid sequence SEQ ID NO: 4, 8, 12, 16, 20, 24, 28, 32, 36, 40, 44, 48, 52, 56, 60, 64, 68, 72, or 76, determined according to Aho, wherein each of the amino acid sequences may have 1, 2, or 3 amino acid substitutions.

Where it is found that not all the three binding CDR regions are critical for binding, the first and second sdAb may be constructed from the above-mentioned combination of CDR regions, but where one of the three CDR regions might have been replaced by another sequence, e.g., been subject to humanisation or other amino acid modifications. In preferred embodiments, the original CDR3 region of the camelid sdAb is maintained as a conserved sequence.

More specifically, the multi-specific construct may comprise as the first or second sdAb, an sdAb comprising a binding region having a combination of CDR1, CDR2, and CDR3 having the respective SEQ ID NOs: 2, 3, and 4; 6, 7, and 8; 10, 11, and 12; 14, 15, and 16; 18, 19, and 20; 22, 23, and 24; 26, 27, and 28; 30, 31, and 32; 34, 35, and 36; 38, 39, and 40; 42, 43, and 44; 46, 47, and 48; 50, 51, and 52; 54, 55, and 56; 58, 59, and 60; 62, 63, and 64; 66, 67, and 68; 70, 71, and 72; or 74, 75, and 76, determined according to Aho.

Multi-specific constructs may comprise a combination of any of the sdAbs/VHH domain described herein insofar that the construct has displacement activity. In preferred embodiments, the first sdAb has displacement activity on its own, such as sdAb 026 (herein named A1) or A2.

Therefore, the multi-specific construct may comprise binding regions from sdAb A1 or A2, Thus, the first sdAb of the construct may comprise binding regions CDR1, CDR2, and CDR3 each comprising or consisting of an amino acid sequence determined according to either Kabat, Chothia, IMTG or Aho numbering schemes in an amino acid sequence selected from any one of SEQ ID NOs: 1 or 5, optionally wherein the CDR1 contain 1, 2, or 3 amino acid substitutions, the CDR2 contain 1, 2, or 3 amino acid substitutions and the CDR3 contain 1, 2, or 3 amino acid substitutions.

Alternatively defined, the first sdAb comprises binding regions CDR1, CDR2, and CDR3 having the respective SEQ ID Nos: 2, 3, and 4; or 6, 7, and 8, wherein each CDR is determined according to Aho numbering scheme.

The second sdAb may be any having IgE binding activity in the presence of the first sdAb. Exemplary second sdAbs comprises binding regions CDR1, CDR2, and CDR3 each comprising or consisting of an amino acid sequence determined according to either Kabat, Chothia, IMTG or Aho numbering scheme in an amino acid sequence selected from any one of SEQ ID NOS: 9, 13, 17, 21, 21, 25, 29, 33, 37, 41, 45, 49, 53, 57, 61, 65, 69, and 73, optionally wherein the CDR1 contain 1, 2, or 3 amino acid substitutions, the CDR2 contain 1, 2, or 3 amino acid substitutions and the CDR3 contain 1, 2, or 3 amino acid substitutions.

In the alternative, a second sdAb comprises binding regions CDR1, CDR2, and CDR3 having the respective SEQ ID Nos: 10, 11, and 12; 14, 15, and 16; 18, 19, and 20; 22, 23, and 24; 26, 27, and 28; 30, 31, and 32; 34, 35, and 36; 38, 39, and 40; 42, 43, and 44; 46, 47, and 48; 50, 51, and 52; 54, 55, and 56; 58, 59, and 60; 62, 63, and 64; 66, 67, and 68; 70, 71, and 72; or 74, 75, and 76, wherein each CDR is determined according to Aho numbering scheme.

Similarly, the second sdAbs may comprise a binding region having a combination of CDR1, CDR2, and CDR3 comprising the respective SEQ ID NOS:

129, 130, and 131; 132, 133, and 134; 135, 136, and 137; 138, 139, and 140; 141, 142, and 143; 144, 145, and 146; 147, 148, and 149; 150, 151, and 152; 153, 154, and 155; 156, 157, and 158; 159, 160, and 161; 162, 163, and 164; 165, 166, and 167; 168, 169, and 170; 171, 172, and 173; 174, 175, and 176; 177, 178, and 179; 180, 181, and 182; or 183, 184 and 185, determined according to Kabat.

Similarly, the second sdAbs may comprise a binding region having a combination of CDR1, CDR2, and CDR3 comprising the respective SEQ ID NOs:

186, 187, and 188; 189, 190, and 191; 192, 193, and 194; 195, 196, and 197;

198, 199, and 200; 201, 202, and 203; 204, 205, and 206; 207, 208, and 209;

210, 211, and 212; 213, 214, and 215; 216, 217, and 218; 219, 220, and 221;

222, 223, and 224; 225, 226, and 227; 228, 229, and 230; 231, 232, and 233;

234, 235, and 236; 237, 238, and 239; or 240, 241 and 242, determined according to Chothia.

Similarly, the second sdAbs may comprise a binding region having a combination of CDR1, CDR2, and CDR3 comprising the respective SEQ ID NOs: 242, 243, and 244; 245, 247, and 248; 249, 250, and 251; 252, 253, and 254; 255, 256, and 257; 258, 259, and 260; 261, 262, and 263; 264, 265, and 266; 267, 268, and 269; 270, 271, and 272; 273, 274, and 275; 276, 277, and 278; 279, 280, and 281; 282, 283, and 284; 285, 286, and 287; 288, 289, and 290; 291, 292, and 293; 294, 295, and 296; or 297, 298 and 299, determined according to IMGT.

As such, a first sdAb of a construct as described herein, may preferably comprise, or consist of any one of SEQ ID NOS: 1 or 2 and a second sdAb may preferably comprise, or consist of any one of SEQ ID NOs: 5, 9, 13, 17, 21, 21, 25, 29, 33, 37, 41, 45, 49, 53, 57, 61, 65, 69, and 73.

Where the first sdAb comprises binding regions of B1, the second sdAb may comprise the binding regions of sdAbs B2, B3, D1, D2, D3, E1, E2, E3, E4, F1, F2, F3, F4, F5, F6 or G1, respectively.

Thus, in still preferred embodiments, a first sdAb of a construct may comprise or consist of any one of SEQ ID NOs: 1, 5 and 9, more preferably a first sdAb of a construct may comprise or consist of SEQ ID NO 1.

In particularly, the first sdAb may be any one of sdAb A1, sdAb A2 or sdAb B1. Thus, a first sdAb may comprise or consists of an amino acid sequence selected from any one of SEQ ID No: 1, 5 and 9, preferably the first sdAb may comprise or consist of the amino acid sequence SEQ ID NO 1.

SdAb A1 may in addition to above, be defined by its three CDR regions, determined using different CDR-calculation methods.

Thus, in a preferred embodiment, a first sdAb of a construct may comprise binding regions CDR1, CDR2, and CDR3 having the respective SEQ ID NOS:

2, 3, and 4 determined according to Aho;
129, 130, and 131 determined according to Kabat;
186, 187, and 188 determined according to Chothia; or
243, 244, and 245 determined according to IMGT, optionally wherein each CDR1 may contain 1, 2, or 3 amino acid substitutions, each CDR2 may contain 1, 2, or 3 amino acid substitutions and each CDR3 may contain 1, 2, or 3 amino acid substitutions.

As well as A1, A2 may in addition be defined by its CDR regions, as described above.

Thus, in one preferred embodiment, a first sdAb of a construct may comprise binding regions CDR1, CDR2, and CDR3 having the respective SEQ ID NOS:

6, 7, and 8 determined according to Aho;
132, 133, and 134 determined according to Kabat;
189, 190, and 191 determined according to Chothia; or
246, 247, and 248 determined according to IMGT, optionally wherein each CDR1 may contain 1, 2, or 3 amino acid substitutions, each CDR2 may contain 1, 2, or 3 amino acid substitutions and each CDR3 may contain 1, 2, or 3 amino acid substitutions.

Further, B1 may in addition to A1 and A2, be defined by CDR regions.

Thus, in one preferred embodiment, a first sdAb of a construct may comprise binding regions CDR1, CDR2, and CDR3 having the respective SEQ ID NOS:

10, 11, and 12 determined according to Aho;
135, 136, and 137 determined according to Kabat;
192, 193, and 194 determined according to Chothia; or
249, 250, and 251 determined according to IMGT, optionally wherein each CDR1 may contain 1, 2, or 3 amino acid substitutions, each CDR2 may contain 1, 2, or 3 amino acid substitutions and each CDR3 may contain 1, 2, or 3 amino acid substitutions.

Alternatively defined, a first sdAb of a construct may comprise binding regions CDR1, CDR2, and CDR3 comprising or consisting of an amino acid sequence as determined according to Kabat, Chothia, IMTH or Aho in the amino acid sequences selected from any one of SEQ ID NOs: 1, 5 or 9, optionally wherein each CDR1 may contain 1, 2, or 3 amino acid substitutions, each CDR2 may contain 1, 2, or 3 amino acid substitutions and each CDR3 may contain 1, 2, or 3 amino acid substitutions.

As further recognised by the present inventors, the multi-specific constructs may exhibit anaphylactogenic activity, however the anaphylactogenic activity may be subject to the test concentration, diluent and sensitivity of the test method. Therefore, preferred embodiments comprise as a first sdAb, the sdAb A1 or an sdAb comprising bindings regions of sdAb A1 and as the second sdAb, an sdAb selected from B1, D2, E1 and F4 or bindings regions of an sdAb selected from B1, D2, E1 and F4.

Accordingly, in the multi-specific construct the first sdAb comprises binding regions CDR1, CDR2, and CDR3 each comprising or consisting of an amino acid sequence determined according to either Kabat, Chothia, IMTG or Aho numbering schemes in an amino acid sequence selected from any one of SEQ ID NOS: 1 or 5, optionally wherein the CDR1 contain 1, 2, or 3 amino acid substitutions, the CDR2 contain 1, 2, or 3 amino acid substitutions and the CDR3 contain 1, 2, or 3 amino acid substitutions; and the second sdAb comprises binding regions CDR1, CDR2, and CDR3 each comprising or consisting of an amino acid sequence determined according to either Kabat, Chothia, IMTG or Aho numbering schemes in an amino acid sequence selected from any one of SEQ ID NOs: 9, 25, 33, 61, optionally wherein the CDR1 contain 1, 2, or 3 amino acid substitutions, the CDR2 contain 1, 2, or 3 amino acid substitutions and the CDR3 contain 1, 2, or 3 amino acid substitutions.

In the alternative, in the multi-specific construct the first sdAb comprises binding regions CDR1, CDR2, and CDR3 having the respective SEQ ID Nos: 2, 3, and 4; or 6, 7, and 8, wherein each CDR is determined according to Aho numbering scheme; and the second sdAb comprises binding regions CDR1, CDR2, and CDR3 having the respective SEQ ID Nos:

10, 11, and 12; 26, 27, and 28; 34, 35, and 36; or
62, 63, and 64, wherein each CDR is determined according to Aho numbering scheme.

In a particular interesting embodiment, the construct comprises binding regions of sdAb A1 and of B1. Thus, a multi-specific construct comprises a first sdAb comprises binding regions CDR1, CDR2, and CDR3 each comprising or consisting of an amino acid sequence determined according to either Kabat, Chothia, IMTG or Aho numbering schemes in an amino acid sequence with SEQ ID NOs: 1, optionally wherein the CDR1 contain 1, 2, or 3 amino acid substitutions, the CDR2 contain 1, 2, or 3 amino acid substitutions and the CDR3 contain 1, 2, or 3 amino acid substitutions; and the second sdAb comprises binding regions CDR1, CDR2, and CDR3 each comprising or consisting of an amino acid sequence determined according to either Kabat, Chothia, IMTG or Aho numbering scheme in an amino acid sequence with SEQ ID NOs: 9, optionally wherein the CDR1 contain 1, 2, or 3 amino acid substitutions, the CDR2 contain 1, 2, or 3 amino acid substitutions and the CDR3 contain 1, 2, or 3 amino acid substitutions.

In the alternative, the multi-specific construct comprises a first sdAb comprising binding regions CDR1, CDR2, and CDR3 having the respective SEQ ID Nos: 2, 3, and 4, wherein each CDR is determined according to Aho numbering scheme; and the second sdAb comprises binding regions CDR1, CDR2, and CDR3 having the respective SEQ ID Nos: 10, 11, and 12, wherein each CDR is determined according to Aho numbering scheme.

Where the second sdAb comprises binding regions from D2, the CDR1, CDR2, and CDR3 may have the respective SEQ ID Nos: 26, 27, and 28 and the sdAb may have the SEQ ID NO: 25.

Where the second sdAb comprises binding regions from E1, the CDR1, CDR2, and CDR3 may have the respective SEQ ID Nos: 34, 35, and 36 and the sdAb may have the SEQ ID NO: 33.

Where the second sdAb comprises binding regions from F4, the CDR1, CDR2, and CDR3 may have the respective SEQ ID Nos: 62, 63, and 64 and the sdAb may have the SEQ ID NO: 61.

In still further embodiments, the first sdAbs A1 or A2 may be replaced with a further variant of A1 such as those described in WO2012175740A1: To be mentioned is the camelid sdAb 39D11 (SEQ ID NO 119 in WO2012/175740A1), the humanised version of 39D11 sdAbs=IGE009 (with mutations: V5L, M77T K83R, Q108L), IGE010 (with mutations: V5L, K83R, M77T, Q108L), IGE011 (with mutations: V5L, M77L K83R, Q108L, W91Y) and IGE012 (with mutations: V5L, M77L, K83R, Q108L, W91Y) having the SEQ ID NO 120-123 in WO2012/175740A1. Among those is IGE009 reported as the preferred one. The affinity-matured versions of IGE009 are IGE025-IGE030 with SEQ ID NO 127-133 in WO2012/175740A1. Among the affinity-matures ones IGE026 and IGE027 are reported as the preferred ones due to 30-50-fold improvement in affinity after maturation. IGE026 is inhere named A1 (SEQ ID NO: 1 in the present application and has SEQ ID NO: 128 in WO2012/175740A1). In here the 39D11 has SEQ ID NO: 316, IGE009 has SEQ ID NO: 317, IGE010 has SEQ ID NO: 318, IGE011 has SEQ ID NO: 319, and IGE012 has SEQ ID NO: 320.

Alternatively, multi-specific constructs comprising a first displacement sdAb may comprise as the second sdAb any sdAb able to bind IgE, such as preferably able to bind IgE at another epitope than the first sdAb and with a high binding affinity in the nanomolar range. Such second sdAbs may be selected among those described in any of the patent applications WO 2004/041867, WO 2012/175740, WO 2014/087010, WO 2020/208177, CN 113461823 and CN 111875706.

Peptide-Linking of sdAbs

As mentioned, an sdAb/VHH domain may be incorporated into a larger construct, such as a multi-specific construct wherein two sdAbs/VHH domains are combined in one construct. Such constructs may have the ability to bind non-identical IgE epitopes of the same IgE. As illustrated by examples herein, multi-specific constructs may comprise at least two distinct sdAbs/VHH domains linked together by a moiety c). In one preferred embodiment, the moiety is a peptide linker (se seen in FIG. 1). In still preferred embodiments, thereof such constructs exhibit improved or increased displacement activity compared to a single sdAbs present in the construct (example 6, table 15 and example 7 table 16).

Table 3 provides the full-length amino acid sequences of exemplary multi-specific constructs comprising at least two distinct sdAbs linked together by a moiety consisting of a peptide linker. Two A1 sdAbs linked together may serve as a control when determining improved displacement activity. As previously described, at least one of the two sdAb has displacement activity on its own. In here A1, A2 or B1 is representing sdAbs with displacement activity on its own.

TABLE 3

| Construct ID | SEQ ID | Construct composition | | |
| --- | --- | --- | --- | --- |
| | | N-terminal | Linker | C-terminal |
| A1A1(G4S)4 | 78 | A1 | (G4S)4 | A1 |
| B3A1(G4S)4 | 79 | B3 | (G4S)4 | A1 |
| A1B3(G4S)4 | 80 | A1 | (G4S)4 | B3 |
| B2A1(G4S)4 | 81 | B2 | (G4S)4 | A1 |
| A1B2(G4S)4 | 82 | A1 | (G4S)4 | B2 |
| D2A1(G4S)4 | 83 | D2 | (G4S)4 | A1 |
| A1D2(G4S)4 | 84 | A1 | (G4S)4 | D2 |
| B1A1(G4S)4 | 85 | B1 | (G4S)4 | A1 |
| A1B1(G4S)4 | 86 | A1 | (G4S)4 | B1 |
| E1A1(G4S)4 | 311 | E1 | (G4S)4 | A1 |
| E2A1(G4S)4 | 312 | E2 | (G4S)4 | A1 |
| E4A1(G4S)4 | 313 | E4 | (G4S)4 | A1 |
| A1E1(G4S)4 | 314 | A1 | (G4S)4 | E1 |
| A1E2(G4S)4 | 315 | A1 | (G4S)4 | E2 |
| A1E4(G4S)4 | 316 | A1 | (G4S)4 | E4 |
| F1A1(G4S)4 | 317 | F1 | (G4S)4 | A1 |
| F3A1(G4S)4 | 318 | F3 | (G4S)4 | A1 |
| F4A1(G4S)4 | 319 | F4 | (G4S)4 | A1 |
| F5A1(G4S)4 | 320 | F5 | (G4S)4 | A1 |
| F6A1(G4S)4 | 321 | F6 | (G4S)4 | A1 |
| A1F1(G4S)4 | 322 | A1 | (G4S)4 | A1 |
| A1F3(G4S)4 | 323 | A1 | (G4S)4 | F1 |
| A1F4(G4S)4 | 324 | A1 | (G4S)4 | F4 |
| A1F5(G4S)4 | 325 | A1 | (G4S)4 | F5 |
| A1F6(G4S)4 | 326 | A1 | (G4S)4 | F6 |
| A1B1(G4S)1 | 458 | A1 | (G4S)1 | B1 |
| A1B1(G4S)2 | 459 | A1 | (G4S)2 | B1 |
| A1B1(G4S)3 | 460 | A1 | (G4S)3 | B1 |
| B1A1(G4S)1 | 461 | B1 | (G4S)1 | A1 |
| B1A1(G4S)2 | 462 | B1 | (G4S)2 | A1 |
| B1A1(G4S)3 | 463 | B1 | (G4S)3 | A1 |

Accordingly, a multi-specific construct may comprise a first and a second sdAb and a moiety that links the first and second sdAb, wherein the moiety is a peptide. Typically, the peptide is a short peptide with up to 30 amino acid residues. By example the peptide may consists of one or more modules of glycine and serine amino acids according to the formula $(G_nS)_n$, wherein n may be an integer from 1 to 6. Thus, a peptide may be GS, $G_2S$, $G_3S$, $(G_2S)_2$ $G_4S$, $(G_4S)_2$, $(G_4S)_3$, $(G_4S)_4$ etc., such as a GS linker selected from SEQ ID NOs: 88-91 or 452-454 or 457 (table 5). Alternatively, the peptide may be an arginine-serine peptide. Further the linker may be EAAAK or $(EAAAK)_2$ with SEQ ID NO 455 or 456.

Table 5 shows an overview of peptide linkers

| Linker | SEQ ID NO | Sequence |
| --- | --- | --- |
| (G4S) | 88 | GGGGS |
| (G4S)2 | 89 | GGGGSGGGGS |
| (G4S)3 | 90 | GGGGSGGGGSGGGGS |
| (G4S)4 | 91 | GGGGSGGGGSGGGGSGGGGS |
| RS | 92* | RS |
| GS | 452 | GS |
| G2S | 453 | GGS |
| G3S | 454 | GGGS |
| EAAAK | 455 | EAAAK |
| (EAAAK)2 | 456 | EAAAKEAAAK |
| G2SG2S | 457 | GGSGGS |

*SEQ ID NO: 92, 452 and 453 are reported as the repeat sequence RSRS, GSGS and GGSGGS, respectively but a single RS, GS and GGS is typically sufficient.

In some embodiments, wherein the multi-specific construct comprises the first and second sdAbs and the moiety is a peptide, the multi-specific construct may comprise one or more further sdAbs operably linked to either the first or second sdAb. For example, the one or more sdAbs may be linked by a peptide, polypeptide, or polysaccharide to either the first or second sdAb. In some embodiments, the one or more additional sdAbs may also be able to bind IgE, preferably the same IgE molecule as the first and second sdAb binds to. In other embodiments, the one or more additional sdAbs may be able to bind human serum albumin (HAS), which may prolong serum half-life.

In embodiments herein, the peptide linker may be selected from the group consisting of SEQ ID NO: 88, 89, 90, 91, 92, 452, 453, 454, 455, 456, and 457. In other words, the peptide linker may be selected from the group consisting of RS, GS, GGS and a peptide with SEQ ID NO: 88, 89, 90, 91, 454, 455, 456 and 457.

It might be understood that the moiety used for linking two or more sdAbs may independently be selected from the group consisting of a peptide, polypeptide, a polymer, and a polysaccharide.

The moiety c) may extend the serum half-life of the multi-specific construct. The extended serum half-life may be determined relative to the serum half-life of each of the first and second sdAbs or the two sdAbs in combination (e.g., wherein the sdAbs are linked together with a peptide moiety).

Alternatively, or additionally, the moiety may add further multi-specificity into the construct by selecting a moiety c) having a binding affinity for another biological relevant target.

Generally, there are several options for selecting a fusion partner for a monomeric sdAb or a multi-specific construct for improving pharmacokinetic properties (Strohl W. 2015). For example:

a. Fusion to a naturally long-half-life protein or protein domain (e.g., Fc fusion, transferrin [Tf] fusion, or albumin fusion).
b. Fusion to an inert polypeptide, e.g., XTEN (also known as recombinant PEG or "rPEG"), a homo-amino acid polymer (HAP; HAPylation, a proline-alanine-serine polymer (PAS; PASylation), or an elastin-like peptide (ELP; ELPylation).
c. Chemical conjugation to repeat chemical moieties, e.g., to PEG (PEGylation or hyaluronic acid).
d. By significantly increasing the negative charge of the monomeric sdAb or the multi-specific construct by polysialylation; or, alternatively, by fusing a negatively charged, highly sialylated peptide (e.g., carboxy-terminal peptide [CTP; of chorionic gonadotropin (CG) β-chain]),
e. Binding non-covalently, via attachment by a peptide linker or protein-binding domain to proteins normally having long-half-life, such as HSA, human IgG, or possibly transferrin.
f. Chemical conjugation to long-half-life proteins such as human IgGs, Fc moieties, or HSA.

It is envisaged that one or more of the options a) to f) may be incorporated in a multi-specific construct disclosed herein.

Fc-fusion of sdAbs.

Fc-fusion between an Fc domain and a therapeutical agent is widely used for providing additional beneficial biological and pharmacological properties (Czajkowsky et al. 2012). The presence of the Fc domain markedly increases plasma half-life, which prolongs therapeutic activity, owing to its interaction with the salvage neonatal Fc-receptor (FcRn) as well as to the slower renal clearance for larger sized molecules. The attached Fc domain also enables these molecules to interact with Fc-receptors (FcRs) found on immune cells. From a biophysical perspective, the Fc domain folds independently and can improve the solubility and stability of the partner molecule (e.g., sdAbs) both in vitro and in vivo, while from a technological viewpoint, the Fc region allows for easy cost-effective purification by protein-G/A affinity chromatography during manufacture.

Therefore, in some embodiments, the moiety c) is a polypeptide which is a fragment of an antibody such as particularly of a human antibody, selected from the group consisting of IgA, IgE, IgG, and IgM, preferably a fragment of IgG. The fragment of IgG may be selected from any fragment of $IgG_1$, $IgG_2$, $IgG_3$, and $IgG_4$, preferably the fragment of IgG is from $IgG_1$ or $IgG_4$, such as particularly the Fc domain of $IgG_1$ or $IgG_4$. The fragment may comprise IgG $C_H1$-$C_H3$, though it may be preferred to use IgG $C_H2$-$C_H3$ (IgG-Fc region). In some embodiments, it might be selected to use a short fragment of IgG, such as either the $C_H1$, $C_H2$ or $C_H3$ region.

Typically, the sdAbs may independently be fused or coupled covalently to $C_H3$ or $C_H2$ of IgG-Fc, optionally via a linker. Thus, the sdAbs may independently be fused or coupled covalently to the N-terminal end of $C_H2$ or to the C-terminal end of $C_H3$, optionally via a linker. In preferred embodiments the IgG-Fc is $IgG_4$-Fc, preferably a human $IgG_4$-Fc. In still further embodiments, thereof, both sdAbs are fused to the C-terminal end or the N-terminal end of the Fc through a peptide linker. In still further interesting embodiments thereof, both sdAbs are fused to the C-terminal end of the Fc through a peptide linker as this seems to protect against anaphylactogenic activity.

Accordingly, multi-specific constructs of interest are wherein the first and second sdAbs are both fused or covalently coupled, directly or via the linker, to $C_H2$ of IgG-Fc,
the first and second sdAbs are both fused or covalently coupled, directly or via the linker, to $C_H3$ of IgG-Fc,
the first sdAb is fused or covalently coupled, directly or via the linker, to $C_H2$ of IgG-Fc and the second sdAb is fused or covalently coupled, directly or via the linker, to $C_H3$ of IgG-Fc, or
the second sdAb is fused or covalently coupled, directly or via the linker, to $C_H2$ of IgG-Fc and the first sdAb is fused or covalently coupled directly or via the linker, to $C_H3$ of IgG-Fc.

In some more interesting embodiments, the first and second sdAb are each fused to $C_H3$ of IgG-Fc (C-terminal end of IgG-Fc) or the first and second sdAb are each fused to $C_H2$ of IgG-Fc (N-terminal end of IgG-Fc), optionally via a linker. In further interesting embodiments, the IgG Fc region is the $IgG_4$-Fc region.

The first and second sdAbs may be fused to the antibody fragment by use of any suitable linker, such as a peptide with up to 30 amino acid residues.

By example, may be used a flexible glycine-serine linker (GS linker), such as a GS linker consisting of one or more modules of $(G_nS)_n$, wherein n may be an integer from 1 to 6. Thus, a peptide may be GS, $G_2S$, $G_3S$, $(G_2S)_2$ $G_4S$, $(G_4S)_2$, $(G_4S)_3$, $(G_4S)_4$ etc., such as a GS linker selected from SEQ ID NOs: 88-91 or 452-454 or 457 (table 5). Alternatively, the peptide may be an arginine-serine (RS) peptide. Further the linker may be EAAAK or $(EAAAK)_2$ with SEQ ID NO 455 or 456.

In one embodiment, the linker is peptide selected from the group consisting of RS, GS, GGS and a peptide with SEQ ID NO: 88, 89, 90, 91, 454, 455, 456 and 457.

As mentioned, the antibody fragment (e.g., Fc region) can be that of any antibody type (e.g., IgG, IgE, IgM, IgD, and IgA), isotype (e.g., IgG1, IgG2, IgG3, IgG4, Ig A1 and Ig A2) or subclass, including engineered subclasses with altered Fc portions that optionally may provide for reduced or enhanced effector cell activity or modification in bio-distribution, serum half-life or excretion rates. The antibody fragment can be derived from any species. For example, the fragment is of human origin. Exemplary effector functions include C1-q binding; GDC; Fc-receptor binding; ADCC; ADCP; down-regulation of cell surface receptors (e.g., B-cell receptor), etc. Such effector functions generally require the Fc region to interact with a receptor, e.g., via the FcγRI; FcγRIIA; FcγRIIBI; FcγRIIB2; FcγRIIIA; FcγRIIIB receptors, and/or the low affinity FcRn receptor. In addition, the Fc-region can be a "dead" Fc, which is one that has been mutagenised to retain activity with respect to, for example, prolonging serum half-life, but which does not activate a high affinity Fc receptor. An Fc may also have decreased binding to complement.

Where it is desirable not to engage Fc interaction with receptors, e.g., FcγRIIB, the antibody fragment may be a CH1 immunoglobulin domains (such as a IgG1-CH1 domain or a IgG4-CH1 domain). Unlike conventionally used IgG-FC domains, they do not engage inhibitory FcγRIIb receptor, do not compete with serum immunoglobulins G for receptor binding, and their cytotoxic activity is independent of Fc glycosylation and FcγRIIIa polymorphism (Rozan et al., 2013)

In certain embodiments, the antibody fragment is from IgG4, such as IgG4-Fc. Examples on antibody fragments are listed in Table 6.

Table 6 shows a list of IgG-Fcs

| Fc construct | SEQ ID NO |
|---|---|
| IgG4 Full hinge region | 125 |
| IgG4 truncated hinge region | 126 |
| IgG4 Fc Knob part, truncated hinge region | 433 |
| IgG4 Fc Hole part, truncated hinge region | 434 |
| IgG4 Fc Knob part Full hinge region | 435 |
| IgG4 Fc Hole part Full hinge region | 436 |

Thus, the moiety c) may be selected from an IgG4 antibody fragment comprising or consisting of an amino acid sequence selected from any one of SEQ ID NOs 125, 126 or alternatively 433, 434, 435, and 436 when the construct is formed by KIH structural Knob and Hole elements. Preferably, the moiety c) may comprise an IgG4 antibody fragment comprising or consisting of an amino acid sequence selected from any one of SEQ ID NOS 125 and 126, optionally fused to a peptide linker. Preferably, the both of the heavy-Fc parts is each fused to an identical peptide linker, thus where the one Fc-chain is fused to for example a GGS peptide the other Fc-chain is also fused to a GGS peptide.

As the Ig-Fc part may contain different mutations, a further embodiment thereof comprises, an IgG4 antibody fragment has an amino acid sequence at least 50%, 60%, 65%, 70%, 75%, 80%, 85%, 90%, 91%, 92%, 93%, 94%, 95%, 96%, 97%, 98%, or 99% identical to the amino acid sequence selected from the group consisting of SEQ ID Nos 125, 126, 433, 434, 435, and 436. As IgG4 is unstable in vivo because of the phenomena "half antibody exchange"

meaning that it becomes bispecific (or functional monomeric in most cases). Therefore, when used therapeutically, a single amino acid mutation might be introduced in the hinge region to prevent this dissociation—the so called S228P mutation.

Another way of preventing the instability of IgG4 in vivo may be to apply the IgG4-Fc scaffold in the knobs-into-holes (KIH) format, which may prevent this dissociation.

One further mutation to implement in an antibody fragment may be a mutation for enhanced FcγRIIb (CD32b) engagement, for example as described in granted U.S. Pat. No. 8,435,517B2. It preferably binds FcγRIIb with a $k_D$ of less than about 100 nM.

Further the Fc-region can be a native-sequence Fc region comprising an amino acid sequence identical to the amino acid sequence of an Fc region found in nature. Native-sequence human Fc regions include a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof or the Fc-region can be a variant Fc region comprising an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein may possess at least about 80% amino acid sequence homology or sequence identity with a native-sequence Fc region and/or with an Fc region of a parent antibody fragment, and most preferably at least about 90% homology therewith, more preferably at least about 95% homology therewith.

In one embodiment, variant Fc sequences may include three amino acid substitutions in the CH2 region to reduce FcγRI binding at EU index positions 234, 235, and 237 (Duncan et al., 1988). Two amino acid substitutions in the complement C1-q binding site at EU index positions 330 and 331 reduce complement fixation (Tao et al., 1993 and Canfield & Morrison, 1991). Substitution into human IgG1 of IgG2 residues at positions 233-236 and IgG4 residues at positions 327, 330 and 331 greatly reduces ADCC and CDC (Armour K L. et al., 1999 and Shields R L. et al., 2001). Other Fc variants are possible, including without limitation one in which a region capable of forming a disulfide bond is deleted, or in which certain amino acid residues are eliminated at the N-terminal end of a native Fc form or a methionine residue is added thereto. Thus, one or more Fc portions of the molecule can comprise one or more mutations in the hinge region to eliminate disulfide bonding. In yet another embodiment, the hinge region of an Fc can be removed entirely. In still another embodiment, the molecule can comprise an Fc variant.

Further, an Fc variant can be constructed by substituting, deleting, or adding amino acid residues to effect complement binding or Fc receptor binding. Techniques of preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

The antibody fragment, e.g., Fc part, may also be modified for constructional (e.g., expression yield) reasons by substituting, deleting, or inserting amino acid residues. Non-limiting examples of mutations introduced to expression yield are described in the following. The antibody fragment may be modified to be in a form having native sugar chains, increased sugar chains compared to a native form or decreased sugar chains compared to the native form or may be in an aglycosylated or deglycosylated form. The increase, decrease, removal or other modification of the sugar chains may be achieved by methods common in the art, such as a chemical method, an enzymatic method or by expressing it in a genetically engineered production cell line. Such cell lines can include microorganisms, e.g., *Pichia pastoris*, and mammalians cell line, e.g., CHO cells, that naturally express glycosylating enzymes. Further, microorganisms or cells can be engineered to express glycosylating enzymes or can be rendered unable to express glycosylation enzymes. As one example of a cell engineered to have altered sialylation activity, the alpha-2, 6-sialyltransferase 1 gene has been engineered into Chinese Hamster Ovary cells and into Sf9 cells. Constructs expressed by these engineered cells are thus sialylated by the exogenous gene product. A further method for obtaining Fc molecules having a modified amount of sugar residues compared to a plurality of native molecules includes separating said plurality of molecules into glycosylated and non-glycosylated fractions, for example, using lectin affinity chromatography. The presence of particularly glycosylation moieties has been shown to alter the function of Immunoglobulins. For example, the removal of sugar chains from an Fc molecule results in a sharp decrease in binding affinity to the C1-q part of the first complement component C1 and a decrease or loss in antibody-dependent cell-mediated cytotoxicity (ADCC) or complement-dependent cytotoxicity (CDC), thereby not inducing unnecessary immune responses in vivo. Additional important modifications include sialylation and fucosylation: the presence of sialic acid in IgG has been correlated with antiinflammatory activity, whereas removal of fucose from the IgG leads to enhanced ADCC activity.

Constructs can have an Fc sequence with enhanced effector functions, e.g., by increasing their binding capacities to FcγRI and increasing ADCC activity. For example, fucose attached to the/V-linked glycan at Asn-297 of Fc sterically hinders the interaction of Fc with FcγRIIIA, and removal of fucose by glyco-engineering can increase the binding to FcγRIIIA, which translates into >50-fold higher ADCC activity compared with wild type IgG1 controls. Protein engineering, through amino acid mutations in the Fc portion of IgG1, has generated multiple variants that increase the affinity of Fc binding to FcγRIIIA. Notably, the triple alanine mutant S298A/E333A/K334A displays 2-fold increase binding to FcγRIIIA and ADCC function. S239D/I332E (2×) and S239D/I332E/A330L (3×) variants have a significant increase in binding affinity to FcγRIIIA and augmentation of ADCC capacity in vitro and in vivo. Other Fc variants identified by yeast display also showed the improved binding to FcγRIIIA. See, for example Liu et al. (2014) JBC 289(6):3571-90, herein specifically incorporated by reference.

The multi-specific construct as described herein can be assembled in different ways.

In a non-limiting example, the multi-specific construct comprises i. a first sdAb selected from the group consisting of SEQ ID NO: 1, 5, 9, 13. 17, 21, 25, 29, 33, 37 41, 45, 49, 53, 57, 61, 65, 69, and 73, preferably selected from sdAb with SEQ ID NO: 1 or 5;

ii. a second sdAb, different from the first sdAb, selected from the group consisting of SEQ ID NO: 1, 5, 9, 13. 17, 21, 25, 29, 33, 37 41, 45, 49, 53, 57, 61, 65, 69, and 73, preferably selected from sdAb with SEQ ID NO: 9, 13. 17, 21, 25, 29, 33, 37 41, 45, 49, 53, 57, 61, 65, 69, and 73 wherein each sdAb is linked to a Fc part, such as iii. a Fc part selected from SEQ ID NO 125 or 126, or Fc part associated by a knob part selected from SEQ ID NO: 433 and 435 and a Hole part selected from SEQ ID NO: 434 and 436, using a linker part to link the sdAb to the Fc part in either the N- or the C-terminal, such as iv. a linker part selected from the group consisting of SEQ ID NO: 88-92 and 452-457.

As mentioned, the amino acid sequence of the first and second sdAbs may be subject to affinity maturation, humanisation, or other amino acid changes of the amino acid sequence, preferably outside the CDR regions. Therefore, the first sdAb may have at least 80%, such as at least 85%, 90%, 95%, 96%, 97%, 98%, or 99%, sequence identity to the group consisting of SEQ ID NO: 1, 5, 9, 13. 17, 21, 25, 29, 33, 37 41, 45, 49, 53, 57, 61, 65, 69, and 73, and the second sdAb, different from the first sdAb, may have at least 80%, such as at least 85%, 90%, 95%, 96%, 97%, 98%, or 99%, sequence identity to the group consisting of SEQ ID NO: 1, 5, 9, 13. 17, 21, 25, 29, 33, 37 41, 45, 49, 53, 57, 61, 65, 69, and 73. Likewise, the Fc part may have any sequence variation described supra under Fc-fused sdAbs.

In a preferred embodiment, the multi-specific construct comprises the first sdAb A1 with SEQ ID NO: 1 or with at least 80% sequence identity to SEQ ID NO: 1, the second sdAb B1 with SEQ ID NO: 9 or with at least 80% sequence identity to SEQ ID NO: 9, wherein each sdAb is linked to the Fc part with SEQ ID NO: 125 or with at least 80% sequence identity to SEQ ID NO: 125, using a linker part with the sequence SEQ ID NO: 88.

In another preferred embodiment, the multi-specific construct comprises the first sdAb A1 with the sequence SEQ ID NO: 1, the second sdAb B1 with the sequence SEQ ID NO: 9, wherein each sdAb are linked to the Fc part with the sequence SEQ ID NO: 126, using a linker part with the sequence SEQ ID NO: 88.

In another non-limiting example the multi-specific construct comprises a first sdAb comprising CDR1, CDR2 and CDR3 regions determined using Kabat, Chothia, IMGT or Aho numbering schemes in the amino acid sequences selected from the group consisting of SEQ ID NO: 1, 5, 9, 13. 17, 21, 25, 29, 33, 37 41, 45, 49, 53, 57, 61, 65, 69, and 73, a second sdAb, different from the first sdAb, comprising CDR1, CDR2 and CDR3 regions determined using Kabat, Chothia, IMGT or Aho numbering schemes in the amino acid sequences selected from the group consisting of SEQ ID NO: 1, 5, 9, 13. 17, 21, 25, 29, 33, 37 41, 45, 49, 53, 57, 61, 65, 69, and 73, wherein each sdAb is linked to a Fc part selected from SEQ ID NO 125 or 126, using a linker part selected from the group consisting of SEQ ID NO: 88-92 and 452-457.

In a preferred embodiment, the multi-specific construct comprises a first sdAb comprising CDR1, CDR2 and CDR3 regions determined using Kabat, Chothia, IMGT or Aho numbering schemes in the amino acid sequence of A1 with the sequence SEQ ID NO: 1, the second sdAb comprising CDR1, CDR2 and CDR3 regions determined using Kabat, Chothia, IMGT or Aho numbering schemes in the amino acid sequence of B1 with the sequence SEQ ID NO: 9, wherein each sdAb is linked to the Fc part with the sequence SEQ IS NO: 125, using a linker part with the sequence SEQ ID NO: 88.

In another preferred embodiment, the multi-specific construct comprises a first sdAb comprising CDR1, CDR2 and CDR3 regions determined using Kabat, Chothia, IMGT or Aho numbering schemes in the amino acid sequence of A1 with the sequence SEQ ID NO: 1, the second sdAb comprising CDR1, CDR2 and CDR3 regions determined using Kabat, Chothia, IMGT or Aho numbering schemes in the amino acid sequence of B1 with the sequence SEQ ID NO: 9, wherein each sdAb are linked to the Fc part with the sequence SEQ IS NO: 126, using a linker part with the sequence SEQ ID NO: 88.

In further preferred embodiment, the multi-specific construct comprises a first sdAb comprising CDR1, CDR2 and CDR3 regions determined using Kabat, Chothia, IMGT or Aho numbering schemes in the amino acid sequence of A1 with the sequence SEQ ID NO: 1, the second sdAb comprising CDR1, CDR2 and CDR3 regions determined using Kabat, Chothia, IMGT or Aho numbering schemes in the amino acid sequence of B1 with the sequence SEQ ID NO: 25, wherein each sdAb are linked to the Fc part with the sequence SEQ IS NO: 125, using a linker part with the sequence SEQ ID NO: 88.

In further preferred embodiment, the multi-specific construct comprises a first sdAb comprising CDR1, CDR2 and CDR3 regions determined using Kabat, Chothia, IMGT or Aho numbering schemes in the amino acid sequence of A1 with the sequence SEQ ID NO: 1, the second sdAb comprising CDR1, CDR2 and CDR3 regions determined using Kabat, Chothia, IMGT or Aho numbering schemes in the amino acid sequence of B1 with the sequence SEQ ID NO: 25, wherein each sdAb are linked to the Fc part with the sequence SEQ IS NO: 126, using a linker part with the sequence SEQ ID NO: 88.

In further preferred embodiment, the multi-specific construct comprises a first sdAb comprising CDR1, CDR2 and CDR3 regions determined using Kabat, Chothia, IMGT or Aho numbering schemes in the amino acid sequence of A1 with the sequence SEQ ID NO: 1, the second sdAb comprising CDR1, CDR2 and CDR3 regions determined using Kabat, Chothia, IMGT or Aho numbering schemes in the amino acid sequence of B1 with the sequence SEQ ID NO: 33, wherein each sdAb are linked to the Fc part with the sequence SEQ IS NO: 125, using a linker part with the sequence SEQ ID NO: 88.

In further preferred embodiment, the multi-specific construct comprises a first sdAb comprising CDR1, CDR2 and CDR3 regions determined using Kabat, Chothia, IMGT or Aho numbering schemes in the amino acid sequence of A1 with the sequence SEQ ID NO: 1, the second sdAb comprising CDR1, CDR2 and CDR3 regions determined using Kabat, Chothia, IMGT or Aho numbering schemes in the amino acid sequence of B1 with the sequence SEQ ID NO: 33, wherein each sdAb are linked to the Fc part with the sequence SEQ IS NO: 126, using a linker part with the sequence SEQ ID NO: 88.

In further preferred embodiment, the multi-specific construct comprises a first sdAb comprising CDR1, CDR2 and CDR3 regions determined using Kabat, Chothia, IMGT or Aho numbering schemes in the amino acid sequence of A1 with the sequence SEQ ID NO: 1, the second sdAb comprising CDR1, CDR2 and CDR3 regions determined using Kabat, Chothia, IMGT or Aho numbering schemes in the amino acid sequence of B1 with the sequence SEQ ID NO: 61, wherein each sdAb are linked to the Fc part with the sequence SEQ IS NO: 125, using a linker part with the sequence SEQ ID NO: 88.

In further preferred embodiment, the multi-specific construct comprises a first sdAb comprising CDR1, CDR2 and CDR3 regions determined using Kabat, Chothia, IMGT or Aho numbering schemes in the amino acid sequence of A1 with the sequence SEQ ID NO: 1, the second sdAb comprising CDR1, CDR2 and CDR3 regions determined using Kabat, Chothia, IMGT or Aho numbering schemes in the amino acid sequence of B1 with the sequence SEQ ID NO: 61, wherein each sdAb are linked to the Fc part with the sequence SEQ IS NO: 126, using a linker part with the sequence SEQ ID NO: 88.

Knob-into-Hole Fc-Fusion

In some embodiments, the multi-specific constructs are expressed as a Knob-Into-Hole (KIH) Fc-fusion. Thus, multi-specific constructs disclosed herein, wherein the first and second sdAb is fused to an IgG-fc, optionally via a linker, the multi-specific construct can be produced as a Knob-Into-Hole (KIH) Fc-fusion constructs.

The KIH technology, which involves engineering CH3 domains to create a "knob" or a "hole" in each heavy chain to promote heterodimerization, can be used to assemble the multi-specific construct.

In one embodiment, the Fc domain included in the multi-specific construct is derived from a human Fc domain and comprises a mutation that induces heterodimerisation. In some embodiments, such mutations include mutations referred to as "knob" and "hole" mutations. For example, amino acid modifications are made at Thr366 within the CH3 domain, which when substituted with a larger amino acid, e.g., Trp (T366W), can preferentially pair with a second CH3 domain in which the amino acids at positions Thr366, Leu368 and Tyr407 are modified to smaller amino acids, e.g., Ser, Ala and Val (T366S/L368A/Y407V), respectively. In some embodiments, the "knob" Fc domain comprises the mutation S354C and T366W. In some embodiments, the "hole" Fc domain comprises the mutations T349C, T366S, L368A, and Y407V. Heterodimerization via modification of CH3 may be further stabilized by introducing disulphide bonds, for example by changing Ser354 to Cys (S354C) and Y349 to Cys (Y349C) on the opposite CH3 domain (reviewed in Carter et al., 2001). In some embodiments, the Fc domain used for heterodimerization comprises an additional mutation, such as mutation S354C on the first member of the heterodimeric Fc pair, which forms an asymmetric disulfide bond with the corresponding mutation Y349C on the second member of the heterodimeric Fc pair. In some embodiments, one member of the heterodimeric Fc pair comprises modifications H435R or H435K to avoid protein a binding while maintaining FcRn binding. In some embodiments, one member of the heterodimeric Fc pair comprises the modification H435R or H435K, while the second member of the heterodimeric Fc pair is not modified at H435. In various embodiments, the hole Fc domain comprises the modification H435R or H435K (in some cases referred to as "hole-R" when the modification is H435R), while the knob Fc domain does not. In some cases, the hole-R mutation improves purification of heterodimers relative to homodimeric hole Fc domains that may be present.

In another embodiment, the Fc polypeptides in the heterodimer include mutations that alter the charge polarity across the Fc dimer interface such that co-expression of electrostatically matched Fc chains supports favourable attractive interactions, thereby promoting desirable Fc heterodimer formation, while unfavourable repulsive charge interactions inhibit undesirable Fc homodimer formation (Gunescaran et al., 2010). When co-expressed in a cell, there is a possibility that the chains bind to each other, but the chains do not substantially bind to each other due to charge repulsion. Other strategies for producing heterodimeric Fc include mixing human IgG with IgA CH3 domain segments to produce complementary CH3 heterodimers, referred to as SEED Fc.

Heterodimerization methods and variants also include those described in published international PCT application WO2014/145806, including "knob and hole" mutations (also referred to as "skew" variants), mutations associated with "electrostatic manipulation" or "charge pair" and pI variants. Heterodimeric variants also include any variant as described in U.S. published application nos. US2012/0149876 or US 2018/011883.

In some embodiments, to promote heterodimerization, both polypeptides of the Fc heterodimer contain paired or complementary amino acid modifications. Exemplary pairwise amino acid modifications of polypeptides in Fc fusions are set forth in table 7.

Table 7 shows examples of mutations in the Fc for the KIH format.

| Fc-Knob | Fc-Hole |
|---|---|
| T366W | T366S/L368W/Y407V |
| T366W/S354C | T366S/L368A/Y407V/Y349C |

-continued

| Fc-Knob | Fc-Hole |
|---|---|
| S364H/F405A | Y349T/Y349F |
| T350V/L351Y/F405A/Y407V | T350V/T366L/K392L/T394W |
| K360D/D399M/Y407A | E345R/Q347R/T366V/K409V |
| K409D/K392D | D399K/E356K |
| K360E/K409W | Q'347R/D399V/F405T |
| L360E/K409W/Y349C | Q347R/399V/F405T/S354C |
| K370E/K409W | E357N/D399V/F405T |
| S354C/T366W | T349C/T366S/L368A/Y407V |

In some embodiments, the modification comprises introducing a protuberance (knob) into the first Fc polypeptide and introducing a cavity (hole) into the second Fc polypeptide such that the protuberance is positional in the cavity to facilitate complexation of the first and second Fc-containing polypeptides. The amino acids targeted for substitution and/or modification to create a protuberance or cavity in a polypeptide are typically interfacial amino acids that interact.

In embodiments herein, an multi-specific construct comprising a first and second sdAb fused to an IgG-fc, optionally via a linker, may be produced as a Knob-Into-Hole (KIH) Fc-fusion construct. In some embodiments, thereof, the Knob part of the KIH comprises IgG4-Fc with SEQ ID NO: 433 or 435. In further embodiments, or in the alternative, the Hole part of the KIH comprises IgG4-Fc with SEQ ID NO: 434 or 436.

Table 8 provides an overview of the full-length amino acid sequences of the two separate parts of the knob-into-hole constructs as disclosed herein.

TABLE 8

| Construct | SEQ ID NO | sdAb | Scaffold | Mutation | linker | Linked terminus |
|---|---|---|---|---|---|---|
| CIgG4A1(RS)Hole | 93 | A1 | Hole | S228P, T349C, T366S, L368A, Y407V | RS | C |
| CIgG4A1(G4S)1Hole | 94 | A1 | Hole | S228P, T349C, T366S, L368A, Y407V | (G4S) | C |
| CIgG4A1(G4S)2Hole | 95 | A1 | Hole | S228P, T349C, T366S, L368A, Y407V | (G4S)2 | C |
| CIgG4A1(G4S)3Hole | 96 | A1 | Hole | S228P, T349C, T366S, L368A, Y407V | (G4S)3 | C |
| CIgG4B3(RS)Knob | 97 | B3 | Knobs | S228P, S354C, T366W | RS | C |
| CIgG4B3(G4S)1Knob | 98 | B3 | Knobs | S228P, S354C, T366W | (G4S) | C |
| CIgG4B3(G4S)2Knob | 99 | B3 | Knobs | S228P, S354C, T366W | (G4S)2 | C |
| CIgG4B3(G4S)3Knob | 100 | B3 | Knobs | S228P, S354C, T366W | (G4S)3 | C |
| CIgG4B1(RS)Knob | 101 | B1 | Knobs | S228P, S354C, T366W | RS | C |
| CIgG4B1(G4S)1Knob | 102 | B1 | Knobs | S228P, S354C, T366W | (G4S) | C |
| CIgG4B1(G4S)2Knob | 103 | B1 | Knobs | S228P, S354C, T366W | (G4S)2 | C |
| CIgG4B1(G4S)3Knob | 104 | B1 | Knobs | S228P, S354C, T366W | (G4S)3 | C |
| CIgG4A1(RS)Knob | 105 | A1 | Knobs | S228P, S354C, T366W | RS | C |
| CIgG4A1(G4S)1Knob | 106 | A1 | Knobs | S228P, S354C, T366W | (G4S) | C |
| CIgG4A1(G4S)2Knob | 107 | A1 | Knobs | S228P, S354C, T366W | (G4S)2 | C |
| CIgG4A1(G4S)3Knob | 108 | A1 | Knobs | S228P, S354C, T366W | (G4S)3 | C |

TABLE 8-continued

| Construct | SEQ ID NO | sdAb | Scaffold | Mutation | linker | Linked terminus |
|---|---|---|---|---|---|---|
| NIgG4A1(RS)Knob | 109 | A1 | Knobs | S228P, S354C, T366W | RS | N |
| NIgG4A1(G4S)1Knob | 110 | A1 | Knobs | S228P, S354C, T366W | (G4S) | N |
| NIgG4A1(G4S)2Knob | 111 | A1 | Knobs | S228P, S354C, T366W | (G4S)2 | N |
| NIgG4A1(G4S)3Knob | 112 | A1 | Knobs | S228P, S354C, T366W | (G4S)3 | N |
| NIgG4A1(RS)Hole | 113 | A1 | Hole | S228P, T349C, T366S, L368A, Y407V | RS | N |
| NIgG4A1(G4S)1Hole | 114 | A1 | Hole | S228P, T349C, T366S, L368A, Y407V | (G4S) | N |
| NIgG4A1(G4S)2Hole | 115 | A1 | Hole | S228P, T349C, T366S, L368A, Y407V | (G4S)2 | N |
| NIgG4A1(G4S)3Hole | 116 | A1 | Hole | S228P, T349C, T366S, L368A, Y407V | (G4S)3 | N |
| NIgG4B3(RS)Knob | 117 | B3 | Knobs | S228P, S354C, T366W | RS | N |
| NIgG4B3(G4S)1Knob | 118 | B3 | Knobs | S228P, S354C, T366W | (G4S) | N |
| NIgG4B3(G4S)2Knob | 119 | B3 | Knobs | S228P, S354C, T366W | (G4S)2 | N |
| NIgG4B3(G4S)3Knob | 120 | B3 | Knobs | S228P, S354C, T366W | (G4S)3 | N |
| NIgG4B1(RS)Knob | 121 | B1 | Knobs | S228P, S354C, T366W | RS | N |
| NIgG4B1(G4S)1Knob | 122 | B1 | Knobs | S228P, S354C, T366W | (G4S) | N |
| NIgG4B1(G4S)2Knob | 123 | B1 | Knobs | S228P, S354C, T366W | (G4S)2 | N |
| NIgG4B1(G4S)3Knob | 124 | B1 | Knobs | S228P, S354C, T366W | (G4S)3 | N |
| CIgG4B2(RS)Knob | 321 | B2 | Knobs | S228P, S354C, T366W | RS | C |
| CIgG4B2(G4S)1Knob | 322 | B2 | Knobs | S228P, S354C, T366W | (G4S) | C |
| CIgG4B2(G4S)2Knob | 323 | B2 | Knobs | S228P, S354C, T366W | (G4S)2 | C |
| CIgG4B2(G4S)3Knob | 324 | B2 | Knobs | S228P, S354C, T366W | (G4S)3 | C |
| NIgG4B2(RS)Knob | 325 | B2 | Knobs | S228P, S354C, T366W | RS | N |
| NIgG4B2(G4S)1Knob | 326 | B2 | Knobs | S228P, S354C, T366W | (G4S) | N |
| NIgG4B2(G4S)2Knob | 327 | B2 | Knobs | S228P, S354C, T366W | (G4S)2 | N |
| NIgG4B2(G4S)3Knob | 328 | B2 | Knobs | S228P, S354C, T366W | (G4S)3 | N |
| CIgG4D1(RS)Knob | 329 | D1 | Knobs | S228P, S354C, T366W | RS | C |
| CIgG4D1(G4S)1Knob | 330 | D1 | Knobs | S228P, S354C, T366W | (G4S) | C |
| CIgG4D1(G4S)2Knob | 331 | D1 | Knobs | S228P, S354C, T366W | (G4S)2 | C |
| CIgG4D1(G4S)3Knob | 332 | D1 | Knobs | S228P, S354C, T366W | (G4S)3 | C |
| NIgG4D1(RS)Knob | 333 | D1 | Knobs | S228P, S354C, T366W | RS | N |
| NIgG4D1(G4S)1Knob | 334 | D1 | Knobs | S228P, S354C, T366W | (G4S) | N |
| NIgG4D1(G4S)2Knob | 335 | D1 | Knobs | S228P, S354C, T366W | (G4S)2 | N |
| NIgG4D1(G4S)3Knob | 336 | D1 | Knobs | S228P, S354C, T366W | (G4S)3 | N |
| CIgG4D2(RS)Knob | 337 | D2 | Knobs | S228P, S354C, T366W | RS | C |
| CIgG4D2(G4S)1Knob | 338 | D2 | Knobs | S228P, S354C, T366W | (G4S) | C |
| CIgG4D2(G4S)2Knob | 339 | D2 | Knobs | S228P, S354C, T366W | (G4S)2 | C |
| CIgG4D2(G4S)3Knob | 340 | D2 | Knobs | S228P, S354C, T366W | (G4S)3 | C |

TABLE 8-continued

| Construct | SEQ ID NO | sdAb | Scaffold | Mutation | linker | Linked terminus |
|-----------|-----------|------|----------|----------|--------|-----------------|
| NIgG4D2(RS)Knob | 341 | D2 | Knobs | S228P, S354C, T366W | RS | N |
| NIgG4D2(G4S)1Knob | 342 | D2 | Knobs | S228P, S354C, T366W | (G4S) | N |
| NIgG4D2(G4S)2Knob | 343 | D2 | Knobs | S228P, S354C, T366W | (G4S)2 | N |
| NIgG4D2(G4S)3Knob | 344 | D2 | Knobs | S228P, S354C, T366W | (G4S)3 | N |
| CIgG4E1(RS)Knob | 345 | E1 | Knobs | S228P, S354C, T366W | RS | C |
| CIgG4E1(G4S)1Knob | 346 | E1 | Knobs | S228P, S354C, T366W | (G4S) | C |
| CIgG4E1(G4S)2Knob | 347 | E1 | Knobs | S228P, S354C, T366W | (G4S)2 | C |
| CIgG4E1(G4S)3Knob | 348 | E1 | Knobs | S228P, S354C, T366W | (G4S)3 | C |
| NIgG4E1(RS)Knob | 349 | E1 | Knobs | S228P, S354C, T366W | RS | N |
| NIgG4E1(G4S)1Knob | 350 | E1 | Knobs | S228P, S354C, T366W | (G4S) | N |
| NIgG4E1(G4S)2Knob | 351 | E1 | Knobs | S228P, S354C, T366W | (G4S)2 | N |
| NIgG4E1(G4S)3Knob | 352 | E1 | Knobs | S228P, S354C, T366W | (G4S)3 | N |
| CIgG4E2(RS)Knob | 353 | E2 | Knobs | S228P, S354C, T366W | RS | C |
| CIgG4E2(G4S)1Knob | 354 | E2 | Knobs | S228P, S354C, T366W | (G4S) | C |
| CIgG4E2(G4S)2Knob | 355 | E2 | Knobs | S228P, S354C, T366W | (G4S)2 | C |
| CIgG4E2(G4S)3Knob | 356 | E2 | Knobs | S228P, S354C, T366W | (G4S)3 | C |
| NIgG4E2(RS)Knob | 357 | E2 | Knobs | S228P, S354C, T366W | RS | N |
| NIgG4E2(G4S)1Knob | 358 | E2 | Knobs | S228P, S354C, T366W | (G4S) | N |
| NIgG4E2(G4S)2Knob | 359 | E2 | Knobs | S228P, S354C, T366W | (G4S)2 | N |
| NIgG4E2(G4S)3Knob | 360 | E2 | Knobs | S228P, S354C, T366W | (G4S)3 | N |
| CIgG4E3(RS)Knob | 361 | E3 | Knobs | S228P, S354C, T366W | RS | C |
| CIgG4E3(G4S)1Knob | 362 | E3 | Knobs | S228P, S354C, T366W | (G4S) | C |
| CIgG4E3(G4S)2Knob | 363 | E3 | Knobs | S228P, S354C, T366W | (G4S)2 | C |
| CIgG4E3(G4S)3Knob | 364 | E3 | Knobs | S228P, S354C, T366W | (G4S)3 | C |
| NIgG4E3(RS)Knob | 365 | E3 | Knobs | S228P, S354C, T366W | RS | N |
| NIgG4E3(G4S)1Knob | 366 | E3 | Knobs | S228P, S354C, T366W | (G4S) | N |
| NIgG4E3(G4S)2Knob | 367 | E3 | Knobs | S228P, S354C, T366W | (G4S)2 | N |
| NIgG4E3(G4S)3Knob | 368 | E3 | Knobs | S228P, S354C, T366W | (G4S)3 | N |
| CIgG4E4(RS)Knob | 369 | E4 | Knobs | S228P, S354C, T366W | RS | C |
| CIgG4E4(G4S)1Knob | 370 | E4 | Knobs | S228P, S354C, T366W | (G4S) | C |
| CIgG4E4(G4S)2Knob | 371 | E4 | Knobs | S228P, S354C, T366W | (G4S)2 | C |
| CIgG4E4(G4S)3Knob | 372 | E4 | Knobs | S228P, S354C, T366W | (G4S)3 | C |
| NIgG4E4(RS)Knob | 373 | E4 | Knobs | S228P, S354C, T366W | RS | N |
| NIgG4E4(G4S)1Knob | 374 | E4 | Knobs | S228P, S354C, T366W | (G4S) | N |
| NIgG4E4(G4S)2Knob | 375 | E4 | Knobs | S228P, S354C, T366W | (G4S)2 | N |
| NIgG4E4(G4S)3Knob | 376 | E4 | Knobs | S228P, S354C, T366W | (G4S)3 | N |
| CIgG4F1(RS)Knob | 377 | F1 | Knobs | S228P, S354C, T366W | RS | C |
| CIgG4F1(G4S)1Knob | 378 | F1 | Knobs | S228P, S354C, T366W | (G4S) | C |

TABLE 8-continued

| Construct | SEQ ID NO | sdAb | Scaffold | Mutation | linker | Linked terminus |
|---|---|---|---|---|---|---|
| CIgG4F1(G4S)2Knob | 379 | F1 | Knobs | S228P, S354C, T366W | (G4S)2 | C |
| CIgG4F1(G4S)3Knob | 380 | F1 | Knobs | S228P, S354C, T366W | (G4S)3 | C |
| NIgG4F1(RS)Knob | 381 | F1 | Knobs | S228P, S354C, T366W | RS | N |
| NIgG4F1(G4S)1Knob | 382 | F1 | Knobs | S228P, S354C, T366W | (G4S) | N |
| NIgG4F1(G4S)2Knob | 383 | F1 | Knobs | S228P, S354C, T366W | (G4S)2 | N |
| NIgG4F1(G4S)3Knob | 384 | F1 | Knobs | S228P, S354C, T366W | (G4S)3 | N |
| CIgG4F2(RS)Knob | 385 | F2 | Knobs | S228P, S354C, T366W | RS | C |
| CIgG4F2(G4S)1Knob | 386 | F2 | Knobs | S228P, S354C, T366W | (G4S) | C |
| CIgG4F2(G4S)2Knob | 387 | F2 | Knobs | S228P, S354C, T366W | (G4S)2 | C |
| CIgG4F2(G4S)3Knob | 388 | F2 | Knobs | S228P, S354C, T366W | (G4S)3 | C |
| NIgG4F2(RS)Knob | 389 | F2 | Knobs | S228P, S354C, T366W | RS | N |
| NIgG4F2(G4S)1Knob | 390 | F2 | Knobs | S228P, S354C, T366W | (G4S) | N |
| NIgG4F2(G4S)2Knob | 391 | F2 | Knobs | S228P, S354C, T366W | (G4S)2 | N |
| NIgG4F2(G4S)3Knob | 392 | F2 | Knobs | S228P, S354C, T366W | (G4S)3 | N |
| CIgG4F3(RS)Knob | 393 | F3 | Knobs | S228P, S354C, T366W | RS | C |
| CIgG4F3(G4S)1Knob | 394 | F3 | Knobs | S228P, S354C, T366W | (G4S) | C |
| CIgG4F3(G4S)2Knob | 395 | F3 | Knobs | S228P, S354C, T366W | (G4S)2 | C |
| CIgG4F3(G4S)3Knob | 396 | F3 | Knobs | S228P, S354C, T366W | (G4S)3 | C |
| NIgG4F3(RS)Knob | 397 | F3 | Knobs | S228P, S354C, T366W | RS | N |
| NIgG4F3(G4S)1Knob | 398 | F3 | Knobs | S228P, S354C, T366W | (G4S) | N |
| NIgG4F3(G4S)2Knob | 399 | F3 | Knobs | S228P, S354C, T366W | (G4S)2 | N |
| NIgG4F3(G4S)3Knob | 400 | F3 | Knobs | S228P, S354C, T366W | (G4S)3 | N |
| CIgG4F4(RS)Knob | 401 | F4 | Knobs | S228P, S354C, T366W | RS | C |
| CIgG4F4(G4S)1Knob | 402 | F4 | Knobs | S228P, S354C, T366W | (G4S) | C |
| CIgG4F4(G4S)2Knob | 403 | F4 | Knobs | S228P, S354C, T366W | (G4S)2 | C |
| CIgG4F4(G4S)3Knob | 404 | F4 | Knobs | S228P, S354C, T366W | (G4S)3 | C |
| NIgG4F4(RS)Knob | 405 | F4 | Knobs | S228P, S354C, T366W | RS | N |
| NIgG4F4(G4S)1Knob | 406 | F4 | Knobs | S228P, S354C, T366W | (G4S) | N |
| NIgG4F4(G4S)2Knob | 407 | F4 | Knobs | S228P, S354C, T366W | (G4S)2 | N |
| NIgG4F4(G4S)3Knob | 408 | F4 | Knobs | S228P, S354C, T366W | (G4S)3 | N |
| CIgG4F5(RS)Knob | 409 | F5 | Knobs | S228P, S354C, T366W | RS | C |
| CIgG4F5(G4S)1Knob | 410 | F5 | Knobs | S228P, S354C, T366W | (G4S) | C |
| CIgG4F5(G4S)2Knob | 411 | F5 | Knobs | S228P, S354C, T366W | (G4S)2 | C |
| CIgG4F5(G4S)3Knob | 412 | F5 | Knobs | S228P, S354C, T366W | (G4S)3 | C |
| NIgG4F5(RS)Knob | 413 | F5 | Knobs | S228P, S354C, T366W | RS | N |
| NIgG4F5(G4S)1Knob | 414 | F5 | Knobs | S228P, S354C, T366W | (G4S) | N |
| NIgG4F5(G4S)2Knob | 415 | F5 | Knobs | S228P, S354C, T366W | (G4S)2 | N |
| NIgG4F5(G4S)3Knob | 416 | F5 | Knobs | S228P, S354C, T366W | (G4S)3 | N |

TABLE 8-continued

| Construct | SEQ ID NO | sdAb | Scaffold | Mutation | linker | Linked terminus |
|---|---|---|---|---|---|---|
| CIgG4F6(RS)Knob | 417 | F6 | Knobs | S228P, S354C, T366W | RS | C |
| CIgG4F6(G4S)1Knob | 418 | F6 | Knobs | S228P, S354C, T366W | (G4S) | C |
| CIgG4F6(G4S)2Knob | 419 | F6 | Knobs | S228P, S354C, T366W | (G4S)2 | C |
| CIgG4F6(G4S)3Knob | 420 | F6 | Knobs | S228P, S354C, T366W | (G4S)3 | C |
| NIgG4F6(RS)Knob | 421 | F6 | Knobs | S228P, S354C, T366W | RS | N |
| NIgG4F6(G4S)1Knob | 422 | F6 | Knobs | S228P, S354C, T366W | (G4S) | N |
| NIgG4F6(G4S)2Knob | 423 | F6 | Knobs | S228P, S354C, T366W | (G4S)2 | N |
| NIgG4F6(G4S)3Knob | 424 | F6 | Knobs | S228P, S354C, T366W | (G4S)3 | N |
| CIgG4A2(RS)Hole | 425 | A2 | Hole | S228P, T349C, T366S, L368A, Y407V | RS | C |
| CIgG4A2(G4S)1Hole | 426 | A2 | Hole | S228P, T349C, T366S, L368A, Y407V | (G4S) | C |
| CIgG4A2(G4S)2Hole | 427 | A2 | Hole | S228P, T349C, T366S, L368A, Y407V | (G4S)2 | C |
| CIgG4A2(G4S)3Hole | 428 | A2 | Hole | S228P, T349C, T366S, L368A, Y407V | (G4S)3 | C |
| NIgG4A2(RS)Hole | 429 | A2 | Hole | S228P, T349C, T366S, L368A, Y407V | RS | N |
| NIgG4A2(G4S)1Hole | 430 | A2 | Hole | S228P, T349C, T366S, L368A, Y407V | (G4S) | N |
| NIgG4A2(G4S)2Hole | 431 | A2 | Hole | S228P, T349C, T366S, L368A, Y407V | (G4S)2 | N |
| NIgG4A2(G4S)3Hole | 432 | A2 | Hole | S228P, T349C, T366S, L368A, Y407V | (G4S)3 | N |
| ClgG4B1(G4S)1Hole | 437 | B1 | Hole | S228P, T349C, T366S, L368A, Y407V | (G4S)1 | C |
| ClgG4B1(GS)Knob | 438 | B1 | Knob | S228P, T349C, T366S, L368A, Y407V | GS | C |
| ClgG4A1(GS)Hole | 439 | A1 | Hole | S228P, T349C, T366S, L368A, Y407V | GS | C |
| ClgG4B1(G2S)Knob | 440 | B1 | Knob | S228P, T349C, T366S, L368A, Y407V | G2S | C |
| ClgG4A1(G2S)Hole | 441 | A1 | Hole | S228P, T349C, T366S, L368A, Y407V | G2S | C |
| ClgG4B1(G3S)Knob | 442 | B1 | Knob | S228P, T349C, T366S, L368A, Y407V | G3S | C |
| ClgG4A1(G3S)Hole | 443 | A1 | Hole | S228P, T349C, T366S, L368A, Y407V | G3S | C |
| ClgG4B1(EAAAK)1Knob | 444 | B1 | Knob | S228P, T349C, T366S, L368A, Y407V | EAAAK | C |
| ClgG4A1(EAAAK)1Hole | 445 | A1 | Hole | S228P, T349C, T366S, L368A, Y407V | EAAAK | C |
| ClgG4B1(EAAAK)2Knob | 446 | B1 | Knob | S228P, T349C, T366S, L368A, Y407V | (EAAAK)2 | C |
| ClgG4A1(EAAAK)2Hole | 447 | A1 | Hole | S228P, T349C, T366S, L368A, Y407V | (EAAAK)2 | C |
| ClgG4B1(G2S)2Knob | 448 | B1 | Knob | S228P, T349C, T366S, L368A, Y407V | (G2S)2 | C |

TABLE 8-continued

| Construct | SEQ ID NO | sdAb | Scaffold | Mutation | linker | Linked terminus |
|---|---|---|---|---|---|---|
| ClgG4A1(G2S)2Hole | 449 | A1 | Hole | S228P, T349C, T366S, L368A, Y407V | (G2S)2 | C |
| ClgG4B1(nolinker)Knob | 450 | B1 | Knob | S228P, T349C, T366S, L368A, Y407V | no linker | C |
| ClgG4A1(no linker)Hole | 451 | A1 | Hole | S228P, T349C, T366S, L368A, Y407V | no linker | C |

The multi-specific construct according to the invention, can be associated by fusing any knob-part with any hole-part shown in Table 8.

It is evident for the skilled person that all constructs in Table 8 described as a "knob" can in addition be made as a "hole" and all constructs described as "hole" in Table 8 can be made as "knob".

As described above, A1 fused to a Fc-hole part may be combined with any sdAb fused to a Fc-knob part, independently on whether the two sdAb is fused in the N- or C-terminal. Therefore, the Hole part with A1 may be selected from any one of SEQ ID Nos: 93-96, 113-116, 445, 447, 449 and 451.

Likewise, when A1 is fused to a Fc-knob part, it may be combined with any sdAb fused to a Fc-Hole part, independently on whether the two sdAb is fused in the N- or C-terminal. Therefore, the Knob part with A1 may be selected from any one of SEQ ID Nos: 105-112.

Further the two sdAbs may be fused to the Fc-hole or knob part using anyone of the linkers mentioned in table 8.

Thus, in one embodiment, the multi-specific construct comprises a hole-part with the amino acid sequence selected from the group consisting of SEQ ID NO: 93, 94, 95, 96, 113, 114, 115, 116, 439, 441, 443, 445, 447, 449, and 451.
and
a knob-part with the amino acid sequence selected from the group consisting of SEQ ID NO: 97, 98, 99, 100, 101, 102, 103, 104, 105, 106, 107, 108, 109, 110, 111, 112, 117, 118, 119, 120, 121, 122, 123, 124, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 438, 440, 442, 444, 446, 448, and 450.

For all embodiments described herein and which relates to a VHH/sdAbs incorporated into the Knob and/or the Hole polypeptide, this VHH/sdAb may be subject to amino acid substitution, such as for affinity maturation or for humanising the sequence. Moreover, the the CDR1 may contain 1, 2, or 3 amino acid substitutions, CDR 2 may contain 1, 2, or 3 amino acid substitutions and CDR3 may contain 1, 2, or 3 amino acid substitutions, such as 1 or 2 amino acid substitutions. The resulting variant sdAb may be evaluated by determining the binding affinity to IgE Fc or determining the displacement activity by an ELISA-based IgE-FcεRIα displacement assay. Desired are variants with comparable activity to the parent sdAb or with improved IgE affinity or improved displacement activity.

According to this invention it is preferred that A1 Fc-hole part, wherein A1 us fused C-terminally, is combined with any other sdAb, also fused C-terminally.

Thus, in a preferred embodiment, the multi-specific construct comprises a Hole-part with the amino acid sequence selected from the group consisting of SEQ ID NO: 93, 94, 95, 96, 439, 441, 443, 445, 447, 449, and 451,
and
a Knob-part with the amino acid sequence selected from the group consisting of SEQ ID NO: 97, 98, 99, 100, 101, 102, 103, 104, 105, 106, 107, 108, 321, 322, 323, 324, 329, 330, 331, 332, 337, 338, 339, 340, 345, 346, 347, 348, 353, 354, 355, 356, 361, 362, 363, 364, 369, 370, 371, 372, 377, 378, 379, 380, 385, 386, 387, 388, 393, 394, 395, 396, 401, 402, 403, 404, 409, 410, 411, 412, 417, 418, 419, 420, 438, 440, 442, 444, 446, 448, and 450.

Similar as described above, it is preferred that A1, N-terminally fused to a Fc-hole part is combined with any sdAb N-terminally fused to a Fc-knob part.

Thus, in another preferred embodiment, the multi-specific construct comprises a Hole-part with the amino acid sequence selected from the group consisting of SEQ ID NO: 113, 114, 115, and 116,
and
109, 110, 111, 112, 117, 118, 119, 120, 121, 122, 123, 124, 325, 326, 327, 328, 333, 334, 335, 336, 341, 342, 343, 344, 349, 350, 351, 352, 357, 358, 359, 360, 365, 366, 367, 368, 373, 374, 375, 376, 381, 382, 383, 384, 389, 390, 391, 392, 397, 398, 399, 400, 405, 406, 407, 408, 413, 414, 415, 416, 421, 422, 423, and 424.

Further, as different linkers can be used to attach the sdAbs to the Fc-knob or hole parts, it is preferred that both sdAbs are C-terminally fused to the Fc-part using the same linker length.

Thus, in yet another embodiment, the multi-specific construct according to the invention is associated having a combination of a hole-part and a knob-part having the respective SEQ ID NO:
93 and 97; 94 and 98; 95 and 99; 96 and 100; 93 and 101; 94 and 102; 95 and 103; 96 and 104; 93 and 105; 94 and 106; 95 and 107; 96 and 108; 93 and 321; 94 and 322; 95 and 323; 96 and 324; 93 and 329; 94 and 330; 95 and 331; 96 and 332; 93 and 337; 94 and 338; 95 and 339; 96 and 340; 93 and 345; 94 and 346; 95 and 347; 96 and 348; 93 and 353; 94 and 354; 95 and 355; 96 and 356; 93 and 361; 94 and 362; 95 and 363; 96 and 364; 93 and 369; 94 and 370; 95 and 371; 96 and 372; 93 and 377; 94 and 378; 95 and 379; 96 and 380; 93 and 385; 94 and 386; 95 and 387; 96 and 388; 93 and 393; 94 and 394; 95 and 395; 96 and 396; 93 and 401; 94 and 402; 95 and 403; 96 and 404; 93 and 409; 94 and 410; 95 and 411; 96 and 412; 93 and 417; 94 and 418; 95 and 419; 96 and 420; 439 and 438; 441 and 440; 443 and 442; 445 and 444; 447 and 446; 449 and 448, or 451 and 450.

According to the above, different linkers can be used to attach the sdAbs to the Fc-knob or hole parts, it is preferred that both sdAbs are N-terminally fused to the Fc-part using the same linker length.

In yet a further embodiment, the multi-specific construct according to the invention is associated having a combination of a hole-part and a knob-part having the respective SEQ ID NO:

113 and 109; 114 and 110; 115 and 111; 116 and 112; 113 and 117; 114 and 118; 115 and 119; 116 and 120; 113 and 121; 114 and 122; 115 and 123; 116 and 124; 113 and 325; 114 and 326; 115 and 327; 116 and 328; 113 and 333; 114 and 334; 115 and 335; 116 and 336; 113 and 341; 114 and 342; 115 and 343; 116 and 344; 113 and 349; 114 and 350; 115 and 351; 116 and 352; 113 and 357; 114 and 358; 115 and 359; 116 and 360; 113 and 365; 114 and 366; 115 and 367; 116 and 368; 113 and 373; 114 and 374; 115 and 375; 116 and 376; 113 and 381; 114 and 382; 115 and 383; 116 and 384; 113 and 389; 114 and 390; 115 and 391; 116 and 392; 113 and 397; 114 and 398; 115 and 399; 116 and 400; 113 and 405; 114 and 406; 115 and 407; 116 and 408; 113 and 413; 114 and 414; 115 and 415; 116 and 416; 113 and 421; 114 and 422; 115 and 423; or 116 and 424.

A multi-specific construct comprises the sdAbs B1 and A1 did show a very high displacement activity when tested in example 6. It is thus preferred to combine the A1 hole part with the B1 knob part N-terminally fused to the Fc-part.

Thus, in a preferred embodiment, the multi-specific construct according to the invention is associated having a combination of a hole-part and a knob-part having the respective SEQ ID NO:

113 and 121;
114 and 122;
115 and 123; or
116 and 124

Similar to above, also B1 combined with A1 C-terminally fused to the Fc-part did show strong displacement activity.

Thus, in a more preferred embodiment, the multi-specific construct according to the invention is associated having a combination of a hole-part and a knob-part having the respective SEQ ID NO:

93 and 101;
94 and 102;
95 and 103; or
96 and 104;

As shown in example 10, some of the constructs may be anaphylactogenic. It is preferred that the multi-specific construct is non-anaphylactogenic. Thus as seen in example 10, a construct comprising B1, A1, linked to IgG4-Fc using (G4S)1 linkers, did not show any anaphylactogenicity.

Thus, in a preferred embodiment, the multi-specific construct according to the invention is associated having a combination of a hole-part and a knob-part having the respective SEQ ID NO: 94 and 102.

Further, when evaluated in mice, in example 9, A1 combined with either D2, E1 or F4 did not induce anaphylaxis in the mice as compared to B1A1 N-terminal linked to the Fc-part, meaning these constructs are not anaphylactogenic.

Thus, in one embodiment, the multi-specific construct according to the invention is associated having a combination of a hole-part and a knob-part having the respective SEQ ID NO: 95 and 339.

In another embodiment, the multi-specific construct according to the invention is associated having a combination of a hole-part and a knob-part having the respective SEQ ID NO: 95 and 347.

In a further embodiment, the multi-specific construct according to the invention is associated having a combination of a hole-part and a knob-part having the respective SEQ ID NO: 95 and 403.

In the above-mentioned constructs, A1 represented one of the two sdAbs in all the examples.

Another non-limiting example is a construct wherein A2 represents one of the two sdAbs and the sdAbs listed in table 1 represents the second sdAb. Thus, in one embodiment, the multi-specific construct comprises a Hole-part with the amino acid sequence selected from the group consisting of SEQ ID NO: 425, 426, 427, 428, 429, 430, 431 and 432 and a knob part with the amino acid sequence selected from the group consisting of SEQ ID NO: 97, 98, 99, 100, 101, 102, 103, 104, 105, 106, 107, 108, 109, 110, 111, 112, 117, 118, 119, 120, 121, 122, 123, 124, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 438, 440, 442, 444, 446, 448, and 450.

The above list represents knob- and hole parts, wherein the sdAb is either N- or C-terminal fused to the Fc-part.

It is preferred that the knob- and hole part is fused to the same terminus, meaning both are either N- or C-terminal.

Thus, In one embodiment, the multi-specific construct comprises a Hole-part with the amino acid sequence selected from the group consisting of SEQ ID NO: 425, 426, 427, and 428 and a Knob-part with the amino acid sequence selected from the group consisting of SEQ ID NO: 97, 98, 99, 100, 101, 102, 103, 104, 105, 106, 107, 108, 321, 322, 323, 324, 329, 330, 331, 332, 337, 338, 339, 340, 345, 346, 347, 348, 353, 354, 355, 356, 361, 362, 363, 364, 369, 370, 371, 372, 377, 378, 379, 380, 385, 386, 387, 388, 393, 394, 395, 396, 401, 402, 403, 404, 409, 410, 411, 412, 417, 418, 419, 420, 438, 440, 442, 444, 446, 448, and 450.

In a further embodiment, the multi-specific construct comprises a Hole-part with the amino acid sequence selected from the group consisting of SEQ ID NO: 429, 430, 431, and 432, and a Knob-part with the amino acid sequence selected from the group consisting of SEQ ID NO: 109, 110, 111, 112, 117, 118, 119, 120, 121, 122, 123, 124, 325, 326, 327, 328, 333, 334, 335, 336, 341, 342, 343, 344, 349, 350, 351, 352, 357, 358, 359, 360, 365, 366, 367, 368, 373, 374, 375, 376, 381, 382, 383, 384, 389, 390, 391, 392, 397, 398, 399, 400, 405, 406, 407, 408, 413, 414, 415, 416, 421, 422, 423, and 424.

Further, as seen in table 8, the knob- and hole part comprises different linkers to fuse the sdAb to the Fc-part. It is preferred that the sdAb fused in the hole- and knob-part are fused to the Fc-part using the same linker.

Thus, in one another embodiment, the multi-specific construct according to the invention is associated having a combination of a hole-part and a knob-part having the respective SEQ ID NO:

425 and 97; 426 and 98; 427 and 99; 428 and 100; 425 and 101; 426 and 102; 427 and 103; 428 and 104; 425 and 105; 426 and 106; 427 and 107; 428 and 108; 425 and 321, 426 and 322, 427 and 323, 428 and 324, 425 and 329, 426 and 330, 427 and 331, 428 and 332, 425 and 337, 426 and 338, 427 and 339, 428 and 340, 425 and 345, 426 and 346, 427 and 347, 428 and 348, 425 and 353, 426 and 354, 427 and 355, 428 and 356, 425 and 361, 426 and 362, 427 and 363, 428 and 364, 425 and 369, 426 and 370, 427 and 371, 428 and 372, 425 and 377, 426 and 378, 427 and 379, 428 and 380, 425 and 385, 426 and 386, 427 and 387, 428 and 388, 425 and 393, 426 and 394, 427 and 395, 428 and 396, 425 and 401, 426 and 402, 427 and 403, 428 and 404, 425 and 409, 426 and 410, 427 and 411, 428 and 412, 425 and 417, 426 and 418, 427 and 419, or 428 and 420.

In yet a further embodiment, the multi-specific construct according to the invention is associated having a combination of a hole-part and a knob-part having the respective SEQ ID NO:

429 and 109; 430 and 110; 431 and 111; 432 and 112; 429 and 117; 430 and 118; 431 and 119; 432 and 120; 429 and 121; 430 and 122; 431 and 123; 432 and 124; 429 and 325, 430 and 326, 431 and 327, 432 and 328, 429 and 333, 430 and 334, 431 and 335, 432 and 336, 429 and 341, 430 and 342, 431 and 343, 32 and 344, 429 and 349, 430 and 350, 431 and 351, 432 and 352, 429 and 357, 430 and 358, 431 and 359, 432 and 360, 429 and 365, 430 and 366, 431 and 367, 432 and 368, 429 and 373, 430 and 374, 431 and 375, 432 and 376, 429 and 381, 430 and 382, 431 and 383, 432 and 384, 429 and 389 430 and 390, 431 and 391, 432 and 392, 429 and 397, 430 and 398, 431 and 399, 432 and 400, 429 and 405, 430 and 406, 431 and 407, 432 and 408, 429 and 413, 430 and 414, 431 and 415, 432 and 416, 429 and 421, 430 and 422, 431 and 423, or 432 and 424.

In a preferred embodiment, the multi-specific construct according to the invention is associated having a combination of a hole-part and a knob-part having the respective SEQ ID NO: 429 and 121; 430 and 122; 431 and 123; or 432 and 124

In a more preferred embodiment, the multi-specific construct according to the invention is associated having a combination of a hole-part and a knob-part having the respective SEQ ID NO: 425 and 101; 426 and 102; 427 and 103; or 428 and 104;

In an even more preferred embodiment, the multi-specific construct according to the invention is associated having a combination of a hole-part and a knob-part having the respective SEQ ID NO: 426 and 102.

Until now, A1 or A2 having disruptive on their own, has been part of the muti-specific construct as the hole-part. Importantly, the construct can be designed where the first sdAb, having disruptive activity on its own, is a knob part.

Thus, in one embodiment, the multi-specific construct comprises a Knob-part with the amino acid sequence selected from the group consisting of SEQ ID NO: 105, 106, 107, 108 and
a Hole-part with the amino acid sequence of SEQ ID NO: 437

Preferably, the multi-specific construct according to the invention is associated having a combination of a hole-part and a knob-part having the respective SEQ ID NO: 437 and 106.

Further, the multi-specific construct may be assembled without a linker between the sdAb and the Fc part, or by using the linkers GS, G2S, G3S, EAAAK or (EAAAK)2.

Thus, in one embodiment, the multi-specific construct comprises a Knob-part with the amino acid sequence selected from the group consisting of SEQ ID NO: 438, 440, 442, 444, 446, 448, and 450 and
a Hole-part with the amino acid sequence selected from the group consisting of SEQ ID NO: 439, 441, 443, 445, 447, 449, and 451.

In a preferred embodiment, the multi-specific construct according to the invention is associated having a combination of a hole-part and a knob-part having the respective SEQ ID NO: 439 and 438.

In another preferred embodiment, the multi-specific construct according to the invention is associated having a combination of a hole-part and a knob-part having the respective SEQ ID NO: 441 and 440.

In a further preferred embodiment, the multi-specific construct according to the invention is associated having a combination of a hole-part and a knob-part having the respective SEQ ID NO: 443 and 442.

In yet another preferred embodiment, the multi-specific construct according to the invention is associated having a combination of a hole-part and a knob-part having the respective SEQ ID NO: 445 and 444.

In yet a further preferred embodiment, the multi-specific construct according to the invention is associated having a combination of a hole-part and a knob-part having the respective SEQ ID NO: 447 and 446.

In a more preferred embodiment, the multi-specific construct according to the invention is associated having a combination of a hole-part and a knob-part having the respective SEQ ID NO: 449 and 448.

In an even more preferred embodiment, the multi-specific construct according to the invention is associated having a combination of a hole-part and a knob-part having the respective SEQ ID NO: 451 and 450.

The Knob-part of the multi-specific construct comprises three parts:
i) one sdAb,
ii) one peptide linker and
iii) one Fc part, wherein the Fc part is linked to ii) in the C-terminal or the N-terminal.
wherein i) is linked to the c-terminal or N-terminal of iii) via ii).

In addition, the hole-part of the multi specific construct comprises three parts;
i) one sdAb, different from the sdAb present on the knob-part
ii) one peptide linker and
iii) one Fc part,
wherein i) is linked to the c-terminal or N-terminal of iii) via ii).
wherein the Fc part is linked to the other parts in the C-terminal and/or the N-terminal. The three parts i) ii) and iii) of the Knob are gathered in one polypeptide whereas the three parts of the Hole are gathered in another polypeptide. Further, for both the knob-part and the hole-part, i) is fused with ii) and ii) is fused with iii), In one embodiment, the knob-part of the multi-specific construct comprises three parts, i), ii) and iii) wherein i) is selected from the group consisting of SEQ ID NO: 1, 5, 9, 13. 17, 21, 25, 33, 37 41, 45, 49, 53, 57, 61, and 65, ii) is selected from the group consisting of SEQ ID NO: 88-92 and 452-457, and iii) is selected from SEQ ID NO: 433 and 435 and the hole-part of the multi-specific construct comprises three parts, i), ii) and iii) wherein i) is different from i) in the knob-part and selected from the group consisting of SEQ ID NO: 1, 5, 9, 13. 17, 21, 25, 33, 37 41, 45, 49, 53, 57, 61, and 65, ii) is selected from the group consisting of SEQ ID NO: 88-92 and 452-457, and iii) is selected from SEQ ID NO: 434 and 436.

More specific embodiments relating to KIH made with sdAbs A1 and B1 are defined in the following:

In a preferred embodiment, the knob-part of the multi-specific construct comprises three parts, i), ii) and iii) wherein i) is SEQ ID NO: 1, ii) is SEQ ID NO: 88, and iii) is SEQ ID NO: 433, and the hole-part of the multi-specific construct comprises three parts, i), ii) and iii) wherein i) is SEQ ID NO: 9, ii) is SEQ ID NO: 88, and iii) is SEQ ID NO: 434.

In another preferred embodiment, the knob-part of the multi-specific construct comprises three parts, i), ii) and iii) wherein i) is SEQ ID NO: 9, ii) is SEQ ID NO: 88, and iii) is SEQ ID NO: 433 and the hole-part of the multi-specific construct comprises three parts, i), ii) and iii) wherein i) is SEQ ID NO: 1, ii) is SEQ ID NO: 88, and iii) is SEQ ID NO: 434.

In a further preferred embodiment, the knob-part of the multi-specific construct comprises three parts, i), ii) and iii) wherein i) is SEQ ID NO: 1, ii) is SEQ ID NO: 88, and iii) is SEQ ID NO: 435 and the hole-part of the multi-specific construct comprises three parts, i), ii) and iii) wherein i) is SEQ ID NO: 9, ii) is SEQ ID NO: 88, and iii) is SEQ ID NO: 436.

In yet a further preferred embodiment, the knob-part of the multi-specific construct comprises three parts, i), ii) and iii) wherein i) is SEQ ID NO: 9, ii) is SEQ ID NO: 88, and iii) is SEQ ID NO: 435 and the hole-part of the multi-specific construct comprises three parts, i), ii) and iii) wherein i) is SEQ ID NO: 1, ii) is SEQ ID NO: 88, and iii) is SEQ ID NO: 436.

In a preferred embodiment, the knob-part of the multi-specific construct comprises three parts, i), ii) and iii) wherein i) is SEQ ID NO: 1, ii) is SEQ ID NO: 88, and iii) is SEQ ID NO: 433, wherein ii) is linked to the C-terminus of iii), and the hole-part of the multi-specific construct comprises three parts, i), ii) and iii) wherein i) is SEQ ID NO: 9, ii) is SEQ ID NO: 88, and iii) is SEQ ID NO: 434, wherein ii) is linked to the C-terminus of iii).

In another preferred embodiment, the knob-part of the multi-specific construct comprises three parts, i), ii) and iii) wherein i) is SEQ ID NO: 9, ii) is SEQ ID NO: 88, and iii) is SEQ ID NO: 433, wherein ii) is linked to the C-terminus of iii)

and the hole-part of the multi-specific construct comprises three parts, i), ii) and iii) wherein i) is SEQ ID NO: 1, ii) is SEQ ID NO: 88, and iii) is SEQ ID NO: 434, wherein ii) is linked to the C-terminus of iii).

In a further preferred embodiment, the knob-part of the multi-specific construct comprises three parts, i), ii) and iii) wherein i) is SEQ ID NO: 1, ii) is SEQ ID NO: 88, and iii) is SEQ ID NO: 435, wherein ii) is linked to the C-terminus of iii)

and the hole-part of the multi-specific construct comprises three parts, i), ii) and iii) wherein i) is SEQ ID NO: 9, ii) is SEQ ID NO: 88, and iii) is SEQ ID NO: 436, wherein ii) is linked to the C-terminus of iii).

In yet a further preferred embodiment, the knob-part of the multi-specific construct comprises three parts, i), ii) and iii) wherein i) is SEQ ID NO: 9, ii) is SEQ ID NO: 88, and iii) is SEQ ID NO: 435, wherein ii) is linked to the C-terminus of iii)

and the hole-part of the multi-specific construct comprises three parts, i), ii) and iii) wherein i) is SEQ ID NO: 1, ii) is SEQ ID NO: 88, and iii) is SEQ ID NO: 436, wherein ii) is linked to the C-terminus of iii).

In a preferred embodiment, the knob-part of the multi-specific construct comprises three parts, i), ii) and iii) wherein i) is SEQ ID NO: 5, ii) is SEQ ID NO: 88, and iii) is SEQ ID NO: 433, and the hole-part of the multi-specific construct comprises three parts, i), ii) and iii) wherein i) is SEQ ID NO: 9, ii) is SEQ ID NO: 88, and iii) is SEQ ID NO: 434.

In another preferred embodiment, the knob-part of the multi-specific construct comprises three parts, i), ii) and iii) wherein i) is SEQ ID NO: 9, ii) is SEQ ID NO: 88, and iii) is SEQ ID NO: 433 and the hole-part of the multi-specific construct comprises three parts, i), ii) and iii) wherein i) is SEQ ID NO: 5, ii) is SEQ ID NO: 88, and iii) is SEQ ID NO: 434.

In a further preferred embodiment, the knob-part of the multi-specific construct comprises three parts, i), ii) and iii) wherein i) is SEQ ID NO: 5, ii) is SEQ ID NO: 88, and iii) is SEQ ID NO: 435 and the hole-part of the multi-specific construct comprises three parts, i), ii) and iii) wherein i) is SEQ ID NO: 9, ii) is SEQ ID NO: 88, and iii) is SEQ ID NO: 436.

In yet a further preferred embodiment, the knob-part of the multi-specific construct comprises three parts, i), ii) and iii) wherein i) is SEQ ID NO: 9, ii) is SEQ ID NO: 88, and iii) is SEQ ID NO: 435 and the hole-part of the multi-specific construct comprises three parts, i), ii) and iii) wherein i) is SEQ ID NO: 5, ii) is SEQ ID NO: 88, and iii) is SEQ ID NO: 436.

In a preferred embodiment, the knob-part of the multi-specific construct comprises three parts, i), ii) and iii) wherein i) is SEQ ID NO: 5, ii) is SEQ ID NO: 88, and iii) is SEQ ID NO: 433, wherein ii) is linked to the C-terminus of iii), and the hole-part of the multi-specific construct comprises three parts, i), ii) and iii) wherein i) is SEQ ID NO: 9, ii) is SEQ ID NO: 88, and iii) is SEQ ID NO: 434, wherein ii) is linked to the C-terminus of iii).

In another preferred embodiment, the knob-part of the multi-specific construct comprises three parts, i), ii) and iii)

wherein i) is SEQ ID NO: 9, ii) is SEQ ID NO: 88, and iii) is SEQ ID NO: 433, wherein ii) is linked to the C-terminus of iii)

and the hole-part of the multi-specific construct comprises three parts, i), ii) and iii) wherein i) is SEQ ID NO: 5, ii) is SEQ ID NO: 88, and iii) is SEQ ID NO: 434, wherein ii) is linked to the C-terminus of iii).

In a further preferred embodiment, the knob-part of the multi-specific construct comprises three parts, i), ii) and iii) wherein i) is SEQ ID NO: 5, ii) is SEQ ID NO: 88, and iii) is SEQ ID NO: 435, wherein ii) is linked to the C-terminus of iii)

and the hole-part of the multi-specific construct comprises three parts, i), ii) and iii) wherein i) is SEQ ID NO: 9, ii) is SEQ ID NO: 88, and iii) is SEQ ID NO: 436, wherein ii) is linked to the C-terminus of iii).

In yet a further preferred embodiment, the knob-part of the multi-specific construct comprises three parts, i), ii) and iii) wherein i) is SEQ ID NO: 9, ii) is SEQ ID NO: 88, and iii) is SEQ ID NO: 435, wherein ii) is linked to the C-terminus of iii)

and the hole-part of the multi-specific construct comprises three parts, i), ii) and iii) wherein i) is SEQ ID NO: 5, ii) is SEQ ID NO: 88, and iii) is SEQ ID NO: 436, wherein ii) is linked to the C-terminus of iii).

Other Linking Moieties (Polymers, Polysaccharides)

In some embodiments, the moiety c) of the multi-specific construct is a polymer, such as particularly a polymer consisting of several repeated units of the monomer ethylene glycol ($C_2H_6O_2$). These polymers are called polyethylene glycol (PEG) and are produced synthetically and can be either linear or branched, and the end group(s) may be either the standard hydroxy group or a methoxy group (denoted mPEG). The attachment of PEG moieties to peptides and proteins is a well-established and efficient method for improving their pharmacokinetic properties, such as plasma/serum half-lives. PEGylation may also alter the hydrophilicity of a peptide or protein and may make PEGylated monomer sdAbs or multi-specific construct described herein less susceptible to renal clearance as well as to protease degradation and may also decrease the immunogenicity.

Other polymers of interest may include poly(N-vinylpyrrolidone) (PVP), polyglycerol (PG), poly(N-(2-hydroxypropyl) methacrylamide) (PHPMA), polyoxazolines (POZs), poly[oligo (ethylene glycol) methyl methacrylate] (POEGMA) and poly(2-methyacryloyloxyethyl phosphorylcholine) (PMPC).

In still other embodiments, the moiety c) of the multi-specific construct is a polysaccharide, such as natural and semi-synthetic polysaccharides, including O- and N-linked oligosaccharides, dextran, hydroxyethyl starch (HES), polysialic acid and hyaluronic acid, as well as unstructured protein polymers such as homo-amino acid polymers, elastin-like polypeptides, XTENs (a class of unstructured biodegradable protein polymers developed by Amunix to increase the half-lives of therapeutic peptides and proteins genetically fused or chemically conjugated to them. XTEN polymers are conceived as non-immunogenic polypeptides consisting of the six hydrophilic, chemically stable amino acids A, E, G, P, S and T) and PAS (a proline-alanine-serine polymer).

Pharmaceutical Compositions

In further aspects, the invention relates to a pharmaceutical composition comprising a multi-specific construct or one or more monomeric sdAbs disclosed herein, and a pharmaceutically acceptable carrier and/or vehicle and/or diluent and/or excipient.

The pharmaceutical composition may be a liquid, a semi-solid, or a solid dosage form (such as freeze dried). The composition/dosage form may be formulated for various administration routes, preferably formulated for being administered by injection, such as intramuscular injection.

Use as a Therapeutic

The multi-specific construct, one or more monomeric sdAbs, or a pharmaceutical composition disclosed herein may be used for displacing IgE prebound to its high affinity receptor in vivo in a subject in need thereof.

Thus, further aspects relate to a method for treatment or prevention of an IgE-related disease or condition, the method comprising administering an effective dose of the multi-specific construct, one or more monomeric sdAbs, or a pharmaceutical composition disclosed herein. The effective dose is expected to be a single dose in range of 10-300 mg, which may be administered once daily, weekly, bi-weekly or monthly.

In other words, further aspects relate to a multi-specific construct, one or more monomeric sdAbs, or a pharmaceutical composition for use as a medicament, preferably for use in anti-IgE therapy, such as for use in the treatment or prevention of an IgE-related disease or condition.

Still alternatively worded further aspects relate to a multi-specific construct, one or more monomeric sdAbs, or a pharmaceutical composition in the manufacture of a medicament, such as a medicament for use in anti-IgE therapy or in the treatment or prevention of an IgE related disease or condition.

In interesting embodiments, the IgE-related disease or disorder is selected from any one of the examples of allergic disease, which are allergic asthma, allergic rhinitis (including seasonal allergic rhinitis and perennial allergic rhinitis) nasal polyps, atopic dermatitis, conjunctivitis, anaphylaxis, hives, food allergy, allergy to non-food related substances including venoms from insects, wasps, bees or spiders and, therapeutic drugs including antibiotic.

Other IgE-related diseases suitable for treatment include other hyper-IgE syndromes, allergic bronchopulmonary aspergilliosis and other aspergilliosis related conditions, idiopathic anaphylaxis, anaphylaxis, bullous pemphigoid, pemphigus vulgaris, urticaria, e.g., chronic urticaria, chronic spontaneous urticaria, nasal polyposis, chronic sinusitis, mastocytosis and other mast cell disorders.

Still other IgE-related diseases that might be treated by constructs disclosed herein might be the same as suggested for Omalizumab (Incorvaia et al., 2014).

The multi-specific construct, one or more monomeric sdAbs, or a pharmaceutical composition may be administered to a subject in need thereof, in particularly a human subject.

Example 1

Immunization and Library Generation

The aim of the present study was to generate a library of sdAbs from a camelid immunized with IgE-Fc.

Material and Methods

Immunization of animals: Single domain antibodies were produced by immunization of Camelids. Immunization was performed by different companies (Capralogics (Hardwick, USA), Eurogentec (Seraing, Belgium) and Preclinics (Potsdam, Germany) using both llamas and alpacas. Animals were immunized with either human IgE or human IgE- according to the immunization protocols shown in Tables 9-12. IgE-Fc were used either Cε2-Cε4 or Cε3-Cε4 Proteins were mixed with Complete Freund's Adjuvant (CFA) or Incomplete Freund's Adjuvant (IFA) before injection.

TABLE 9

| Immunization schedule and tissue collection for Llama RAY. | | | |
|---|---|---|---|
| Day | Type of antigen | Amount of antigen | Tissue collection |
| 0 | IgE | 100 μg | 15-20 mL blood |
| 21 | IgE | 100 μg | |
| 42 | IgE | 100 μg | |
| 52 | | | 25 mL |
| 63 | IgE | 100 μg | |
| 73 | | | 500 mL |

TABLE 10

| Immunization schedule and tissue collection for Llama TOM. | | | |
|---|---|---|---|
| Day | Type of antigen | Amount of antigen | Tissue collection |
| 0 | IgE-Fc Cε2-Cε4 | 100 μg | 15-20 mL blood |
| 21 | IgE-Fc Cε2-Cε4 | 100 μg | |
| 42 | IgE-Fc Cε2-Cε4 | 100 μg | |
| 52 | | | 25 mL |
| 63 | IgE-Fc Cε2-Cε4 | 100 μg | |
| 73 | | | 500 mL |

TABLE 11

| Immunization schedule and tissue collection for Llama MAX and Alpaca ZOE. | | | |
|---|---|---|---|
| Day | Type of antigen | Amount of antigen | Tissue collection |
| 0 | IgE-Fc Cε2-Cε4 | 100 μg | 3-4 mL blood |
| 14 | IgE-Fc Cε2-Cε4 | 100 μg | |
| 28 | IgE-Fc Cε2-Cε4 | 100 μg | 3-4 mL blood |
| 35 | IgE-Fc Cε2-Cε4 | 100 μg | |
| 43 | | | 300 mL |

Library generation: an sdAb library was constructed from each animal by purifying PBMCs from blood isolated from the animals using a Ficoll® (Cytiva) gradient. RNA was extracted from purified PBMCs using NucleoSpin® RNA kit (Macherey-Nagel). cDNA was synthetized from RNA using Superscript III First-Strand kit (Invitrogen). SdAb genes were amplified from cDNA by PCR using primers 1 and 2 (IgG2) and primers 1 and 3 (IgG3). Using amplified sdAb genes, the library was built into a Yeast Display plasmid named pNT by homologous recombination in *Saccharomyces cerevisiae* EBY100 (ATCC).

Libraries were generated using the following primers:

```
Primer 1:
taagATGCAGTTACTTCGCTGTTTTTCAATATTTTCTGTTATTGCTA

GCGTTTTAGCAGCTGGAGATGTGCAGCTGCAGGAGTCTGGRGGAGG

Primer 2:
CCTCCACCGCCagcgtagtctggaacgtcgtatgggtatctaccttc aaTACTAGTGGGGTCTTCGCTGTGGTGCG
```

-continued

```
Primer 3:
CCTCCACCGCCagcgtagtctggaacgtcgtatgggtatctaccttc aaTACTAGTAGGTTGTGGTTTTGGTGTCTTGGG
```

Results

A yeast library of >10⁷ transformed cells is obtained for each animal immunized. Quality control of the libraries by sequencing colony PCR show that all libraries contain 50-90% sdAbs in the correct reading frame.

Example 2

Selection of sdAbs that Binds IgE-Fc

The aim of the present study was to select sdAbs capable of binding towards IgE-Fc.

Material and Methods

For selection of sdAbs capable of binding IgE-Fc, a starter culture of the library obtained in example 1 was inoculated with 10× the library size (>10⁸ cells) in 1 L glucose minimal media (SD-CAA) and incubated overnight at 30° C. and 180 rpm. Next day, the culture was passaged to $OD_{600}$=0.2-0.3 and cultivated at 30° C. and 180 rpm until it reached early exponential phase ($OD_{600}$=0.8-1.0). Cells were pelleted by centrifugation and resuspended in galactose minimal media (SG-CAA) to induce display of the sdAb on the surface of the yeast cells (sdAb genes under GAL1 promotor). The culture was incubated overnight at 20° C. and 180 rpm. Next day, cells were pelleted by centrifugation and resuspended in PBS 5% BSA. A first round of selection for the cell's capability of binding IgE-Fc Cε2-Cε4 was performed by either Magnetic Activated Cell Sorting (MACS) and/or Fluorescent Activated Cell Sorting (FACS) against biotinylated IgE-Fc Cε2-Cε4.

MACS: 2×10⁸ cells were Negatively Selected Against 200 μL Streptavidin

Dynabeads™ MyOne™ C1 (Invitrogen) using a magnet (Dynal). First, a negative selection was performed following a positive selection using biotinylated IgE-Fc Cε2-Cε4: cells were incubated for 1 h with 1 μM biotinylated IgE-Fc Cε2-Cε4, washed with PBS 5% BSA, incubated with 100 μL Streptavidin Dynabeads™ MyOne™ C1 (Invitrogen) for 30 min, washed with PBS 5% BSA and sorted using a magnet (Dynal).

FACS: 3×10⁷ cells were incubated for 1 h with 1 μM biotinylated IgE-Fc Cε2-Cε4 in PBS 1% BSA. Cells were washed with PBS 1% BSA and incubated 15 min with anti-HA PE/Cy7 (BioLegend) and streptavidin PerCP/Cy5.5 (BioLegend) both at 1:100. Cells were washed with PBS 1% BSA and sorted using a SH800 cell sorter (SONY).

Sorted cells from both MACS and FACS were pooled and cultivated in SD-CAA. Subsequent rounds of selection were performed against biotinylated IgE-Fc Cε2-Cε4, biotinylated IgE-Fc Cε3-Cε4 335 or biotinylated IgE-Fc Cε2-Cε4/FcεRIα complex, with the same setup as the first round of selection. Rounds of selection were repeated with decreasing target concentration (1000 nM, 200 nM, 50 nM, 10 nM) until one or several positive populations were visible, two to four rounds of selection were needed depending on the library.

When the selection process was completed, positive cells were cultivated on SD-CAA plates and CFU were subsequently sequenced by Sanger sequencing to identify sdAbs of interest.

Results

The immune library generated from Llama RAY (table 9) was incubated with 1 µM biotinylated IgE-Fc Cε2-Cε4 and analysed by FACS using two parameters (sdAb expression and IgE-Fc binding) before starting selection. Here a large population positive for sdAb expression is visible, within this, a small population positive for IgE-Fc binding can be observed (FIG. 2A). First round of selection was performed by MACS against 1 µM biotinylated IgE-Fc Cε2-Cε4. During the first round of selection <1% of the cells were positively selected. The positive population was taken for a second round of selection performed by FACS against 200 nM biotinylated IgE-Fc Cε2-Cε4 or 200 nM complex biotinylated IgE-Fc Cε2-Cε4: FcεRIα. Round 2 against IgE-Fc Cε2-Cε4 shows two populations positive on sdAb expression and IgE-Fc binding. These two populations were sorted in gate C and together they represent 18.31% of the cells (FIG. 2B). Cells selected from rounds 2 (FIG. 2B, gate C) were cultivated and sdAbs were identified by Sanger sequencing. 10 colonies were sequenced from the population, and showed two dominant sdAbs, B1 and B3 (table 1).

The above method was repeated for all generated libraries. Table 1, page 15 lists the resulting sdAbs and shows the full-length amino acid sequence of each hit and tables 2a-d show CDRs for each hit determined by different methods.

Example 3

Expression of Single Domain Antibodies

The aim of the present study was to express both sdAb mono- and dimers, with different types of linkers.

Material and Methods

SdAb monomers of interest (table 1) and identified in example 2 were amplified from pNT plasmid by PCR and recloned in pET22b plasmid by SLICE cloning reaction. Thereby, a pelB signal sequence and a C-terminal his/HA tag were added to the sdAbs allowing for secretion into periplasmic space and subsequent purification and detection. SdAbs were expressed in *E. coli* Rosetta (DE3) cells using 2YT media. Expression was induced in early exponential phase with 0.5 mM IPTG and carried overnight at 20° C.-25° C. Purification of sdAbs from supernatant or supernatant+periplasmic extract was performed by IMAC using HisTrap excel column (Cytiva) as first step and by SEC with a Hiload 16-600 Superdex® 75 pg (Cytiva) column as second step. Size and purity of each sdAbs were evaluated on a 15% acrylamide SDS-PAGE. Then, immunoreactivity of sdAbs against immobilized IgE-Fc Cε2-4 and IgE-Fc Cε3-4 was analysed by ELISA. IgE-Fc were coated at 2 µg/mL overnight in a Nunc MaxiSorp plate (ThermoFisher). After blocking sdAbs were added at a 1:10 dilution in TBS and incubated 3 h at room temperature. Detection was performed using a mouse anti-HA antibody (ThermoFisher) and an anti-mouse IgG AP conjugated (Sigma Aldrich).

Following expression, relative epitope mapping (binding) was done for each individual sdAb monomers relatively to a different sdAb by use of Octet RED96e system (FortéBIO). Here biotinylated IgE Fc (made in-house ALK, Denmark) was immobilised on SAX (High precision streptavidin) sensors (FortéBIO) to max 1 nm using Kinetic buffer (PBS, 0.02% Tween20, 0.1% BSA) as a diluent. Then, a first sdAb (100 nM) was incubated for 300 s with the IgE Fc loaded streptavidin sensor, then a second sdAb (100 nM) was incubated with the sensor for 300 s. This method was performed for all sdAb combinations. Data were analyzed and a matrix generated in the Octet Data Analysis HT 11.1 Software (FortéBIO) using the epitope binning function.

Constructs Comprising Two sdAbs Linked by Peptide Linker

Constructs comprising two sdAbs were made with sdAbs able to bind simultaneously to the IgE-Fc as detected by the relative epitope mapping above.

Constructs comprising two sdAbs ("dimers") genes were built by PCR. First, each sdAbs was amplified using primers containing $(G_4S)_4$ linker. The sdAbs were then assembled to form a "dimer" by a second step PCR before cloning. Expression and purification were performed as described for sdAb monomers. The purification of the "dimers" were done as described for the monomers.

Constructs Comprising Two sdAbs Linked by IgG-Fc

Another way of combining two distinct sdAbs is through Fc-fusion (FIG. 1). In here $IgG_4$-Fc is used as an example. Heterodimerization of sdAbs fused to $IgG_4$-Fc is achieved with "knobs-into-holes" mutations in the $IgG_4$ Fc domain (Carter et al., 1998) and by use of peptide linker, such as RS or $(G_4S)_n$ linker between sdAb and $IgG_4$-Fc (FIG. 1). Plasmids coding for a first sdAb fused to the "knobs" $IgG_4$-Fc (with mutation in S354C, or T366W) (FIG. 1A) and second sdAb fused to "holes" IgG4 Fc (with mutations in T349C, T366S, L368A, or Y407V) (FIG. 1B) are co-transfects in human embryonic kidney cells (Expi293). Expression supernatant is collected after six days, centrifuged, and filtered. The bispecific IgG4 antibody constructs are purified using a Protein A column. After application of the supernatant, the column is washed with 10 CV of 20 mM sodium phosphate buffer pH 7 and bound proteins are eluted with 0.1 M citric acid pH 3. Elution fractions are neutralized immediately with 1 M Tris-HCl pH 9. Furthermore, elution fractions are applied to a size exclusion chromatography (SEC) column with PBS as running buffer. Elution fractions are combined, concentrated and sterile filtered through a 0.2 µm syringe filter.

Results

Selected monomeric sdAbs (table 1) and A1 (comparator sdAb 026) were cloned in pET22b plasmid. All were expressed by *E. coli* Rosetta (DE3) with different yield of expression depending on the sdAb (1-10 mg/L of culture). SdAb size and purity were controlled on a 15% acrylamide SDS-PAGE and Coomassie blue staining (data not shown). As shown for monomer sdAb B1, the size of the compound of interest was in the expected range between 15 kDa and 20 kDa (data not shown). After first step of purification an extra compound or aggregate around 130 kDa was visible above the sdAb band. The second step of purification allow to remove this contaminant and show monomer of high purity (data not shown).

SdAb monomers binding toward IgE-Fc was validated by ELISA. All sdAbs showed immunoreactivity against IgE-Fc Cε2-4 (table 13). However, only four monomer sdAbs (A1, D3, F6 and G1) showed immunoreactivity against IgE-Fc Cε3-4 (table 13). This indicate that the majority of the selected sdAbs bind IgE-Fc through Cε2 domain.

TABLE 13

| Assessment of sdAb binding against IgE-Fc Cε2-4 and IgE-Fc Cε3-4 by ELISA | | |
|---|---|---|
| sdAb | IgE-Fc Cε2-4 | IgE-Fc Cε3-4 |
| A1 | YES | YES |
| B1 | YES | NO |

TABLE 13-continued

Assessment of sdAb binding against IgE-Fc Cε2-4
and IgE-Fc Cε3-4 by ELISA

| sdAb | IgE-Fc Cε2-4 | IgE-Fc Cε3-4 |
|------|-------------|-------------|
| B2 | YES | NO |
| B3 | YES | NO |
| D1 | YES | NO |
| D2 | YES | NO |
| D3 | YES | YES |
| E1 | YES | NO |
| E2 | YES | NO |
| E3 | YES | NO |
| E4 | YES | NO |
| F1 | YES | NO |
| F3 | YES | NO |
| F4 | YES | NO |
| F5 | YES | NO |
| F6 | YES | YES |
| G1 | YES | YES |

Relative epitope mapping of the expressed sdAbs showed that most of the monomeric sdAbs bind simultaneously with A1 to IgE antibody and thus to another IgE-binding epitope than A1 (FIG. 3). Here, the sdAbs B3, B1, D1 and D2 share a similar epitope, which is different from the epitope of B2 or A1. Such sdAbs might be used in combination with either A1, A2 or other sdAbs having a different binding site at IgE to modify the overall anti-IgE activity of one sdAb. For example, to improve the dissociation of receptor bound IgE.

The epitope mapping was used to determine the combination of sdAbs for dimerization, both with and without IgG4 fusion.

Various examples on sdAb "dimers" fused through a (G4S)4 linker were cloned and expressed (table 3). Dimer formed with N-terminal B1 and C-terminal A1 (B1A1(G4S) 4) is shown as an example. The elution of the first purification shows a visible clear band at the expected size between 35 kDa and 45 kDa on an SDS-PAGE after Coomassie blue staining. However, a lot of contaminant compounds of various size are also displayed The second step of purification allows to remove these contaminants and to refine the purity of the sdAb "dimers" (data not shown).

For heterodimerization of sdAbs fused to IgG4-Fc, table 8 shows other examples of "dimers" (the combination of sdAb, IgG$_4$-Fc and linker).

Conclusion

Both mono- and dimer single domain antibodies as well as IgG$_4$-Fc fused sdAbs were expressed and purified showing a high degree of purity and having the expected size on SDS-PAGE analysis.

Example 4

Mutation of Single Domain Antibodies

The aim of the present study was to study the effect of single point mutation on sdAb A1 to generate a mutant with improved displacement activity.

Material and Methods

From A1 (SEQ ID NO 1), two libraries were built. Library 1 was covering amino acids of A1 from position 11 to 61 and library 2 was covering position 62 to 112. Each library was generated by SOE PCR using oligopools from Integrated DNA Technologies to introduce a NNK codon at each position. Resulting DNA library contained all possible single amino acid mutants on position 11 to 61 for library 1 and 62 to 112 for library 2. To assess the effect of these mutations, the library is cloned into a Yeast Display plasmid named pNT by homologous recombination in *Saccharomyces cerevisiae* EBY100 (ATCC) following the procedure described by (Benatuil et al., 2010).

Each library was cultivated, expression induced and stained using three colors staining as described in example 2. A single round of selection by FACS against biotinylated IgE: FcεRIα complex at a concentration corresponding to K$_D$ on yeast of the sdAb (determined by titration) was performed as described in example 2. Two populations were selected: a negative one (Anti-HA+, Streptavidin−) and a positive one (Anti-HA+, Streptavidin+, Anti-FcεRIα−).

Selected populations were cultivated in SD-CAA media at 30° C. Plasmids were extracted separately from non-selected library, negative population and positive populations using Zymoprep Yeast Plasmid Miniprep II kit (Zymo Research). sdAb genes from extracted plasmids were amplified by PCR. Purified PCR products were sent to Deeptope (France) for deep sequencing using Illumina technology and data analysis.

Mutations were inserted in A1 by site-directed mutagenesis PCR directly on pET22b containing A1 gene. A1 triple mutant was expressed and purified like previously described in example 2.

Results

SdAb A1 displayed on yeast showed a K$_D$ of 0.345 nM for biotinylated IgE: FcεRIα complex (data not shown. Thus, selection of A1 DMS libraries was performed at this concentration to monitor the effect of mutation on the binding. A negative population of sdAbs expressed on yeast but not binding biotinylated IgE is selected (data not shown). A positive population of sdAbs expressed on yeast, binding biotinylated IgE but negative for FcεRIα is selected (data not shown). sdAbs from library before selection, negative population and positive population were sequenced using deep sequencing and the frequency of each nanobody in the library was determined before and after selection. Thus, the effect of each single mutation on A1 can be assessed by calculation of the enrichment scores (Enrichment=Frequency of the mutant after selection/Frequency before selection) (FIG. 4). A mutation with a high enrichment score in the negative population is deleterious for the activity of A1 and will most likely be depleted in the positive population like mutation P45K. A mutation with a high enrichment score in the positive population and depleted in the negative population like mutation V93E will improve A1 affinity for IgE-Fc.

Using Deep Mutational Scanning data, three mutations (T28R, P45Y and V93E) enriched in positive population and depleted in negative population were selected to build a mutated version of sdAb A1, named A2. A2 was expressed, purified and its binding toward IgE-Fc was confirmed like previously described in example 2.

Other mutations were enriched in the positive population as well and will thus, improve A1 affinity to IgE-Fc as for the three selected mutations described above. The following mutations can be used, either alone or in combination to build a mutated version of A1: L11F, L11K, V12F, V12Y, V12G, Q13V, P14M, P14E, P14R, R19K, A23K, A23R, S25K, S25R, G26K, G26R, T28K, T28R, F29Y, G30F, G30W, G30Y, G30D, G30H, G30K, G30K, G30R, K43R, P45W, P45Y, F68W, T69W, T69G, T69N, T69R, I70V, S71N, D73F, D73W, D73Y, D73M, D73I, D73L, D73V, D73A, D73G, D73S, D73T, D73N, D73Q, D73E, D73H, D73K, D73R, A75W, A75Y, A75P, A75M, A75G, A75S, A75N, A75K, A75R, N77Y, N77K, N77R, M78K, M78R, L79F, L79V, L79A, L79A, L79N, L79H, Q82W, Q82Y, M83I, T91A, T91G, T91Q, T91D, T91E, T91H, V93M, V93T, V93E and L104M.

The above method was applied for sdAb B2 and B3 as well and the following mutations were enriched in the positive population as well and will thus, improve the affinity to IgE-Fc. These mutations can be used either alone or in combination to build a mutated version of B2 or B3 respectively.

B2: V12T, A23Q, A23D, T28Q, T28H, D35M, D35A, D36V, Q39F, Q39W, Q39Y, Q39I, Q39V, Q39E, Q44P, D74P, D74I, S105I, S105N, S105D and S105E B3: S21E, A23D, A23E, S25D, W36I, V37W, V37Y, A40C, A40R, G44P, G44D, G44E, G44H, F45P, F45M, F45M, F45I, F45L, F45V, F45A, S45A, S45G, T58D, N59E, K65M, K65A, T69Q, S71I, N77G, R78M, R78V, R78E, Q82Y, N84D, N84E, K87L, K87G, K87C, K87S, K87N, K87D, K87E, K87H, P88D, T91A, T91G, T91N, T91Q, T91D, T91E, A97M, A97I, A97L, A97V, N105P, N105D, R108F, R108M, R108I, R108V, R108N, R108Q and R108K

Conclusion

Using Deep Mutational Scanning, the effect of all single mutation of sdAb A1, B2 and B3 on the interaction with IgE-Fc/FcεRIα was assessed. It was possible to generate a list of mutations that can improve the binding affinity of A1, B2 and B3 to IgE-Fc. Further, a triple mutant of A1, named A2, has been generated and successfully expressed and purified.

Example 5

Affinity Determination

The aim of the present study was to test the affinity of the sdAbs obtained in the prior examples to IgE-Fc.

Material and Methods

The affinity of the mono, dimer sdAbs and multi-specific construct to IgE-Fc were tested at Octet RED96e system (FortéBIO) using Kinetic buffer (PBS, 0.02% Tween20, 0.1% BSA) as a diluent. The biotinylated IgE Fc (made in-house ALK, Denmark) was immobilised on SAX (High precision streptavidin) sensors (FortéBIO) to max 1 nm. The association (240 s) and dissociation (600 s) were measured for the analytes in a serial dilution (from 10 nM to 0.37 nM). Data were subtracted to blank reference sensors exposed to the same serial analyte dilutions, aligned, and analysed in the Octet Data Analysis HT 11.1 Software (FortéBIO) using a 1:1 fitting model.

Results

The affinity to IgE Fc was measured for five individual sdAbs and compared to A1 (table 14). The $k_{on}$ is a constant used to characterize how quickly the sdAbs bind to IgE, whereas $k_{off}$ characterizes how quickly the sdAbs dissociate from IgE. The ratio of $k_{off}/k_{on}$ results in the equilibrium dissociation constant $K_D$. The lower the $K_D$ value the higher the affinity of the sdAb to IgE. Typically, sdAb bind their antigen with a $k_{on}$ of $10^5$-$10^6$ $(M^{-1}s^{-1})$ and $k_{off}$ rate of $10^{-3}$ $(s^{-1})$ resulting in binding events in the low nM affinity range. Here, B2 and B3 showed the highest affinity towards IgE which is comparable to A1 in the low nM affinity range ($\sim 1 \times 10^{-10}$ M). B1 and D2 showed a lower affinity ($6$-$8 \times 10^{-8}$ M).

TABLE 14

| Affinity determination of sdAb using biolayer interferometry (BLI, octet) and a global 1:1 fit. | | | |
|---|---|---|---|
| sdAb construct | $k_{on}$ $(M^{-1}s^{-1})$ | $k_{off}$ $(s^{-1})$ | $k_D$ (M) |
| A1 | $1.0 \times 10^6$ | $2.0 \times 10^{-4}$ | $1.9 \times 10^{-10}$ |
| B1 | $7.6 \times 10^5$ | $4.9 \times 10^{-2}$ | $6.5 \times 10^{-8}$ |
| B2 | $7.0 \times 10^5$ | $7.8 \times 10^{-5}$ | $1.1 \times 10^{-10}$ |
| B3 | $8.8 \times 10^5$ | $2.5 \times 10^{-4}$ | $2.8 \times 10^{-10}$ |
| D1 | $1.4 \times 10^5$ | $4.5 \times 10^{-4}$ | $3.2 \times 10^{-9}$ |
| D2 | $2.4 \times 10^5$ | $2.0 \times 10^{-2}$ | $8.1 \times 10^{-8}$ |

The affinity of the additional sdAbs described herein to IgE-Fc will be measured by the same procedure.

Conclusion

The selected, non-optimised sdAb show high affinity towards IgE in the high to low nM range comparable to the A1.

Example 6

Displacement Effect of Single Domain Antibodies Measured by ELISA

Aim

The aim of the present example was to evaluate the ability of the sdAbs to displace the binding between human IgE and the high affinity human IgE receptor (FcεRIα) using a biochemical ELISA assay.

Material and Methods

The displacement effect was tested using IgE-FcεRIα displacement ELISA assay. Maxisorp® microtiter plates (Thermo Scientific Nunc, Roskilde, Denmark) were coated with 100 μl streptavidin, 5 μg/ml (Thermo Scientific, Waltham, MA) for 18 h at 4° C. followed by wash with 300 μl washing buffer (PBS containing 0.05% Tween 20) using an AquaMax® 2000 plate washer (Molecular Devices, San Jose, CA). Remaining binding sites were blocked with 250 μl blocking buffer (PBS containing 2% BSA) for 2 h and washed with 300 μl washing buffer. Subsequently, the bound streptavidin was loaded with 100 μl (0.1 μg/ml) recombinant human FcεRIα (site specific biotinylated via avi-tag, made in-house, ALK, Hørsholm, Denmark) for 1 h and plates washed twice with 300 μl washing buffer. The bound receptor was then loaded with 100 μl recombinant human IgE (made in-house, ALK, Hørsholm, Denmark), 13 ng/ml (pre-titrated to reach an $OD_{450}$ signal in the range of 1.5-2.5 in the absence of displacement components) for 1 h followed by three washes of 300 μl washing buffer.

displacement step: 100 μl sdAbs diluted in concentration series (pM-μM range) or blocking buffer only as a non-displacement negative control, were added to the ELISA wells and incubated for 1 h. Any IgE, displaced from the receptor by a sdAb was washed away by three washes of 300 μl washing buffer.

The remaining, non-displaced IgE was detected by addition of 100 μl HRP-conjugated anti human lambda light chain (Bethyl Laboratories, Montgomery, Tx), diluted 1:20.000 in blocking buffer for 1 h followed by three washes of 300 μl. Then 100 μl TMB One (Kementec, Taastrup, Denmark) was added to the wells and incubated for 15 minutes, and the reaction stopped by addition of 100 μl 1N sulfuric acid.

Finally, absorbance at $OD_{450}$ was measured on a Glomax Discover plate reader (Promega, Madison, Wi).

Results were analysed using GraphPad Prism ver. 9.3.0 (GraphPad Software, San Diego, CA) and the percent displacement effect was determined as the relative reduction in signal compared to the control with no sdAb added. The $EC_{50}$ values and the maximal effect were determined from the graphs (not shown) as listed in table 15.

All types of sdAbs, both mono- and dimers, as well as sdAb-Fc fusion complexes can be tested using this procedure.

Results

Table 1 lists the sdAbs tested in the IgE-FcεRIα displacement ELISA assay as either monomers, or combined pairs build as dimers or as multi-specific constructs. The sdAbs B1, B2, B3, D1, D2, E1, E2, E3, E4, F1, F2, F3, F4, F5, F6 was in combination with A1 and fused to IgG4-Fc (as seen in FIG. 1). $IgG_4$-Fc fusion was either n-terminal or c-terminal, using different linkers between sdAbs and $IgG_4$. Further the sdAb A2 was combined with B1 in the same way. Table 15 shows all the tested sdAbs and constructs and the results of the Fc fusion constructs.

The ability of the various sdAbs to displace IgE from the receptor (FcεRIα) was evaluated by use of the ELISA based IgE-FcεRIα displacement assay. The percent displacement effect was calculated as the relative reduction in signal compared to the control with no sdAb added. The $EC_{50}$ values and the maximal effects were determined (table 15).

Table 15 shows the displacement effect in terms of $EC_{50}$ and "max effect" for monomer sdAbs and multi-specific constructs.

| Test compound | SEQ ID NO | $EC_{50}$ (nM) | Max effect |
|---|---|---|---|
| Dimers | | | |
| B1A1(G4S)4 | 85 | 1.9 | >95% |
| A1B1(G4S)4 | 86 | 0.9 | >95% |
| B2A1(G4S)4 | 81 | 30 | >95% |
| A1B2(G4S)4 | 82 | 1.4 | >95% |
| B3A1(G4S)4 | 79 | 0.3 | >95% |
| A1B3(G4S)4 | 80 | 190 | 80% |
| D2A1(G4S)4 | 83 | 8.0 | >95% |
| A1D2(G4S)4 | 84 | 10 | >95% |
| A1A1(G4S)4 | 78 | 250 | 90% |
| A1E1(G4S)4 | 314 | 4.9 | >95% |
| E1A1(G4S)4 | 311 | 1.2 | >95% |
| A1E2(G4S)4 | 315 | 500 | 80% |
| E2A1(G4S)4 | 312 | n.d. | 40% |
| A1E4(G4S)4 | 316 | 18 | >95% |
| E4A1(G4S)4 | 313 | 23 | >95% |
| A1F1(G4S)4 | 322 | 230 | 70% |
| F1A1(G4S)4 | 317 | 4000 | >95% |
| A1F3(G4S)4 | 323 | 30 | >95% |
| F3A1(G4S)4 | 318 | n.d. | 40% |
| A1F4(G4S)4 | 324 | 0.6 | >95% |
| F4A1(G4S)4 | 319 | 22 | >95% |
| A1F5(G4S)4 | 325 | 110 | >95% |
| F5A1(G4S)4 | 320 | 1100 | 75% |
| A1F6(G4S)4 | 326 | 0.7 | >95% |
| F6A1(G4S)4 | 321 | 4000 | 65% |
| A1B1(G4S)1 | 458 | 1.0 | >95% |
| A1B1(G4S)2 | 459 | 0.7 | >95% |
| A1B1(G4S)3 | 460 | 0.6 | >95% |
| B1A1(G4S)1 | 461 | 5.3 | >95% |
| B1A1(G4S)2 | 462 | 10 | >95% |
| B1A1(G4S)3 | 463 | 5.3 | >95% |
| Single sdAbs | | | |
| A1 | 1 | 800 | >95% |
| A2 | 5 | 250 | >95% |
| B1 | 9 | 200 | 65% |
| B2 | 13 | n.d. | <20% |

-continued

| Test compound | SEQ ID NO | $EC_{50}$ (nM) | Max effect |
|---|---|---|---|
| B3 | 17 | n.d. | 0% |
| D1 | 21 | n.d. | 0% |
| D2 | 25 | 10,000 | 50% |
| E1 | 33 | n.d. | <20% |
| E2 | 37 | n.d. | 0% |
| E3 | 41 | n.d. | 0% |
| F1 | 49 | n.d. | 0% |
| F3 | 57 | n.d. | 0% |
| F4 | 61 | n.d. | <20% |
| F5 | 65 | n.d. | 35% |
| F6 | 69 | n.d. | <20% |
| G1 | 73 | n.d. | n.d. |
| SdAb mixes (controls) | | | |
| A1 + B1 | 1 + 9 | 19 | >95% |
| A1 + B2 | 1 + 13 | 22 | >95% |
| A1 + B3 | 1 + 17 | 280 | 95% |
| A1 + D1 | 1 + 21 | 140 | 90% |
| A1 + D2 | 1 + 25 | 200 | >95% |
| A1 + E1 | 1 + 33 | 80 | >95% |
| A1 + E2 | 1 + 37 | 1300 | 90% |
| A1 + E3 | 1 + 41 | 115 | >95% |
| A1 + F1 | 1 + 49 | 800 | 95% |
| A1 + F3 | 1 + 57 | 400 | >95% |
| A1 + F4 | 1 + 61 | 120 | >95% |
| A1 + F5 | 1 + 65 | 230 | >95% |
| A1 + F6 | 1 + 69 | 180 | >95% |
| Comparator | | | |
| KIH_E7_79 | 128 | 0.5 | >95% |
| IgG4-Fc fusion | | | |
| NIgG4B1A1(RS) | 121 + 113 | 1.9 | >95% |
| NIgG4B1A1(G4S)1 | 122 + 114 | 1.1 | >95% |
| NIgG4B1A1(G4S)2 | 123 + 115 | 1.4 | >95% |
| NIgG4B1A1(G4S)3 | 124 + 116 | 0.9 | >95% |
| CIgG4B1A1(RS) | 101 + 93 | 9.8 | >95% |
| CIgG4B1A1(G4S)1 | 102 + 94 | 3.1 | >95% |
| CIgG4B1A1(G4S)2 | 103 + 95 | 4.0 | >95% |
| CIgG4B1A1(G4S3) | 104 + 96 | 3.5 | >95% |
| NIgG4A1A1(RS) | 109 + 113 | 490 | ~60% |
| NIgG4A1A1(G4S)1 | 110 + 114 | 260 | ~65% |
| NIgG4A1A1(G4S)2 | 111 + 115 | 230 | ~70% |
| NIgG4A1A1(G4S)3 | 112 + 116 | 310 | ~60% |
| CIgG4A1A1(RS) | 105 + 93 | n.d. | <20% |
| CIgE4A1A1(GS)1 | 106 + 94 | n.d. | ~40% |
| CIgE4A1A1(GS)2 | 107 + 95 | 145 | ~70% |
| CIgE4A1A1(GS3) | 108 + 96 | 36 | ~85% |
| NIgG4B1A2(RS) | 121 + 429 | 0.8 | >95% |
| NIgG4B1A2(G4S)1 | 122 + 430 | 0.6 | >95% |
| NIgG4B1A2(G4S)2 | 123 + 431 | 0.5 | >95% |
| NIgG4B1A2(G4S)3 | 124 + 432 | 0.2 | >95% |
| CIgG4B1A2(RS) | 101 + 425 | 5 | >95% |
| CIgG4B1A2(G4S)1 | 102 + 426 | 3 | >95% |
| CIgG4B1A2(G4S)2 | 103 + 427 | 2.7 | >95% |
| CIgG4B1A2(G4S)3 | 104 + 428 | 2.5 | >95% |
| NIgG4B2A1(RS) | 321 + 113 | 11 | >95% |
| NIgG4B2A1(G4S)1 | 322 + 114 | 5 | >95% |
| NIgG4B2A1(G4S)2 | 323 + 115 | 2.4 | >95% |
| NIgG4B2A1(G4S)3 | 324 + 116 | 1.2 | >95% |
| CIgG4B2A1(RS) | 325 + 93 | 130 | 70% |
| CIgG4B2A1(G4S)1 | 326 + 94 | 0.8 | >95% |
| CIgG4B2A1(G4S)2 | 327 + 95 | 0.7 | >95% |
| CIgG4B2A1(G4S)3 | 328 + 96 | 2.1 | >95% |
| NIgG4B3A1(RS) | 117 + 113 | 145 | 55% |
| NIgG4B3A1(G4S)1 | 118 + 114 | 61 | 70% |
| NIgG4B3A1(G4S)2 | 119 + 115 | 12 | 70% |
| NIgG4B3A1(G4S)3 | 120 + 116 | 1.7 | 85% |
| CIgG4B3A1(RS) | 97 + 93 | n.d. | 0% |
| CIgG4B3A1(G4S)1 | 98 + 94 | n.d. | 45% |
| CIgG4B3A1(G4S)2 | 99 + 95 | 32 | 85% |
| CIgG4B3A1(G4S)3 | 100 + 96 | 5.4 | 95% |
| NIgG4D1A1(RS) | 333 + 113 | 30 | 80% |
| NIgG4D1A1(G4S)1 | 334 + 114 | 7 | >95% |
| NIgG4D1A1(G4S)2 | 335 + 115 | 3.1 | >95% |
| NIgG4D1A1(G4S)3 | 336 + 116 | 2.1 | >95% |
| CIgG4D1A1(RS) | 329 + 93 | n.d. | 30% |

-continued

| Test compound | SEQ ID NO | $EC_{50}$ (nM) | Max effect |
|---|---|---|---|
| CIgG4D1A1(G4S)1 | 330 + 94 | 52 | 90% |
| CIgG4D1A1(G4S)2 | 331 + 95 | 30 | >95% |
| CIgG4D1A1(G4S)3 | 332 + 96 | 14 | >95% |
| NIgG4D2A1(RS) | 341 + 113 | 10 | >95% |
| NIgG4D2A1(G4S)1 | 342 + 114 | 9 | >95% |
| NIgG4D2A1(G4S)2 | 343 + 115 | 0.8 | >95% |
| NIgG4D2A1(G4S)3 | 344 + 116 | 4 | 85% |
| CIgG4D2A1(RS) | 337 + 93 | n.d. | 35% |
| CIgG4D2A1(G4S)1 | 338 + 94 | 25 | >95% |
| CIgG4D2A1(G4S)2 | 339 + 95 | 7 | >95% |
| CIgG4D2A1(G4S)3 | 340 + 96 | 4.8 | >95% |
| NIgG4E1A1(RS) | 349 + 113 | 14 | >95% |
| NIgG4E1A1(G4S)1 | 350 + 114 | 8.5 | >95% |
| NIgG4E1A1(G4S)2 | 351 + 115 | 0.9 | >95% |
| NIgG4E1A1(G4S)3 | 352 + 116 | 4 | >95% |
| CIgG4E1A1(RS) | 345 + 93 | 480 | 65% |
| CIgG4E1A1(G4S)1 | 346 + 94 | 30 | >95% |
| CIgG4E1A1(G4S)2 | 347 + 95 | 10 | >95% |
| CIgG4E1A1(G4S)3 | 348 + 96 | 9 | >95% |
| NIgG4E2A1(RS) | 357 + 113 | 1000 | 50% |
| NIgG4E2A1(G4S)1 | 358 + 114 | n.d. | 45% |
| NIgG4E2A1(G4S)2 | 359 + 115 | 22 | 75% |
| NIgG4E2A1(G4S)3 | 360 + 116 | 7 | 85% |
| CIgG4E2A1(RS) | 353 + 93 | n.d. | 25% |
| CIgG4E2A1(G4S)1 | 354 + 94 | 1000 | 50% |
| CIgG4E2A1(G4S)2 | 355 + 95 | 410 | 65% |
| CIgG4E2A1(G4S)3 | 356 + 96 | 160 | 75% |
| NIgG4E3A1(RS) | 365 + 113 | 31 | >95% |
| NIgG4E3A1(G4S)1 | 366 + 114 | 9 | >95% |
| NIgG4E3A1(G4S)2 | 367 + 115 | 7.2 | 90% |
| NIgG4E3A1(G4S)3 | 368 + 116 | 3 | 90% |
| CIgG4E3A1(RS) | 361 + 93 | n.d. | 30% |
| CIgG4E3A1(G4S)1 | 362 + 94 | 130 | 85% |
| CIgG4E3A1(G4S)2 | 363 + 95 | 50 | >95% |
| CIgG4E3A1(G4S)3 | 364 + 96 | 36 | 90% |
| NIgG4E4A1(RS) | 373 + 113 | 68 | 80% |
| NIgG4E4A1(G4S)1 | 374 + 114 | 17 | 95% |
| NIgG4E4A1(G4S)2 | 375 + 115 | 12 | >95% |
| NIgG4E4A1(G4S)3 | 376 + 116 | 10 | >95% |
| CIgG4E4A1(RS) | 369 + 93 | n.d. | 40% |
| CIgG4E4A1(G4S)1 | 370 + 94 | 130 | 85% |
| CIgG4E4A1(G4S)2 | 371 + 95 | 48 | 90% |
| CIgG4E4A1(G4S)3 | 372 + 96 | 22 | 95% |
| NIgG4F1A1(RS) | 381 + 113 | 1000 | 50% |
| NIgG4F1A1(G4S)1 | 382 + 114 | 60 | 70% |
| NIgG4F1A1(G4S)2 | 383 + 115 | 22 | 85% |
| NIgG4F1A1(G4S)3 | 384 + 116 | 8 | 85% |
| CIgG4F1A1(RS) | 377 + 93 | n.d. | 0% |
| CIgG4F1A1(G4S)1 | 378 + 94 | n.d. | 30% |
| CIgG4F1A1(G4S)2 | 379 + 95 | 800 | 55% |
| CIgG4F1A1(G4S)3 | 380 + 96 | 480 | 65% |
| NIgG4F2A1(RS) | 389 + 113 | n.d. | 30% |
| NIgG4F2A1(G4S)1 | 390 + 114 | 600 | 50% |
| NIgG4F2A1(G4S)2 | 391 + 115 | 35 | 80% |
| NIgG4F2A1(G4S)3 | 392 + 116 | 13 | 85% |
| CIgG4F2A1(RS) | 385 + 93 | n.d. | 10% |
| CIgG4F2A1(G4S)1 | 386 + 94 | n.d. | 20% |
| CIgG4F2A1(G4S)2 | 387 + 95 | n.d. | 35% |
| CIgG4F2A1(G4S)3 | 388 + 96 | n.d. | 45% |
| NIgG4F3A1(RS) | 397 | 21 | 65% |
| NIgG4F3A1(G4S)1 | 398 | 5.1 | 70% |
| NIgG4F3A1(G4S)2 | 399 | 4.9 | 80% |
| NIgG4F3A1(G4S)3 | 400 | 12 | 80% |
| CIgG4F3A1(RS) | 393 | n.d. | 30% |
| CIgG4F3A1(G4S)1 | 394 | 1000 | 50% |
| CIgG4F3A1(G4S)2 | 395 | 41 | 80% |
| CIgG4F3A1(G4S)3 | 396 | 24 | 90% |
| NIgG4F4A1(RS) | 405 | 22 | >95% |
| NIgG4F4A1(G4S)1 | 406 | 2.5 | >95% |
| NIgG4F4A1(G4S)2 | 407 | 1 | >95% |
| NIgG4F4A1(G4S)3 | 408 | 0.7 | >95% |
| CIgG4F4A1(RS) | 401 | 90 | 70% |
| CIgG4F4A1(G4S)1 | 402 | 17 | 90% |
| CIgG4F4A1(G4S)2 | 403 | 30 | 90% |
| CIgG4F4A1(G4S)3 | 404 | 50 | 90% |
| NIgG4F5A1(RS) | 413 | 310 | 60% |
| NIgG4F5A1(G4S)1 | 414 | 90 | 75% |

-continued

| Test compound | SEQ ID NO | $EC_{50}$ (nM) | Max effect |
|---|---|---|---|
| NIgG4F5A1(G4S)2 | 415 | 90 | 75% |
| NIgG4F5A1(G4S)3 | 416 | 29 | 70% |
| CIgG4F5A1(RS) | 409 | n.d. | 15% |
| CIgG4F5A1(G4S)1 | 410 | n.d. | 30% |
| CIgG4F5A1(G4S)2 | 411 | 580 | 55% |
| CIgG4F5A1(G4S)3 | 412 | 400 | 65% |
| NIgG4F6A1(RS) | 421 | 600 | 55% |
| NIgG4F6A1(G4S)1 | 422 | 0.6 | >95% |
| NIgG4F6A1(G4S)2 | 423 | 0.5 | >95% |
| NIgG4F6A1(G4S)3 | 424 | 0.7 | 90% |
| CIgG4F6A1(RS) | 417 | n.d. | 20% |
| CIgG4F6A1(G4S)1 | 418 | n.d. | 25% |
| CIgG4F6A1(G4S)2 | 419 | 8 | 75% |
| CIgG4F6A1(G4S)3 | 420 | 3.3 | 90% |
| CIgG4A1B1(G4S)1 | 437 + 106 | 2.9 | >95% |
| CIgG4B1A1(no linker) | 450 + 451 | 14 | 90% |
| CIgG4B1A1(GS) | 438 + 439 | 9.1 | >95% |
| CIgG4B1A1(G2S) | 440 + 441 | 3.4 | >95% |
| CIgG4B1A1(G3S) | 442 + 443 | 3.1 | >95% |
| CIgG4B1A1(G2SG2S) | 444 + 445 | 3.8 | >95% |
| CIgG4B1A1(EAAAK) | 446 + 447 | 3.0 | >95% |
| CIgG4B1A1(EAAAK)2 | 448 + 449 | 4.1 | >95% |

Overall, it is observed that only a few of the monomeric sdAbs had displacement activity: A1, A2, and B1. Notably, this displacement activity could be greatly increased by pairing an sdAb having displacement activity with another sdAb able to bind a distinct epitope on the IgE-Fc, either as simple mixtures two sdAbs, dimers or fused to IgG-Fc.

The most efficient constructs were identified among the multimeric constructs, which seem far more effective than the sdAb monomers. The most efficient multimeric construct showed $EC_{50}$ values in the sub nanomolar to single digit nanomolar range and with maximal effects >95% at the highest tested concentrations. In comparison, the comparator construct KIH_E07_79 was also highly potent in this assay ($EC_{50}$=0.6 nM and Max effect >95%). To the extent that the monomeric sdAbs of the multimeric constructs binds distinct IgE epitopes, they are considered multispecific constructs.

The relative orientation of the two linked sdAb-entities within the sdAb dimers had a pronounced effect in some instances e.g., B3A1(G4S)4 was much more efficient ($EC_{50}$=0.3 nM) than the reverse orientation A1B3 (G4S)4 ($EC_{50}$=190 nM). Still, there were also examples where the relative orientation seemed less important e.g., D2A1(G4S)4 vs. A1D2(G4S)4 showing $EC_{50}$ values in the same range (8 nM and 10 nM, respectively).

Mixes of sdAb A1 with an additional sdAb monomer (but not linked together-see sdAb mixes, (table 15)), showed synergetic effects as the $EC_{50}$ values in most cases were considerably lower than any of the two sdAbs alone. Still, none of these combinations were as efficient as the most potent linked sdAb dimers.

A2 was more efficient at displacing IgE from the receptor than A1 ($EC_{50}$ of 250 nM and 800 nM, respectively).

Conclusion

Several of the linked sdAb dimers and sdAb-IgG4Fc fusion constructs showed $EC_{50}$ values in the sub nanomolar to single digit nanomolar range and were able to displace >95% IgE from the receptor.

Example 7

Cellular Evaluation of sdAbs Displacement Activity Using RBL Assay

The aim of the present study was to evaluate the ability of the sdAbs to displace the binding between human IgE and the high affinity human IgE receptor (FcεRIα) expressed in a cellular system.

Material and Methods

The ability of the sdAbs to displace IgE from the receptor was tested using RBL assay.

Rat basophilic leukemia cells (RBL SX-38) were cultured in complete MEM/cMEM: MEM (Gibco 11095-080)+100 mM Na-Pyrovate (Gibco 11360-+70)+15% FCS+pen/strep (Lonza DE17-602E)+1 mg/ml G418 (Gibco 10131-027) in horizontal TC-culture flasks. For IgE sensitization the cells were detached from TC-culture flasks after washing out protein from the cells with PBS before addition of Trypsin-Versene (LONZA cat no 17-161E), after 5 min incubation at 37° C. the cells seeded in 200 μl cMEM with $10^5$ cells/well in 96 well plate in (Nunc 167008). The cells were incubated overnight (5% $CO_2$, 37° C.).

Sensitization of RBL SX-38 with IgE was done after removal of supernatant: A mixture of three Der p 2 specific recombinant human IgE clones: H10, H12, P4E (Christensen et al. 2008) was used. 100 μl cMEM with 1 μg/ml recombinant human IgE were added to each well and incubated 2 hours in CO2 incubator (5% $CO_2$, 37° C.). Wells for non-sensitized controls were incubated with cMEM only for comparison.

Displacement of bound IgE: To the sensitized RBL SX-38 cells 50 μl/well SdAbs or comparator were added. Peptide-linked, as well as IgG-Fc fused sdAbs were tested in 1 μM concentrations and 10 folds dilutions thereof, while single sdAb were tested in 1 μM concentrations. In addition, mix of sdAb A1 with individual single sdAb were also tested with 1 μM of each. The cells were incubated 1 hour in CO2 incubator (5% $CO_2$, 37° C.).

FACS stain of surface bound IgE: Cells from the RBL assay was separately washed twice with FACS staining buffer (BD FACS flow+0.5% BSA) by centrifugation 5 min 500×g and cell pellet stained with a-FcεR1 FITC (Invitrogen 11-5899-42) and anti-IgE APC (Invitrogen 17-6886-42). The cell were incubated on ice for 30 min followed by wash with FACS staining buffer before fixation 15 min, RT, with 200 μl cell fix (BD 340181)/well. After additional wash the cells were analyzed on flowcytometer: Cytek Aurora with plate loader. FACS data were analysed using SpectroFlo software and the relevant cells were identified and gated based on scatter and FcεR1 expression. IgE mean fluorescence, readout for the assay were analysed using GraphPad Prism ver. 9.3.0 (GraphPad Software, San Diego, CA) and the percent displacement effect were determined as the relative reduction in signal compared to the control with no sdAb added. The maximal displacement effect and $EC_{50}$, (sdAb concentration resulting in 50% inhibition relative to control with no sdAb added) were determined from dose-response graphs of IgE expression (mean fluorescence) using nonlinear curve fit of log transformed data with GraphPad Prism.

Results

The sdAbs of interest (table 16) were tested in a RBL assay for displacement activity using Rat Basophilic Leukemia cells (RBL-SX38). The sdAbs were tested in different combinations, either as sdAb monomers, as sdAb dimers (bispecific or bivalent) linked together both with and without an Fc domain, or combination of two individual sdAb monomers added in the same setup. The displacement effect is listed in (table 16) with $EC_{50}$ and Maximal effect for linked sdAb and (A1 and KIH_E7_79 for comparison) and effect 1 μM for remaining sdAb.

The sdAbs was in (individual) combination with A1 or A2, fused to IgG4-Fc (as schematically seen in FIG. 1), either n-terminal or c-terminal, using different linkers (as described in table 8 and table 15). Table 16 shows the results of the tested constructs.

The activity of each tested construct is shown in form of $EC_{50}$ and maximal displacement activity.

All linked sdAb dimers showed efficient displacement of IgE from FcER1 on RBL-SX38 cells in contrast to the monospecific, bivalent A1A1(G4S)4 construct (table 16). The 11 most efficient dimers completely displaced IgE with a $EC_{50}$ of 2 nM or less: B1A1(G4S)4, A1B1 (G4S)4, A1B2 (G4S)4, B2A1(G4S)4, A1B3 (G4S)4, A1E1 (G4S)4, A1E4 (G4S)4, F3A1(G4S)4, F4A1(G4S)4, A1F6 (G4S)4, F6A1 (G4S)4 (table 16).

Data indicate that the order of linkage play a role as D2A1(G4S)4 was less potent than A1D2(G4S)4 with $EC_{50}$~78 nM vs~4 nM and the same for B2A1(G4S)4 vs B2A1(G4S)4 with $EC_{50}$~6 nM vs~1 nM.

Mix of sdAb monomer A1 with different sdAb monomers (non-linked) improve the displacement in all cases, most efficient for mixes with B1 and B2 with an effect ~100% using 1 μM sdAb (table 16).

Displacement with single sdAb indicate that B1 displace IgE more efficient than A1 at 1 μM.

For the multi-specific construct, where two sdAbs are linked to a Fc domain, most of the tested constructs, showed an effective displacement activity, compared to the individual, unlinked sdAbs.

Table 16 lists the data from displacement with sdAbs tested with RBL-SX36 cells, both mono- and dimers and combinations.

|  | | RBL-SX38 | |
| --- | --- | --- | --- |
| SdAb construct | SEQ ID | $EC_{50}$ (nM) | Max effect/ effect 1 μM |
| Peptide Linked sdAbs | | | |
| B1A1(G4S)4 | 85 | 1.4 | 100 |
| A1B1(G4S)4 | 86 | 1.4 | 100 |
| B2A1(G4S)4 | 81 | 5.8 | 92 |
| A1B2(G4S)4 | 82 | 0.8 | 100 |
| B3A1(G4S)4 | 79 | 2.0 | 100 |
| A1B3(G4S)4 | 80 | 0.4 | 99 |
| D2A1(G4S)4 | 83 | 78.7 | 83 |
| A1D2(G4S)4 | 84 | 4.3 | 98 |
| A1A1(G4S)4 | 78 | 401.7 | 45 |
| A1E1(G4S)4 | 314 | 0.6 | 100 |
| A1E4(G4S)4 | 316 | 0.3 | 100 |
| F3A1(G4S)4 | 318 | 0.8 | 91 |
| F4A1(G4S)4 | 319 | 0.3 | 99 |
| A1F6(G4S)4 | 326 | 0.8 | 92 |
| F6A1(G4S)4 | 321 | 0.4 | 88 |
| Single sdAbs | | | |
| A1 | 1 | n.d. | 40 |
| B1 | 9 | n.d. | 54 |
| B2 | 13 | n.d. | 23 |
| B3 | 17 | n.d. | 7 |
| D2 | 25 | n.d. | 22 |
| D1 | 21 | n.d. | 12 |
| E1 | 33 | n.d. | 0 |
| E2 | 37 | n.d. | n.d. |

75

-continued

| | | RBL-SX38 | |
|---|---|---|---|
| SdAb construct | SEQ ID | EC$_{50}$ (nM) | Max effect/effect 1 µM |
| E3 | 41 | n.d. | n.d. |
| E4 | 45 | n.d. | n.d. |
| F1 | 49 | n.d. | n.d. |
| F2 | 53 | n.d. | n.d. |
| F3 | 57 | n.d. | 5.6 |
| F4 | 61 | n.d. | 17 |
| F5 | 65 | n.d. | n.d. |
| F6 | 69 | n.d. | 26 |
| G1 | 73 | n.d. | n.d. |
| Not-linked SdAb mixes | | | |
| A1 + B1 | 1 + 9 | n.d. | 100 |
| A1 + B2 | 1 + 13 | n.d. | 98 |
| A1 + B3 | 1 + 17 | n.d. | 64 |
| A1 + D2 | 1 + 25 | n.d. | 80 |
| A1 + E1 | 1 + 33 | 69.8 | 99 |
| A1 + F4 | 1 + 61 | 188 | 64 |
| A1 + F4 | 1 + 61 | 218 | 97 |
| A1 + F6 | 1 + 69 | 565 | 56 |
| Comparator | | | |
| KIH_E07_79 | 128 | 0.8 | 98 |
| IgG4 FC fusions | | n.d. | n.d. |
| NIgG4B1A1(RS) | 121 + 113 | 3 | 99 |
| NIgG4B1A1(G4S)1 | 122 + 114 | 3 | 99 |
| NIgG4B1A1(G4S)2 | 123 + 115 | 3 | 99 |
| NIgG4B1A1(G4S)3 | 124 + 116 | 2.6 | 99 |
| CIgG4B1A1(RS) | 101 + 93 | 84.9 | 92 |
| CIgG4B1A1(G4S)1 | 102 + 94 | 22.4 | 99 |
| CIgG4B1A1(G4S)2 | 103 + 95 | 19.5 | 99 |
| CIgG4B1A1(G4S3) | 104 + 96 | 14.1 | 99 |
| NIgG4A1A1(RS) | 109 + 113 | n.d. | 45 |
| NIgG4A1A1(G4S)1 | 110 + 114 | n.d. | 44 |
| NIgG4A1A1(G4S)2 | 111 + 115 | n.d. | 36 |
| NIgG4A1A1(G4S)3 | 112 + 116 | n.d. | 40 |
| CIgG4A1A1(RS) | 105 + 93 | n.d. | 11 |
| CIgE4A1A1(GS)1 | 106 + 94 | n.d. | 7 |
| CIgE4A1A1(GS)2 | 107 + 95 | n.d. | 19 |
| CIgE4A1A1(GS3) | 108 + 96 | n.d. | 10 |
| CIgG4B3A1(RS) | 97 + 93 | n.d. | 1 |
| CIgG4B3A1(GS)1 | 98 + 94 | n.d. | 12 |
| CIgG4B3A1(GS)2 | 99 + 95 | n.d. | 28 |
| CIgG4B3A1(GS)3 | 100 + 96 | n.d. | 76 |
| NIgG4B3A1(RS) | 117 + 113 | n.d. | 94 |
| NIgG4B3A1(GS)1 | 118 + 114 | n.d. | 94 |
| NIgG4B3A1(GS)2 | 119 + 115 | n.d. | 94 |
| NIgG4B3A1(GS)3 | 120 + 116 | n.d. | 93 |
| NIgG4B1A2(RS) | 121 + 429 | 0.6 | 99 |
| NIgG4B1A2(G4S)1 | 122 + 430 | 0.4 | 100 |
| NIgG4B1A2(G4S)2 | 123 + 431 | 0.4 | 100 |
| NIgG4B1A2(G4S)3 | 124 + 432 | 0.5 | 100 |
| CIgG4B1A2(RS) | 101 + 425 | 11.9 | 99 |
| CIgG4B1A2(G4S)1 | 102 + 426 | 8.1 | 100 |
| CIgG4B1A2(G4S)2 | 103 + 427 | 6.1 | 100 |
| CIgG4B1A2(G4S)3 | 104 + 428 | 5.3 | 100 |
| NIgG4B2A1(RS) | 325 + 113 | 0.4 | 99 |
| NIgG4B2A1(G4S)1 | 326 + 114 | 0.3 | 97 |
| NIgG4B2A1(G4S)2 | 327 + 115 | 0.3 | 98 |
| NIgG4B2A1(G4S)3 | 328 + 116 | 0.5 | 98 |
| CIgG4B2A1(RS) | 321 + 93 | 273 | 70 |
| CIgG4B2A1(G4S)1 | 322 + 94 | 8.8 | 93 |
| CIgG4B2A1(G4S)2 | 323 + 95 | 1.6 | 99 |
| CIgG4B2A1(G4S)3 | 324 + 96 | 1.5 | 98 |
| NIgG4D1A1(RS) | 333 + 113 | 1.6 | 97 |
| NIgG4D1A1(G4S)1 | 334 + 114 | 1.4 | 99 |
| NIgG4D1A1(G4S)2 | 335 + 115 | 1.6 | 100 |
| NIgG4D1A1(G4S)3 | 336 + 116 | 2.0 | 99 |
| CIgG4D1A1(RS) | 329 + 93 | n.d. | 16 |
| CIgG4D1A1(G4S)1 | 330 + 94 | 65.8 | 96 |
| CIgG4D1A1(G4S)2 | 331 + 95 | 87.2 | 96 |
| CIgG4D1A1(G4S)3 | 332 + 96 | 64.6 | 96 |
| NIgG4D2A1(RS) | 341 + 113 | 12.3 | 97 |
| NIgG4D2A1(G4S)1 | 342 + 114 | 8.7 | 97 |
| NIgG4D2A1(G4S)2 | 343 + 115 | 6.3 | 96 |

76

-continued

| | | RBL-SX38 | |
|---|---|---|---|
| SdAb construct | SEQ ID | EC$_{50}$ (nM) | Max effect/effect 1 µM |
| NIgG4D2A1(G4S)3 | 344 + 116 | 3.7 | 88 |
| CIgG4D2A1(RS) | 337 + 93 | n.d. | 6 |
| CIgG4D2A1(G4S)1 | 338 + 94 | 125.9 | 95 |
| CIgG4D2A1(G4S)2 | 339 + 95 | 39.0 | 99 |
| CIgG4D2A1(G4S)3 | 340 + 96 | 28.8 | 99 |
| NIgG4E1A1(RS) | 349 + 113 | 8.7 | 97 |
| NIgG4E1A1(G4S)1 | 350 + 114 | 7.1 | 96 |
| NIgG4E1A1(G4S)2 | 351 + 115 | 4.8 | 94 |
| NIgG4E1A1(G4S)3 | 352 + 116 | 3.7 | 98 |
| CIgG4E1A1(RS) | 345 + 93 | n.d. | 9 |
| CIgG4E1A1(G4S)1 | 346 + 94 | 96.1 | 95 |
| CIgG4E1A1(G4S)2 | 347 + 95 | 35.6 | 99 |
| CIgG4E1A1(G4S)3 | 348 + 96 | 24.1 | 99 |
| NIgG4E2A1(RS) | 357 + 113 | 2.0 | 97 |
| NIgG4E2A1(G4S)1 | 358 + 114 | 2.3 | 95 |
| NIgG4E2A1(G4S)2 | 359 + 115 | 1.9 | 98 |
| NIgG4E2A1(G4S)3 | 360 + 116 | 2.0 | 97 |
| CIgG4E2A1(RS) | 353 + 93 | n.d. | 6 |
| CIgG4E2A1(G4S)1 | 354 + 94 | n.d. | 22 |
| CIgG4E2A1(G4S)2 | 355 + 95 | 571.6 | 45 |
| CIgG4E2A1(G4S)3 | 356 + 96 | 531.6 | 45 |
| NIgG4E3A1(RS) | 365 + 113 | 2.2 | 100 |
| NIgG4E3A1(G4S)1 | 366 + 114 | 2.0 | 99 |
| NIgG4E3A1(G4S)2 | 367 + 115 | 2.1 | 99 |
| NIgG4E3A1(G4S)3 | 368 + 116 | 2.2 | 97 |
| CIgG4E3A1(RS) | 361 + 93 | n.d. | 21 |
| CIgG4E3A1(G4S)1 | 362 + 94 | 276.6 | 76 |
| CIgG4E3A1(G4S)2 | 363 + 95 | 172.2 | 94 |
| CIgG4E3A1(G4S)3 | 364 + 96 | 161.5 | 73 |
| NIgG4E4A1(RS) | 373 + 113 | 6.2 | 90 |
| NIgG4E4A1(G4S)1 | 374 + 114 | 17.0 | 97 |
| NIgG4E4A1(G4S)2 | 375 + 115 | 16.4 | 98 |
| NIgG4E4A1(G4S)3 | 376 + 116 | 36.0 | 92 |
| CIgG4E4A1(RS) | 369 + 93 | n.d. | 0 |
| CIgG4E4A1(G4S)1 | 370 + 94 | 241.5 | 87 |
| CIgG4E4A1(G4S)2 | 371 + 95 | 107.0 | 94 |
| CIgG4E4A1(G4S)3 | 372 + 96 | 31.6 | 98 |
| NIgG4F1A1(RS) | 381 + 113 | 3.5 | 88 |
| NIgG4F1A1(G4S)1 | 382 + 114 | 2.6 | 92 |
| NIgG4F1A1(G4S)2 | 383 + 115 | 2.1 | 95 |
| NIgG4F1A1(G4S)3 | 384 + 116 | 35.5 | 92 |
| CIgG4F1A1(RS) | 377 + 93 | n.d. | 0 |
| CIgG4F1A1(G4S)1 | 378 + 94 | n.d. | 8 |
| CIgG4F1A1(G4S)2 | 379 + 95 | n.d. | 18 |
| CIgG4F1A1(G4S)3 | 380 + 96 | n.d. | 0 |
| NIgG4F2A1(RS) | 389 + 113 | 2.0 | 88 |
| NIgG4F2A1(G4S)1 | 390 + 114 | 2.0 | 92 |
| NIgG4F2A1(G4S)2 | 391 + 115 | 2.0 | 94 |
| NIgG4F2A1(G4S)3 | 392 + 116 | 2.0 | 95 |
| CIgG4F2A1(RS) | 385 + 93 | n.d. | 3 |
| CIgG4F2A1(G4S)1 | 386 + 94 | n.d. | 11 |
| CIgG4F2A1(G4S)2 | 387 + 95 | n.d. | 0 |
| CIgG4F2A1(G4S)3 | 388 + 96 | n.d. | 2 |
| NIgG4F3A1(RS) | 397 + 113 | 2.0 | 93 |
| NIgG4F3A1(G4S)1 | 398 + 114 | 2.0 | 93 |
| NIgG4F3A1(G4S)2 | 399 + 115 | 2.0 | 95 |
| NIgG4F3A1(G4S)3 | 400 + 116 | 0.9 | 94 |
| CIgG4F3A1(RS) | 401 + 93 | n.d. | 9 |
| CIgG4F3A1(G4S)1 | 402 + 94 | n.d. | 35 |
| CIgG4F3A1(G4S)2 | 403 + 95 | n.d. | 0 |
| CIgG4F3A1(G4S)3 | 404 + 96 | n.d. | 2 |
| NIgG4F4A1(RS) | 405 + 113 | 331.4 | 74 |
| NIgG4F4A1(G4S)1 | 406 + 114 | 21.6 | 100 |
| NIgG4F4A1(G4S)2 | 407 + 115 | 21.1 | 97 |
| NIgG4F4A1(G4S)3 | 408 + 116 | 44.49 | 85 |
| CIgG4F4A1(RS) | 401 + 93 | 1.2 | 99 |
| CIgG4F4A1(G4S)1 | 402 + 94 | 0.9 | 100 |
| CIgG4F4A1(G4S)2 | 403 + 95 | 0.9 | 100 |
| CIgG4F4A1(G4S)3 | 404 + 96 | 1.2 | 97 |
| NIgG4F5A1(RS) | 413 + 113 | 0.7 | 99 |
| NIgG4F5A1(G4S)1 | 414 + 114 | 28.9 | 67 |
| NIgG4F5A1(G4S)2 | 415 + 115 | 21.2 | 75 |
| NIgG4F5A1(G4S)3 | 416 + 116 | 34.8 | 48 |
| CIgG4F5A1(RS) | 409 + 93 | n.d. | 0 |

-continued

| | | RBL-SX38 | |
| SdAb construct | SEQ ID | EC$_{50}$ (nM) | Max effect/ effect 1 μM |
|---|---|---|---|
| CIgG4F5A1(G4S)1 | 410 + 94 | n.d. | 19 |
| CIgG4F5A1(G4S)2 | 411 + 95 | n.d. | 25 |
| CIgG4F5A1(G4S)3 | 412 + 96 | n.d. | 27 |
| NIgG4F6A1(RS) | 421 + 113 | 3.2 | 26 |
| NIgG4F6A1(G4S)1 | 422 + 114 | 2.2 | 68 |
| NIgG4F6A1(G4S)2 | 423 + 115 | 2.3 | 76 |
| NIgG4F6A1(G4S)3 | 424 + 116 | 2.7 | 87 |
| CIgG4F6A1(RS) | 417 + 93 | n.d. | 96 |
| CIgG4F6A1(G4S)1 | 418 + 94 | 59.9 | 95 |
| CIgG4F6A1(G4S)2 | 419 + 95 | 16.6 | 98 |
| CIgG4F6A1(G4S)3 | 420 + 96 | 7.9 | 90 |

Example 8

Inhibition of Effector Cell Degranulation.

The aim is to evaluate whether sdAbs can inhibit effector cell degranulation up on allergen challenge.

Material and Method

PBMC were isolated from heparinized whole blood from allergic donors by method with Lymfoprep (Fresenius Kabi 1114547) and Leuceptubes (Greiner 227290). After isolation the cells was washed and resuspended in RPMI, HSA: (RPMI 1640 (Gibco 72400-021)+0.5% HSA (Sigma A1653)) to 1/16 of original blood volume and used for displacement with sdAB construct by incubating with different concentrations for 1 h at 37 C. The preincubated cells is washed in RPMI, HSA and resuspended to 1/8 of blood volume in RPMI, HSA added IL-3 (RD peprotec cat 200-03)$_2$ ng/ml.

The IgE displace cells and controls are used for Basophil activation with a-IgE or allergen diluted in RPMI+0.5% HSA and stimulated with different concentrations of rDerp2, rBetv1 or Derp extract (ALK internal), depended on the donor sensitization and anti-IgE (Dako A0094), 1000-100-10 ng/ml.

Following 1 hours incubation in CO2 incubator (5% CO$_2$, 37° C.), the reaction was stopped by addition of BD FACS flow+0.5% BSA+10 mM EDTA.

FACS stain of activated cells: Cells were washed twice with FACS staining buffer (BD FACS flow+0.5% BSA) by centrifugation 5 min 500×G and cell pellet stained with a-CD63 FIC (BD92467), a-CD203c APC (e-bioscience, 324610), CD123 PE (BD034345). The cell were incubated on ice for 30 min followed by wash with FACS staining buffer before fixation 15 min, RT, with 200 μl cell fix (BD 340181)/well. After additional wash the cells were analyzed on flowcytometer: Cytek Aurora with plate loader. For comparison to IgE displacement efficiency sample of cells not used for activation assay was stained for IgE with a-IgE APC (ebioscience 17-6986) and FcER1 Cra1 BV605 (BD 747785) combined with CD123 PE like descibed above. Data were analysed using SpectroFlo software and the Basophils were identified as cells with low side-scatter and high CD203c+CD123 expression. Pct of basophils with high CD63 expression were depicted in graphs using Graph Prisma as % activated basophils.

The method above was further used in a more physiological setup. Here whole heparinized blood was used in stead of PBMC for direct incubation 1+1 with dilutions of sdAb constructs. After wash the blood was reconstituted with RPMI, HSA added IL-3 and assay performed as described with PBMC Results treatment of basophils with sdAb lead to decreased activation of basophils following stimulation with allergen or a-IgE. (FIG. 5A-C).

Dose response induced activation by rDerp2 in HDM allergic donor was ~10 fold decreased after treatment with 1 μM sdAb A1, with cells that show 16% displacement effect measured by IgE expression (table 17)

Efficient treatment was observed when combining sdAb A2 with single sdAb B1 or B2 while no effect were observed when combining sdAb A2 with B3, here the activation were comparable with A2 alone (FIG. 5B-C). These findings reflect the effect of displacement on IgE surface expression (table 17) where sdAb A2 in combination with B1 or B2 show ~100% effect while A2 in combination with B3 and A2 alone show comparable displacement effect ~70%.

The multispecific construct (CIgG4B1A1(G4S)1 was able to reduce the activation of basophils in PBMC (FIG. 5 D) and whole blood (FIG. 5 E-F) in a dose dependent matter demonstrated with concentration ranging from 10-1000 nM. (FIG. 5D-F) with a construct showing no direct cellular activation.

Conclusion

In conclusion cellular evaluation of sdAb-mediated IgE displacement reveal that efficient displacement of IgE from the FcER1 receptor situated on the cell surface, can be obtained using displacing sdAb A1 or A2 in combination with some of the other tested sdAbs or as linked sdAb.

The displacement of IgE was demonstrated with RBL-SX38 cells sensitized with recombinant IgE.

In addition, the displacement of IgE from human basophils from allergic donors and impact hereof on a following challenge of the basophils with either allergen or anti-IgE was demonstrated as well.

Example 9

Evaluation of the Ability to Prevent Anaphylaxis in Murine Model

The aim of the present example is to evaluate the ability of the sdAbs to prevent anaphylaxis in vivo.

Material and Methods

B6.Cg-Fcer1a$^{tm1Knt}$ Tg(FCER1A)1Bhk/J mice were originally obtained from The Jackson Laboratory and then bred in house for use in a passive systemic anaphylaxis (PSA) or a passive cutaneous anaphylaxis (PCA) model. For the PSA model, mice were sensitized by intraperitoneal (i.p.) injection of a mixture of three Der p 2-specific recombinant human IgE clones: H10, H12, P4E (Christensen et al. 2008), 200 μl per mouse with 16.67 μg/ml of each Ab in PBS. 24 hours later, the mice were injected i.p. with 200 μl of either sterile PBS or the sdAb CIgG4B1A1(G4S)1 at different concentrations (150 μM, 10 μM, 2 μM, 0.4 μM and 0.08 μM, in PBS), followed 4 hours later by allergen challenge (i.p. injection of 200 μl 0.05 μg/ml rDer p 2 (ALK internal)). Core body temperature was measured using temperature transponders (IPTT-300, implanted subcutaneously at least a day before experiment start), directly before inhibitor injection or allergen challenge and every 5 minutes thereafter for one hour or until serum collection 90 min post-challenge (BD Microtainer SST tubes, 365968). Serum mouse mast cell protease 1 (mMCPT1) concentration was determined using the MCPT-1 (mMCP-1) Mouse Uncoated ELISA Kit (Invitrogen, 88-7503-88) as per the manufacturer's recommendations (FIG. 6A). For the PCA model, mice were sensitized with the same three anti-Der p 2 antibodies, but 20 µl intradermally, with 2.5 µg/ml of each antibody. Usually, mice would be injected with the inhibitors either intradermally or intraperitoneally the next day, six hours before intravenous challenge with rDer p 2 (10 µg per mouse, 100 µl) in 1% Evan's Blue (Sigma-Aldrich, E2129) solution in sterile NaCl solution. However, for anaphylactogenicity testing, the inhibitor was injected intradermally with concurrent i.v. injection of the Evan's Blue solution without rDer p 2. A half hour after dye injection, mice were sacrificed and the area of dye extravasation on the back measured. Back skin was then harvested for dye extraction using formamide (Merck, S4117). The optical density of the extracted dye was measured at 600 nm (FIG. 8B).

Results

Figure 7A:
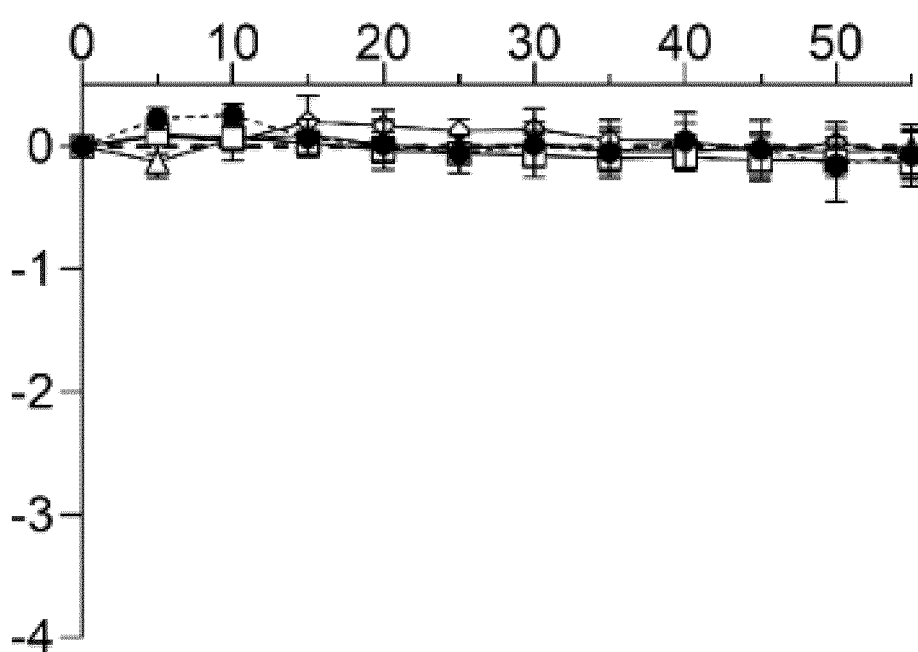

CIgG4B1A1(G4S)1 prevented anaphylaxis in the PSA model in a dose dependent manner. While the mice showed no changes in core body temperature after injection with the inhibitors alone (FIG. 6B), the animals treated with the lowest concentration of CIgG4B1A1(G4S)1 (0.08 µM) responded similarly to mice in the control group (injected with PBS) for both reduction in body temperature as well as serum mMCPT1 elevation. After treatment with a 0.4 µM dose mice were partially protected, and anaphylaxis was almost entirely prevented after treatment with the two highest doses of CIgG4B1A1(G4S)1 (FIG. 6C-E). Similarly, the constructs CIgG4D2A1(G4S)2, CIgG4E1A1(G4S)2, and CIgG4F4A1(G4S)1 were not anaphylactogenic on their own (FIG. 7A) but were able to disrupt anaphylaxis with varying efficiency (FIG. 7B). On the other hand, the N-linked construct NIgG4B1A1(G4S)3 induced core body temperature decreases in mice during the PSA model (FIG. 8A) and dye extravasation into sensitized skin areas in the PCA model for anaphylactogenicity testing (FIG. 8C).

Conclusion

The sdAbs CIgG4B1A1(G4S)1, CIgG4D2A1(G4S)2, CIgG4E1A1(G4S)2, and CIgG4F4A1(G4S)1 were able to prevent anaphylaxis in vivo in a murine passive systemic anaphylaxis model.

Example 10

Evaluation of Potential Anaphylactogenic Constructs.

The aim of the present study was to evaluate the ability of the sdAbs alone or as part of the construct, to activate basophils.

Material and Methods

PBMC isolated from heparinized whole blood (as described in example 8) or whole heparinized blood from allergic donors was incubated with incubating with different concentrations of sdAb constructs diluted in RPMI, 5% HSA for 1 hour in CO2 incubator (5% $CO_2$, 37° C.). The reaction was stopped by addition of BD FACS flow+0.5% BSA+10 mM EDTA and FACS stain of the cells for measuring CD63 and IgE expression was performed with the same method and reagents as described in example 8.

Results

An example is seen in FIG. 9, showing the displacement activity of different constructs at increasing concentrations (similar setup as in example 7). Further, FIG. 9A+C shows an example of the percentage activation of basophils triggered by the same constructs at different concentration. Overall constructs fused in the N-terminal showed a high activation in the mentioned interval, whereas C-terminal fused constructs were less anaphylactogenic. Further as seen in FIG. 9A+C, the linker in the C-terminal fused constructed, influenced the anaphylactogenic activity as well. The construct CIgG4B1A1(G4S)1 was tested in cells isolated from more than 20 different donors and did not show any anaphylactogenic activity in any concentration in any of the donors. On the other hand, the construct NIgG4B1A1(G4S)1 was tested in a similar number of donors and did show anaphylactogenic activity in all the donors. Interestingly, the comparator KIH_E7_79, did show anaphylactogenic activity. In some donors KIH_E7_79 only activated in high concentrations, whereas in other donors the activation was seen in lower concentrations as well. The rest of the constructs listed in table 15, showed a high variation in term of anaphylactogenic activity among different donors, but also within the same donor, meaning a clear conclusion cannot be drawn from this assay alone but may be confirmed in mice as seen in example 9.

Conclusion

Overall, this example shows that N-terminal-linked multispecific constructs were in general activating the basophils and thus, had anaphylactogenic activity, whereas most of the C-terminal linked did not, dependent on the linker. Importantly, CIgG4B1A1(G4S)1 did not show any anaphylactogenic activity when tested in more than 200 donors. The comparator KIH_E7_79 did show a high degree of anaphylactogenic activity compared to CIgG4B1A1(G4S)1. This setup is an easy and simple way of testing if a specific construct has the potential to have anaphylactogenic activity or not. The anaphylactogenic activity might be confirmed in murine models.

Example 11

Humanization of the sdAbs

Aim

Humanization of therapeutic antibodies derived from animal immunizations is often required to minimize immunogenicity risks in humans, which can cause potentially harmful and serious side effects and reduce antibody efficacy. Thus, the aim of the present study is to humanize the sdAbs described herein.

Material and Methods

The CDRs and Framework of the sdAbs for humanization are determined as described herein, which gives each sdAb, 3 individual CDR regions (CDR1-3) and 4 framework regions (FR1-4).

Each of the 4 framework regions (FR1-FR4) are initially fully humanized by identifying the closest human germline VH sequence and replacing these sequences with the camelid framework sections. This will give a degree of humanization at 100%.

Next step is to test the functionality of the humanized sdAbs as to whether the original functionally is maintained.

If the adjusted sequence is not affected by the humanization, or if an acceptable decrease in functionality is observed (which may be a weakened antigen-binding or less effective displacement), the humanization procedure is ended, and the final degree of humanization is 100%.

On the other hand, if the functionality is unacceptable affected at a degree of humanization at 100%, the sdAbs is subjected to "back-mutational procedures", with the purpose of decreasing the degree of humanization by re-introducing the original camelid amino acid sequences into the individual frames, one by one. Following the re-introduction of original camelid amino acid sequences, the functionality of the sdAbs is determined. When the loss of functionality, due to humanization, is re-established following back-mutational procedures, the degree of humanization is re-calculated, and the humanization procedure is ended. The final degree of humanization (0-100%) is dependent of the effect on the functionality of the humanized construct and cannot be predicted.

LIST OF REFERENCES

Almagro J C (2004), 'Identification of differences in the specificity-determining residues of antibodies that recognize antigens of different size: implications for the rational design of antibody repertoires', Journal of Molecular Recognition, doi.org/10.1002/jmr.659

Armour K L, Clark M R, Handly A G, Williamson L M. (1999) 'Recombinant human IgG molecules lacking Fcgamma receptor I binding and monocyte triggering activities' Euro J Immunol. DOI: 10.1002/(SICI)1521-4141(199908)29:08<2613::AID-IMMU2613>3.0.CO;2-J Balbino, Conde, Marichal, Starkl and Reber (2018) 'Approaches to target IgE antibodies in allergic diseases', Pharmacology and Therapeutics. Elsevier. doi: 10.1016/j.pharmthera.2018.05.015.

Baumann, M. J., Eggel, A., Amstutz, P., Stadler, B. M. and Vogel, M. (2010) 'DARPins against a functional IgE epitope', Immunology Letters. Elsevier. doi: 10.1016/j.imlet.2010.07.005.

Canfield S M, and Morrison S L. (1991) 'The binding affinity of human IgG for its high affinity Fc receptor is determined by multiple amino acids in the CH2 domain and is modulated by the hinge region' J. Exp. Med. DOI: 10.1084/jem.173.6.1483

Carter P., (2001) 'Bispecific human IgG by design' Journal of Immunological Methods. DOI: 10.1016/s0022-1759(00)00339-2

Chang Tse Wen (2000) 'The pharmacological basis of anti-IgE therapy', Nature Biotechnology. Nature Publishing Group. doi: 10.1038/72601.

Czajkowsky, D. M., Hu, J., Shao, Z. and Pleass, R. J. (2012) 'Fc-fusion proteins: new developments and future perspectives', EMBO Molecular Medicine. EMBO Press. doi: 10.1002/emmm.201201379.

Dhaliwal, B., Yuan, D., Pang, M. O. Y., Henry, A. J., Cain, K., Oxbrow, A., Fabiane, S. M., Beavil, A. J., McDonnell, J. M., Gould, H. J. and Sutton, B. J. (2012) 'Crystal structure of IgE bound to its B-cell receptor CD23 reveals a mechanism of reciprocal allosteric inhibition with high affinity receptor FcεRI', Proceedings of the National Academy of Sciences of the United States of America. National Academy of Sciences. doi: 10.1073/pnas.1207278109.

Drinkwater Nyssa, Cossins Benjamin P, Keeble Anthony H, Wright Michael, Cain Katharine, Hailu Hanna, Oxbrow Amanda, Delgado Jean, Shuttleworth Lindsay K, Kao Michael W-P, McDonnell James M, Beavil Andrew J and

82

Henry (2014) 'Human immunoglobulin E flexes between acutely bent and extended conformations', Nature Structural & Molecular Biology. Nature Publishing Group. doi: 10.1038/nsmb.2795.

Dondelinger M, Filee P, Sauvage E, Quinting B, Muydermans S, Galleni M and Vandevenne M (2018) 'Understanding the Significance and Implications of Antibody Numbering and Antigen-Binding Surface/Residue Definition'frontiers in immunology. doi.org/10.3389/fimmu.2018.02278

Duncan A R, Woof J M N, Partridge L J, Burton D R, and Winter G., (1988) 'Localization of the binding site for the human high-affinity Fc receptor on IgG', Nature, DOI: 10.1038/332563a0

Eggel, A., Baravalle, G., Hobi, G., Kim, B., Buschor, P., Forrer, P., Shin, J. S., Vogel, M., Stadler, B. M., Dahinden, C. A. and Jardetzky, T. S. (2014) 'Accelerated dissociation of IgE-FcεRI complexes by disruptive inhibitors actively desensitizes allergic effector cells.', Journal of Allergy and Clinical Immunology, The. Mosby. doi: 10.1016/j.jaci.2014.02.005.

Holdom, M. (2011) 'Conformational changes in IgE contribute to its uniquely slow dissociationrate from receptor Fc epsilon RI', Nature Structural & Molecular Biology. Nature Publishing Group.

Incorvaia, C., Mauro, M., Russello, M., Formigoni, C., Riario-Sforza, G. G. and Ridolo, E. (2014) 'Omalizumab, an anti-immunoglobulin E antibody: state of the art', Drug Design, Development and Therapy. Dove Press Ltd. doi: 10.2147/DDDT.S49409.

Jabs Frederic, Plum Melanie, Laursen Nick, Jensen Rasmus, Mølgaard Brian, Miehe Michaela, Mandolesi Marco, Rauber Michèle, Pfützner Wolfgang, Jakob Thilo, Mobs Christian, Andersen Gregers and Spillner Edzard (2018) 'Trapping IgE in a closed conformation by mimicking CD23 binding prevents and disrupts FcεRI interaction', Nature Communications. Nature Publishing Group UK. doi: 10.1038/s41467-017-02312-7.

Lefranc M P, (2002) 'IMGT, the international ImMunoGeneTics database: a high-quality information system for comparative immunogenetics and immunology', Developmental and Comparative Immunology. doi.org/10.1016/S0145-305X(02)00026-5

Kim Beomkyu, Eggel Alexander, Tarchevskaya Svetlana S., Vogel Monique, Prinz Heino and Jardetzky Theodore S. (2012) 'Accelerated disassembly of IgE-receptor complexes by a disruptive macromolecular inhibitor', Nature. Nature Publishing Group UK. doi: 10.1038/nature11546.

Mitchelle L S & Colwell L J, (2018) 'Comparative analysis of nanobody sequence and structure data' Proteins, DOI: 10.1002/prot.25497.

Ofran Y, Schlessinger and Rost B, (2008) 'Automated identification of complementarity determining regions (CDRs) reveals peculiar characteristics of CDRs and B cell epitopes', J Immunol, DOI: 10.4049/jimmunol.181.9.6230

Padlan E A, Abergel C and Tipper J P (1995), 'Identification of specificity-determining residues in antibodies.' Faseb J. doi.org/10.1096/fasebj.9.1.7821752

Pennington, Gasser, Brigger, Guntern, Eggel and Jardetzky (2021) 'Structure-guided design of ultrapotent disruptive IgE inhibitors to rapidly terminate acute allergic reactions', Journal of Allergy and Clinical Immunology, The. Mosby. doi: 10.1016/j.jaci.2021.03.050.

Riechmann and Muyldemans (1999) 'Single domain antibodies: comparison of camel V H and camelised human V H domains', J Immunol Methods. DOI: 10.1016/s0022-1759 (99)00138-6

Rossotti, M. A., Bélanger, K., Henry, K. A. and Tanha, J. (2021) 'Immunogenicity and humanization of single-domain antibodies', FEBS Journal, The. John Wiley & Sons, Inc. doi: 10.1111/febs.15809.

Rozan, C., Cornillon, A., Petiard, C., Chartier, M., Behar, G., Boix, C., Kerfelec, B., Robert, B., Pèlegrin, A., Chames, P., Teillaud, J.-L. and Baty, D. (2013) 'Single-Domain Antibody-Based and Linker-Free Bispecific Antibodies Targeting FcγRIII Induce Potent Antitumor Activity without Recruiting Regulatory T Cells', Molecular cancer therapeutics. American Association for Cancer Research. doi: 10.1158/1535-7163.MCT-12-1012.

Shields R L., Namenuk A K, Hong K, Meng Y G, Rae J, Briggs J, Xie D, Lai J, Stadlen A, LiB, Fox, J A, Presta L G (2001) 'High Resolution Mapping of the Binding Site

84 on Human IgG1 for FcγRI, FcγRII, FcγRIII, and FcRn and Design of IgG1 Variants with Improved Binding to the FcγR*', J Biol Chem. DOI:https://doi.org/10.1074/jbc.M009483200

Strohl, W. (2015) 'Fusion Proteins for Half-Life Extension of Biologics as a Strategy to Make Biobetters', BioDrugs. Adis. doi: 10.1007/s40259-015-0133-6.

Sulea, T. (2022) 'Humanization of Camelid Single-Domain Antibodies', Methods in Molecular Biology. Humana Press. doi: 10.1007/978-1-0716-2075-5_14.

Tao M H, Smith R I and Morrison S L., (1993) 'Structural features of human immunoglobulin G that determine isotype-specific differences in complement activation' J. Exp. Med. 178:661. DOI: 10.1084/jem.178.2.661

Wurzburg, Kim, Tarchevskaya, Eggel, Vogel and Jardetzky (2012) 'An Engineered Disulfide Bond Reversibly Traps the IgE-Fc3-4 in a Closed, Nonreceptor Binding Conformation*', Journal of Biological Chemistry. American Society for Biochemistry and Molecular Biology. doi: 10.1074/jbc.M112.407502.

The invention claimed is:

1. A multi-specific construct comprising
   a. a first single domain antibody (sdAb) able to displace bound IgE from FcεRI,
   b. a second sdAb that binds to IgE,
   c. a moiety that links the first and second sdAb,
   wherein
      the first and second sdAb bind non-identical epitopes of IgE, and
      the multi-specific construct can displace bound IgE from the IgE high-affinity receptor (FcεRI) with improved displacement activity compared to the first or second sdAb,
   wherein the moiety that links the first and second sdAb comprises
      an Fc region from an IgG antibody or from an Fc region comprising a mutation that induces heterodimerisation, and the first sdAb and second sdAb are fused or coupled covalently to the C-terminal end of a first Fc region polypeptide and a second Fc region polypeptide, respectively,
   wherein the first sdAb comprises a first CDR1, CDR2, and CDR3 binding regions each comprising or consisting of an amino acid sequence in the amino acid sequence set forth in SEQ ID NO: 1, wherein the amino acid sequence of the first CDR1, CDR2, and CDR3 binding regions are determined according to a single numbering scheme, wherein said numbering scheme is either Kabat, Chothia, IMTG or Aho numbering scheme, and
   the second sdAb comprises a second CDR1, CDR2, and CDR3 binding regions each comprising or consisting of an amino acid sequence in the amino acid sequence set forth in SEQ ID NO: 9 or 25, wherein the amino acid sequence of the second CDR1, CDR2, and CDR3 binding regions are determined according to a single numbering scheme, wherein said numbering scheme is either Kabat, Chothia, IMTG or Aho numbering scheme.

2. The multi-specific construct according to claim 1, wherein the IgG antibody is selected from IgG1, IgG2, IgG3, and IgG4.

3. The multi-specific construct according to claim 1, wherein the Fc region is from a human Fc region.

4. The multi-specific construct according to claim 3, wherein when IgG is IgG4, the Fc region comprises a truncated IgG4 hinge region.

5. The multi-specific construct according to claim 1, wherein the first sdAb or the second sdAb or both sdAbs consist(s) of affinity-matured, human or humanized amino acid sequences in the non-CDR regions.

6. The multi-specific construct according to claim 1, wherein the multi-specific construct is modified to add or remove glycosylation sites.

7. The multi-specific construct according to claim 1, wherein the Fc-region is modified to increase serum half-life of the multi-specific construct, compared to natural Fc-region.

8. The multi-specific construct according to claim 1, wherein the first and second sdAb are fused or coupled to the moiety via a linker.

9. The multi-specific construct according to claim 8, wherein the linker is a G4S linker.

10. The multi-specific construct according to claim 9, wherein the mutation that induces heterodimerisation comprises mutations in each polypeptide of the IgG-Fc, wherein the first polypeptide comprises the mutations T349C, T366S, L368A, and Y407V, and the second polypeptide comprises the mutations S354C and T366W, wherein numbering is per the EU numbering index.

11. The multi-specific construct according claim 10, wherein when IgG is IgG4, the Fc regions comprise the mutation S228P in IgG4, wherein numbering is per the EU numbering index.

12. A multi-specific construct comprising:
a. a first single domain antibody (sdAb) able to displace bound IgE from FcεRI;
b. a second sdAb that binds to IgE; and
c. a Fc region,
wherein the multi-specific construct comprises two polypeptides having the respective SEQ ID NOs: 94 and 102 or SEQ ID NOs: 94 and 338, wherein non-CDR regions of at least one of said polypeptides are modified to comprise human or humanized amino acid sequences; and wherein the multi-specific construct is able to displace bound IgE from FcεRI with improved displacement activity compared to the first or second sdAb.

* * * * *